US011434484B2

(12) United States Patent
Wang et al.

(10) Patent No.: US 11,434,484 B2
(45) Date of Patent: Sep. 6, 2022

(54) THREE-COMPONENT CRISPR/CAS COMPLEX SYSTEM AND USES THEREOF

(71) Applicant: The Jackson Laboratory, Bar Harbor, ME (US)

(72) Inventors: Haoyi Wang, Beijing (CN); Albert Cheng, Unionville, CT (US); Nathaniel Jillette, Farmington, CT (US)

(73) Assignee: The Jackson Laboratory, Bar Harbor, ME (US)

(*) Notice: Subject to any disclaimer, the term of this patent is extended or adjusted under 35 U.S.C. 154(b) by 964 days.

(21) Appl. No.: 15/702,944

(22) Filed: Sep. 13, 2017

(65) Prior Publication Data

US 2018/0094257 A1   Apr. 5, 2018

Related U.S. Application Data

(63) Continuation of application No. PCT/US2016/021491, filed on Mar. 9, 2016.

(60) Provisional application No. 62/221,249, filed on Sep. 21, 2015, provisional application No. 62/132,644, filed on Mar. 13, 2015.

(51) Int. Cl.
*C12N 9/22* (2006.01)
*C12N 15/11* (2006.01)
*C12N 15/90* (2006.01)

(52) U.S. Cl.
CPC ............... *C12N 15/11* (2013.01); *C12N 9/22* (2013.01); *C12N 15/111* (2013.01); *C12N 15/907* (2013.01); *C12N 2310/20* (2017.05); *C12N 2310/531* (2013.01); *C12N 2800/80* (2013.01)

(58) Field of Classification Search
CPC ......... C12N 15/11; C12N 15/111; C12N 9/22; C12N 2310/20; C12N 2310/531
See application file for complete search history.

(56) References Cited

U.S. PATENT DOCUMENTS

| | | | |
|---|---|---|---|
| 2010/0204259 A1 | 8/2010 | Tygesen et al. | |
| 2013/0129701 A1* | 5/2013 | Wang | C12N 15/86 424/94.3 |
| 2014/0010873 A1 | 1/2014 | Tygesen et al. | |
| 2019/0218261 A1* | 7/2019 | Cheng | C07K 14/315 |
| 2020/0071369 A1* | 3/2020 | Cheng | C07K 14/4702 |

FOREIGN PATENT DOCUMENTS

| | | |
|---|---|---|
| WO | 2011/160052 A2 | 12/2011 |
| WO | WO 2012/068627 A1 | 5/2012 |

OTHER PUBLICATIONS

Zalatan et al.; Engineering Complex Synthetic Transcriptional Programs with CRISPR RNA Scaffolds; Cell; vol. 160, Nos. 1-2, pp. 339-350, published online Dec. 18, 2014, and supplemental data (Year: 2014).*
Qi et al.; Repurposing CRISPR as an RNA-Guided Platform for Sequence-Specific Control of Gene Expression; Cell, vol. 152, No. 5, pp. 1173-1183, published Feb. 28, 2013 (Year: 2013).*
Stratagene; 1988 catalog, p. 39 (Year: 1988).*
Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.
Cheng et al.: "Casilio: a versatile CRISPR-Cas9-Pumilio hybrid for gene regulation and genomic labeling", Cell Research—Xibao Yanjiu, vol. 26, No. 2, Jan. 15, 2016, pp. 254-257.
Zalatan et al., "Engineering complex synthetic transcriptional programs with CRISPR RNA scaffolds", Cell, vol. 160, No. 1, Jan. 15, 2015, pp. 339-350.
Mali et al., "CAS9 transcriptional activators for target specificity screening and paired nickases for cooperative genome engineering", Nature Biotechnology, vol. 31, No. 9, Aug. 1, 2013, pp. 833-838.
International Preliminary Report on Patentability for PCT/US2016/021491 dated Sep. 19, 2017, pp. 1-7.

* cited by examiner

*Primary Examiner* — Antonio Galisteo Gonzalez
(74) *Attorney, Agent, or Firm* — Wolf, Greenfield & Sacks, P.C.

(57) ABSTRACT

The invention described herein provides compositions and reagents for assembling a tripartite complex at a specific location of a target DNA. The invention also provides methods for using the complex to, for example, label a specific genomic locus, to regulate the expression of a target gene, or to create a gene regulatory network.

18 Claims, 22 Drawing Sheets

Specification includes a Sequence Listing.

| | Samples |
|---|---|
| 1 | dCas9/sgControl-5xPBS32/PUF(3-2)::VP64 |
| 2 | dCas9/sgTetO-5xPBS32/PUF(3-2)::VP64 |
| 3 | dCas9/sgControl-5xPBS6272/KRAB::PUF(6-2/7-2) |
| 4 | dCas9/sgSV40-5xPBS6272/KRAB::PUF(6-2/7-2) |
| 5 | dCas9/sgControl-5xPBS32/PUF(3-2)::VP64/sgControl-5xPBS6272/KRAB::PUF(6-2/7-2) |
| 6 | dCas9/sgTetO-5xPBS32/PUF(3-2)::VP64/sgSV40-5xPBS6272/KRAB::PUF(6-2/7-2) |

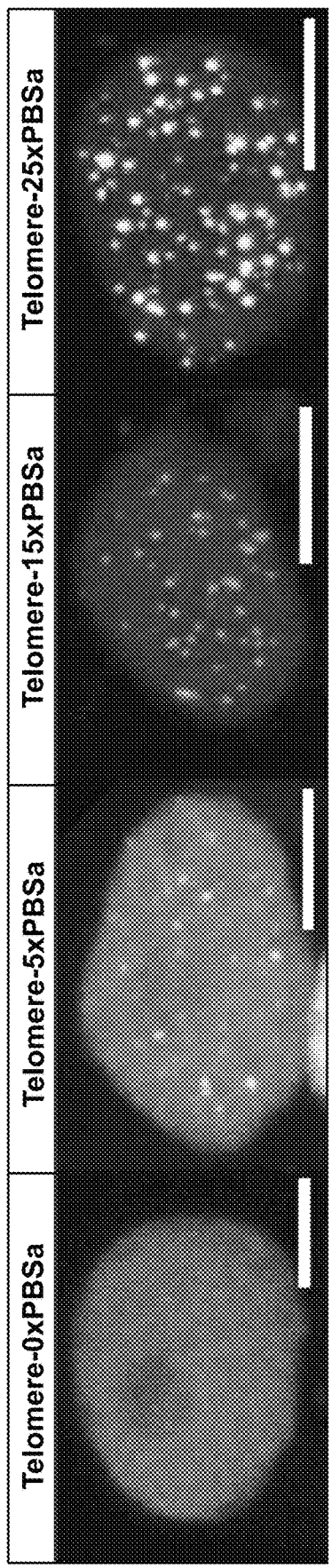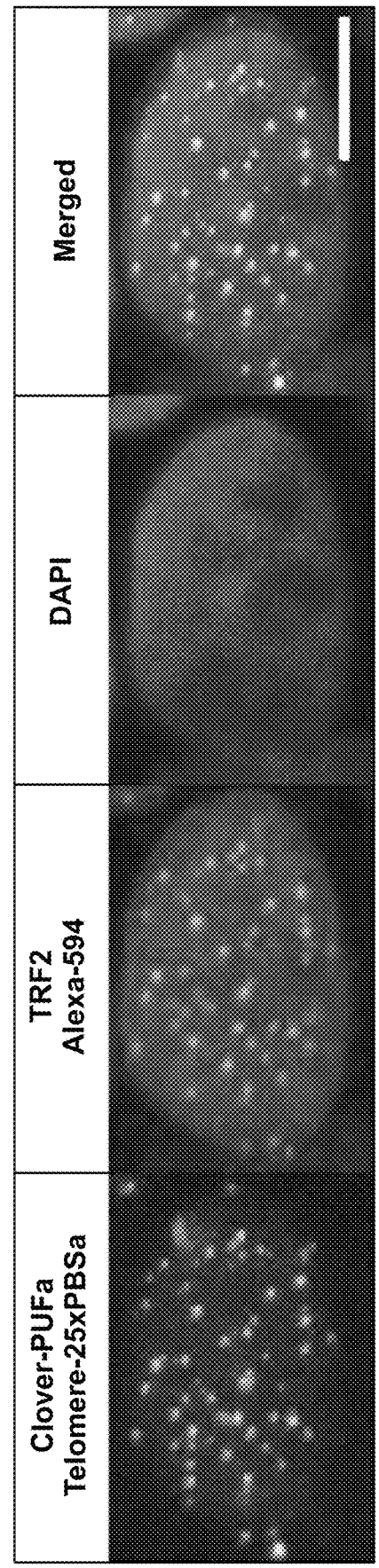
FIG. 6B
FIG. 6C

Multiplexing

Multimerization

Complex formation

SEQUENCE LISTING

<160> NUMBER OF SEQ ID NOS: 173

<210> SEQ ID NO 1
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1
gttttagagc tagaaatagc aagttaaaat aaggcta         37

<210> SEQ ID NO 2
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 2
gtttaagagc tatgctggaa acagcatagc aagtttaaat aaggcta    47

<210> SEQ ID NO 3
<211> LENGTH: 349
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Cys Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Ser Tyr Val Ile Glu His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

```
Leu Glu Lys Tyr Tyr Met Lys Asn Gly Val Asp Leu Gly
            340                 345
```

<210> SEQ ID NO 4
<211> LENGTH: 349
<212> TYPE: PRT
<213> ORGANISM: Homo sapiens

<400> SEQUENCE: 4

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Asn Tyr Val Ile Gln His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly
            340                 345
```

```
<210> SEQ ID NO 5
<211> LENGTH: 349
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (36)..(36)
<223> OTHER INFORMATION: /replace="Ser" or "Gly" or "Ala" or "Thr" or
      "Asn"
<220> FEATURE:
<221> NAME/KEY: VARIANT
<222> LOCATION: (40)..(40)
<223> OTHER INFORMATION: /replace="Arg" or "Glu"
<220> FEATURE:
<221> NAME/KEY: VARIANT
<222> LOCATION: (72)..(72)
<223> OTHER INFORMATION: /replace="Ser" or "Gly" or "Ala" or "Thr" or
      "Asn"
<220> FEATURE:
<221> NAME/KEY: VARIANT
<222> LOCATION: (73)..(73)
<223> OTHER INFORMATION: /replace="Tyr"
<220> FEATURE:
<221> NAME/KEY: VARIANT
<222> LOCATION: (76)..(76)
<223> OTHER INFORMATION: /replace="Arg" or "Glu"
<220> FEATURE:
<221> NAME/KEY: VARIANT
<222> LOCATION: (108)..(108)
<223> OTHER INFORMATION: /replace="Ser" or "Gly" or "Ala" or "Thr" or
      "Asn"
<220> FEATURE:
<221> NAME/KEY: VARIANT
<222> LOCATION: (112)..(112)
<223> OTHER INFORMATION: /replace="Arg" or "Glu"
<220> FEATURE:
<221> NAME/KEY: VARIANT
<222> LOCATION: (144)..(144)
<223> OTHER INFORMATION: /replace="Ser" or "Gly" or "Ala" or "Thr" or
      "Asn"
<220> FEATURE:
<221> NAME/KEY: VARIANT
<222> LOCATION: (145)..(145)
<223> OTHER INFORMATION: /replace="His"
<220> FEATURE:
<221> NAME/KEY: VARIANT
<222> LOCATION: (148)..(148)
<223> OTHER INFORMATION: /replace="Arg" or "Glu"
<220> FEATURE:
<221> NAME/KEY: VARIANT
<222> LOCATION: (180)..(180)
<223> OTHER INFORMATION: /replace="Ser" or "Gly" or "Ala" or "Thr" or
      "Asn"
<220> FEATURE:
<221> NAME/KEY: VARIANT
<222> LOCATION: (184)..(184)
<223> OTHER INFORMATION: /replace="Arg" or "Glu"
<220> FEATURE:
<221> NAME/KEY: VARIANT
<222> LOCATION: (216)..(216)
<223> OTHER INFORMATION: /replace="Ser" or "Gly" or "Ala" or "Thr" or
      "Asn"
<220> FEATURE:
<221> NAME/KEY: VARIANT
<222> LOCATION: (217)..(217)
<223> OTHER INFORMATION: /replace="Tyr"
<220> FEATURE:
<221> NAME/KEY: VARIANT
<222> LOCATION: (220)..(220)
<223> OTHER INFORMATION: /replace="Arg" or "Glu"
<220> FEATURE:
<221> NAME/KEY: VARIANT
<222> LOCATION: (252)..(252)
<223> OTHER INFORMATION: /replace="Ser" or "Gly" or "Ala" or "Thr" or
      "Asn"
```

```
<220> FEATURE:
<221> NAME/KEY: VARIANT
<222> LOCATION: (253)..(253)
<223> OTHER INFORMATION: /replace="Asn"
<220> FEATURE:
<221> NAME/KEY: VARIANT
<222> LOCATION: (256)..(256)
<223> OTHER INFORMATION: /replace="Arg" or "Glu"
<220> FEATURE:
<221> NAME/KEY: VARIANT
<222> LOCATION: (295)..(295)
<223> OTHER INFORMATION: /replace="Ser" or "Gly" or "Ala" or "Thr" or
      "Asn"
<220> FEATURE:
<221> NAME/KEY: VARIANT
<222> LOCATION: (296)..(296)
<223> OTHER INFORMATION: /replace="Tyr"
<220> FEATURE:
<221> NAME/KEY: VARIANT
<222> LOCATION: (299)..(299)
<223> OTHER INFORMATION: /replace="Arg" or "Glu"
<220> FEATURE:
<221> NAME/KEY: MISC_FEATURE
<222> LOCATION: (1)..(349)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 5

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Cys Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Cys Arg Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Cys
    130                 135                 140

Arg Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Cys Arg Val Ile Gln His Val Leu Glu
    210                 215                 220

His Gly Arg Pro Glu Asp Lys Ser Lys Ile Val Ala Glu Ile Arg Gly
225                 230                 235                 240
```

```
Asn Val Leu Val Leu Ser Gln His Lys Phe Ala Cys Arg Val Val Gln
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Cys Arg Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly
                340                 345
```

<210> SEQ ID NO 6
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

```
Gln His Gly Cys Arg Phe Ile Gln Leu Lys Leu Glu Arg Ala
1               5                   10
```

<210> SEQ ID NO 7
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

```
Gln His Gly Ser Arg Phe Ile Gln Leu Lys Leu Glu Arg Ala
1               5                   10
```

<210> SEQ ID NO 8
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

```
Gln His Gly Ser Arg Phe Ile Arg Leu Lys Leu Glu Arg Ala
1               5                   10
```

<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

```
Gln His Gly Gly Arg Phe Ile Arg Leu Lys Leu Glu Arg Ala
```

1               5                   10

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gln His Gly Ala Arg Phe Ile Arg Leu Lys Leu Glu Arg Ala
1               5                   10

<210> SEQ ID NO 11
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gln His Gly Thr Arg Phe Ile Arg Leu Lys Leu Glu Arg Ala
1               5                   10

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln His Gly Cys Arg Phe Ile Arg Leu Lys Leu Glu Arg Ala
1               5                   10

<210> SEQ ID NO 13
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gln His Gly Ser Arg Phe Ile Glu Leu Lys Leu Glu Arg Ala
1               5                   10

<210> SEQ ID NO 14
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gln His Gly Asn Arg Phe Ile Gln Leu Lys Leu Glu Arg Ala
1               5                   10

<210> SEQ ID NO 15

```
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Val Phe Gly Cys Arg Val Ile Gln Lys Phe Phe Glu Phe Gly
1               5                   10

<210> SEQ ID NO 16
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Val Phe Gly Ser Arg Val Ile Gln Lys Phe Phe Glu Phe Gly
1               5                   10

<210> SEQ ID NO 17
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Val Phe Gly Cys Tyr Val Ile Gln Lys Phe Phe Glu Phe Gly
1               5                   10

<210> SEQ ID NO 18
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Val Phe Gly Ser Tyr Val Ile Gln Lys Phe Phe Glu Phe Gly
1               5                   10

<210> SEQ ID NO 19
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Val Phe Gly Ser Tyr Val Ile Arg Lys Phe Phe Glu Phe Gly
1               5                   10

<210> SEQ ID NO 20
<211> LENGTH: 14
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 20

Val Phe Gly Gly Tyr Val Ile Arg Lys Phe Phe Glu Phe Gly
1               5                   10

<210> SEQ ID NO 21
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Phe Gly Ala Tyr Val Ile Arg Lys Phe Phe Glu Phe Gly
1               5                   10

<210> SEQ ID NO 22
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Val Phe Gly Thr Tyr Val Ile Arg Lys Phe Phe Glu Phe Gly
1               5                   10

<210> SEQ ID NO 23
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Val Phe Gly Cys Tyr Val Ile Arg Lys Phe Phe Glu Phe Gly
1               5                   10

<210> SEQ ID NO 24
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Val Phe Gly Ser Tyr Val Ile Glu Lys Phe Phe Glu Phe Gly
1               5                   10

<210> SEQ ID NO 25
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 25

Val Phe Gly Asn Tyr Val Ile Gln Lys Phe Phe Glu Phe Gly
1               5                   10

<210> SEQ ID NO 26
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Met Tyr Gly Cys Arg Val Ile Gln Lys Ala Leu Glu Phe Ile
1               5                   10

<210> SEQ ID NO 27
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Met Tyr Gly Ser Arg Val Ile Gln Lys Ala Leu Glu Phe Ile
1               5                   10

<210> SEQ ID NO 28
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Met Tyr Gly Ser Arg Val Ile Arg Lys Ala Leu Glu Phe Ile
1               5                   10

<210> SEQ ID NO 29
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Met Tyr Gly Gly Arg Val Ile Arg Lys Ala Leu Glu Phe Ile
1               5                   10

<210> SEQ ID NO 30
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Met Tyr Gly Ala Arg Val Ile Arg Lys Ala Leu Glu Phe Ile
1               5                   10
```

```
<210> SEQ ID NO 31
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Met Tyr Gly Thr Arg Val Ile Arg Lys Ala Leu Glu Phe Ile
1               5                   10

<210> SEQ ID NO 32
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Met Tyr Gly Cys Arg Val Ile Arg Lys Ala Leu Glu Phe Ile
1               5                   10

<210> SEQ ID NO 33
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Met Tyr Gly Ser Arg Val Ile Glu Lys Ala Leu Glu Phe Ile
1               5                   10

<210> SEQ ID NO 34
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Met Tyr Gly Asn Arg Val Ile Gln Lys Ala Leu Glu Phe Ile
1               5                   10

<210> SEQ ID NO 35
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gln Asn Gly Cys Arg Val Val Gln Lys Cys Ile Glu Cys Val
1               5                   10

<210> SEQ ID NO 36
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gln Asn Gly Ser Arg Val Val Gln Lys Cys Ile Glu Cys Val
1               5                   10

<210> SEQ ID NO 37
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gln Asn Gly Cys His Val Val Gln Lys Cys Ile Glu Cys Val
1               5                   10

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gln Asn Gly Ser His Val Val Gln Lys Cys Ile Glu Cys Val
1               5                   10

<210> SEQ ID NO 39
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gln Asn Gly Ser His Val Val Arg Lys Cys Ile Glu Cys Val
1               5                   10

<210> SEQ ID NO 40
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gln Asn Gly Gly His Val Val Arg Lys Cys Ile Glu Cys Val
1               5                   10

<210> SEQ ID NO 41
<211> LENGTH: 14
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 41

Gln Asn Gly Ala His Val Val Arg Lys Cys Ile Glu Cys Val
1               5                   10

<210> SEQ ID NO 42
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gln Asn Gly Thr His Val Val Arg Lys Cys Ile Glu Cys Val
1               5                   10

<210> SEQ ID NO 43
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gln Asn Gly Cys His Val Val Arg Lys Cys Ile Glu Cys Val
1               5                   10

<210> SEQ ID NO 44
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gln Asn Gly Ser His Val Val Glu Lys Cys Ile Glu Cys Val
1               5                   10

<210> SEQ ID NO 45
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gln Asn Gly Asn His Val Val Gln Lys Cys Ile Glu Cys Val
1               5                   10

<210> SEQ ID NO 46
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Pro Tyr Gly Cys Arg Val Ile Gln Arg Ile Leu Glu His Cys
1               5                   10

<210> SEQ ID NO 47
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Pro Tyr Gly Ser Arg Val Ile Gln Arg Ile Leu Glu His Cys
1               5                   10

<210> SEQ ID NO 48
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Pro Tyr Gly Ser Arg Val Ile Arg Arg Ile Leu Glu His Cys
1               5                   10

<210> SEQ ID NO 49
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Pro Tyr Gly Gly Arg Val Ile Arg Arg Ile Leu Glu His Cys
1               5                   10

<210> SEQ ID NO 50
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Pro Tyr Gly Ala Arg Val Ile Arg Arg Ile Leu Glu His Cys
1               5                   10

<210> SEQ ID NO 51
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Pro Tyr Gly Thr Arg Val Ile Arg Arg Ile Leu Glu His Cys
1               5                   10

```
<210> SEQ ID NO 52
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Pro Tyr Gly Cys Arg Val Ile Arg Arg Ile Leu Glu His Cys
1               5                   10

<210> SEQ ID NO 53
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Pro Tyr Gly Ser Arg Val Ile Glu Arg Ile Leu Glu His Cys
1               5                   10

<210> SEQ ID NO 54
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Pro Tyr Gly Asn Arg Val Ile Gln Arg Ile Leu Glu His Cys
1               5                   10

<210> SEQ ID NO 55
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gln Tyr Gly Cys Arg Val Ile Gln His Val Leu Glu His Gly
1               5                   10

<210> SEQ ID NO 56
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gln Tyr Gly Ser Arg Val Ile Gln His Val Leu Glu His Gly
1               5                   10

<210> SEQ ID NO 57
<211> LENGTH: 14
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gln Tyr Gly Cys Tyr Val Ile Gln His Val Leu Glu His Gly
1               5                   10

<210> SEQ ID NO 58
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gln Tyr Gly Ser Tyr Val Ile Gln His Val Leu Glu His Gly
1               5                   10

<210> SEQ ID NO 59
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Tyr Gly Ser Tyr Val Ile Arg His Val Leu Glu His Gly
1               5                   10

<210> SEQ ID NO 60
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gln Tyr Gly Gly Tyr Val Ile Arg His Val Leu Glu His Gly
1               5                   10

<210> SEQ ID NO 61
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gln Tyr Gly Ala Tyr Val Ile Arg His Val Leu Glu His Gly
1               5                   10

<210> SEQ ID NO 62
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

```
                Synthetic peptide"

<400> SEQUENCE: 62

Gln Tyr Gly Thr Tyr Val Ile Arg His Val Leu Glu His Gly
1               5                   10

<210> SEQ ID NO 63
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gln Tyr Gly Cys Tyr Val Ile Arg His Val Leu Glu His Gly
1               5                   10

<210> SEQ ID NO 64
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gln Tyr Gly Ser Tyr Val Ile Glu His Val Leu Glu His Gly
1               5                   10

<210> SEQ ID NO 65
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gln Tyr Gly Asn Tyr Val Ile Gln His Val Leu Glu His Gly
1               5                   10

<210> SEQ ID NO 66
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Lys Phe Ala Cys Arg Val Val Gln Lys Cys Val Thr His Ala
1               5                   10

<210> SEQ ID NO 67
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67
```

```
Lys Phe Ala Ser Arg Val Val Gln Lys Cys Val Thr His Ala
1               5                   10
```

<210> SEQ ID NO 68
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

```
Lys Phe Ala Cys Asn Val Val Gln Lys Cys Val Thr His Ala
1               5                   10
```

<210> SEQ ID NO 69
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

```
Lys Phe Ala Ser Asn Val Val Gln Lys Cys Val Thr His Ala
1               5                   10
```

<210> SEQ ID NO 70
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

```
Lys Phe Ala Ser Asn Val Val Arg Lys Cys Val Thr His Ala
1               5                   10
```

<210> SEQ ID NO 71
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

```
Lys Phe Ala Gly Asn Val Val Arg Lys Cys Val Thr His Ala
1               5                   10
```

<210> SEQ ID NO 72
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

```
Lys Phe Ala Ala Asn Val Val Arg Lys Cys Val Thr His Ala
1               5                   10
```

```
<210> SEQ ID NO 73
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Lys Phe Ala Thr Asn Val Val Arg Lys Cys Val Thr His Ala
1               5                   10

<210> SEQ ID NO 74
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Lys Phe Ala Cys Asn Val Val Arg Lys Cys Val Thr His Ala
1               5                   10

<210> SEQ ID NO 75
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Lys Phe Ala Ser Asn Val Val Glu Lys Cys Val Thr His Ala
1               5                   10

<210> SEQ ID NO 76
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Lys Phe Ala Asn Asn Val Val Gln Lys Cys Val Thr His Ala
1               5                   10

<210> SEQ ID NO 77
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Gln Tyr Ala Cys Arg Val Val Gln Lys Met Ile Asp Val Ala
1               5                   10

<210> SEQ ID NO 78
<211> LENGTH: 14
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 78

Gln Tyr Ala Ser Arg Val Val Gln Lys Met Ile Asp Val Ala
1               5                   10

<210> SEQ ID NO 79
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gln Tyr Ala Cys Tyr Val Val Gln Lys Met Ile Asp Val Ala
1               5                   10

<210> SEQ ID NO 80
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gln Tyr Ala Ser Tyr Val Val Gln Lys Met Ile Asp Val Ala
1               5                   10

<210> SEQ ID NO 81
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gln Tyr Ala Ser Tyr Val Val Arg Lys Met Ile Asp Val Ala
1               5                   10

<210> SEQ ID NO 82
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gln Tyr Ala Gly Tyr Val Val Arg Lys Met Ile Asp Val Ala
1               5                   10

<210> SEQ ID NO 83
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 83

Gln Tyr Ala Ala Tyr Val Val Arg Lys Met Ile Asp Val Ala
1               5                   10

<210> SEQ ID NO 84
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Gln Tyr Ala Thr Tyr Val Val Arg Lys Met Ile Asp Val Ala
1               5                   10

<210> SEQ ID NO 85
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gln Tyr Ala Cys Tyr Val Val Arg Lys Met Ile Asp Val Ala
1               5                   10

<210> SEQ ID NO 86
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gln Tyr Ala Ser Tyr Val Val Glu Lys Met Ile Asp Val Ala
1               5                   10

<210> SEQ ID NO 87
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Gln Tyr Ala Asn Tyr Val Val Gln Lys Met Ile Asp Val Ala
1               5                   10

<210> SEQ ID NO 88
<211> LENGTH: 349
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Gly Arg Ser Arg Leu Leu Glu Asp Phe Arg Asn Asn Arg Tyr Pro Asn

Leu Gln Leu Arg Glu Ile Ala Gly His Ile Met Glu Phe Ser Gln Asp
                  20                  25                  30

Gln His Gly Ser Arg Phe Ile Gln Leu Lys Leu Glu Arg Ala Thr Pro
              35                  40                  45

Ala Glu Arg Gln Leu Val Phe Asn Glu Ile Leu Gln Ala Ala Tyr Gln
          50                  55                  60

Leu Met Val Asp Val Phe Gly Asn Tyr Val Ile Gln Lys Phe Phe Glu
 65                  70                  75                  80

Phe Gly Ser Leu Glu Gln Lys Leu Ala Leu Ala Glu Arg Ile Arg Gly
                  85                  90                  95

His Val Leu Ser Leu Ala Leu Gln Met Tyr Gly Ser Arg Val Ile Glu
              100                 105                 110

Lys Ala Leu Glu Phe Ile Pro Ser Asp Gln Gln Asn Glu Met Val Arg
          115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
              180                 185                 190

Asp Gln Thr Leu Pro Ile Leu Glu Glu Leu His Gln His Thr Glu Gln
          195                 200                 205

Leu Val Gln Asp Gln Tyr Gly Asn Tyr Val Ile Gln His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
              260                 265                 270

Glu Val Cys Thr Met Asn Asp Gly Pro His Ser Ala Leu Tyr Thr Met
          275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly
              340                 345

<210> SEQ ID NO 89
<211> LENGTH: 349
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Gly Arg Ser Arg Leu Leu Glu Asp Phe Arg Asn Asn Arg Tyr Pro Asn
 1               5                  10                  15

Leu Gln Leu Arg Glu Ile Ala Gly His Ile Met Glu Phe Ser Gln Asp
                20                  25                  30

Gln His Gly Ser Arg Phe Ile Gln Leu Lys Leu Glu Arg Ala Thr Pro
            35                  40                  45

Ala Glu Arg Gln Leu Val Phe Asn Glu Ile Leu Gln Ala Ala Tyr Gln
50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Ser Tyr Val Ile Glu His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly
            340                 345

<210> SEQ ID NO 90
<211> LENGTH: 349
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 90

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Glu Leu Lys Leu Glu Arg Ala Thr Pro
            35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Ser Arg Val Ile Glu Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Asn Tyr Val Ile Gln His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly
            340                 345

<210> SEQ ID NO 91
<211> LENGTH: 341
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp

```
            20                  25                  30
Gln His Gly Ser Arg Phe Ile Glu Leu Lys Leu Glu Arg Ala Thr Pro
            35                  40                  45

Ala Glu Arg Gln Leu Val Phe Asn Glu Ile Leu Gln Ala Ala Tyr Gln
 50                  55                  60

Leu Met Val Asp Val Phe Gly Cys Arg Val Ile Gln Lys Phe Phe Glu
 65                  70                  75                  80

Phe Gly Ser Leu Glu Gln Lys Leu Ala Leu Ala Glu Arg Ile Arg Gly
                 85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
            115                 120                 125

Glu Leu Asp Gly His Val Leu Lys Cys Val Lys Asp Gln Asn Gly Asn
            130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
            195                 200                 205

Leu Val Gln Asp Gln Tyr Gly Ser Tyr Val Ile Glu His Val Leu Glu
            210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
            275                 280                 285

Met Lys Asp Gln Tyr Ala Ser Tyr Val Val Glu Lys Met Ile Asp Val
            290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr
            340

<210> SEQ ID NO 92
<211> LENGTH: 341
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gly Arg Ser Arg Leu Leu Glu Asp Phe Arg Asn Asn Arg Tyr Pro Asn
1               5                  10                  15

Leu Gln Leu Arg Glu Ile Ala Gly His Ile Met Glu Phe Ser Gln Asp
            20                  25                  30
```

-continued

Gln His Gly Asn Arg Phe Ile Gln Leu Lys Leu Glu Arg Ala Thr Pro
          35                  40                  45

Ala Glu Arg Gln Leu Val Phe Asn Glu Ile Leu Gln Ala Ala Tyr Gln
 50                  55                  60

Leu Met Val Asp Val Phe Gly Ser Tyr Val Ile Glu Lys Phe Phe Glu
 65                  70                  75                  80

Phe Gly Ser Leu Glu Gln Lys Leu Ala Leu Ala Glu Arg Ile Arg Gly
              85                  90                  95

His Val Leu Ser Leu Ala Leu Gln Met Tyr Gly Ser Arg Val Ile Glu
             100                 105                 110

Lys Ala Leu Glu Phe Ile Pro Ser Asp Gln Gln Asn Glu Met Val Arg
             115                 120                 125

Glu Leu Asp Gly His Val Leu Lys Cys Val Lys Asp Gln Asn Gly Asn
130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                 165                 170                 175

Pro Tyr Gly Ser Arg Val Ile Glu Arg Ile Leu Glu His Cys Leu Pro
             180                 185                 190

Asp Gln Thr Leu Pro Ile Leu Glu Glu Leu His Gln His Thr Glu Gln
             195                 200                 205

Leu Val Gln Asp Gln Tyr Gly Ser Tyr Val Ile Glu His Val Leu Glu
 210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Cys Asn Val Val Gln
                 245                 250                 255

Lys Cys Val Thr His Ala Ser Arg Thr Glu Arg Ala Val Leu Ile Asp
             260                 265                 270

Glu Cys Val Thr Met Asn Asp Gly Pro His Ser Ala Leu Tyr Thr Met
             275                 280                 285

Met Lys Asp Gln Tyr Ala Ser Tyr Val Val Glu Lys Met Ile Asp Val
 290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                 325                 330                 335

Leu Glu Lys Tyr Tyr
             340

<210> SEQ ID NO 93
<211> LENGTH: 341
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
             20                  25                  30

-continued

```
Gln His Gly Cys Arg Phe Ile Gln Leu Lys Leu Glu Arg Ala Thr Pro
         35                  40                  45

Ala Glu Arg Gln Leu Val Phe Asn Glu Ile Leu Gln Ala Ala Tyr Gln
 50                  55                  60

Leu Met Val Asp Val Phe Gly Ser Tyr Val Ile Glu Lys Phe Phe Glu
 65                  70                  75                  80

Phe Gly Ser Leu Glu Gln Lys Leu Ala Leu Ala Glu Arg Ile Arg Gly
                 85                  90                  95

His Val Leu Ser Leu Ala Leu Gln Met Tyr Gly Asn Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Ser Tyr Val Ile Glu His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Cys Asn Val Val Gln
                245                 250                 255

Lys Cys Val Thr His Ala Ser Arg Thr Glu Arg Ala Val Leu Ile Asp
            260                 265                 270

Glu Cys Val Thr Met Asn Asp Gly Pro His Ser Ala Leu Tyr Thr Met
        275                 280                 285

Met Lys Asp Gln Tyr Ala Cys Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr
            340

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Pro Pro Lys Lys Lys Arg Lys Val
1               5

<210> SEQ ID NO 95
<211> LENGTH: 6
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 95

His His His His His His
1               5

<210> SEQ ID NO 96
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96
```

| Met | Gly | Ile | Leu | Pro | Pro | Lys | Lys | Arg | Lys | Val | Ser | Arg | Gly | Arg |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ser | Arg | Leu | Leu | Glu | Asp | Phe | Arg | Asn | Asn | Arg | Tyr | Pro | Asn | Leu | Gln |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Arg | Glu | Ile | Ala | Gly | His | Ile | Met | Glu | Phe | Ser | Gln | Asp | Gln | His |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Ser | Arg | Phe | Ile | Gln | Leu | Lys | Leu | Glu | Arg | Ala | Thr | Pro | Ala | Glu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Arg | Gln | Leu | Val | Phe | Asn | Glu | Ile | Leu | Gln | Ala | Ala | Tyr | Gln | Leu | Met |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Asp | Val | Phe | Gly | Asn | Tyr | Val | Ile | Gln | Lys | Phe | Phe | Glu | Phe | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ser | Leu | Glu | Gln | Lys | Leu | Ala | Leu | Ala | Glu | Arg | Ile | Arg | Gly | His | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Ser | Leu | Ala | Leu | Gln | Met | Tyr | Gly | Ser | Arg | Val | Ile | Glu | Lys | Ala |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Leu | Glu | Phe | Ile | Pro | Ser | Asp | Gln | Gln | Asn | Glu | Met | Val | Arg | Glu | Leu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Asp | Gly | His | Val | Leu | Lys | Cys | Val | Lys | Asp | Gln | Asn | Gly | Asn | His | Val |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Val | Gln | Lys | Cys | Ile | Glu | Cys | Val | Gln | Pro | Gln | Ser | Leu | Gln | Phe | Ile |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ile | Asp | Ala | Phe | Lys | Gly | Gln | Val | Phe | Ala | Leu | Ser | Thr | His | Pro | Tyr |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Gly | Cys | Arg | Val | Ile | Gln | Arg | Ile | Leu | Glu | His | Cys | Leu | Pro | Asp | Gln |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Thr | Leu | Pro | Ile | Leu | Glu | Glu | Leu | His | Gln | His | Thr | Glu | Gln | Leu | Val |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gln | Asp | Gln | Tyr | Gly | Asn | Tyr | Val | Ile | Gln | His | Val | Leu | Glu | His | Gly |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Arg | Pro | Glu | Asp | Lys | Ser | Lys | Ile | Val | Ala | Glu | Ile | Arg | Gly | Asn | Val |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Leu | Val | Leu | Ser | Gln | His | Lys | Phe | Ala | Ser | Asn | Val | Val | Glu | Lys | Cys |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Val | Thr | His | Ala | Ser | Arg | Thr | Glu | Arg | Ala | Val | Leu | Ile | Asp | Glu | Val |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Cys | Thr | Met | Asn | Asp | Gly | Pro | His | Ser | Ala | Leu | Tyr | Thr | Met | Met | Lys |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

```
Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
            325                 330                 335

Thr Leu Arg Lys Tyr Thr Tyr Gly Lys His Ile Leu Ala Lys Leu Glu
        340                 345                 350

Lys Tyr Tyr Met Lys Asn Gly Val Asp Leu Gly Gly Pro Ala Gly Ser
            355                 360                 365

Gly Arg Ala Asp Ala Leu Asp Phe Asp Leu Asp Met Leu Gly Ser
        370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
            405                 410                 415

Asp Leu Asp Met Leu Tyr Ile Asp
            420
```

<210> SEQ ID NO 97
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 97

```
Met Gly Ile Leu Pro Pro Lys Lys Arg Lys Val Ser Arg Gly Arg
1               5                   10                  15

Ser Arg Leu Leu Glu Asp Phe Arg Asn Asn Arg Tyr Pro Asn Leu Gln
            20                  25                  30

Leu Arg Glu Ile Ala Gly His Ile Met Glu Phe Ser Gln Asp Gln His
        35                  40                  45

Gly Ser Arg Phe Ile Gln Leu Lys Leu Glu Arg Ala Thr Pro Ala Glu
    50                  55                  60

Arg Gln Leu Val Phe Asn Glu Ile Leu Gln Ala Ala Tyr Gln Leu Met
65                  70                  75                  80

Val Asp Val Phe Gly Asn Tyr Val Ile Gln Lys Phe Phe Glu Phe Gly
                85                  90                  95

Ser Leu Glu Gln Lys Leu Ala Leu Ala Glu Arg Ile Arg Gly His Val
            100                 105                 110

Leu Ser Leu Ala Leu Gln Met Tyr Gly Cys Arg Val Ile Gln Lys Ala
        115                 120                 125

Leu Glu Phe Ile Pro Ser Asp Gln Gln Asn Glu Met Val Arg Glu Leu
    130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
                165                 170                 175

Ile Asp Ala Phe Lys Gly Gln Val Phe Ala Leu Ser Thr His Pro Tyr
            180                 185                 190

Gly Cys Arg Val Ile Gln Arg Ile Leu Glu His Cys Leu Pro Asp Gln
        195                 200                 205

Thr Leu Pro Ile Leu Glu Glu Leu His Gln His Thr Glu Gln Leu Val
    210                 215                 220
```

-continued

```
Gln Asp Gln Tyr Gly Ser Tyr Val Ile Glu His Val Leu Glu His Gly
225                 230                 235                 240

Arg Pro Glu Asp Lys Ser Lys Ile Val Ala Glu Ile Arg Gly Asn Val
            245                 250                 255

Leu Val Leu Ser Gln His Lys Phe Ala Asn Asn Val Val Gln Lys Cys
        260                 265                 270

Val Thr His Ala Ser Arg Thr Glu Arg Ala Val Leu Ile Asp Glu Val
    275                 280                 285

Cys Thr Met Asn Asp Gly Pro His Ser Ala Leu Tyr Thr Met Met Lys
290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
            325                 330                 335

Thr Leu Arg Lys Tyr Thr Tyr Gly Lys His Ile Leu Ala Lys Leu Glu
        340                 345                 350

Lys Tyr Tyr Met Lys Asn Gly Val Asp Leu Gly Gly Pro Ala Gly Ser
    355                 360                 365

Gly Arg Ala Asp Ala Leu Asp Asp Phe Asp Leu Asp Met Leu Gly Ser
370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
            405                 410                 415

Asp Leu Asp Met Leu Tyr Ile Asp
            420
```

<210> SEQ ID NO 98
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

```
Met Gly Ile Leu Pro Lys Lys Arg Lys Val Ser Arg Gly Arg
1               5                   10                  15

Ser Arg Leu Leu Glu Asp Phe Arg Asn Asn Arg Tyr Pro Asn Leu Gln
            20                  25                  30

Leu Arg Glu Ile Ala Gly His Ile Met Glu Phe Ser Gln Asp Gln His
        35                  40                  45

Gly Ser Arg Phe Ile Gln Leu Lys Leu Glu Arg Ala Thr Pro Ala Glu
    50                  55                  60

Arg Gln Leu Val Phe Asn Glu Ile Leu Gln Ala Ala Tyr Gln Leu Met
65                  70                  75                  80

Val Asp Val Phe Gly Asn Tyr Val Ile Gln Lys Phe Phe Glu Phe Gly
            85                  90                  95

Ser Leu Glu Gln Lys Leu Ala Leu Ala Glu Arg Ile Arg Gly His Val
        100                 105                 110

Leu Ser Leu Ala Leu Gln Met Tyr Gly Cys Arg Val Ile Gln Lys Ala
    115                 120                 125

Leu Glu Phe Ile Pro Ser Asp Gln Gln Asn Glu Met Val Arg Glu Leu
130                 135                 140

Asp Gly His Val Leu Lys Cys Val Lys Asp Gln Asn Gly Asn His Val
```

```
                145                 150                 155                 160
        Val Gln Lys Cys Ile Glu Cys Val Gln Pro Gln Ser Leu Gln Phe Ile
                        165                 170                 175

Ile Asp Ala Phe Lys Gly Gln Val Phe Ala Leu Ser Thr His Pro Tyr
                        180                 185                 190

Gly Cys Arg Val Ile Gln Arg Ile Leu Glu His Cys Leu Pro Asp Gln
                        195                 200                 205

Thr Leu Pro Ile Leu Glu Glu Leu His Gln His Thr Glu Gln Leu Val
                210                 215                 220

Gln Asp Gln Tyr Gly Asn Tyr Val Ile Gln His Val Leu Glu His Gly
        225                 230                 235                 240

Arg Pro Glu Asp Lys Ser Lys Ile Val Ala Glu Ile Arg Gly Asn Val
                        245                 250                 255

Leu Val Leu Ser Gln His Lys Phe Ala Ser Asn Val Val Glu Lys Cys
                        260                 265                 270

Val Thr His Ala Ser Arg Thr Glu Arg Ala Val Leu Ile Asp Glu Val
                        275                 280                 285

Cys Thr Met Asn Asp Gly Pro His Ser Ala Leu Tyr Thr Met Met Lys
                290                 295                 300

Asp Gln Tyr Ala Asn Tyr Val Val Gln Lys Met Ile Asp Val Ala Glu
        305                 310                 315                 320

Pro Gly Gln Arg Lys Ile Val Met His Lys Ile Arg Pro His Ile Ala
                        325                 330                 335

Thr Leu Arg Lys Tyr Thr Tyr Gly Lys His Ile Leu Ala Lys Leu Glu
                        340                 345                 350

Lys Tyr Tyr Met Lys Asn Gly Val Asp Leu Gly Gly Pro Ala Gly Ser
                        355                 360                 365

Gly Arg Ala Asp Ala Leu Asp Asp Phe Asp Leu Asp Met Leu Gly Ser
                370                 375                 380

Asp Ala Leu Asp Asp Phe Asp Leu Asp Met Leu Gly Ser Asp Ala Leu
        385                 390                 395                 400

Asp Asp Phe Asp Leu Asp Met Leu Gly Ser Asp Ala Leu Asp Asp Phe
                        405                 410                 415

Asp Leu Asp Met Leu Tyr Ile Asp
                        420

<210> SEQ ID NO 99
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Met Gly Ile Leu Pro Pro Lys Lys Lys Arg Lys Val Ser Arg Gly Arg
        1               5                   10                  15

Ser Arg Leu Leu Glu Asp Phe Arg Asn Asn Arg Tyr Pro Asn Leu Gln
                        20                  25                  30

Leu Arg Glu Ile Ala Gly His Ile Met Glu Phe Ser Gln Asp Gln His
                        35                  40                  45

Gly Ser Arg Phe Ile Gln Leu Lys Leu Glu Arg Ala Thr Pro Ala Glu
                50                  55                  60

Arg Gln Leu Val Phe Asn Glu Ile Leu Gln Ala Ala Tyr Gln Leu Met
        65                  70                  75                  80
```

Val Asp Val Phe Gly Asn Tyr Val Ile Gln Lys Phe Phe Glu Phe Gly
            85                  90                  95

Ser Leu Glu Gln Lys Leu Ala Leu Ala Glu Arg Ile Arg Gly His Val
            100                 105                 110

Leu Ser Leu Ala Leu Gln Met Tyr Gly Ser Arg Val Ile Glu Lys Ala
            115                 120                 125

Leu Glu Phe Ile Pro Ser Asp Gln Gln Asn Glu Met Val Arg Glu Leu
        130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
                165                 170                 175

Ile Asp Ala Phe Lys Gly Gln Val Phe Ala Leu Ser Thr His Pro Tyr
            180                 185                 190

Gly Cys Arg Val Ile Gln Arg Ile Leu Glu His Cys Leu Pro Asp Gln
            195                 200                 205

Thr Leu Pro Ile Leu Glu Glu Leu His Gln His Thr Glu Gln Leu Val
        210                 215                 220

Gln Asp Gln Tyr Gly Ser Tyr Val Ile Glu His Val Leu Glu His Gly
225                 230                 235                 240

Arg Pro Glu Asp Lys Ser Lys Ile Val Ala Glu Ile Arg Gly Asn Val
                245                 250                 255

Leu Val Leu Ser Gln His Lys Phe Ala Asn Asn Val Val Gln Lys Cys
            260                 265                 270

Val Thr His Ala Ser Arg Thr Glu Arg Ala Val Leu Ile Asp Glu Val
            275                 280                 285

Cys Thr Met Asn Asp Gly Pro His Ser Ala Leu Tyr Thr Met Met Lys
        290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
                325                 330                 335

Thr Leu Arg Lys Tyr Thr Tyr Gly Lys His Ile Leu Ala Lys Leu Glu
            340                 345                 350

Lys Tyr Tyr Met Lys Asn Gly Val Asp Leu Gly Gly Pro Ala Gly Ser
            355                 360                 365

Gly Arg Ala Asp Ala Leu Asp Asp Phe Asp Leu Asp Met Leu Gly Ser
        370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
                405                 410                 415

Asp Leu Asp Met Leu Tyr Ile Asp
            420

<210> SEQ ID NO 100
<211> LENGTH: 621
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

```
Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Val Ala Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser His Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys Ser
225                 230                 235                 240

Arg Gly Pro Tyr Ser Ile Val Ser Pro Lys Cys Gly Gly Gly Ser
                245                 250                 255

Gly Pro Ala Gly Ile Leu Pro Pro Lys Lys Arg Lys Val Ser Arg
            260                 265                 270

Gly Arg Ser Arg Leu Leu Glu Asp Phe Arg Asn Asn Arg Tyr Pro Asn
    275                 280                 285

Leu Gln Leu Arg Glu Ile Ala Gly His Ile Met Glu Phe Ser Gln Asp
        290                 295                 300

Gln His Gly Ser Arg Phe Ile Gln Leu Lys Leu Glu Arg Ala Thr Pro
305                 310                 315                 320

Ala Glu Arg Gln Leu Val Phe Asn Glu Ile Leu Gln Ala Ala Tyr Gln
                325                 330                 335

Leu Met Val Asp Val Phe Gly Asn Tyr Val Ile Gln Lys Phe Phe Glu
            340                 345                 350

Phe Gly Ser Leu Glu Gln Lys Leu Ala Leu Ala Glu Arg Ile Arg Gly
        355                 360                 365

His Val Leu Ser Leu Ala Leu Gln Met Tyr Gly Ser Arg Val Ile Glu
    370                 375                 380

Lys Ala Leu Glu Phe Ile Pro Ser Asp Gln Asn Glu Met Val Arg
385                 390                 395                 400

Glu Leu Asp Gly His Val Leu Lys Cys Val Lys Asp Gln Asn Gly Asn
                405                 410                 415

His Val Val Gln Lys Cys Ile Glu Cys Val Gln Pro Gln Ser Leu Gln
```

```
                420             425             430
Phe Ile Ile Asp Ala Phe Lys Gly Gln Val Phe Ala Leu Ser Thr His
                435             440             445

Pro Tyr Gly Cys Arg Val Ile Gln Arg Ile Leu Glu His Cys Leu Pro
    450             455             460

Asp Gln Thr Leu Pro Ile Leu Glu Glu Leu His Gln His Thr Glu Gln
465             470             475             480

Leu Val Gln Asp Gln Tyr Gly Asn Tyr Val Ile Gln His Val Leu Glu
                485             490             495

His Gly Arg Pro Glu Asp Lys Ser Lys Ile Val Ala Glu Ile Arg Gly
            500             505             510

Asn Val Leu Val Leu Ser Gln His Lys Phe Ala Ser Asn Val Val Glu
            515             520             525

Lys Cys Val Thr His Ala Ser Arg Thr Glu Arg Ala Val Leu Ile Asp
            530             535             540

Glu Val Cys Thr Met Asn Asp Gly Pro His Ser Ala Leu Tyr Thr Met
545             550             555             560

Met Lys Asp Gln Tyr Ala Asn Tyr Val Val Gln Lys Met Ile Asp Val
                565             570             575

Ala Glu Pro Gly Gln Arg Lys Ile Val Met His Lys Ile Arg Pro His
            580             585             590

Ile Ala Thr Leu Arg Lys Tyr Thr Tyr Gly Lys His Ile Leu Ala Lys
            595             600             605

Leu Glu Lys Tyr Tyr Met Lys Asn Gly Val Asp Leu Gly
            610             615             620
```

<210> SEQ ID NO 101
<211> LENGTH: 621
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 101

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
                20                  25                  30

Glu Gly Glu Gly Asp Ala Thr Asn Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Phe Gly Tyr Gly Val Ala Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Phe Asn Ser His Asn Val Tyr Ile Thr Ala Asp Lys Gln Lys Asn
145                 150                 155                 160
```

```
Gly Ile Lys Ala Asn Phe Lys Ile Arg His Asn Val Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser His Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Lys Ser
225                 230                 235                 240

Arg Gly Pro Tyr Ser Ile Val Ser Pro Lys Cys Gly Gly Gly Gly Ser
            245                 250                 255

Gly Pro Ala Gly Ile Leu Pro Pro Lys Lys Arg Lys Val Ser Arg
            260                 265                 270

Gly Arg Ser Arg Leu Leu Glu Asp Phe Arg Asn Asn Arg Tyr Pro Asn
            275                 280                 285

Leu Gln Leu Arg Glu Ile Ala Gly His Ile Met Glu Phe Ser Gln Asp
            290                 295                 300

Gln His Gly Ser Arg Phe Ile Gln Leu Lys Leu Glu Arg Ala Thr Pro
305                 310                 315                 320

Ala Glu Arg Gln Leu Val Phe Asn Glu Ile Leu Gln Ala Ala Tyr Gln
            325                 330                 335

Leu Met Val Asp Val Phe Gly Asn Tyr Val Ile Gln Lys Phe Phe Glu
            340                 345                 350

Phe Gly Ser Leu Glu Gln Lys Leu Ala Leu Ala Glu Arg Ile Arg Gly
            355                 360                 365

His Val Leu Ser Leu Ala Leu Gln Met Tyr Gly Ser Arg Val Ile Glu
            370                 375                 380

Lys Ala Leu Glu Phe Ile Pro Ser Asp Gln Gln Asn Glu Met Val Arg
385                 390                 395                 400

Glu Leu Asp Gly His Val Leu Lys Cys Val Lys Asp Gln Asn Gly Asn
            405                 410                 415

His Val Val Gln Lys Cys Ile Glu Cys Val Gln Pro Gln Ser Leu Gln
            420                 425                 430

Phe Ile Ile Asp Ala Phe Lys Gly Gln Val Phe Ala Leu Ser Thr His
            435                 440                 445

Pro Tyr Gly Cys Arg Val Ile Gln Arg Ile Leu Glu His Cys Leu Pro
            450                 455                 460

Asp Gln Thr Leu Pro Ile Leu Glu Glu Leu His Gln His Thr Glu Gln
465                 470                 475                 480

Leu Val Gln Asp Gln Tyr Gly Ser Tyr Val Ile Glu His Val Leu Glu
            485                 490                 495

His Gly Arg Pro Glu Asp Lys Ser Lys Ile Val Ala Glu Ile Arg Gly
            500                 505                 510

Asn Val Leu Val Leu Ser Gln His Lys Phe Ala Asn Asn Val Val Gln
            515                 520                 525

Lys Cys Val Thr His Ala Ser Arg Thr Glu Arg Ala Val Leu Ile Asp
530                 535                 540

Glu Val Cys Thr Met Asn Asp Gly Pro His Ser Ala Leu Tyr Thr Met
545                 550                 555                 560

Met Lys Asp Gln Tyr Ala Asn Tyr Val Val Gln Lys Met Ile Asp Val
            565                 570                 575
```

Ala Glu Pro Gly Gln Arg Lys Ile Val Met His Lys Ile Arg Pro His
            580                 585                 590

Ile Ala Thr Leu Arg Lys Tyr Thr Tyr Gly Lys His Ile Leu Ala Lys
        595                 600                 605

Leu Glu Lys Tyr Tyr Met Lys Asn Gly Val Asp Leu Gly
    610                 615                 620

<210> SEQ ID NO 102
<211> LENGTH: 641
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Met Val Arg Gly Ser His His His His His Gly Met Ala Ser Met
1               5                   10                  15

Thr Gly Gly Gln Gln Met Gly Arg Asp Leu Tyr Asp Asp Asp Lys
            20                  25                  30

Asp Pro Met Val Ser Lys Gly Glu Glu Leu Ile Lys Glu Asn Met Arg
        35                  40                  45

Met Lys Val Val Met Glu Gly Ser Val Asn Gly His Gln Phe Lys Cys
    50                  55                  60

Thr Gly Glu Gly Glu Gly Asn Pro Tyr Met Gly Thr Gln Thr Met Arg
65                  70                  75                  80

Ile Lys Val Ile Glu Gly Gly Pro Leu Pro Phe Ala Phe Asp Ile Leu
                85                  90                  95

Ala Thr Ser Phe Met Tyr Gly Ser Arg Thr Phe Ile Lys Tyr Pro Lys
            100                 105                 110

Gly Ile Pro Asp Phe Phe Lys Gln Ser Phe Pro Glu Gly Phe Thr Trp
        115                 120                 125

Glu Arg Val Thr Arg Tyr Glu Asp Gly Gly Val Val Thr Val Met Gln
    130                 135                 140

Asp Thr Ser Leu Glu Asp Gly Cys Leu Val Tyr His Val Gln Val Arg
145                 150                 155                 160

Gly Val Asn Phe Pro Ser Asn Gly Pro Val Met Gln Lys Lys Thr Lys
                165                 170                 175

Gly Trp Glu Pro Asn Thr Glu Met Met Tyr Pro Ala Asp Gly Gly Leu
            180                 185                 190

Arg Gly Tyr Thr His Met Ala Leu Lys Val Asp Gly Gly His Leu
        195                 200                 205

Ser Cys Ser Phe Val Thr Thr Tyr Arg Ser Lys Lys Thr Val Gly Asn
    210                 215                 220

Ile Lys Met Pro Gly Ile His Ala Val Asp His Arg Leu Glu Arg Leu
225                 230                 235                 240

Glu Glu Ser Asp Asn Glu Met Phe Val Val Gln Arg Glu His Ala Val
                245                 250                 255

Ala Lys Phe Ala Gly Leu Gly Gly Gly Met Asp Glu Leu Tyr Lys Gly
            260                 265                 270

Gly Gly Gly Ser Gly Pro Ala Gly Ile Leu Pro Lys Lys Lys Arg
        275                 280                 285

Lys Val Ser Arg Gly Arg Ser Arg Leu Leu Glu Asp Phe Arg Asn Asn
    290                 295                 300

Arg Tyr Pro Asn Leu Gln Leu Arg Glu Ile Ala Gly His Ile Met Glu

```
            305                 310                 315                 320
        Phe Ser Gln Asp Gln His Gly Ser Arg Phe Ile Gln Leu Lys Leu Glu
                        325                 330                 335

Arg Ala Thr Pro Ala Glu Arg Gln Leu Val Phe Asn Glu Ile Leu Gln
                        340                 345                 350

Ala Ala Tyr Gln Leu Met Val Asp Val Phe Gly Asn Tyr Val Ile Gln
                        355                 360                 365

Lys Phe Phe Glu Phe Gly Ser Leu Glu Gln Lys Leu Ala Leu Ala Glu
                        370                 375                 380

Arg Ile Arg Gly His Val Leu Ser Leu Ala Leu Gln Met Tyr Gly Ser
        385                 390                 395                 400

Arg Val Ile Glu Lys Ala Leu Glu Phe Ile Pro Ser Asp Gln Gln Asn
                        405                 410                 415

Glu Met Val Arg Glu Leu Asp Gly His Val Leu Lys Cys Val Lys Asp
                        420                 425                 430

Gln Asn Gly Asn His Val Val Gln Lys Cys Ile Glu Cys Val Gln Pro
                        435                 440                 445

Gln Ser Leu Gln Phe Ile Ile Asp Ala Phe Lys Gly Gln Val Phe Ala
                        450                 455                 460

Leu Ser Thr His Pro Tyr Gly Cys Arg Val Ile Gln Arg Ile Leu Glu
        465                 470                 475                 480

His Cys Leu Pro Asp Gln Thr Leu Pro Ile Leu Glu Glu Leu His Gln
                        485                 490                 495

His Thr Glu Gln Leu Val Gln Asp Gln Tyr Gly Asn Tyr Val Ile Gln
                        500                 505                 510

His Val Leu Glu His Gly Arg Pro Glu Asp Lys Ser Lys Ile Val Ala
                        515                 520                 525

Glu Ile Arg Gly Asn Val Leu Val Leu Ser Gln His Lys Phe Ala Ser
                        530                 535                 540

Asn Val Val Glu Lys Cys Val Thr His Ala Ser Arg Thr Glu Arg Ala
        545                 550                 555                 560

Val Leu Ile Asp Glu Val Cys Thr Met Asn Asp Gly Pro His Ser Ala
                        565                 570                 575

Leu Tyr Thr Met Met Lys Asp Gln Tyr Ala Asn Tyr Val Val Gln Lys
                        580                 585                 590

Met Ile Asp Val Ala Glu Pro Gly Gln Arg Lys Ile Val Met His Lys
                        595                 600                 605

Ile Arg Pro His Ile Ala Thr Leu Arg Lys Tyr Thr Tyr Gly Lys His
                        610                 615                 620

Ile Leu Ala Lys Leu Glu Lys Tyr Tyr Met Lys Asn Gly Val Asp Leu
        625                 630                 635                 640

Gly

<210> SEQ ID NO 103
<211> LENGTH: 709
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Met Gly Ile Leu Pro Pro Lys Lys Lys Arg Lys Val Ser Arg Gly Arg
1               5                   10                  15
```

-continued

```
Ser Arg Leu Leu Glu Asp Phe Arg Asn Asn Arg Tyr Pro Asn Leu Gln
             20                  25                  30

Leu Arg Glu Ile Ala Gly His Ile Met Glu Phe Ser Gln Asp Gln His
         35                  40                  45

Gly Ser Arg Phe Ile Gln Leu Lys Leu Glu Arg Ala Thr Pro Ala Glu
     50                  55                  60

Arg Gln Leu Val Phe Asn Glu Ile Leu Gln Ala Ala Tyr Gln Leu Met
 65                  70                  75                  80

Val Asp Val Phe Gly Asn Tyr Val Ile Gln Lys Phe Phe Glu Phe Gly
                 85                  90                  95

Ser Leu Glu Gln Lys Leu Ala Leu Ala Glu Arg Ile Arg Gly His Val
            100                 105                 110

Leu Ser Leu Ala Leu Gln Met Tyr Gly Ser Arg Val Ile Glu Lys Ala
        115                 120                 125

Leu Glu Phe Ile Pro Ser Asp Gln Gln Asn Glu Met Val Arg Glu Leu
    130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
                165                 170                 175

Ile Asp Ala Phe Lys Gly Gln Val Phe Ala Leu Ser Thr His Pro Tyr
            180                 185                 190

Gly Cys Arg Val Ile Gln Arg Ile Leu Glu His Cys Leu Pro Asp Gln
        195                 200                 205

Thr Leu Pro Ile Leu Glu Glu Leu His Gln His Thr Glu Gln Leu Val
    210                 215                 220

Gln Asp Gln Tyr Gly Asn Tyr Val Ile Gln His Val Leu Glu His Gly
225                 230                 235                 240

Arg Pro Glu Asp Lys Ser Lys Ile Val Ala Glu Ile Arg Gly Asn Val
                245                 250                 255

Leu Val Leu Ser Gln His Lys Phe Ala Ser Asn Val Val Glu Lys Cys
            260                 265                 270

Val Thr His Ala Ser Arg Thr Glu Arg Ala Val Leu Ile Asp Glu Val
        275                 280                 285

Cys Thr Met Asn Asp Gly Pro His Ser Ala Leu Tyr Thr Met Met Lys
    290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
                325                 330                 335

Thr Leu Arg Lys Tyr Thr Tyr Gly Lys His Ile Leu Ala Lys Leu Glu
            340                 345                 350

Lys Tyr Tyr Met Lys Asn Gly Val Asp Leu Gly Gly Pro Ala Gly Gly
        355                 360                 365

Gly Gly Ser Gly Gly Gly Gly Ser Gly Gly Gly Gly Ser Gly Pro Lys
    370                 375                 380

Lys Lys Arg Lys Val Ala Ala Ala Gly Ser Pro Ser Gly Gln Ile Ser
385                 390                 395                 400

Asn Gln Ala Leu Ala Leu Ala Pro Ser Ser Ala Pro Val Leu Ala Gln
                405                 410                 415

Thr Met Val Pro Ser Ser Ala Met Val Pro Leu Ala Gln Pro Pro Ala
            420                 425                 430

Pro Ala Pro Val Leu Thr Pro Gly Pro Pro Gln Ser Leu Ser Ala Pro
```

```
                    435                 440                 445
Val Pro Lys Ser Thr Gln Ala Gly Glu Gly Thr Leu Ser Glu Ala Leu
    450                 455                 460

Leu His Leu Gln Phe Asp Ala Asp Glu Asp Leu Gly Ala Leu Leu Gly
465                 470                 475                 480

Asn Ser Thr Asp Pro Gly Val Phe Thr Asp Leu Ala Ser Val Asp Asn
                485                 490                 495

Ser Glu Phe Gln Gln Leu Leu Asn Gln Gly Val Ser Met Ser His Ser
            500                 505                 510

Thr Ala Glu Pro Met Leu Met Glu Tyr Pro Glu Ala Ile Thr Arg Leu
        515                 520                 525

Val Thr Gly Ser Gln Arg Pro Pro Asp Pro Ala Pro Thr Pro Leu Gly
    530                 535                 540

Thr Ser Gly Leu Pro Asn Gly Leu Ser Gly Asp Glu Asp Phe Ser Ser
545                 550                 555                 560

Ile Ala Asp Met Asp Phe Ser Ala Leu Leu Ser Gln Ile Ser Ser Ser
                565                 570                 575

Gly Gln Gly Gly Gly Gly Ser Gly Phe Ser Val Asp Thr Ser Ala Leu
            580                 585                 590

Leu Asp Leu Phe Ser Pro Ser Val Thr Val Pro Asp Met Ser Leu Pro
        595                 600                 605

Asp Leu Asp Ser Ser Leu Ala Ser Ile Gln Glu Leu Leu Ser Pro Gln
    610                 615                 620

Glu Pro Pro Arg Pro Pro Glu Ala Glu Asn Ser Ser Pro Asp Ser Gly
625                 630                 635                 640

Lys Gln Leu Val His Tyr Thr Ala Gln Pro Leu Phe Leu Leu Asp Pro
                645                 650                 655

Gly Ser Val Asp Thr Gly Ser Asn Asp Leu Pro Val Leu Phe Glu Leu
            660                 665                 670

Gly Glu Gly Ser Tyr Phe Ser Glu Gly Asp Gly Phe Ala Glu Asp Pro
        675                 680                 685

Thr Ile Ser Leu Leu Thr Gly Ser Glu Pro Pro Lys Ala Lys Asp Pro
    690                 695                 700

Thr Val Ser Ile Asp
705

<210> SEQ ID NO 104
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Met Gly Ser Pro Lys Lys Arg Lys Val Glu Ala Ser Met Asp Ala
1               5                   10                  15

Lys Ser Leu Thr Ala Trp Ser Arg Thr Leu Val Thr Phe Lys Asp Val
            20                  25                  30

Phe Val Asp Phe Thr Arg Glu Glu Trp Lys Leu Leu Asp Thr Ala Gln
        35                  40                  45

Gln Ile Val Tyr Arg Asn Val Met Leu Glu Asn Tyr Lys Asn Leu Val
    50                  55                  60

Ser Leu Gly Tyr Gln Leu Thr Lys Pro Asp Val Ile Leu Arg Leu Glu
65                  70                  75                  80
```

Lys Gly Glu Glu Pro Trp Leu Val Ser Arg Gly Ser Ile Val Gly Ile
            85                  90                  95

Leu Pro Pro Lys Lys Arg Lys Val Ser Arg Gly Arg Ser Arg Leu
            100                 105                 110

Leu Glu Asp Phe Arg Asn Asn Arg Tyr Pro Asn Leu Gln Leu Arg Glu
            115                 120                 125

Ile Ala Gly His Ile Met Glu Phe Ser Gln Asp Gln His Gly Ser Arg
130                 135                 140

Phe Ile Gln Leu Lys Leu Glu Arg Ala Thr Pro Ala Glu Arg Gln Leu
145                 150                 155                 160

Val Phe Asn Glu Ile Leu Gln Ala Ala Tyr Gln Leu Met Val Asp Val
                165                 170                 175

Phe Gly Asn Tyr Val Ile Gln Lys Phe Phe Glu Phe Gly Ser Leu Glu
                180                 185                 190

Gln Lys Leu Ala Leu Ala Glu Arg Ile Arg Gly His Val Leu Ser Leu
            195                 200                 205

Ala Leu Gln Met Tyr Gly Ser Arg Val Ile Glu Lys Ala Leu Glu Phe
210                 215                 220

Ile Pro Ser Asp Gln Gln Asn Glu Met Val Arg Glu Leu Asp Gly His
225                 230                 235                 240

Val Leu Lys Cys Val Lys Asp Gln Asn Gly Asn His Val Val Gln Lys
                245                 250                 255

Cys Ile Glu Cys Val Gln Pro Gln Ser Leu Gln Phe Ile Ile Asp Ala
                260                 265                 270

Phe Lys Gly Gln Val Phe Ala Leu Ser Thr His Pro Tyr Gly Cys Arg
            275                 280                 285

Val Ile Gln Arg Ile Leu Glu His Cys Leu Pro Asp Gln Thr Leu Pro
290                 295                 300

Ile Leu Glu Glu Leu His Gln His Thr Glu Gln Leu Val Gln Asp Gln
305                 310                 315                 320

Tyr Gly Asn Tyr Val Ile Gln His Val Leu Glu His Gly Arg Pro Glu
                325                 330                 335

Asp Lys Ser Lys Ile Val Ala Glu Ile Arg Gly Asn Val Leu Val Leu
            340                 345                 350

Ser Gln His Lys Phe Ala Ser Asn Val Val Glu Lys Cys Val Thr His
            355                 360                 365

Ala Ser Arg Thr Glu Arg Ala Val Leu Ile Asp Glu Val Cys Thr Met
370                 375                 380

Asn Asp Gly Pro His Ser Ala Leu Tyr Thr Met Met Lys Asp Gln Tyr
385                 390                 395                 400

Ala Asn Tyr Val Val Gln Lys Met Ile Asp Val Ala Glu Pro Gly Gln
                405                 410                 415

Arg Lys Ile Val Met His Lys Ile Arg Pro His Ile Ala Thr Leu Arg
            420                 425                 430

Lys Tyr Thr Tyr Gly Lys His Ile Leu Ala Lys Leu Glu Lys Tyr Tyr
            435                 440                 445

Met Lys Asn Gly Val Asp Leu Gly
    450                 455

<210> SEQ ID NO 105
<211> LENGTH: 727
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 105
```

| | | | | | | | | | | | | | | |
|---|---|---|---|---|---|---|---|---|---|---|---|---|---|---|
| Met | Ala | Tyr | Pro | Tyr | Asp | Val | Pro | Asp | Tyr | Ala | Ser | Leu | Gly | Ser | Gly |
| 1 | | | | 5 | | | | | 10 | | | | | 15 | |
| Ser | Pro | Lys | Lys | Lys | Arg | Lys | Val | Glu | Asp | Pro | Lys | Lys | Lys | Arg | Lys |
| | | | 20 | | | | | 25 | | | | | 30 | | |
| Val | Asp | Gly | Ile | Gly | Ser | Gly | Ser | Asn | Gly | Ser | Ser | Gly | Ser | Ser | Glu |
| | | | 35 | | | | | 40 | | | | | 45 | | |
| Leu | Ile | Lys | Glu | Asn | Met | His | Met | Lys | Leu | Tyr | Met | Glu | Gly | Thr | Val |
| | 50 | | | | | 55 | | | | | 60 | | | | |
| Asp | Asn | His | His | Phe | Lys | Cys | Thr | Ser | Glu | Gly | Glu | Gly | Lys | Pro | Tyr |
| 65 | | | | | 70 | | | | | 75 | | | | | 80 |
| Glu | Gly | Thr | Gln | Thr | Met | Arg | Ile | Lys | Val | Val | Glu | Gly | Gly | Pro | Leu |
| | | | | 85 | | | | | 90 | | | | | 95 | |
| Pro | Phe | Ala | Phe | Asp | Ile | Leu | Ala | Thr | Ser | Phe | Leu | Tyr | Gly | Ser | Lys |
| | | | 100 | | | | | 105 | | | | | 110 | | |
| Thr | Phe | Ile | Asn | His | Thr | Gln | Gly | Ile | Pro | Asp | Phe | Phe | Lys | Gln | Ser |
| | | | 115 | | | | | 120 | | | | | 125 | | |
| Phe | Pro | Glu | Gly | Phe | Thr | Trp | Glu | Arg | Val | Thr | Thr | Tyr | Glu | Asp | Gly |
| | 130 | | | | | 135 | | | | | 140 | | | | |
| Gly | Val | Leu | Thr | Ala | Thr | Gln | Asp | Thr | Ser | Leu | Gln | Asp | Gly | Cys | Leu |
| 145 | | | | | 150 | | | | | 155 | | | | | 160 |
| Ile | Tyr | Asn | Val | Lys | Ile | Arg | Gly | Val | Asn | Phe | Thr | Ser | Asn | Gly | Pro |
| | | | | 165 | | | | | 170 | | | | | 175 | |
| Val | Met | Gln | Lys | Lys | Thr | Leu | Gly | Trp | Glu | Ala | Phe | Thr | Glu | Thr | Leu |
| | | | 180 | | | | | 185 | | | | | 190 | | |
| Tyr | Pro | Ala | Asp | Gly | Gly | Leu | Glu | Gly | Arg | Asn | Asp | Met | Ala | Leu | Lys |
| | | | 195 | | | | | 200 | | | | | 205 | | |
| Leu | Val | Gly | Gly | Ser | His | Leu | Ile | Ala | Asn | Ile | Lys | Thr | Thr | Tyr | Arg |
| | 210 | | | | | 215 | | | | | 220 | | | | |
| Ser | Lys | Lys | Pro | Ala | Lys | Asn | Leu | Lys | Met | Pro | Gly | Val | Tyr | Tyr | Val |
| 225 | | | | | 230 | | | | | 235 | | | | | 240 |
| Asp | Tyr | Arg | Leu | Glu | Arg | Ile | Lys | Glu | Ala | Asn | Asn | Glu | Thr | Tyr | Val |
| | | | | 245 | | | | | 250 | | | | | 255 | |
| Glu | Gln | His | Glu | Val | Ala | Val | Ala | Arg | Tyr | Cys | Asp | Leu | Pro | Ser | Lys |
| | | | 260 | | | | | 265 | | | | | 270 | | |
| Leu | Gly | His | Lys | Leu | Asn | Gly | Gly | Gly | Gly | Met | Asp | Ala | Lys | Ser | |
| | | | 275 | | | | | 280 | | | | | 285 | | |
| Leu | Thr | Ala | Trp | Ser | Arg | Thr | Leu | Val | Thr | Phe | Lys | Asp | Val | Phe | Val |
| | 290 | | | | | 295 | | | | | 300 | | | | |
| Asp | Phe | Thr | Arg | Glu | Glu | Trp | Lys | Leu | Leu | Asp | Thr | Ala | Gln | Gln | Ile |
| 305 | | | | | 310 | | | | | 315 | | | | | 320 |
| Val | Tyr | Arg | Asn | Val | Met | Leu | Glu | Asn | Tyr | Lys | Asn | Leu | Val | Ser | Leu |
| | | | | 325 | | | | | 330 | | | | | 335 | |
| Gly | Tyr | Gln | Leu | Thr | Lys | Pro | Asp | Val | Ile | Leu | Arg | Leu | Glu | Lys | Gly |
| | | | 340 | | | | | 345 | | | | | 350 | | |
| Glu | Glu | Pro | Gly | Gly | Ser | Gly | Gly | Ser | Gly | Pro | Ala | Gly | Ile | Leu | |
| | | | 355 | | | | | 360 | | | | | 365 | | |
| Pro | Pro | Lys | Lys | Lys | Arg | Lys | Val | Ser | Arg | Gly | Arg | Ser | Arg | Leu | Leu |
| | 370 | | | | | 375 | | | | | 380 | | | | |
| Glu | Asp | Phe | Arg | Asn | Asn | Arg | Tyr | Pro | Asn | Leu | Gln | Leu | Arg | Glu | Ile |

```
                385                 390                 395                 400
        Ala Gly His Ile Met Glu Phe Ser Gln Asp Gln His Gly Ser Arg Phe
                            405                 410                 415
        Ile Gln Leu Lys Leu Glu Arg Ala Thr Pro Ala Glu Arg Gln Leu Val
                            420                 425                 430
        Phe Asn Glu Ile Leu Gln Ala Ala Tyr Gln Leu Met Val Asp Val Phe
                            435                 440                 445
        Gly Asn Tyr Val Ile Gln Lys Phe Phe Glu Phe Gly Ser Leu Glu Gln
                            450                 455                 460
        Lys Leu Ala Leu Ala Glu Arg Ile Arg Gly His Val Leu Ser Leu Ala
        465                 470                 475                 480
        Leu Gln Met Tyr Gly Ser Arg Val Ile Glu Lys Ala Leu Glu Phe Ile
                            485                 490                 495
        Pro Ser Asp Gln Gln Asn Glu Met Val Arg Glu Leu Asp Gly His Val
                            500                 505                 510
        Leu Lys Cys Val Lys Asp Gln Asn Gly Asn His Val Val Gln Lys Cys
                            515                 520                 525
        Ile Glu Cys Val Gln Pro Gln Ser Leu Gln Phe Ile Ile Asp Ala Phe
                            530                 535                 540
        Lys Gly Gln Val Phe Ala Leu Ser Thr His Pro Tyr Gly Cys Arg Val
        545                 550                 555                 560
        Ile Gln Arg Ile Leu Glu His Cys Leu Pro Asp Gln Thr Leu Pro Ile
                            565                 570                 575
        Leu Glu Glu Leu His Gln His Thr Glu Gln Leu Val Gln Asp Gln Tyr
                            580                 585                 590
        Gly Asn Tyr Val Ile Gln His Val Leu Glu His Gly Arg Pro Glu Asp
                            595                 600                 605
        Lys Ser Lys Ile Val Ala Glu Ile Arg Gly Asn Val Leu Val Leu Ser
                            610                 615                 620
        Gln His Lys Phe Ala Ser Asn Val Val Glu Lys Cys Val Thr His Ala
        625                 630                 635                 640
        Ser Arg Thr Glu Arg Ala Val Leu Ile Asp Glu Val Cys Thr Met Asn
                            645                 650                 655
        Asp Gly Pro His Ser Ala Leu Tyr Thr Met Met Lys Asp Gln Tyr Ala
                            660                 665                 670
        Asn Tyr Val Val Gln Lys Met Ile Asp Val Ala Glu Pro Gly Gln Arg
                            675                 680                 685
        Lys Ile Val Met His Lys Ile Arg Pro His Ile Ala Thr Leu Arg Lys
                            690                 695                 700
        Tyr Thr Tyr Gly Lys His Ile Leu Ala Lys Leu Glu Lys Tyr Tyr Met
        705                 710                 715                 720
        Lys Asn Gly Val Asp Leu Gly
                            725

<210> SEQ ID NO 106
<211> LENGTH: 1673
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Met Ile Asp Gly Gly Gly Gly Ser Gly Gly Gly Gly Ser Gly Gly Gly
        1               5                   10                  15
```

-continued

```
Gly Ser Met Tyr Pro Tyr Asp Val Pro Asp Tyr Ala Ser Pro Lys Lys
            20                  25                  30

Lys Arg Lys Val Glu Ala Ser Asp Lys Lys Tyr Ser Ile Gly Leu Ala
        35                  40                  45

Ile Gly Thr Asn Ser Val Gly Trp Ala Val Ile Thr Asp Glu Tyr Lys
50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Arg Tyr Thr Arg
            100                 105                 110

Arg Lys Asn Arg Ile Cys Tyr Leu Gln Glu Ile Phe Ser Asn Glu Met
        115                 120                 125

Ala Lys Val Asp Asp Ser Phe Phe His Arg Leu Glu Glu Ser Phe Leu
130                 135                 140

Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
            180                 185                 190

Tyr Leu Ala Leu Ala His Met Ile Lys Phe Arg Gly His Phe Leu Ile
        195                 200                 205

Glu Gly Asp Leu Asn Pro Asp Asn Ser Asp Val Asp Lys Leu Phe Ile
210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
            260                 265                 270

Asn Gly Leu Phe Gly Asn Leu Ile Ala Leu Ser Leu Gly Leu Thr Pro
        275                 280                 285

Asn Phe Lys Ser Asn Phe Asp Leu Ala Glu Asp Ala Lys Leu Gln Leu
290                 295                 300

Ser Lys Asp Thr Tyr Asp Asp Asp Leu Asp Asn Leu Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
            340                 345                 350

Ala Pro Leu Ser Ala Ser Met Ile Lys Arg Tyr Asp Glu His His Gln
        355                 360                 365

Asp Leu Thr Leu Leu Lys Ala Leu Val Arg Gln Gln Leu Pro Glu Lys
370                 375                 380

Tyr Lys Glu Ile Phe Phe Asp Gln Ser Lys Asn Gly Tyr Ala Gly Tyr
385                 390                 395                 400

Ile Asp Gly Gly Ala Ser Gln Glu Glu Phe Tyr Lys Phe Ile Lys Pro
                405                 410                 415

Ile Leu Glu Lys Met Asp Gly Thr Glu Glu Leu Leu Val Lys Leu Asn
            420                 425                 430
```

```
Arg Glu Asp Leu Leu Arg Lys Gln Arg Thr Phe Asp Asn Gly Ser Ile
            435                 440                 445

Pro His Gln Ile His Leu Gly Glu Leu His Ala Ile Leu Arg Arg Gln
450                 455                 460

Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
            500                 505                 510

Pro Trp Asn Phe Glu Glu Val Val Asp Lys Gly Ala Ser Ala Gln Ser
            515                 520                 525

Phe Ile Glu Arg Met Thr Asn Phe Asp Lys Asn Leu Pro Asn Glu Lys
530                 535                 540

Val Leu Pro Lys His Ser Leu Leu Tyr Glu Tyr Phe Thr Val Tyr Asn
545                 550                 555                 560

Glu Leu Thr Lys Val Lys Tyr Val Thr Glu Gly Met Arg Lys Pro Ala
                565                 570                 575

Phe Leu Ser Gly Glu Gln Lys Lys Ala Ile Val Asp Leu Leu Phe Lys
            580                 585                 590

Thr Asn Arg Lys Val Thr Val Lys Gln Leu Lys Glu Asp Tyr Phe Lys
            595                 600                 605

Lys Ile Glu Cys Phe Asp Ser Val Glu Ile Ser Gly Val Glu Asp Arg
            610                 615                 620

Phe Asn Ala Ser Leu Gly Thr Tyr His Asp Leu Leu Lys Ile Ile Lys
625                 630                 635                 640

Asp Lys Asp Phe Leu Asp Asn Glu Glu Asn Glu Asp Ile Leu Glu Asp
                645                 650                 655

Ile Val Leu Thr Leu Thr Leu Phe Glu Asp Arg Glu Met Ile Glu Glu
            660                 665                 670

Arg Leu Lys Thr Tyr Ala His Leu Phe Asp Asp Lys Val Met Lys Gln
            675                 680                 685

Leu Lys Arg Arg Arg Tyr Thr Gly Trp Gly Arg Leu Ser Arg Lys Leu
690                 695                 700

Ile Asn Gly Ile Arg Asp Lys Gln Ser Gly Lys Thr Ile Leu Asp Phe
705                 710                 715                 720

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
            740                 745                 750

Gly Gln Gly Asp Ser Leu His Glu His Ile Ala Asn Leu Ala Gly Ser
            755                 760                 765

Pro Ala Ile Lys Lys Gly Ile Leu Gln Thr Val Lys Val Val Asp Glu
770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815

Glu Arg Met Lys Arg Ile Glu Glu Gly Ile Lys Glu Leu Gly Ser Gln
            820                 825                 830

Ile Leu Lys Glu His Pro Val Glu Asn Thr Gln Leu Gln Asn Glu Lys
            835                 840                 845

Leu Tyr Leu Tyr Tyr Leu Gln Asn Gly Arg Asp Met Tyr Val Asp Gln
```

```
                850                 855                 860
Glu Leu Asp Ile Asn Arg Leu Ser Asp Tyr Asp Val Asp Ala Ile Val
865                 870                 875                 880

Pro Gln Ser Phe Leu Lys Asp Asp Ser Ile Asp Asn Lys Val Leu Thr
                885                 890                 895

Arg Ser Asp Lys Asn Arg Gly Lys Ser Asp Asn Val Pro Ser Glu Glu
                900                 905                 910

Val Val Lys Lys Met Lys Asn Tyr Trp Arg Gln Leu Leu Asn Ala Lys
                915                 920                 925

Leu Ile Thr Gln Arg Lys Phe Asp Asn Leu Thr Lys Ala Glu Arg Gly
            930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
                965                 970                 975

Met Asn Thr Lys Tyr Asp Glu Asn Asp Lys Leu Ile Arg Glu Val Lys
            980                 985                 990

Val Ile Thr Leu Lys Ser Lys Leu Val Ser Asp Phe Arg Lys Asp Phe
            995                 1000                1005

Gln Phe Tyr Lys Val Arg Glu Ile Asn Asn Tyr His His Ala His
        1010                1015                1020

Asp Ala Tyr Leu Asn Ala Val Val Gly Thr Ala Leu Ile Lys Lys
        1025                1030                1035

Tyr Pro Lys Leu Glu Ser Glu Phe Val Tyr Gly Asp Tyr Lys Val
        1040                1045                1050

Tyr Asp Val Arg Lys Met Ile Ala Lys Ser Glu Gln Glu Ile Gly
        1055                1060                1065

Lys Ala Thr Ala Lys Tyr Phe Phe Tyr Ser Asn Ile Met Asn Phe
        1070                1075                1080

Phe Lys Thr Glu Ile Thr Leu Ala Asn Gly Glu Ile Arg Lys Arg
        1085                1090                1095

Pro Leu Ile Glu Thr Asn Gly Glu Thr Gly Glu Ile Val Trp Asp
        1100                1105                1110

Lys Gly Arg Asp Phe Ala Thr Val Arg Lys Val Leu Ser Met Pro
        1115                1120                1125

Gln Val Asn Ile Val Lys Lys Thr Glu Val Gln Thr Gly Gly Phe
        1130                1135                1140

Ser Lys Glu Ser Ile Leu Pro Lys Arg Asn Ser Asp Lys Leu Ile
        1145                1150                1155

Ala Arg Lys Lys Asp Trp Asp Pro Lys Lys Tyr Gly Gly Phe Asp
        1160                1165                1170

Ser Pro Thr Val Ala Tyr Ser Val Leu Val Val Ala Lys Val Glu
        1175                1180                1185

Lys Gly Lys Ser Lys Lys Leu Lys Ser Val Lys Glu Leu Leu Gly
        1190                1195                1200

Ile Thr Ile Met Glu Arg Ser Ser Phe Glu Lys Asn Pro Ile Asp
        1205                1210                1215

Phe Leu Glu Ala Lys Gly Tyr Lys Glu Val Lys Lys Asp Leu Ile
        1220                1225                1230

Ile Lys Leu Pro Lys Tyr Ser Leu Phe Glu Leu Glu Asn Gly Arg
        1235                1240                1245

Lys Arg Met Leu Ala Ser Ala Gly Glu Leu Gln Lys Gly Asn Glu
        1250                1255                1260
```

```
Leu Ala Leu Pro Ser Lys Tyr Val Asn Phe Leu Tyr Leu Ala Ser
    1265             1270                 1275

His Tyr Glu Lys Leu Lys Gly Ser Pro Glu Asp Asn Glu Gln Lys
    1280             1285                 1290

Gln Leu Phe Val Glu Gln His Lys His Tyr Leu Asp Glu Ile Ile
    1295             1300                 1305

Glu Gln Ile Ser Glu Phe Ser Lys Arg Val Ile Leu Ala Asp Ala
    1310             1315                 1320

Asn Leu Asp Lys Val Leu Ser Ala Tyr Asn Lys His Arg Asp Lys
    1325             1330                 1335

Pro Ile Arg Glu Gln Ala Glu Asn Ile Ile His Leu Phe Thr Leu
    1340             1345                 1350

Thr Asn Leu Gly Ala Pro Ala Ala Phe Lys Tyr Phe Asp Thr Thr
    1355             1360                 1365

Ile Asp Arg Lys Arg Tyr Thr Ser Thr Lys Glu Val Leu Asp Ala
    1370             1375                 1380

Thr Leu Ile His Gln Ser Ile Thr Gly Leu Tyr Glu Thr Arg Ile
    1385             1390                 1395

Asp Leu Ser Gln Leu Gly Gly Asp Ser Pro Lys Lys Lys Arg Lys
    1400             1405                 1410

Val Glu Ala Ser Gly Gly Gly Gly Ser Gly Gly Gly Ser Gly
    1415             1420                 1425

Gly Gly Gly Ser Gly Pro Ala Met Val Ser Lys Gly Glu Glu Asp
    1430             1435                 1440

Asn Met Ala Ile Ile Lys Glu Phe Met Arg Phe Lys Val His Met
    1445             1450                 1455

Glu Gly Ser Val Asn Gly His Glu Phe Glu Ile Glu Gly Glu Gly
    1460             1465                 1470

Glu Gly Arg Pro Tyr Glu Gly Thr Gln Thr Ala Lys Leu Lys Val
    1475             1480                 1485

Thr Lys Gly Gly Pro Leu Pro Phe Ala Trp Asp Ile Leu Ser Pro
    1490             1495                 1500

Gln Phe Met Tyr Gly Ser Lys Ala Tyr Val Lys His Pro Ala Asp
    1505             1510                 1515

Ile Pro Asp Tyr Leu Lys Leu Ser Phe Pro Glu Gly Phe Lys Trp
    1520             1525                 1530

Glu Arg Val Met Asn Phe Glu Asp Gly Gly Val Val Thr Val Thr
    1535             1540                 1545

Gln Asp Ser Ser Leu Gln Asp Gly Glu Phe Ile Tyr Lys Val Lys
    1550             1555                 1560

Leu Arg Gly Thr Asn Phe Pro Ser Asp Gly Pro Val Met Gln Lys
    1565             1570                 1575

Lys Thr Met Gly Trp Glu Ala Ser Ser Glu Arg Met Tyr Pro Glu
    1580             1585                 1590

Asp Gly Ala Leu Lys Gly Glu Ile Lys Gln Arg Leu Lys Leu Lys
    1595             1600                 1605

Asp Gly Gly His Tyr Asp Ala Glu Val Lys Thr Thr Tyr Lys Ala
    1610             1615                 1620

Lys Lys Pro Val Gln Leu Pro Gly Ala Tyr Asn Val Asn Ile Lys
    1625             1630                 1635

Leu Asp Ile Thr Ser His Asn Glu Asp Tyr Thr Ile Val Glu Gln
    1640             1645                 1650
```

Tyr Glu Arg Ala Glu Gly Arg His Ser Thr Gly Gly Met Asp Glu
    1655                1660                1665

Leu Tyr Lys Ile Asp
    1670

<210> SEQ ID NO 107
<211> LENGTH: 1220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Met Ile Phe Lys Pro Glu Glu Leu Arg Gln Ala Leu Met Pro Thr Leu
1               5                   10                  15

Glu Ala Leu Tyr Arg Gln Asp Pro Glu Ser Leu Pro Phe Arg Gln Pro
            20                  25                  30

Val Asp Pro Gln Leu Leu Gly Ile Pro Asp Tyr Phe Asp Ile Val Lys
        35                  40                  45

Asn Pro Met Asp Leu Ser Thr Ile Lys Arg Lys Leu Asp Thr Gly Gln
50                  55                  60

Tyr Gln Glu Pro Trp Gln Tyr Val Asp Val Trp Leu Met Phe Asn
65              70                  75                  80

Asn Ala Trp Leu Tyr Asn Arg Lys Thr Ser Arg Val Tyr Lys Phe Cys
                85                  90                  95

Ser Lys Leu Ala Glu Val Phe Glu Gln Glu Ile Asp Pro Val Met Gln
            100                 105                 110

Ser Leu Gly Tyr Cys Cys Gly Arg Lys Tyr Glu Phe Ser Pro Gln Thr
        115                 120                 125

Leu Cys Cys Tyr Gly Lys Gln Leu Cys Thr Ile Pro Arg Asp Ala Ala
    130                 135                 140

Tyr Tyr Ser Tyr Gln Asn Arg Tyr His Phe Cys Glu Lys Cys Phe Thr
145                 150                 155                 160

Glu Ile Gln Gly Glu Asn Val Thr Leu Gly Asp Asp Pro Ser Gln Pro
                165                 170                 175

Gln Thr Thr Ile Ser Lys Asp Gln Phe Glu Lys Lys Lys Asn Asp Thr
            180                 185                 190

Leu Asp Pro Glu Pro Phe Val Asp Cys Lys Glu Cys Gly Arg Lys Met
        195                 200                 205

His Gln Ile Cys Val Leu His Tyr Asp Ile Ile Trp Pro Ser Gly Phe
    210                 215                 220

Val Cys Asp Asn Cys Leu Lys Lys Thr Gly Arg Pro Arg Lys Glu Asn
225                 230                 235                 240

Lys Phe Ser Ala Lys Arg Leu Gln Thr Thr Arg Leu Gly Asn His Leu
                245                 250                 255

Glu Asp Arg Val Asn Lys Phe Leu Arg Arg Gln Asn His Pro Glu Ala
            260                 265                 270

Gly Glu Val Phe Val Arg Val Ala Ser Ser Asp Lys Thr Val Glu
        275                 280                 285

Val Lys Pro Gly Met Lys Ser Arg Phe Val Asp Ser Gly Glu Met Ser
    290                 295                 300

Glu Ser Phe Pro Tyr Arg Thr Lys Ala Leu Phe Ala Phe Glu Glu Ile
305                 310                 315                 320

Asp Gly Val Asp Val Cys Phe Phe Gly Met His Val Gln Glu Tyr Gly 325                 330                 335
Ser Asp Cys Pro Pro Asn Thr Arg Arg Val Tyr Ile Ser Tyr Leu
            340                 345                 350

Asp Ser Ile His Phe Phe Arg Pro Arg Cys Leu Arg Thr Ala Val Tyr
            355                 360                 365

His Glu Ile Leu Ile Gly Tyr Leu Glu Tyr Val Lys Lys Leu Gly Tyr
    370                 375                 380

Val Thr Gly His Ile Trp Ala Cys Pro Pro Ser Glu Gly Asp Asp Tyr
385                 390                 395                 400

Ile Phe His Cys His Pro Pro Asp Gln Lys Ile Pro Lys Pro Lys Arg
                405                 410                 415

Leu Gln Glu Trp Tyr Lys Lys Met Leu Asp Lys Ala Phe Ala Glu Arg
            420                 425                 430

Ile Ile Asn Asp Tyr Lys Asp Ile Phe Lys Gln Ala Asn Glu Asp Arg
            435                 440                 445

Leu Thr Ser Ala Lys Glu Leu Pro Tyr Phe Glu Gly Asp Phe Trp Pro
    450                 455                 460

Asn Val Leu Glu Glu Ser Ile Lys Glu Leu Glu Gln Glu Glu Glu Glu
465                 470                 475                 480

Arg Lys Lys Glu Glu Ser Thr Ala Ala Ser Glu Thr Pro Glu Gly Ser
                485                 490                 495

Gln Gly Asp Ser Lys Asn Ala Lys Lys Lys Asn Asn Lys Lys Thr Asn
            500                 505                 510

Lys Asn Lys Ser Ser Ile Ser Arg Ala Asn Lys Lys Lys Pro Ser Met
        515                 520                 525

Pro Asn Val Ser Asn Asp Leu Ser Gln Lys Leu Tyr Ala Thr Met Glu
    530                 535                 540

Lys His Lys Glu Val Phe Phe Val Ile His Leu His Ala Gly Pro Val
545                 550                 555                 560

Ile Ser Thr Gln Pro Pro Ile Val Asp Pro Asp Pro Leu Leu Ser Cys
            565                 570                 575

Asp Leu Met Asp Gly Arg Asp Ala Phe Leu Thr Leu Ala Arg Asp Lys
            580                 585                 590

His Trp Glu Phe Ser Ser Leu Arg Arg Ser Lys Trp Ser Thr Leu Cys
        595                 600                 605

Met Leu Val Glu Leu His Thr Gln Gly Gln Asp Arg Phe Val Tyr Thr
    610                 615                 620

Cys Asn Glu Cys Lys His His Val Glu Thr Arg Trp His Cys Thr Val
625                 630                 635                 640

Cys Glu Asp Tyr Asp Leu Cys Ile Asn Cys Tyr Asn Thr Lys Ser His
                645                 650                 655

Thr His Lys Met Val Lys Trp Gly Leu Gly Leu Asp Asp Glu Gly Ser
            660                 665                 670

Ser Gln Gly Glu Pro Gln Ser Lys Ser Pro Gln Glu Ser Arg Arg Leu
        675                 680                 685

Ser Ile Gln Arg Cys Ile Gln Ser Leu Val His Ala Cys Gln Cys Arg
    690                 695                 700

Asn Ala Asn Cys Ser Leu Pro Ser Cys Gln Lys Met Lys Arg Val Val
705                 710                 715                 720

Gln His Thr Lys Gly Cys Lys Arg Lys Thr Asn Gly Gly Cys Pro Val
                725                 730                 735

Cys Lys Gln Leu Ile Ala Leu Cys Cys Tyr His Ala Lys His Cys Gln
            740                 745                 750

```
Glu Asn Lys Cys Pro Val Pro Phe Cys Leu Asn Ile Asn Asp Gly Gly
            755                 760                 765
Gly Gly Ser Asp Pro Lys Lys Arg Lys Val Asp Pro Lys Lys Lys
    770                 775                 780
Arg Lys Val Asp Pro Lys Lys Arg Lys Val Gly Ser Thr Gly Ser
785                 790                 795                 800
Arg Asn Asp Gly Gly Gly Ser Gly Gly Gly Ser Gly Gly Gly
                805                 810                 815
Gly Ser Gly Arg Ala Gly Ile Leu Pro Pro Lys Lys Arg Lys Val
            820                 825                 830
Ser Arg Gly Arg Ser Arg Leu Leu Glu Asp Phe Arg Asn Asn Arg Tyr
            835                 840                 845
Pro Asn Leu Gln Leu Arg Glu Ile Ala Gly His Ile Met Glu Phe Ser
850                 855                 860
Gln Asp Gln His Gly Ser Arg Phe Ile Gln Leu Lys Leu Glu Arg Ala
865                 870                 875                 880
Thr Pro Ala Glu Arg Gln Leu Val Phe Asn Glu Ile Leu Gln Ala Ala
                885                 890                 895
Tyr Gln Leu Met Val Asp Val Phe Gly Asn Tyr Val Ile Gln Lys Phe
            900                 905                 910
Phe Glu Phe Gly Ser Leu Glu Gln Lys Leu Ala Leu Ala Glu Arg Ile
            915                 920                 925
Arg Gly His Val Leu Ser Leu Ala Leu Gln Met Tyr Gly Ser Arg Val
            930                 935                 940
Ile Glu Lys Ala Leu Glu Phe Ile Pro Ser Asp Gln Gln Asn Glu Met
945                 950                 955                 960
Val Arg Glu Leu Asp Gly His Val Leu Lys Cys Val Lys Asp Gln Asn
                965                 970                 975
Gly Asn His Val Val Gln Lys Cys Ile Glu Cys Val Gln Pro Gln Ser
            980                 985                 990
Leu Gln Phe Ile Ile Asp Ala Phe Lys Gly Gln Val Phe Ala Leu Ser
        995                 1000                1005
Thr His Pro Tyr Gly Cys Arg Val Ile Gln Arg Ile Leu Glu His
    1010                1015                1020
Cys Leu Pro Asp Gln Thr Leu Pro Ile Leu Glu Glu Leu His Gln
    1025                1030                1035
His Thr Glu Gln Leu Val Gln Asp Gln Tyr Gly Asn Tyr Val Ile
    1040                1045                1050
Gln His Val Leu Glu His Gly Arg Pro Glu Asp Lys Ser Lys Ile
    1055                1060                1065
Val Ala Glu Ile Arg Gly Asn Val Leu Val Leu Ser Gln His Lys
    1070                1075                1080
Phe Ala Ser Asn Val Val Glu Lys Cys Val Thr His Ala Ser Arg
    1085                1090                1095
Thr Glu Arg Ala Val Leu Ile Asp Glu Val Cys Thr Met Asn Asp
    1100                1105                1110
Gly Pro His Ser Ala Leu Tyr Thr Met Met Lys Asp Gln Tyr Ala
    1115                1120                1125
Asn Tyr Val Val Gln Lys Met Ile Asp Val Ala Glu Pro Gly Gln
    1130                1135                1140
Arg Lys Ile Val Met His Lys Ile Arg Pro His Ile Ala Thr Leu
    1145                1150                1155
```

Arg Lys Tyr Thr Tyr Gly Lys His Ile Leu Ala Lys Leu Glu Lys
    1160                1165                1170

Tyr Tyr Met Lys Asn Gly Val Asp Leu Gly Asp Pro Lys Lys Lys
    1175                1180                1185

Arg Lys Val Asp Pro Lys Lys Arg Lys Val Gly Gly Arg Gly
    1190                1195                1200

Gly Gly Gly Ser Gly Gly Gly Gly Ser Gly Gly Gly Gly Ser Gly
    1205                1210                1215

Pro Ala
    1220

<210> SEQ ID NO 108
<211> LENGTH: 1220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Met Ile Asp Gly Gly Gly Ser Asp Pro Lys Lys Lys Arg Lys Val
1               5                   10                  15

Asp Pro Lys Lys Lys Arg Lys Val Asp Pro Lys Lys Lys Arg Lys Val
                20                  25                  30

Gly Ser Thr Gly Ser Arg Asn Asp Gly Gly Gly Gly Ser Gly Gly Gly
                35                  40                  45

Gly Ser Gly Gly Gly Gly Ser Gly Arg Ala Gly Ile Leu Pro Pro Lys
    50                  55                  60

Lys Lys Arg Lys Val Ser Arg Gly Arg Ser Arg Leu Leu Glu Asp Phe
65                  70                  75                  80

Arg Asn Asn Arg Tyr Pro Asn Leu Gln Leu Arg Glu Ile Ala Gly His
                85                  90                  95

Ile Met Glu Phe Ser Gln Asp Gln His Gly Ser Arg Phe Ile Gln Leu
                100                 105                 110

Lys Leu Glu Arg Ala Thr Pro Ala Glu Arg Gln Leu Val Phe Asn Glu
            115                 120                 125

Ile Leu Gln Ala Ala Tyr Gln Leu Met Val Asp Val Phe Gly Asn Tyr
            130                 135                 140

Val Ile Gln Lys Phe Phe Glu Phe Gly Ser Leu Glu Gln Lys Leu Ala
145                 150                 155                 160

Leu Ala Glu Arg Ile Arg Gly His Val Leu Ser Leu Ala Leu Gln Met
                165                 170                 175

Tyr Gly Ser Arg Val Ile Glu Lys Ala Leu Glu Phe Ile Pro Ser Asp
                180                 185                 190

Gln Gln Asn Glu Met Val Arg Glu Leu Asp Gly His Val Leu Lys Cys
            195                 200                 205

Val Lys Asp Gln Asn Gly Asn His Val Val Gln Lys Cys Ile Glu Cys
210                 215                 220

Val Gln Pro Gln Ser Leu Gln Phe Ile Ile Asp Ala Phe Lys Gly Gln
225                 230                 235                 240

Val Phe Ala Leu Ser Thr His Pro Tyr Gly Cys Arg Val Ile Gln Arg
                245                 250                 255

Ile Leu Glu His Cys Leu Pro Asp Gln Thr Leu Pro Ile Leu Glu Glu
                260                 265                 270

Leu His Gln His Thr Glu Gln Leu Val Gln Asp Gln Tyr Gly Asn Tyr

```
              275                 280                 285
Val Ile Gln His Val Leu Glu His Gly Arg Pro Glu Asp Lys Ser Lys
290                 295                 300
Ile Val Ala Glu Ile Arg Gly Asn Val Leu Val Leu Ser Gln His Lys
305                 310                 315                 320
Phe Ala Ser Asn Val Val Glu Lys Cys Val Thr His Ala Ser Arg Thr
                325                 330                 335
Glu Arg Ala Val Leu Ile Asp Glu Val Cys Thr Met Asn Asp Gly Pro
                340                 345                 350
His Ser Ala Leu Tyr Thr Met Met Lys Asp Gln Tyr Ala Asn Tyr Val
                355                 360                 365
Val Gln Lys Met Ile Asp Val Ala Glu Pro Gly Gln Arg Lys Ile Val
                370                 375                 380
Met His Lys Ile Arg Pro His Ile Ala Thr Leu Arg Lys Tyr Thr Tyr
385                 390                 395                 400
Gly Lys His Ile Leu Ala Lys Leu Glu Lys Tyr Tyr Met Lys Asn Gly
                405                 410                 415
Val Asp Leu Gly Asp Pro Lys Lys Arg Lys Val Asp Pro Lys Lys
                420                 425                 430
Lys Arg Lys Val Gly Gly Arg Gly Gly Gly Ser Gly Gly Gly
                435                 440                 445
Ser Gly Gly Gly Ser Gly Pro Ala Ile Phe Lys Pro Glu Glu Leu
450                 455                 460
Arg Gln Ala Leu Met Pro Thr Leu Glu Ala Leu Tyr Arg Gln Asp Pro
465                 470                 475                 480
Glu Ser Leu Pro Phe Arg Gln Pro Val Asp Pro Gln Leu Leu Gly Ile
                485                 490                 495
Pro Asp Tyr Phe Asp Ile Val Lys Asn Pro Met Asp Leu Ser Thr Ile
                500                 505                 510
Lys Arg Lys Leu Asp Thr Gly Gln Tyr Gln Glu Pro Trp Gln Tyr Val
                515                 520                 525
Asp Asp Val Trp Leu Met Phe Asn Asn Ala Trp Leu Tyr Asn Arg Lys
                530                 535                 540
Thr Ser Arg Val Tyr Lys Phe Cys Ser Lys Leu Ala Glu Val Phe Glu
545                 550                 555                 560
Gln Glu Ile Asp Pro Val Met Gln Ser Leu Gly Tyr Cys Cys Gly Arg
                565                 570                 575
Lys Tyr Glu Phe Ser Pro Gln Thr Leu Cys Cys Tyr Gly Lys Gln Leu
                580                 585                 590
Cys Thr Ile Pro Arg Asp Ala Ala Tyr Tyr Ser Tyr Gln Asn Arg Tyr
                595                 600                 605
His Phe Cys Glu Lys Cys Phe Thr Glu Ile Gln Gly Glu Asn Val Thr
                610                 615                 620
Leu Gly Asp Asp Pro Ser Gln Pro Gln Thr Thr Ile Ser Lys Asp Gln
625                 630                 635                 640
Phe Glu Lys Lys Lys Asn Asp Thr Leu Asp Pro Glu Pro Phe Val Asp
                645                 650                 655
Cys Lys Glu Cys Gly Arg Lys Met His Gln Ile Cys Val Leu His Tyr
                660                 665                 670
Asp Ile Ile Trp Pro Ser Gly Phe Val Cys Asp Asn Cys Leu Lys Lys
                675                 680                 685
Thr Gly Arg Pro Arg Lys Glu Asn Lys Phe Ser Ala Lys Arg Leu Gln
                690                 695                 700
```

```
Thr Thr Arg Leu Gly Asn His Leu Glu Asp Arg Val Asn Lys Phe Leu
705                 710                 715                 720

Arg Arg Gln Asn His Pro Glu Ala Gly Glu Val Phe Val Arg Val Val
            725                 730                 735

Ala Ser Ser Asp Lys Thr Val Glu Val Lys Pro Gly Met Lys Ser Arg
            740                 745                 750

Phe Val Asp Ser Gly Glu Met Ser Glu Ser Phe Pro Tyr Arg Thr Lys
            755                 760                 765

Ala Leu Phe Ala Phe Glu Glu Ile Asp Gly Val Asp Val Cys Phe Phe
770                 775                 780

Gly Met His Val Gln Glu Tyr Gly Ser Asp Cys Pro Pro Asn Thr
785                 790                 795                 800

Arg Arg Val Tyr Ile Ser Tyr Leu Asp Ser Ile His Phe Phe Arg Pro
                805                 810                 815

Arg Cys Leu Arg Thr Ala Val Tyr His Glu Ile Leu Ile Gly Tyr Leu
            820                 825                 830

Glu Tyr Val Lys Lys Leu Gly Tyr Val Thr Gly His Ile Trp Ala Cys
            835                 840                 845

Pro Pro Ser Glu Gly Asp Asp Tyr Ile Phe His Cys His Pro Pro Asp
850                 855                 860

Gln Lys Ile Pro Lys Pro Lys Arg Leu Gln Glu Trp Tyr Lys Lys Met
865                 870                 875                 880

Leu Asp Lys Ala Phe Ala Glu Arg Ile Ile Asn Asp Tyr Lys Asp Ile
                885                 890                 895

Phe Lys Gln Ala Asn Glu Asp Arg Leu Thr Ser Ala Lys Glu Leu Pro
            900                 905                 910

Tyr Phe Glu Gly Asp Phe Trp Pro Asn Val Leu Glu Glu Ser Ile Lys
            915                 920                 925

Glu Leu Glu Gln Glu Glu Glu Arg Lys Lys Glu Glu Ser Thr Ala
930                 935                 940

Ala Ser Glu Thr Pro Glu Gly Ser Gln Gly Asp Ser Lys Asn Ala Lys
945                 950                 955                 960

Lys Lys Asn Asn Lys Lys Thr Asn Lys Asn Lys Ser Ser Ile Ser Arg
                965                 970                 975

Ala Asn Lys Lys Lys Pro Ser Met Pro Asn Val Ser Asn Asp Leu Ser
            980                 985                 990

Gln Lys Leu Tyr Ala Thr Met Glu Lys His Lys Glu Val Phe Phe Val
        995                 1000                1005

Ile His Leu His Ala Gly Pro Val Ile Ser Thr Gln Pro Pro Ile
    1010                1015                1020

Val Asp Pro Asp Pro Leu Leu Ser Cys Asp Leu Met Asp Gly Arg
    1025                1030                1035

Asp Ala Phe Leu Thr Leu Ala Arg Asp Lys His Trp Glu Phe Ser
    1040                1045                1050

Ser Leu Arg Arg Ser Lys Trp Ser Thr Leu Cys Met Leu Val Glu
    1055                1060                1065

Leu His Thr Gln Gly Gln Asp Arg Phe Val Tyr Thr Cys Asn Glu
    1070                1075                1080

Cys Lys His His Val Glu Thr Arg Trp His Cys Thr Val Cys Glu
    1085                1090                1095

Asp Tyr Asp Leu Cys Ile Asn Cys Tyr Asn Thr Lys Ser His Thr
    1100                1105                1110
```

| His | Lys | Met | Val | Lys | Trp | Gly | Leu | Gly | Leu | Asp | Asp | Glu | Gly | Ser |
|-----|-----|-----|-----|-----|-----|-----|-----|-----|-----|-----|-----|-----|-----|-----|
| 1115 | | | | | 1120 | | | | | 1125 | | | | |

| Ser | Gln | Gly | Glu | Pro | Gln | Ser | Lys | Ser | Pro | Gln | Glu | Ser | Arg | Arg |
|-----|-----|-----|-----|-----|-----|-----|-----|-----|-----|-----|-----|-----|-----|-----|
| 1130 | | | | | 1135 | | | | | 1140 | | | | |

| Leu | Ser | Ile | Gln | Arg | Cys | Ile | Gln | Ser | Leu | Val | His | Ala | Cys | Gln |
|-----|-----|-----|-----|-----|-----|-----|-----|-----|-----|-----|-----|-----|-----|-----|
| 1145 | | | | | 1150 | | | | | 1155 | | | | |

| Cys | Arg | Asn | Ala | Asn | Cys | Ser | Leu | Pro | Ser | Cys | Gln | Lys | Met | Lys |
|-----|-----|-----|-----|-----|-----|-----|-----|-----|-----|-----|-----|-----|-----|-----|
| 1160 | | | | | 1165 | | | | | 1170 | | | | |

| Arg | Val | Val | Gln | His | Thr | Lys | Gly | Cys | Lys | Arg | Lys | Thr | Asn | Gly |
|-----|-----|-----|-----|-----|-----|-----|-----|-----|-----|-----|-----|-----|-----|-----|
| 1175 | | | | | 1180 | | | | | 1185 | | | | |

| Gly | Cys | Pro | Val | Cys | Lys | Gln | Leu | Ile | Ala | Leu | Cys | Cys | Tyr | His |
|-----|-----|-----|-----|-----|-----|-----|-----|-----|-----|-----|-----|-----|-----|-----|
| 1190 | | | | | 1195 | | | | | 1200 | | | | |

| Ala | Lys | His | Cys | Gln | Glu | Asn | Lys | Cys | Pro | Val | Pro | Phe | Cys | Leu |
|-----|-----|-----|-----|-----|-----|-----|-----|-----|-----|-----|-----|-----|-----|-----|
| 1205 | | | | | 1210 | | | | | 1215 | | | | |

Asn Ile
    1220

<210> SEQ ID NO 109
<211> LENGTH: 454
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 109
gagggcctat ttcccatgat tccttcatat ttgcatatac gatacaaggc tgttagagag      60
ataattggaa ttaatttgac tgtaaacaca agatattag tacaaaatac gtgacgtaga     120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccn nnnnnnnnn nnnnnnnnng tttaagagct atgctggaaa cagcatagca    300
agtttaaata aggctagtcc gttatcaact tgaaaaagtg gcaccgagtc ggtgccaatt    360
gggtctccag atcttttttt gttttagagc tagaaatagc aagttaaaat aaggctagtc    420
cgtagcgcgt gcgccaattc tgcagacaaa tggc                                454

<210> SEQ ID NO 110
<211> LENGTH: 472
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 110
gagggcctat ttcccatgat tccttcatat ttgcatatac gatacaaggc tgttagagag      60
ataattggaa ttaatttgac tgtaaacaca agatattag tacaaaatac gtgacgtaga     120
aagtaataat ttcttgggta gtttgcagtt ttaaaattat gttttaaaat ggactatcat    180
atgcttaccg taacttgaaa gtatttcgat ttcttggctt tatatatctt gtggaaagga    240

```
cgaaacaccn nnnnnnnnnn nnnnnnnnng tttaagagct atgctggaaa cagcatagca      300
agtttaaata aggctagtcc gttatcaact tgaaaaagtg gcaccgagtc ggtgccaatt      360
gggtctccag atgcctgtat gtagccagat cttttttttgt tttagagcta gaaatagcaa    420
gttaaaataa ggctagtccg tagcgcgtgc gccaattctg cagacaaatg gc             472
```

<210> SEQ ID NO 111
<211> LENGTH: 510
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 111

```
gagggcctat ttcccatgat tccttcatat ttgcatatac gatacaaggc tgttagagag       60
ataattggaa ttaatttgac tgtaaacaca aagatattag tacaaaatac gtgacgtaga      120
aagtaataat ttcttgggta gtttgcagtt ttaaaattat gttttaaaat ggactatcat      180
atgcttaccg taacttgaaa gtatttcgat ttccttggctt tatatatctt gtggaaagga    240
cgaaacaccn nnnnnnnnn nnnnnnnnng tttaagagct atgctggaaa cagcatagca      300
agtttaaata aggctagtcc gttatcaact tgaaaaagtg gcaccgagtc ggtgccaatt      360
gggtctccag attgtatgta gcctgtatgt agcctgtatg tagcctgtat gtagcctgta    420
tgtaagatct ttttttgttt tagagctaga aatagcaagt taaaataagg ctagtccgta    480
gcgcgtgcgc caattctgca gacaaatggc                                      510
```

<210> SEQ ID NO 112
<211> LENGTH: 621
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 112

```
gagggcctat ttcccatgat tccttcatat ttgcatatac gatacaaggc tgttagagag       60
ataattggaa ttaatttgac tgtaaacaca aagatattag tacaaaatac gtgacgtaga      120
aagtaataat ttcttgggta gtttgcagtt ttaaaattat gttttaaaat ggactatcat      180
atgcttaccg taacttgaaa gtatttcgat ttccttggctt tatatatctt gtggaaagga    240
cgaaacaccn nnnnnnnnn nnnnnnnnng tttaagagct atgctggaaa cagcatagca      300
agtttaaata aggctagtcc gttatcaact tgaaaaagtg gcaccgagtc ggtgccaatt      360
gggtctccag attgtatgta gcctgtatgt agcctgtatg tagcctgtat gtagcctgta    420
tgtaagattg tatgtagctg tatgtagcct gtatgtagcc tgtatgtagc ctgtatgtaa    480
gattgtatgt agcctgtatg tagcctgtat gtagcctgta tgtagcctgt atgtaagatc    540
tttttttgtt ttagagctag aaatagcaag ttaaaataag gctagtccgt agcgcgtgcg    600
```

<210> SEQ ID NO 113
<211> LENGTH: 734
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 113

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag attgtatgta gcctgtatgt agcctgtatg tagcctgtat gtagcctgta   420
tgtaagattg tatgtagcct gtatgtagcc tgtatgtagc ctgtatgtag cctgtatgta   480
agattgtatg tagcctgtat gtagcctgta tgtagcctgt atgtagcctg tatgtaagat   540
tgtatgtagc ctgtatgtag cctgtatgta gcctgtatgt agcctgtatg taagattgta   600
tgtagcctgt atgtagcctg tatgtagcct gtatgtagcc tgtatgtaag atcttttttt   660
gttttagagc tagaaatagc aagttaaaat aaggctagtc cgtagcgcgt gcgccaattc   720
tgcagacaaa tggc                                                   734
```

<210> SEQ ID NO 114
<211> LENGTH: 472
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 114

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atgccttgat atagccagat cttttttttgt tttagagcta gaaatagcaa   420
gttaaaataa ggctagtccg tagcgcgtgc gccaattctg cagacaaatg gc           472
```

<210> SEQ ID NO 115
<211> LENGTH: 477

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 115

| | |
|---|---|
| gagggcctat ttcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacaccn nnnnnnnnn nnnnnnnnng tttaagagct atgctggaaa cagcatagca | 300 |
| agtttaaata aggctagtcc gttatcaact tgaaaaagtg gcaccgagtc ggtgccaatt | 360 |
| gggtctccag atttgatata gccttgatat aagatctttt tttgttttag agctagaaat | 420 |
| agcaagttaa ataaggcta gtccgtagcg cgtgcgccaa ttctgcagac aaatggc | 477 |

<210> SEQ ID NO 116
<211> LENGTH: 510
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 116

| | |
|---|---|
| gagggcctat ttcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacaccn nnnnnnnnn nnnnnnnnng tttaagagct atgctggaaa cagcatagca | 300 |
| agtttaaata aggctagtcc gttatcaact tgaaaaagtg gcaccgagtc ggtgccaatt | 360 |
| gggtctccag atttgatata gccttgatat agccttgata tagccttgat atagccttga | 420 |
| tataagatct tttttttgttt tagagctaga aatagcaagt taaataagg ctagtccgta | 480 |
| gcgcgtgcgc caattctgca gacaaatggc | 510 |

<210> SEQ ID NO 117
<211> LENGTH: 566
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 117

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atttgatata gccttgatat agccttgata tagccttgat atagccttga   420
tataagattt gatatagcct tgatatagcc ttgatatagc cttgatatag ccttgatata   480
agatcttttt ttgttttaga gctagaaata gcaagttaaa ataaggctag tccgtagcgc   540
gtgcgccaat tctgcagaca aatggc                                        566
```

```
<210> SEQ ID NO 118
<211> LENGTH: 622
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 118
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atttgatata gccttgatat agccttgata tagccttgat atagccttga   420
tataagattt gatatagcct tgatatagcc ttgatatagc cttgatatag ccttgatata   480
agatttgata tagccttgat atagccttga tatagccttg atatagcctt gatataagat   540 cttttttttgt tttagagcta gaaatagcaa gttaaaataa ggctagtccg tagcgcgtgc   600
gccaattctg cagacaaatg gc                                            622
```

```
<210> SEQ ID NO 119
<211> LENGTH: 678
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 119
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
```

```
atgcttaccg taacttgaaa gtatttcgat ttcttggctt tatatatctt gtggaaagga    240
cgaaacaccn nnnnnnnnn nnnnnnnnng tttaagagct atgctggaaa cagcatagca    300
agtttaaata aggctagtcc gttatcaact tgaaaagtg gcaccgagtc ggtgccaatt    360
gggtctccag atttgatata gccttgatat agccttgata tagccttgat atagccttga    420
tataagattt gatatagcct tgatatagcc ttgatatagc cttgatatag ccttgatata    480
agatttgata tagccttgat atagccttga tatagccttg atatagcctt gatataagat    540
ttgatatagc cttgatatag ccttgatata gccttgatat agccttgata taagatcttt    600
ttttgtttta gagctagaaa tagcaagtta aataaggct agtccgtagc gcgtgcgcca    660
attctgcaga caaatggc    678
```

<210> SEQ ID NO 120
<211> LENGTH: 734
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 120

```
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccn nnnnnnnnn nnnnnnnnng tttaagagct atgctggaaa cagcatagca    300
agtttaaata aggctagtcc gttatcaact tgaaaagtg gcaccgagtc ggtgccaatt    360
gggtctccag atttgatata gccttgatat agccttgata tagccttgat atagccttga    420
tataagattt gatatagcct tgatatagcc ttgatatagc cttgatatag ccttgatata    480
agatttgata tagccttgat atagccttga tatagccttg atatagcctt gatataagat    540
ttgatatagc cttgatatag ccttgatata gccttgatat agccttgata taagatttga    600
tatagccttg atatagcctt gatatagcct tgatatagcc ttgatataag atcttttttt    660
gttttagagc tagaaatagc aagttaaaat aaggctagtc cgtagcgcgt gcgccaattc    720
tgcagacaaa tggc    734
```

<210> SEQ ID NO 121
<211> LENGTH: 979
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 121

```
gagggcctat ttcccatgat tccttcatat ttgcatatac gatacaaggc tgttagagag     60
```

```
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccn nnnnnnnnnn nnnnnnnnng tttaagagct atgctggaaa cagcatagca     300
agtttaaata aggctagtcc gttatcaact tgaaaaagtg gcaccgagtc ggtgccaatt     360
gggtctccag atttgatata gccttgatat agccttgata tagccttgat atagccttga     420
tataagattt gatatagcct tgatatagcc ttgatatagc cttgatatag ccttgatata     480
agatttgata taccttgata tagccttgat atagccttga tatagccttg atataagatt     540
tgatatagcc ttgatatagc cttgatatag ccttgatata gccttgatat agccttgata     600
tagccttgat ataagatttg atatagcctt gatatagcct tgatatagcc ttgatatagc     660
cttgatataa gatttgatat agccttgata tagccttgat atagccttga tatagccttg     720
atataagatt tgatatagcc ttgatatagc cttgatatag ccttgatata gccttgatat     780
aagatttgat atagccttga tatagccttg atatagcctt gatatagcct tgatataaga     840
tttgatatag ccttgatata gccttgatat agccttgata tagccttgat ataagatctt     900
tttttgtttt agagctagaa atagcaagtt aaaataaggc tagtccgtag cgcgtgcgcc     960
aattctgcag acaaatggc                                                 979
```

<210> SEQ ID NO 122
<211> LENGTH: 490
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 122

```
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccn nnnnnnnnnn nnnnnnnnng tttaagagct atgctggaaa cagcatagca     300
agtttaaata aggctagtcc gttatcaact tgaaaaagtg gcaccgagtc ggtgccaatt     360
gggtctccag atgccttgat atagccagat gccttgatat agccagatct tttttgttt      420 tagagctaga aatagcaagt taaaataagg ctagtccgta gcgcgtgcgc caattctgca     480
gacaaatggc                                                            490
```

<210> SEQ ID NO 123
<211> LENGTH: 562
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 123

```
gagggcctat ttcccatgat tccttcatat ttgcatatac gatacaaggc tgttagagag        60
ataattggaa ttaatttgac tgtaaacaca aagatattag tacaaaatac gtgacgtaga       120
aagtaataat ttcttgggta gtttgcagtt ttaaaattat gttttaaaat ggactatcat       180
atgcttaccg taacttgaaa gtatttcgat ttcttggctt tatatatctt gtggaaagga       240
cgaaacaccn nnnnnnnnn nnnnnnnnng tttaagagct atgctggaaa cagcatagca       300
agtttaaata aggctagtcc gttatcaact tgaaaaagtg gcaccgagtc ggtgccaatt       360
gggtctccag atgccttgat atagccagat gccttgatat agccagatgc cttgatatag       420
ccagatgcct tgatatagcc agatgccttg atatagccag atgccttgat atagccagat       480
cttttttgt tttagagcta gaaatagcaa gttaaaataa ggctagtccg tagcgcgtgc        540
gccaattctg cagacaaatg gc                                                562
```

<210> SEQ ID NO 124
<211> LENGTH: 724
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 124

```
gagggcctat ttcccatgat tccttcatat ttgcatatac gatacaaggc tgttagagag        60
ataattggaa ttaatttgac tgtaaacaca aagatattag tacaaaatac gtgacgtaga       120
aagtaataat ttcttgggta gtttgcagtt ttaaaattat gttttaaaat ggactatcat       180
atgcttaccg taacttgaaa gtatttcgat ttcttggctt tatatatctt gtggaaagga       240
cgaaacaccn nnnnnnnnn nnnnnnnnng tttaagagct atgctggaaa cagcatagca       300
agtttaaata aggctagtcc gttatcaact tgaaaaagtg gcaccgagtc ggtgccaatt       360
gggtctccag atgccttgat atagccagat gccttgatat agccagatgc cttgatatag       420
ccagatgcct tgatatagcc agatgccttg atatagccag atgccttgat atagccagat       480
gccttgatat agccagatgc cttgatatag ccagatgcct tgatatagcc agatgccttg       540
atatagccag atgccttgat atagccagat gccttgatat agccagatgc cttgatatag       600
ccagatgcct tgatatagcc agatgccttg atatagccag atctttttt gttttagagc       660
tagaaatagc aagttaaaat aaggctagtc cgtagcgcgt gcgccaattc tgcagacaaa       720
tggc                                                                    724
```

<210> SEQ ID NO 125
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 125

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng tttaagagct atgctggaaa cagcatagca   300
agtttaaata aggctagtcc gttatcaact tgaaaaagtg gcaccgagtc ggtgccaatt   360
gggtctccag atgccttgat atagccagat gccttgatat agccagatgc cttgatatag   420
ccagatgcct tgatatagcc agatgccttg atatagccag atgccttgat atagccagat   480
gccttgatat agccagatgc cttgatatag ccagatgcct tgatatagcc agatgccttg   540
atatagccag atgccttgat atagccagat gccttgatat agccagatgc cttgatatag   600
ccagatgcct tgatatagcc agatgccttg atatagccag atgccttgat atagccagat   660
gccttgatat agccagatgc cttgatatag ccagatcctt gatatagcca gatgccttga   720
tatagccaga tctttttttg ttttagagct agaaatagca agttaaaata aggctagtcc   780
gtagcgcgtg cgccaattct gcagacaaat ggc                                813
```

<210> SEQ ID NO 126
<211> LENGTH: 515
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (330)..(349)
<223> OTHER INFORMATION: a, c, t, g, unknown or other

<400> SEQUENCE: 126

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccg caattgggtc tccagattgt atgtagcctg tatgtagcct gtatgtagcc   300
tgtatgtagc ctgtatgtaa gatctcaccn nnnnnnnnn nnnnnnnnng tttaagagct   360
atgctggaaa cagcatagca agtttaaata aggctagtcc gttatcaact tgaaaaagtg   420
gcaccgagtc ggtgcttttt tgttttagag ctagaaatag caagttaaaa taaggctagt   480
ccgtagcgcg tgcgccaatt ctgcagacaa atggc                               515
```

<210> SEQ ID NO 127
<211> LENGTH: 510
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 127

| | |
|---|---|
| gagggcctat ttcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacaccn nnnnnnnnn nnnnnnnnng tttaagagct atgctggaaa cagcatagca | 300 |
| agtttaaata aggctagtcc gttatcaact tgaaaaagtg gcaccgagtc ggtgccaatt | 360 |
| gggtctccag attgtatgta gtctattgat atagtcttgt ctatgtatgt agtctattga | 420 |
| tataagatct ttttttgttt tagagctaga aatagcaagt taaataagg ctagtccgta | 480 |
| gcgcgtgcgc caattctgca gacaaatggc | 510 |

```
<210> SEQ ID NO 128
<211> LENGTH: 678
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 128
```

| | |
|---|---|
| gagggcctat ttcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacaccn nnnnnnnnn nnnnnnnnng tttaagagct atgctggaaa cagcatagca | 300 |
| agtttaaata aggctagtcc gttatcaact tgaaaaagtg gcaccgagtc ggtgccaatt | 360 |
| gggtctccag attgtatgta gtctattgat atagtcttgt ctatgtatgt agtctattga | 420 |
| tataagattg tatgtagtct attgatatag tcttgtctat gtatgtagtc tattgatata | 480 |
| agattgtatg tagtctattg atatagtctt gtctatgtat gtagtctatt gatataagat | 540 |
| tgtatgtagt ctattgatat agtcttgtct atgtatgtag tctattgata taagatcttt | 600 |
| ttttgtttta gagctagaaa tagcaagtta aaataaggct agtccgtagc gcgtgcgcca | 660 |
| attctgcaga caaatggc | 678 |

```
<210> SEQ ID NO 129
<211> LENGTH: 566
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 129
```

| | |
|---|---|
| gagggcctat ttcccatgat tccttcatat ttgcatatac gatacaaggc tgttagagag | 60 |
| ataattggaa ttaatttgac tgtaaacaca aagatattag tacaaaatac gtgacgtaga | 120 |

```
aagtaataat ttcttgggta gtttgcagtt ttaaaattat gttttaaaat ggactatcat      180
atgcttaccg taacttgaaa gtatttcgat ttcttggctt tatatatctt gtggaaagga      240
cgaaacaccn nnnnnnnnn nnnnnnnnng tttaagagct atgctggaaa cagcatagca      300
agtttaaata aggctagtcc gttatcaact tgaaaaagtg gcaccgagtc ggtgccaatt      360
gggtctccag attgtatgta gtctattgat atagtcttgt ctatgtatgt agtctattga      420
tataagattg tatgtagtct attgatatag tcttgtctat gtatgtagtc tattgatata      480 agatctttt ttgttttaga gctagaaata gcaagttaaa ataaggctag tccgtagcgc      540
gtgcgccaat tctgcagaca aatggc                                            566
```

<210> SEQ ID NO 130
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130

```
gttctcttgc tgaaagctcg a                                                  21
```

<210> SEQ ID NO 131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131

```
gcttttctct atcactgata                                                    20
```

<210> SEQ ID NO 132
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132

```
gcatacttct gcctgctggg gagcctg                                            27
```

<210> SEQ ID NO 133
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133

```
gaaagtcccc aggctcccca gc                                                 22
```

<210> SEQ ID NO 134
<211> LENGTH: 22
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 134
gcatctcaat tagtcagcaa cc                                              22

<210> SEQ ID NO 135
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
gttagggtta gggttagggt ta                                              22

<210> SEQ ID NO 136
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
gttgaggcct tcgttggaaa c                                               21

<210> SEQ ID NO 137
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
gaagagtgga ggccgtgcgc gg                                              22

<210> SEQ ID NO 138
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
gcaagcaagg gaagcgacaa gg                                              22

<210> SEQ ID NO 139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
gatgtttcag gactaggctg a                                               21

<210> SEQ ID NO 140
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
gagctgggcc aggagaggag a                                              21

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141 gagggggtctg tggagagttt                                               20

<210> SEQ ID NO 142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
ggcttggtgt attcagaatg                                                20

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
gtagagatgc cgccccgccc                                                20

<210> SEQ ID NO 144
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
ggccccgccc cctggatggg                                                20

<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
``` gggggggagaa actgaggcga                                                 20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
ggtggtggca atggtgtctg                                                  20

<210> SEQ ID NO 147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
gacacaactg gcgcccctcc                                                  20

<210> SEQ ID NO 148
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
ggcccctact tccccttcaa                                                  20

<210> SEQ ID NO 149
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
gagtgataag acacccgctt                                                  20

<210> SEQ ID NO 150
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
gcctgggagg gactggggga                                                  20

<210> SEQ ID NO 151
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 151
ggacaatccc ggtccccaga                                                   20

<210> SEQ ID NO 152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 152
ggtctgccgg aaggtctaca                                                   20

<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 153
ggcaggtaga ttatggggcc                                                   20

<210> SEQ ID NO 154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
gaagacggcc tctcagagga                                                   20

<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
gtatttctgg cctgggcaag                                                   20

<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
gcatgtgacg ggggctgtca                                                   20

-continued

```
<210> SEQ ID NO 157
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
gctgccgggt tttgcatgaa                                                      20

<210> SEQ ID NO 158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
gccggccgcg cgggggaggc                                                      20

<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
ggcaggcgag gaggggagg                                                       20

<210> SEQ ID NO 160
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
gcatacttct gcctgctggg gagcctg                                              27

<210> SEQ ID NO 161
<211> LENGTH: 1399
<212> TYPE: PRT
<213> ORGANISM: Streptococcus pyogenes

<400> SEQUENCE: 161
```

Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Ala Ile Gly
            20                  25                  30

Thr Asn Ser Val Gly Trp Ala Val Ile Thr Asp Glu Tyr Lys Val Pro
        35                  40                  45

Ser Lys Lys Phe Lys Val Leu Gly Asn Thr Asp Arg His Ser Ile Lys
    50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Arg Tyr Thr Arg Arg Lys

```
                    85                  90                  95
Asn Arg Ile Cys Tyr Leu Gln Glu Ile Phe Ser Asn Glu Met Ala Lys
                100                 105                 110

Val Asp Asp Ser Phe Phe His Arg Leu Glu Glu Ser Phe Leu Val Glu
            115                 120                 125

Glu Asp Lys Lys His Glu Arg His Pro Ile Phe Gly Asn Ile Val Asp
        130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
                180                 185                 190

Asp Leu Asn Pro Asp Asn Ser Asp Val Asp Lys Leu Phe Ile Gln Leu
            195                 200                 205

Val Gln Thr Tyr Asn Gln Leu Phe Glu Glu Asn Pro Ile Asn Ala Ser
        210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
                260                 265                 270

Lys Ser Asn Phe Asp Leu Ala Glu Asp Ala Lys Leu Gln Leu Ser Lys
            275                 280                 285

Asp Thr Tyr Asp Asp Asp Leu Asp Asn Leu Leu Ala Gln Ile Gly Asp
        290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
                340                 345                 350

Thr Leu Leu Lys Ala Leu Val Arg Gln Gln Leu Pro Glu Lys Tyr Lys
            355                 360                 365

Glu Ile Phe Phe Asp Gln Ser Lys Asn Gly Tyr Ala Gly Tyr Ile Asp
        370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
        435                 440                 445

Phe Tyr Pro Phe Leu Lys Asp Asn Arg Glu Lys Ile Glu Lys Ile Leu
        450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510
```

```
Glu Arg Met Thr Asn Phe Asp Lys Asn Leu Pro Asn Glu Lys Val Leu
        515                 520                 525

Pro Lys His Ser Leu Leu Tyr Glu Tyr Phe Thr Val Tyr Asn Glu Leu
        530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
                580                 585                 590

Glu Cys Phe Asp Ser Val Glu Ile Ser Gly Val Glu Asp Arg Phe Asn
        595                 600                 605

Ala Ser Leu Gly Thr Tyr His Asp Leu Leu Lys Ile Ile Lys Asp Lys
        610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
                660                 665                 670

Arg Arg Arg Tyr Thr Gly Trp Gly Arg Leu Ser Arg Lys Leu Ile Asn
        675                 680                 685

Gly Ile Arg Asp Lys Gln Ser Gly Lys Thr Ile Leu Asp Phe Leu Lys
        690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
                725                 730                 735

Gly Asp Ser Leu His Glu His Ile Ala Asn Leu Ala Gly Ser Pro Ala
                740                 745                 750

Ile Lys Lys Gly Ile Leu Gln Thr Val Lys Val Val Asp Glu Leu Val
        755                 760                 765

Lys Val Met Gly Arg His Lys Pro Glu Asn Ile Val Ile Glu Met Ala
        770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
                805                 810                 815

Lys Glu His Pro Val Glu Asn Thr Gln Leu Gln Asn Glu Lys Leu Tyr
                820                 825                 830

Leu Tyr Tyr Leu Gln Asn Gly Arg Asp Met Tyr Val Asp Gln Glu Leu
        835                 840                 845

Asp Ile Asn Arg Leu Ser Asp Tyr Asp Val Asp Ala Ile Val Pro Gln
        850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
                885                 890                 895

Lys Lys Met Lys Asn Tyr Trp Arg Gln Leu Leu Asn Ala Lys Leu Ile
                900                 905                 910

Thr Gln Arg Lys Phe Asp Asn Leu Thr Lys Ala Glu Arg Gly Gly Leu
        915                 920                 925
```

```
Ser Glu Leu Asp Lys Ala Gly Phe Ile Lys Arg Gln Leu Val Glu Thr
930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
                980                 985                 990

Tyr Lys Val Arg Glu Ile Asn Asn Tyr His His Ala His Asp Ala Tyr
            995                 1000                1005

Leu Asn Ala Val Val Gly Thr Ala Leu Ile Lys Lys Tyr Pro Lys
    1010                1015                1020

Leu Glu Ser Glu Phe Val Tyr Gly Asp Tyr Lys Val Tyr Asp Val
    1025                1030                1035

Arg Lys Met Ile Ala Lys Ser Glu Gln Glu Ile Gly Lys Ala Thr
    1040                1045                1050

Ala Lys Tyr Phe Phe Tyr Ser Asn Ile Met Asn Phe Phe Lys Thr
    1055                1060                1065

Glu Ile Thr Leu Ala Asn Gly Glu Ile Arg Lys Arg Pro Leu Ile
    1070                1075                1080

Glu Thr Asn Gly Glu Thr Gly Glu Ile Val Trp Asp Lys Gly Arg
    1085                1090                1095

Asp Phe Ala Thr Val Arg Lys Val Leu Ser Met Pro Gln Val Asn
    1100                1105                1110

Ile Val Lys Lys Thr Glu Val Gln Thr Gly Gly Phe Ser Lys Glu
    1115                1120                1125

Ser Ile Leu Pro Lys Arg Asn Ser Asp Lys Leu Ile Ala Arg Lys
    1130                1135                1140

Lys Asp Trp Asp Pro Lys Lys Tyr Gly Gly Phe Asp Ser Pro Thr
    1145                1150                1155

Val Ala Tyr Ser Val Leu Val Ala Lys Val Glu Lys Gly Lys
    1160                1165                1170

Ser Lys Lys Leu Lys Ser Val Lys Glu Leu Leu Gly Ile Thr Ile
    1175                1180                1185

Met Glu Arg Ser Ser Phe Glu Lys Asn Pro Ile Asp Phe Leu Glu
    1190                1195                1200

Ala Lys Gly Tyr Lys Glu Val Lys Lys Asp Leu Ile Ile Lys Leu
    1205                1210                1215

Pro Lys Tyr Ser Leu Phe Glu Leu Glu Asn Gly Arg Lys Arg Met
    1220                1225                1230

Leu Ala Ser Ala Gly Glu Leu Gln Lys Gly Asn Glu Leu Ala Leu
    1235                1240                1245

Pro Ser Lys Tyr Val Asn Phe Leu Tyr Leu Ala Ser His Tyr Glu
    1250                1255                1260

Lys Leu Lys Gly Ser Pro Glu Asp Asn Glu Gln Lys Gln Leu Phe
    1265                1270                1275

Val Glu Gln His Lys His Tyr Leu Asp Glu Ile Ile Glu Gln Ile
    1280                1285                1290

Ser Glu Phe Ser Lys Arg Val Ile Leu Ala Asp Ala Asn Leu Asp
    1295                1300                1305

Lys Val Leu Ser Ala Tyr Asn Lys His Arg Asp Lys Pro Ile Arg
    1310                1315                1320

Glu Gln Ala Glu Asn Ile Ile His Leu Phe Thr Leu Thr Asn Leu
```

<210> SEQ ID NO 162
<211> LENGTH: 1399
<212> TYPE: PRT
<213> ORGANISM: Streptococcus pyogenes

<400> SEQUENCE: 162

```
Gly Ala Pro Ala Ala Phe Lys Tyr Phe Asp Thr Thr Ile Asp Arg
            1340                1345                1350
Lys Arg Tyr Thr Ser Thr Lys Glu Val Leu Asp Ala Thr Leu Ile
            1355                1360                1365
His Gln Ser Ile Thr Gly Leu Tyr Glu Thr Arg Ile Asp Leu Ser
            1370                1375                1380
Gln Leu Gly Gly Asp Ser Pro Lys Lys Lys Arg Lys Val Glu Ala
            1385                1390                1395
Ser

Met Tyr Pro Tyr Asp Val Pro Asp Tyr Ala Ser Pro Lys Lys Lys Arg
1               5                   10                  15
Lys Val Glu Ala Ser Asp Lys Lys Tyr Ser Ile Gly Leu Asp Ile Gly
                20                  25                  30
Thr Asn Ser Val Gly Trp Ala Val Ile Thr Asp Glu Tyr Lys Val Pro
            35                  40                  45
Ser Lys Lys Phe Lys Val Leu Gly Asn Thr Asp Arg His Ser Ile Lys
        50                  55                  60
Lys Asn Leu Ile Gly Ala Leu Leu Phe Asp Ser Gly Glu Thr Ala Glu
65                  70                  75                  80
Ala Thr Arg Leu Lys Arg Thr Ala Arg Arg Arg Tyr Thr Arg Arg Lys
                85                  90                  95
Asn Arg Ile Cys Tyr Leu Gln Glu Ile Phe Ser Asn Glu Met Ala Lys
            100                 105                 110
Val Asp Asp Ser Phe Phe His Arg Leu Glu Glu Ser Phe Leu Val Glu
        115                 120                 125
Glu Asp Lys Lys His Glu Arg His Pro Ile Phe Gly Asn Ile Val Asp
    130                 135                 140
Glu Val Ala Tyr His Glu Lys Tyr Pro Thr Ile Tyr His Leu Arg Lys
145                 150                 155                 160
Lys Leu Val Asp Ser Thr Asp Lys Ala Asp Leu Arg Leu Ile Tyr Leu
                165                 170                 175
Ala Leu Ala His Met Ile Lys Phe Arg Gly His Phe Leu Ile Glu Gly
            180                 185                 190
Asp Leu Asn Pro Asp Asn Ser Asp Val Asp Lys Leu Phe Ile Gln Leu
        195                 200                 205
Val Gln Thr Tyr Asn Gln Leu Phe Glu Glu Asn Pro Ile Asn Ala Ser
    210                 215                 220
Gly Val Asp Ala Lys Ala Ile Leu Ser Ala Arg Leu Ser Lys Ser Arg
225                 230                 235                 240
Arg Leu Glu Asn Leu Ile Ala Gln Leu Pro Gly Glu Lys Lys Asn Gly
                245                 250                 255
Leu Phe Gly Asn Leu Ile Ala Leu Ser Leu Gly Leu Thr Pro Asn Phe
            260                 265                 270
Lys Ser Asn Phe Asp Leu Ala Glu Asp Ala Lys Leu Gln Leu Ser Lys
        275                 280                 285
Asp Thr Tyr Asp Asp Asp Leu Asp Asn Leu Leu Ala Gln Ile Gly Asp
```

-continued

```
            290                 295                 300
Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
                340                 345                 350

Thr Leu Leu Lys Ala Leu Val Arg Gln Gln Leu Pro Glu Lys Tyr Lys
            355                 360                 365

Glu Ile Phe Phe Asp Gln Ser Lys Asn Gly Tyr Ala Gly Tyr Ile Asp
        370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
                420                 425                 430

Gln Ile His Leu Gly Glu Leu His Ala Ile Leu Arg Arg Gln Glu Asp
            435                 440                 445

Phe Tyr Pro Phe Leu Lys Asp Asn Arg Glu Lys Ile Glu Lys Ile Leu
        450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
                500                 505                 510

Glu Arg Met Thr Asn Phe Asp Lys Asn Leu Pro Asn Glu Lys Val Leu
            515                 520                 525

Pro Lys His Ser Leu Leu Tyr Glu Tyr Phe Thr Val Tyr Asn Glu Leu
        530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
                580                 585                 590

Glu Cys Phe Asp Ser Val Glu Ile Ser Gly Val Glu Asp Arg Phe Asn
            595                 600                 605

Ala Ser Leu Gly Thr Tyr His Asp Leu Leu Lys Ile Ile Lys Asp Lys
        610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
                660                 665                 670

Arg Arg Arg Tyr Thr Gly Trp Gly Arg Leu Ser Arg Lys Leu Ile Asn
            675                 680                 685

Gly Ile Arg Asp Lys Gln Ser Gly Lys Thr Ile Leu Asp Phe Leu Lys
        690                 695                 700

Ser Asp Gly Phe Ala Asn Arg Asn Phe Met Gln Leu Ile His Asp Asp
705                 710                 715                 720
```

```
Ser Leu Thr Phe Lys Glu Asp Ile Gln Lys Ala Gln Val Ser Gly Gln
            725                 730                 735

Gly Asp Ser Leu His Glu His Ile Ala Asn Leu Ala Gly Ser Pro Ala
            740                 745                 750

Ile Lys Lys Gly Ile Leu Gln Thr Val Lys Val Val Asp Glu Leu Val
            755                 760                 765

Lys Val Met Gly Arg His Lys Pro Glu Asn Ile Val Ile Glu Met Ala
            770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
            805                 810                 815

Lys Glu His Pro Val Glu Asn Thr Gln Leu Gln Asn Glu Lys Leu Tyr
            820                 825                 830

Leu Tyr Tyr Leu Gln Asn Gly Arg Asp Met Tyr Val Asp Gln Glu Leu
            835                 840                 845

Asp Ile Asn Arg Leu Ser Asp Tyr Asp Val Asp His Ile Val Pro Gln
            850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
            885                 890                 895

Lys Lys Met Lys Asn Tyr Trp Arg Gln Leu Leu Asn Ala Lys Leu Ile
            900                 905                 910

Thr Gln Arg Lys Phe Asp Asn Leu Thr Lys Ala Glu Arg Gly Gly Leu
            915                 920                 925

Ser Glu Leu Asp Lys Ala Gly Phe Ile Lys Arg Gln Leu Val Glu Thr
            930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
            980                 985                 990

Tyr Lys Val Arg Glu Ile Asn Asn Tyr His His Ala His Asp Ala Tyr
            995                 1000                1005

Leu Asn Ala Val Val Gly Thr Ala Leu Ile Lys Lys Tyr Pro Lys
            1010                1015                1020

Leu Glu Ser Glu Phe Val Tyr Gly Asp Tyr Lys Val Tyr Asp Val
            1025                1030                1035

Arg Lys Met Ile Ala Lys Ser Glu Gln Glu Ile Gly Lys Ala Thr
            1040                1045                1050

Ala Lys Tyr Phe Phe Tyr Ser Asn Ile Met Asn Phe Phe Lys Thr
            1055                1060                1065

Glu Ile Thr Leu Ala Asn Gly Glu Ile Arg Lys Arg Pro Leu Ile
            1070                1075                1080

Glu Thr Asn Gly Glu Thr Gly Glu Ile Val Trp Asp Lys Gly Arg
            1085                1090                1095

Asp Phe Ala Thr Val Arg Lys Val Leu Ser Met Pro Gln Val Asn
            1100                1105                1110

Ile Val Lys Lys Thr Glu Val Gln Thr Gly Gly Phe Ser Lys Glu
            1115                1120                1125
```

Ser Ile Leu Pro Lys Arg Asn Ser Asp Lys Leu Ile Ala Arg Lys
    1130                1135                1140

Lys Asp Trp Asp Pro Lys Lys Tyr Gly Gly Phe Asp Ser Pro Thr
1145                1150                1155

Val Ala Tyr Ser Val Leu Val Ala Lys Val Glu Lys Gly Lys
1160                1165                1170

Ser Lys Lys Leu Lys Ser Val Lys Glu Leu Leu Gly Ile Thr Ile
1175                1180                1185

Met Glu Arg Ser Ser Phe Glu Lys Asn Pro Ile Asp Phe Leu Glu
1190                1195                1200

Ala Lys Gly Tyr Lys Glu Val Lys Lys Asp Leu Ile Ile Lys Leu
1205                1210                1215

Pro Lys Tyr Ser Leu Phe Glu Leu Glu Asn Gly Arg Lys Arg Met
1220                1225                1230

Leu Ala Ser Ala Gly Glu Leu Gln Lys Gly Asn Glu Leu Ala Leu
1235                1240                1245

Pro Ser Lys Tyr Val Asn Phe Leu Tyr Leu Ala Ser His Tyr Glu
1250                1255                1260

Lys Leu Lys Gly Ser Pro Glu Asp Asn Glu Gln Lys Gln Leu Phe
1265                1270                1275

Val Glu Gln His Lys His Tyr Leu Asp Glu Ile Ile Glu Gln Ile
1280                1285                1290

Ser Glu Phe Ser Lys Arg Val Ile Leu Ala Asp Ala Asn Leu Asp
1295                1300                1305

Lys Val Leu Ser Ala Tyr Asn Lys His Arg Asp Lys Pro Ile Arg
1310                1315                1320

Glu Gln Ala Glu Asn Ile Ile His Leu Phe Thr Leu Thr Asn Leu
1325                1330                1335

Gly Ala Pro Ala Ala Phe Lys Tyr Phe Asp Thr Thr Ile Asp Arg
1340                1345                1350

Lys Arg Tyr Thr Ser Thr Lys Glu Val Leu Asp Ala Thr Leu Ile
1355                1360                1365

His Gln Ser Ile Thr Gly Leu Tyr Glu Thr Arg Ile Asp Leu Ser
1370                1375                1380

Gln Leu Gly Gly Asp Ser Pro Lys Lys Arg Lys Val Glu Ala
1385                1390                1395

Ser

<210> SEQ ID NO 163
<211> LENGTH: 1399
<212> TYPE: PRT
<213> ORGANISM: Streptococcus pyogenes

<400> SEQUENCE: 163

Met Tyr Pro Tyr Asp Val Pro Asp Tyr Ala Ser Pro Lys Lys Arg
1               5                   10                  15

Lys Val Glu Ala Ser Asp Lys Lys Tyr Ser Ile Gly Leu Ala Ile Gly
                20                  25                  30

Thr Asn Ser Val Gly Trp Ala Val Ile Thr Asp Glu Tyr Lys Val Pro
            35                  40                  45

Ser Lys Lys Phe Lys Val Leu Gly Asn Thr Asp Arg His Ser Ile Lys
        50                  55                  60

Lys Asn Leu Ile Gly Ala Leu Leu Phe Asp Ser Gly Glu Thr Ala Glu
65                  70                  75                  80

-continued

```
Ala Thr Arg Leu Lys Arg Thr Ala Arg Arg Tyr Thr Arg Arg Lys
                85                  90                  95
Asn Arg Ile Cys Tyr Leu Gln Glu Ile Phe Ser Asn Glu Met Ala Lys
            100                 105                 110
Val Asp Asp Ser Phe Phe His Arg Leu Glu Glu Ser Phe Leu Val Glu
            115                 120                 125
Glu Asp Lys Lys His Glu Arg His Pro Ile Phe Gly Asn Ile Val Asp
            130                 135                 140
Glu Val Ala Tyr His Glu Lys Tyr Pro Thr Ile Tyr His Leu Arg Lys
145                 150                 155                 160
Lys Leu Val Asp Ser Thr Asp Lys Ala Asp Leu Arg Leu Ile Tyr Leu
                165                 170                 175
Ala Leu Ala His Met Ile Lys Phe Arg Gly His Phe Leu Ile Glu Gly
            180                 185                 190
Asp Leu Asn Pro Asp Asn Ser Asp Val Asp Lys Leu Phe Ile Gln Leu
            195                 200                 205
Val Gln Thr Tyr Asn Gln Leu Phe Glu Glu Asn Pro Ile Asn Ala Ser
            210                 215                 220
Gly Val Asp Ala Lys Ala Ile Leu Ser Ala Arg Leu Ser Lys Ser Arg
225                 230                 235                 240
Arg Leu Glu Asn Leu Ile Ala Gln Leu Pro Gly Glu Lys Lys Asn Gly
                245                 250                 255
Leu Phe Gly Asn Leu Ile Ala Leu Ser Leu Gly Leu Thr Pro Asn Phe
            260                 265                 270
Lys Ser Asn Phe Asp Leu Ala Glu Asp Ala Lys Leu Gln Leu Ser Lys
            275                 280                 285
Asp Thr Tyr Asp Asp Asp Leu Asp Asn Leu Leu Ala Gln Ile Gly Asp
            290                 295                 300
Gln Tyr Ala Asp Leu Phe Leu Ala Ala Lys Asn Leu Ser Asp Ala Ile
305                 310                 315                 320
Leu Leu Ser Asp Ile Leu Arg Val Asn Thr Glu Ile Thr Lys Ala Pro
                325                 330                 335
Leu Ser Ala Ser Met Ile Lys Arg Tyr Asp Glu His His Gln Asp Leu
            340                 345                 350
Thr Leu Leu Lys Ala Leu Val Arg Gln Gln Leu Pro Glu Lys Tyr Lys
            355                 360                 365
Glu Ile Phe Phe Asp Gln Ser Lys Asn Gly Tyr Ala Gly Tyr Ile Asp
            370                 375                 380
Gly Gly Ala Ser Gln Glu Glu Phe Tyr Lys Phe Ile Lys Pro Ile Leu
385                 390                 395                 400
Glu Lys Met Asp Gly Thr Glu Glu Leu Leu Val Lys Leu Asn Arg Glu
                405                 410                 415
Asp Leu Leu Arg Lys Gln Arg Thr Phe Asp Asn Gly Ser Ile Pro His
            420                 425                 430
Gln Ile His Leu Gly Glu Leu His Ala Ile Leu Arg Arg Gln Glu Asp
            435                 440                 445
Phe Tyr Pro Phe Leu Lys Asp Asn Arg Glu Lys Ile Glu Lys Ile Leu
            450                 455                 460
Thr Phe Arg Ile Pro Tyr Tyr Val Gly Pro Leu Ala Arg Gly Asn Ser
465                 470                 475                 480
Arg Phe Ala Trp Met Thr Arg Lys Ser Glu Glu Thr Ile Thr Pro Trp
                485                 490                 495
Asn Phe Glu Glu Val Val Asp Lys Gly Ala Ser Ala Gln Ser Phe Ile
```

-continued

```
            500                 505                 510
Glu Arg Met Thr Asn Phe Asp Lys Asn Leu Pro Asn Glu Lys Val Leu
            515                 520                 525
Pro Lys His Ser Leu Leu Tyr Glu Tyr Phe Thr Val Tyr Asn Glu Leu
            530                 535                 540
Thr Lys Val Lys Tyr Val Thr Glu Gly Met Arg Lys Pro Ala Phe Leu
545                 550                 555                 560
Ser Gly Glu Gln Lys Lys Ala Ile Val Asp Leu Leu Phe Lys Thr Asn
            565                 570                 575
Arg Lys Val Thr Val Lys Gln Leu Lys Glu Asp Tyr Phe Lys Lys Ile
            580                 585                 590
Glu Cys Phe Asp Ser Val Glu Ile Ser Gly Val Glu Asp Arg Phe Asn
            595                 600                 605
Ala Ser Leu Gly Thr Tyr His Asp Leu Leu Lys Ile Ile Lys Asp Lys
            610                 615                 620
Asp Phe Leu Asp Asn Glu Glu Asn Glu Asp Ile Leu Glu Asp Ile Val
625                 630                 635                 640
Leu Thr Leu Thr Leu Phe Glu Asp Arg Glu Met Ile Glu Glu Arg Leu
            645                 650                 655
Lys Thr Tyr Ala His Leu Phe Asp Asp Lys Val Met Lys Gln Leu Lys
            660                 665                 670
Arg Arg Arg Tyr Thr Gly Trp Gly Arg Leu Ser Arg Lys Leu Ile Asn
            675                 680                 685
Gly Ile Arg Asp Lys Gln Ser Gly Lys Thr Ile Leu Asp Phe Leu Lys
            690                 695                 700
Ser Asp Gly Phe Ala Asn Arg Asn Phe Met Gln Leu Ile His Asp Asp
705                 710                 715                 720
Ser Leu Thr Phe Lys Glu Asp Ile Gln Lys Ala Gln Val Ser Gly Gln
            725                 730                 735
Gly Asp Ser Leu His Glu His Ile Ala Asn Leu Ala Gly Ser Pro Ala
            740                 745                 750
Ile Lys Lys Gly Ile Leu Gln Thr Val Lys Val Val Asp Glu Leu Val
            755                 760                 765
Lys Val Met Gly Arg His Lys Pro Glu Asn Ile Val Ile Glu Met Ala
            770                 775                 780
Arg Glu Asn Gln Thr Thr Gln Lys Gly Gln Lys Asn Ser Arg Glu Arg
785                 790                 795                 800
Met Lys Arg Ile Glu Glu Gly Ile Lys Glu Leu Gly Ser Gln Ile Leu
            805                 810                 815
Lys Glu His Pro Val Glu Asn Thr Gln Leu Gln Asn Glu Lys Leu Tyr
            820                 825                 830
Leu Tyr Tyr Leu Gln Asn Gly Arg Asp Met Tyr Val Asp Gln Glu Leu
            835                 840                 845
Asp Ile Asn Arg Leu Ser Asp Tyr Asp Val Asp His Ile Val Pro Gln
            850                 855                 860
Ser Phe Leu Lys Asp Asp Ser Ile Asp Asn Lys Val Leu Thr Arg Ser
865                 870                 875                 880
Asp Lys Asn Arg Gly Lys Ser Asp Asn Val Pro Ser Glu Glu Val Val
            885                 890                 895
Lys Lys Met Lys Asn Tyr Trp Arg Gln Leu Leu Asn Ala Lys Leu Ile
            900                 905                 910
Thr Gln Arg Lys Phe Asp Asn Leu Thr Lys Ala Glu Arg Gly Gly Leu
            915                 920                 925
```

```
Ser Glu Leu Asp Lys Ala Gly Phe Ile Lys Arg Gln Leu Val Glu Thr
        930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
                980                 985                 990

Tyr Lys Val Arg Glu Ile Asn Asn Tyr His His Ala His Asp Ala Tyr
            995                 1000                1005

Leu Asn Ala Val Val Gly Thr Ala Leu Ile Lys Lys Tyr Pro Lys
    1010                1015                1020

Leu Glu Ser Glu Phe Val Tyr Gly Asp Tyr Lys Val Tyr Asp Val
    1025                1030                1035

Arg Lys Met Ile Ala Lys Ser Glu Gln Glu Ile Gly Lys Ala Thr
    1040                1045                1050

Ala Lys Tyr Phe Phe Tyr Ser Asn Ile Met Asn Phe Phe Lys Thr
    1055                1060                1065

Glu Ile Thr Leu Ala Asn Gly Glu Ile Arg Lys Arg Pro Leu Ile
    1070                1075                1080

Glu Thr Asn Gly Glu Thr Gly Glu Ile Val Trp Asp Lys Gly Arg
    1085                1090                1095

Asp Phe Ala Thr Val Arg Lys Val Leu Ser Met Pro Gln Val Asn
    1100                1105                1110

Ile Val Lys Lys Thr Glu Val Gln Thr Gly Gly Phe Ser Lys Glu
    1115                1120                1125

Ser Ile Leu Pro Lys Arg Asn Ser Asp Lys Leu Ile Ala Arg Lys
    1130                1135                1140

Lys Asp Trp Asp Pro Lys Lys Tyr Gly Gly Phe Asp Ser Pro Thr
    1145                1150                1155

Val Ala Tyr Ser Val Leu Val Val Ala Lys Val Glu Lys Gly Lys
    1160                1165                1170

Ser Lys Lys Leu Lys Ser Val Lys Glu Leu Leu Gly Ile Thr Ile
    1175                1180                1185

Met Glu Arg Ser Ser Phe Glu Lys Asn Pro Ile Asp Phe Leu Glu
    1190                1195                1200

Ala Lys Gly Tyr Lys Glu Val Lys Lys Asp Leu Ile Ile Lys Leu
    1205                1210                1215

Pro Lys Tyr Ser Leu Phe Glu Leu Glu Asn Gly Arg Lys Arg Met
    1220                1225                1230

Leu Ala Ser Ala Gly Glu Leu Gln Lys Gly Asn Glu Leu Ala Leu
    1235                1240                1245

Pro Ser Lys Tyr Val Asn Phe Leu Tyr Leu Ala Ser His Tyr Glu
    1250                1255                1260

Lys Leu Lys Gly Ser Pro Glu Asp Asn Glu Gln Lys Gln Leu Phe
    1265                1270                1275

Val Glu Gln His Lys His Tyr Leu Asp Glu Ile Ile Glu Gln Ile
    1280                1285                1290

Ser Glu Phe Ser Lys Arg Val Ile Leu Ala Asp Ala Asn Leu Asp
    1295                1300                1305

Lys Val Leu Ser Ala Tyr Asn Lys His Arg Asp Lys Pro Ile Arg
    1310                1315                1320
```

-continued

```
Glu Gln Ala Glu Asn Ile Ile His Leu Phe Thr Leu Thr Asn Leu
    1325                1330                1335

Gly Ala Pro Ala Ala Phe Lys Tyr Phe Asp Thr Thr Ile Asp Arg
    1340                1345                1350

Lys Arg Tyr Thr Ser Thr Lys Glu Val Leu Asp Ala Thr Leu Ile
    1355                1360                1365

His Gln Ser Ile Thr Gly Leu Tyr Glu Thr Arg Ile Asp Leu Ser
    1370                1375                1380

Gln Leu Gly Gly Asp Ser Pro Lys Lys Lys Arg Lys Val Glu Ala
    1385                1390                1395

Ser
```

<210> SEQ ID NO 164
<211> LENGTH: 1399
<212> TYPE: PRT
<213> ORGANISM: Streptococcus pyogenes

<400> SEQUENCE: 164

```
Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Asp Ile Gly
            20                  25                  30

Thr Asn Ser Val Gly Trp Ala Val Ile Thr Asp Glu Tyr Lys Val Pro
        35                  40                  45

Ser Lys Lys Phe Lys Val Leu Gly Asn Thr Asp Arg His Ser Ile Lys
    50                  55                  60

Lys Asn Leu Ile Gly Ala Leu Leu Phe Asp Ser Gly Glu Thr Ala Glu
65                  70                  75                  80

Ala Thr Arg Leu Lys Arg Thr Ala Arg Arg Tyr Thr Arg Arg Lys
                85                  90                  95

Asn Arg Ile Cys Tyr Leu Gln Glu Ile Phe Ser Asn Glu Met Ala Lys
                100                 105                 110

Val Asp Asp Ser Phe Phe His Arg Leu Glu Glu Ser Phe Leu Val Glu
            115                 120                 125

Glu Asp Lys Lys His Glu Arg His Pro Ile Phe Gly Asn Ile Val Asp
    130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
        195                 200                 205

Val Gln Thr Tyr Asn Gln Leu Phe Glu Glu Asn Pro Ile Asn Ala Ser
    210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
        275                 280                 285
```

```
Asp Thr Tyr Asp Asp Asp Leu Asp Asn Leu Leu Ala Gln Ile Gly Asp
    290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
        355                 360                 365

Glu Ile Phe Phe Asp Gln Ser Lys Asn Gly Tyr Ala Gly Tyr Ile Asp
    370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
        435                 440                 445

Phe Tyr Pro Phe Leu Lys Asp Asn Arg Glu Lys Ile Glu Lys Ile Leu
    450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510

Glu Arg Met Thr Asn Phe Asp Lys Asn Leu Pro Asn Glu Lys Val Leu
        515                 520                 525

Pro Lys His Ser Leu Leu Tyr Glu Tyr Phe Thr Val Tyr Asn Glu Leu
    530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
            580                 585                 590

Glu Cys Phe Asp Ser Val Glu Ile Ser Gly Val Glu Asp Arg Phe Asn
        595                 600                 605

Ala Ser Leu Gly Thr Tyr His Asp Leu Leu Lys Ile Ile Lys Asp Lys
    610                 615                 620

Asp Phe Leu Asp Asn Glu Glu Asn Glu Asp Ile Leu Glu Asp Ile Val
625                 630                 635                 640

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
            660                 665                 670

Arg Arg Arg Tyr Thr Gly Trp Gly Arg Leu Ser Arg Lys Leu Ile Asn
        675                 680                 685

Gly Ile Arg Asp Lys Gln Ser Gly Lys Thr Ile Leu Asp Phe Leu Lys
    690                 695                 700

Ser Asp Gly Phe Ala Asn Arg Asn Phe Met Gln Leu Ile His Asp Asp
```

```
            705                 710                 715                 720
        Ser Leu Thr Phe Lys Glu Asp Ile Gln Lys Ala Gln Val Ser Gly Gln
                        725                 730                 735
        Gly Asp Ser Leu His Glu His Ile Ala Asn Leu Ala Gly Ser Pro Ala
                        740                 745                 750
        Ile Lys Lys Gly Ile Leu Gln Thr Val Lys Val Val Asp Glu Leu Val
                        755                 760                 765
        Lys Val Met Gly Arg His Lys Pro Glu Asn Ile Val Ile Glu Met Ala
                        770                 775                 780
        Arg Glu Asn Gln Thr Thr Gln Lys Gly Gln Lys Asn Ser Arg Glu Arg
        785                 790                 795                 800
        Met Lys Arg Ile Glu Glu Gly Ile Lys Glu Leu Gly Ser Gln Ile Leu
                        805                 810                 815
        Lys Glu His Pro Val Glu Asn Thr Gln Leu Gln Asn Glu Lys Leu Tyr
                        820                 825                 830
        Leu Tyr Tyr Leu Gln Asn Gly Arg Asp Met Tyr Val Asp Gln Glu Leu
                        835                 840                 845
        Asp Ile Asn Arg Leu Ser Asp Tyr Asp Val Asp Ala Ile Val Pro Gln
        850                 855                 860
        Ser Phe Leu Lys Asp Asp Ser Ile Asp Asn Lys Val Leu Thr Arg Ser
        865                 870                 875                 880
        Asp Lys Asn Arg Gly Lys Ser Asp Asn Val Pro Ser Glu Glu Val Val
                        885                 890                 895
        Lys Lys Met Lys Asn Tyr Trp Arg Gln Leu Leu Asn Ala Lys Leu Ile
                        900                 905                 910
        Thr Gln Arg Lys Phe Asp Asn Leu Thr Lys Ala Glu Arg Gly Gly Leu
                        915                 920                 925
        Ser Glu Leu Asp Lys Ala Gly Phe Ile Lys Arg Gln Leu Val Glu Thr
                        930                 935                 940
        Arg Gln Ile Thr Lys His Val Ala Gln Ile Leu Asp Ser Arg Met Asn
        945                 950                 955                 960
        Thr Lys Tyr Asp Glu Asn Asp Lys Leu Ile Arg Glu Val Lys Val Ile
                        965                 970                 975
        Thr Leu Lys Ser Lys Leu Val Ser Asp Phe Arg Lys Asp Phe Gln Phe
                        980                 985                 990
        Tyr Lys Val Arg Glu Ile Asn Asn Tyr His His Ala His Asp Ala Tyr
                        995                 1000                1005
        Leu Asn Ala Val Val Gly Thr Ala Leu Ile Lys Lys Tyr Pro Lys
            1010                1015                1020
        Leu Glu Ser Glu Phe Val Tyr Gly Asp Tyr Lys Val Tyr Asp Val
            1025                1030                1035
        Arg Lys Met Ile Ala Lys Ser Glu Gln Glu Ile Gly Lys Ala Thr
            1040                1045                1050
        Ala Lys Tyr Phe Phe Tyr Ser Asn Ile Met Asn Phe Phe Lys Thr
            1055                1060                1065
        Glu Ile Thr Leu Ala Asn Gly Glu Ile Arg Lys Arg Pro Leu Ile
            1070                1075                1080
        Glu Thr Asn Gly Glu Thr Gly Glu Ile Val Trp Asp Lys Gly Arg
            1085                1090                1095
        Asp Phe Ala Thr Val Arg Lys Val Leu Ser Met Pro Gln Val Asn
            1100                1105                1110
        Ile Val Lys Lys Thr Glu Val Gln Thr Gly Gly Phe Ser Lys Glu
            1115                1120                1125
```

Ser Ile Leu Pro Lys Arg Asn Ser Asp Lys Leu Ile Ala Arg Lys
    1130                1135                1140

Lys Asp Trp Asp Pro Lys Lys Tyr Gly Gly Phe Asp Ser Pro Thr
    1145                1150                1155

Val Ala Tyr Ser Val Leu Val Ala Lys Val Glu Lys Gly Lys
    1160                1165                1170

Ser Lys Lys Leu Lys Ser Val Lys Glu Leu Leu Gly Ile Thr Ile
    1175                1180                1185

Met Glu Arg Ser Ser Phe Glu Lys Asn Pro Ile Asp Phe Leu Glu
    1190                1195                1200

Ala Lys Gly Tyr Lys Glu Val Lys Lys Asp Leu Ile Ile Lys Leu
    1205                1210                1215

Pro Lys Tyr Ser Leu Phe Glu Leu Glu Asn Gly Arg Lys Arg Met
    1220                1225                1230

Leu Ala Ser Ala Gly Glu Leu Gln Lys Gly Asn Glu Leu Ala Leu
    1235                1240                1245

Pro Ser Lys Tyr Val Asn Phe Leu Tyr Leu Ala Ser His Tyr Glu
    1250                1255                1260

Lys Leu Lys Gly Ser Pro Glu Asp Asn Glu Gln Lys Gln Leu Phe
    1265                1270                1275

Val Glu Gln His Lys His Tyr Leu Asp Glu Ile Ile Glu Gln Ile
    1280                1285                1290

Ser Glu Phe Ser Lys Arg Val Ile Leu Ala Asp Ala Asn Leu Asp
    1295                1300                1305

Lys Val Leu Ser Ala Tyr Asn Lys His Arg Asp Lys Pro Ile Arg
    1310                1315                1320

Glu Gln Ala Glu Asn Ile Ile His Leu Phe Thr Leu Thr Asn Leu
    1325                1330                1335

Gly Ala Pro Ala Ala Phe Lys Tyr Phe Asp Thr Thr Ile Asp Arg
    1340                1345                1350

Lys Arg Tyr Thr Ser Thr Lys Glu Val Leu Asp Ala Thr Leu Ile
    1355                1360                1365

His Gln Ser Ile Thr Gly Leu Tyr Glu Thr Arg Ile Asp Leu Ser
    1370                1375                1380

Gln Leu Gly Gly Asp Ser Pro Lys Lys Lys Arg Lys Val Glu Ala
    1385                1390                1395

Ser

<210> SEQ ID NO 165
<211> LENGTH: 641
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 165

Met Val Arg Gly Ser His His His His His His Gly Met Ala Ser Met
1               5                   10                  15

Thr Gly Gly Gln Gln Met Gly Arg Asp Leu Tyr Asp Asp Asp Lys
                20                  25                  30

Asp Pro Met Val Ser Lys Gly Glu Glu Leu Ile Lys Glu Asn Met Arg
            35                  40                  45

Met Lys Val Val Met Glu Gly Ser Val Asn Gly His Gln Phe Lys Cys

```
              50                  55                  60
Thr Gly Glu Gly Glu Gly Asn Pro Tyr Met Gly Thr Gln Thr Met Arg
65                  70                  75                  80

Ile Lys Val Ile Glu Gly Gly Pro Leu Pro Phe Ala Phe Asp Ile Leu
                    85                  90                  95

Ala Thr Ser Phe Met Tyr Gly Ser Arg Thr Phe Ile Lys Tyr Pro Lys
                100                 105                 110

Gly Ile Pro Asp Phe Phe Lys Gln Ser Phe Pro Glu Gly Phe Thr Trp
            115                 120                 125

Glu Arg Val Thr Arg Tyr Glu Asp Gly Gly Val Val Thr Val Met Gln
130                 135                 140

Asp Thr Ser Leu Glu Asp Gly Cys Leu Val Tyr His Val Gln Val Arg
145                 150                 155                 160

Gly Val Asn Phe Pro Ser Asn Gly Pro Val Met Gln Lys Lys Thr Lys
                165                 170                 175

Gly Trp Glu Pro Asn Thr Glu Met Met Tyr Pro Ala Asp Gly Gly Leu
                180                 185                 190

Arg Gly Tyr Thr His Met Ala Leu Lys Val Asp Gly Gly His Leu
            195                 200                 205

Ser Cys Ser Phe Val Thr Thr Tyr Arg Ser Lys Lys Thr Val Gly Asn
    210                 215                 220

Ile Lys Met Pro Gly Ile His Ala Val Asp His Arg Leu Glu Arg Leu
225                 230                 235                 240

Glu Glu Ser Asp Asn Glu Met Phe Val Val Gln Arg Glu His Ala Val
                245                 250                 255

Ala Lys Phe Ala Gly Leu Gly Gly Gly Met Asp Glu Leu Tyr Lys Gly
                260                 265                 270

Gly Gly Gly Ser Gly Pro Ala Gly Ile Leu Pro Pro Lys Lys Lys Arg
            275                 280                 285

Lys Val Ser Arg Gly Arg Ser Arg Leu Leu Glu Asp Phe Arg Asn Asn
    290                 295                 300

Arg Tyr Pro Asn Leu Gln Leu Arg Glu Ile Ala Gly His Ile Met Glu
305                 310                 315                 320

Phe Ser Gln Asp Gln His Gly Ser Arg Phe Ile Gln Leu Lys Leu Glu
                325                 330                 335

Arg Ala Thr Pro Ala Glu Arg Gln Leu Val Phe Asn Glu Ile Leu Gln
                340                 345                 350

Ala Ala Tyr Gln Leu Met Val Asp Val Phe Gly Asn Tyr Val Ile Gln
                355                 360                 365

Lys Phe Phe Glu Phe Gly Ser Leu Glu Gln Lys Leu Ala Leu Ala Glu
    370                 375                 380

Arg Ile Arg Gly His Val Leu Ser Leu Ala Leu Gln Met Tyr Gly Ser
385                 390                 395                 400

Arg Val Ile Glu Lys Ala Leu Glu Phe Ile Pro Ser Asp Gln Gln Asn
                405                 410                 415

Glu Met Val Arg Glu Leu Asp Gly His Val Leu Lys Cys Val Lys Asp
                420                 425                 430

Gln Asn Gly Asn His Val Val Gln Lys Cys Ile Glu Cys Val Gln Pro
            435                 440                 445

Gln Ser Leu Gln Phe Ile Ile Asp Ala Phe Lys Gly Gln Val Phe Ala
    450                 455                 460

Leu Ser Thr His Pro Tyr Gly Cys Arg Val Ile Gln Arg Ile Leu Glu
465                 470                 475                 480
```

```
His Cys Leu Pro Asp Gln Thr Leu Pro Ile Leu Glu Glu Leu His Gln
                485                 490                 495

His Thr Glu Gln Leu Val Gln Asp Gln Tyr Gly Asn Tyr Val Ile Gln
                500                 505                 510

His Val Leu Glu His Gly Arg Pro Glu Asp Lys Ser Lys Ile Val Ala
                515                 520                 525

Glu Ile Arg Gly Asn Val Leu Val Leu Ser Gln His Lys Phe Ala Ser
                530                 535                 540

Asn Val Val Glu Lys Cys Val Thr His Ala Ser Arg Thr Glu Arg Ala
545                 550                 555                 560

Val Leu Ile Asp Glu Val Cys Thr Met Asn Asp Gly Pro His Ser Ala
                565                 570                 575

Leu Tyr Thr Met Met Lys Asp Gln Tyr Ala Asn Tyr Val Val Gln Lys
                580                 585                 590

Met Ile Asp Val Ala Glu Pro Gly Gln Arg Lys Ile Val Met His Lys
                595                 600                 605

Ile Arg Pro His Ile Ala Thr Leu Arg Lys Tyr Thr Tyr Gly Lys His
                610                 615                 620

Ile Leu Ala Lys Leu Glu Lys Tyr Tyr Met Lys Asn Gly Val Asp Leu
625                 630                 635                 640

Gly

<210> SEQ ID NO 166
<211> LENGTH: 641
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

Met Val Arg Gly Ser His His His His His Gly Met Ala Ser Met
1               5                   10                  15

Thr Gly Gly Gln Gln Met Gly Arg Asp Leu Tyr Asp Asp Asp Asp Lys
                20                  25                  30

Asp Pro Met Val Ser Lys Gly Glu Glu Leu Ile Lys Glu Asn Met Arg
                35                  40                  45

Met Lys Val Val Met Glu Gly Ser Val Asn Gly His Gln Phe Lys Cys
                50                  55                  60

Thr Gly Glu Gly Glu Gly Asn Pro Tyr Met Gly Thr Gln Thr Met Arg
65                  70                  75                  80

Ile Lys Val Ile Glu Gly Gly Pro Leu Pro Phe Ala Phe Asp Ile Leu
                85                  90                  95

Ala Thr Ser Phe Met Tyr Gly Ser Arg Thr Phe Ile Lys Tyr Pro Lys
                100                 105                 110

Gly Ile Pro Asp Phe Phe Lys Gln Ser Phe Pro Glu Gly Phe Thr Trp
                115                 120                 125

Glu Arg Val Thr Arg Tyr Glu Asp Gly Gly Val Val Thr Val Met Gln
                130                 135                 140

Asp Thr Ser Leu Glu Asp Gly Cys Leu Val Tyr His Val Gln Val Arg
145                 150                 155                 160

Gly Val Asn Phe Pro Ser Asn Gly Pro Val Met Gln Lys Lys Thr Lys
                165                 170                 175

Gly Trp Glu Pro Asn Thr Glu Met Met Tyr Pro Ala Asp Gly Gly Leu
```

```
            180                 185                 190
Arg Gly Tyr Thr His Met Ala Leu Lys Val Asp Gly Gly His Leu
            195                 200                 205
Ser Cys Ser Phe Val Thr Thr Tyr Arg Ser Lys Lys Thr Val Gly Asn
            210                 215                 220
Ile Lys Met Pro Gly Ile His Ala Val Asp His Arg Leu Glu Arg Leu
225                 230                 235                 240
Glu Glu Ser Asp Asn Glu Met Phe Val Val Gln Arg Glu His Ala Val
            245                 250                 255
Ala Lys Phe Ala Gly Leu Gly Gly Met Asp Glu Leu Tyr Lys Gly
            260                 265                 270
Gly Gly Gly Ser Gly Pro Ala Gly Ile Leu Pro Pro Lys Lys Arg
            275                 280                 285
Lys Val Ser Arg Gly Arg Ser Arg Leu Leu Glu Asp Phe Arg Asn Asn
            290                 295                 300
Arg Tyr Pro Asn Leu Gln Leu Arg Glu Ile Ala Gly His Ile Met Glu
305                 310                 315                 320
Phe Ser Gln Asp Gln His Gly Ser Arg Phe Ile Gln Leu Lys Leu Glu
            325                 330                 335
Arg Ala Thr Pro Ala Glu Arg Gln Leu Val Phe Asn Glu Ile Leu Gln
            340                 345                 350
Ala Ala Tyr Gln Leu Met Val Asp Val Phe Gly Asn Tyr Val Ile Gln
            355                 360                 365
Lys Phe Phe Glu Phe Gly Ser Leu Glu Gln Lys Leu Ala Leu Ala Glu
            370                 375                 380
Arg Ile Arg Gly His Val Leu Ser Leu Ala Leu Gln Met Tyr Gly Cys
385                 390                 395                 400
Arg Val Ile Gln Lys Ala Leu Glu Phe Ile Pro Ser Asp Gln Gln Asn
            405                 410                 415
Glu Met Val Arg Glu Leu Asp Gly His Val Leu Lys Cys Val Lys Asp
            420                 425                 430
Gln Asn Gly Asn His Val Val Gln Lys Cys Ile Glu Cys Val Gln Pro
            435                 440                 445
Gln Ser Leu Gln Phe Ile Ile Asp Ala Phe Lys Gly Gln Val Phe Ala
            450                 455                 460
Leu Ser Thr His Pro Tyr Gly Cys Arg Val Ile Gln Arg Ile Leu Glu
465                 470                 475                 480
His Cys Leu Pro Asp Gln Thr Leu Pro Ile Leu Glu Glu Leu His Gln
            485                 490                 495
His Thr Glu Gln Leu Val Gln Asp Gln Tyr Gly Ser Tyr Val Ile Glu
            500                 505                 510
His Val Leu Glu His Gly Arg Pro Glu Asp Lys Ser Lys Ile Val Ala
            515                 520                 525
Glu Ile Arg Gly Asn Val Leu Val Leu Ser Gln His Lys Phe Ala Asn
            530                 535                 540
Asn Val Val Gln Lys Cys Val Thr His Ala Ser Arg Thr Glu Arg Ala
545                 550                 555                 560
Val Leu Ile Asp Glu Val Cys Thr Met Asn Asp Gly Pro His Ser Ala
            565                 570                 575
Leu Tyr Thr Met Met Lys Asp Gln Tyr Ala Asn Tyr Val Val Gln Lys
            580                 585                 590
Met Ile Asp Val Ala Glu Pro Gly Gln Arg Lys Ile Val Met His Lys
            595                 600                 605
```

Ile Arg Pro His Ile Ala Thr Leu Arg Lys Tyr Thr Tyr Gly Lys His
610                 615                 620

Ile Leu Ala Lys Leu Glu Lys Tyr Tyr Met Lys Asn Gly Val Asp Leu
625                 630                 635                 640

Gly

<210> SEQ ID NO 167
<211> LENGTH: 621
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
                20                  25                  30

Glu Gly Glu Gly Asp Ala Thr Asn Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Phe Gly Tyr Gly Val Ala Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser His Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Lys Ser
225                 230                 235                 240

Arg Gly Pro Tyr Ser Ile Val Ser Pro Lys Cys Gly Gly Gly Ser
                245                 250                 255

Gly Pro Ala Gly Ile Leu Pro Pro Lys Lys Arg Lys Val Ser Arg
            260                 265                 270

Gly Arg Ser Arg Leu Leu Glu Asp Phe Arg Asn Asn Arg Tyr Pro Asn
        275                 280                 285

Leu Gln Leu Arg Glu Ile Ala Gly His Ile Met Glu Phe Ser Gln Asp
290                 295                 300

Gln His Gly Ser Arg Phe Ile Gln Leu Lys Leu Glu Arg Ala Thr Pro

```
              305                 310                 315                 320
Ala Glu Arg Gln Leu Val Phe Asn Glu Ile Leu Gln Ala Ala Tyr Gln
                325                 330                 335

Leu Met Val Asp Val Phe Gly Asn Tyr Val Ile Gln Lys Phe Phe Glu
                340                 345                 350

Phe Gly Ser Leu Glu Gln Lys Leu Ala Leu Ala Glu Arg Ile Arg Gly
                355                 360                 365

His Val Leu Ser Leu Ala Leu Gln Met Tyr Gly Ser Arg Val Ile Glu
                370                 375                 380

Lys Ala Leu Glu Phe Ile Pro Ser Asp Gln Gln Asn Glu Met Val Arg
385                 390                 395                 400

Glu Leu Asp Gly His Val Leu Lys Cys Val Lys Asp Gln Asn Gly Asn
                405                 410                 415

His Val Val Gln Lys Cys Ile Glu Cys Val Gln Pro Gln Ser Leu Gln
                420                 425                 430

Phe Ile Ile Asp Ala Phe Lys Gly Gln Val Phe Ala Leu Ser Thr His
                435                 440                 445

Pro Tyr Gly Cys Arg Val Ile Gln Arg Ile Leu Glu His Cys Leu Pro
                450                 455                 460

Asp Gln Thr Leu Pro Ile Leu Glu Glu Leu His Gln His Thr Glu Gln
465                 470                 475                 480

Leu Val Gln Asp Gln Tyr Gly Asn Tyr Val Ile Gln His Val Leu Glu
                485                 490                 495

His Gly Arg Pro Glu Asp Lys Ser Lys Ile Val Ala Glu Ile Arg Gly
                500                 505                 510

Asn Val Leu Val Leu Ser Gln His Lys Phe Ala Ser Asn Val Val Glu
                515                 520                 525

Lys Cys Val Thr His Ala Ser Arg Thr Glu Arg Ala Val Leu Ile Asp
                530                 535                 540

Glu Val Cys Thr Met Asn Asp Gly Pro His Ser Ala Leu Tyr Thr Met
545                 550                 555                 560

Met Lys Asp Gln Tyr Ala Asn Tyr Val Val Gln Lys Met Ile Asp Val
                565                 570                 575

Ala Glu Pro Gly Gln Arg Lys Ile Val Met His Lys Ile Arg Pro His
                580                 585                 590

Ile Ala Thr Leu Arg Lys Tyr Thr Tyr Gly Lys His Ile Leu Ala Lys
                595                 600                 605

Leu Glu Lys Tyr Tyr Met Lys Asn Gly Val Asp Leu Gly
                610                 615                 620

<210> SEQ ID NO 168
<211> LENGTH: 621
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
                20                  25                  30

Glu Gly Glu Gly Asp Ala Thr Asn Gly Lys Leu Thr Leu Lys Phe Ile
                35                  40                  45
```

```
Cys Thr Thr Gly Lys Leu Pro Val Pro Trp Pro Thr Leu Val Thr Thr
    50                  55                  60

Phe Gly Tyr Gly Val Ala Cys Phe Ser Arg Tyr Pro Asp His Met Lys
65                      70                  75                  80

Gln His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser His Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys Ser
225                 230                 235                 240

Arg Gly Pro Tyr Ser Ile Val Ser Pro Lys Cys Gly Gly Gly Gly Ser
                245                 250                 255

Gly Pro Ala Gly Ile Leu Pro Pro Lys Lys Arg Lys Val Ser Arg
            260                 265                 270

Gly Arg Ser Arg Leu Leu Glu Asp Phe Arg Asn Asn Arg Tyr Pro Asn
        275                 280                 285

Leu Gln Leu Arg Glu Ile Ala Gly His Ile Met Glu Phe Ser Gln Asp
    290                 295                 300

Gln His Gly Ser Arg Phe Ile Gln Leu Lys Leu Glu Arg Ala Thr Pro
305                 310                 315                 320

Ala Glu Arg Gln Leu Val Phe Asn Glu Ile Leu Gln Ala Ala Tyr Gln
                325                 330                 335

Leu Met Val Asp Val Phe Gly Asn Tyr Val Ile Gln Lys Phe Phe Glu
            340                 345                 350

Phe Gly Ser Leu Glu Gln Lys Leu Ala Leu Ala Glu Arg Ile Arg Gly
        355                 360                 365

His Val Leu Ser Leu Ala Leu Gln Met Tyr Gly Cys Arg Val Ile Gln
    370                 375                 380

Lys Ala Leu Glu Phe Ile Pro Ser Asp Gln Gln Asn Glu Met Val Arg
385                 390                 395                 400

Glu Leu Asp Gly His Val Leu Lys Cys Val Lys Asp Gln Asn Gly Asn
                405                 410                 415

His Val Val Gln Lys Cys Ile Glu Cys Val Gln Pro Gln Ser Leu Gln
            420                 425                 430

Phe Ile Ile Asp Ala Phe Lys Gly Gln Val Phe Ala Leu Ser Thr His
        435                 440                 445

Pro Tyr Gly Cys Arg Val Ile Gln Arg Ile Leu Glu His Cys Leu Pro
    450                 455                 460
```

-continued

```
Asp Gln Thr Leu Pro Ile Leu Glu Glu Leu His Gln His Thr Glu Gln
465                 470                 475                 480

Leu Val Gln Asp Gln Tyr Gly Ser Tyr Val Ile Glu His Val Leu Glu
            485                 490                 495

His Gly Arg Pro Glu Asp Lys Ser Lys Ile Val Ala Glu Ile Arg Gly
        500                 505                 510

Asn Val Leu Val Leu Ser Gln His Lys Phe Ala Asn Val Val Gln
            515                 520                 525

Lys Cys Val Thr His Ala Ser Arg Thr Glu Arg Ala Val Leu Ile Asp
    530                 535                 540

Glu Val Cys Thr Met Asn Asp Gly Pro His Ser Ala Leu Tyr Thr Met
545                 550                 555                 560

Met Lys Asp Gln Tyr Ala Asn Tyr Val Val Gln Lys Met Ile Asp Val
                565                 570                 575

Ala Glu Pro Gly Gln Arg Lys Ile Val Met His Lys Ile Arg Pro His
            580                 585                 590

Ile Ala Thr Leu Arg Lys Tyr Thr Tyr Gly Lys His Ile Leu Ala Lys
        595                 600                 605

Leu Glu Lys Tyr Tyr Met Lys Asn Gly Val Asp Leu Gly
    610                 615                 620

<210> SEQ ID NO 169
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Met Gly Ile Leu Pro Pro Lys Lys Arg Lys Val Ser Arg Gly Arg
1               5                   10                  15

Ser Arg Leu Leu Glu Asp Phe Arg Asn Asn Arg Tyr Pro Asn Leu Gln
            20                  25                  30

Leu Arg Glu Ile Ala Gly His Ile Met Glu Phe Ser Gln Asp Gln His
        35                  40                  45

Gly Ser Arg Phe Ile Gln Leu Lys Leu Glu Arg Ala Thr Pro Ala Glu
    50                  55                  60

Arg Gln Leu Val Phe Asn Glu Ile Leu Gln Ala Ala Tyr Gln Leu Met
65                  70                  75                  80

Val Asp Val Phe Gly Asn Tyr Val Ile Gln Lys Phe Phe Glu Phe Gly
                85                  90                  95

Ser Leu Glu Gln Lys Leu Ala Leu Ala Glu Arg Ile Arg Gly His Val
            100                 105                 110

Leu Ser Leu Ala Leu Gln Met Tyr Gly Ser Arg Val Ile Glu Lys Ala
        115                 120                 125

Leu Glu Phe Ile Pro Ser Asp Gln Gln Asn Glu Met Val Arg Glu Leu
    130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
                165                 170                 175

Ile Asp Ala Phe Lys Gly Gln Val Phe Ala Leu Ser Thr His Pro Tyr
            180                 185                 190

Gly Cys Arg Val Ile Gln Arg Ile Leu Glu His Cys Leu Pro Asp Gln
```

```
                195                 200                 205
Thr Leu Pro Ile Leu Glu Glu Leu His Gln His Thr Glu Gln Leu Val
    210                 215                 220

Gln Asp Gln Tyr Gly Asn Tyr Val Ile Gln His Val Leu Glu His Gly
225                 230                 235                 240

Arg Pro Glu Asp Lys Ser Lys Ile Val Ala Glu Ile Arg Gly Asn Val
                245                 250                 255

Leu Val Leu Ser Gln His Lys Phe Ala Ser Asn Val Val Glu Lys Cys
            260                 265                 270

Val Thr His Ala Ser Arg Thr Glu Arg Ala Val Leu Ile Asp Glu Val
        275                 280                 285

Cys Thr Met Asn Asp Gly Pro His Ser Ala Leu Tyr Thr Met Met Lys
290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
                325                 330                 335

Thr Leu Arg Lys Tyr Thr Tyr Gly Lys His Ile Leu Ala Lys Leu Glu
            340                 345                 350

Lys Tyr Tyr Met Lys Asn Gly Val Asp Leu Gly Gly Pro Ala Gly Ser
        355                 360                 365

Gly Arg Ala Asp Ala Leu Asp Asp Phe Asp Leu Asp Met Leu Gly Ser
370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
                405                 410                 415

Asp Leu Asp Met Leu Tyr Ile Asp
            420
```

<210> SEQ ID NO 170
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 170

```
Met Gly Ile Leu Pro Pro Lys Lys Arg Lys Val Ser Arg Gly Arg
1               5                   10                  15

Ser Arg Leu Leu Glu Asp Phe Arg Asn Asn Arg Tyr Pro Asn Leu Gln
            20                  25                  30

Leu Arg Glu Ile Ala Gly His Ile Met Glu Phe Ser Gln Asp Gln His
        35                  40                  45

Gly Ser Arg Phe Ile Gln Leu Lys Leu Glu Arg Ala Thr Pro Ala Glu
    50                  55                  60

Arg Gln Leu Val Phe Asn Glu Ile Leu Gln Ala Ala Tyr Gln Leu Met
65                  70                  75                  80

Val Asp Val Phe Gly Asn Tyr Val Ile Gln Lys Phe Phe Glu Phe Gly
                85                  90                  95

Ser Leu Glu Gln Lys Leu Ala Leu Ala Glu Arg Ile Arg Gly His Val
            100                 105                 110

Leu Ser Leu Ala Leu Gln Met Tyr Gly Cys Arg Val Ile Gln Lys Ala
        115                 120                 125
```

Leu Glu Phe Ile Pro Ser Asp Gln Gln Asn Glu Met Val Arg Glu Leu
        130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
                165                 170                 175

Ile Asp Ala Phe Lys Gly Gln Val Phe Ala Leu Ser Thr His Pro Tyr
            180                 185                 190

Gly Cys Arg Val Ile Gln Arg Ile Leu Glu His Cys Leu Pro Asp Gln
        195                 200                 205

Thr Leu Pro Ile Leu Glu Glu Leu His Gln His Thr Glu Gln Leu Val
    210                 215                 220

Gln Asp Gln Tyr Gly Ser Tyr Val Ile Glu His Val Leu Glu His Gly
225                 230                 235                 240

Arg Pro Glu Asp Lys Ser Lys Ile Val Ala Glu Ile Arg Gly Asn Val
                245                 250                 255

Leu Val Leu Ser Gln His Lys Phe Ala Asn Asn Val Val Gln Lys Cys
            260                 265                 270

Val Thr His Ala Ser Arg Thr Glu Arg Ala Val Leu Ile Asp Glu Val
        275                 280                 285

Cys Thr Met Asn Asp Gly Pro His Ser Ala Leu Tyr Thr Met Met Lys
    290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
                325                 330                 335

Thr Leu Arg Lys Tyr Thr Tyr Gly Lys His Ile Leu Ala Lys Leu Glu
            340                 345                 350

Lys Tyr Tyr Met Lys Asn Gly Val Asp Leu Gly Gly Pro Ala Gly Ser
        355                 360                 365

Gly Arg Ala Asp Ala Leu Asp Asp Phe Asp Leu Asp Met Leu Gly Ser
    370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
                405                 410                 415

Asp Leu Asp Met Leu Tyr Ile Asp
            420

<210> SEQ ID NO 171
<211> LENGTH: 709
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Met Gly Ile Leu Pro Pro Lys Lys Lys Arg Lys Val Ser Arg Gly Arg
1               5                   10                  15

Ser Arg Leu Leu Glu Asp Phe Arg Asn Asn Arg Tyr Pro Asn Leu Gln
            20                  25                  30

Leu Arg Glu Ile Ala Gly His Ile Met Glu Phe Ser Gln Asp Gln His
        35                  40                  45

```
Gly Ser Arg Phe Ile Gln Leu Lys Leu Glu Arg Ala Thr Pro Ala Glu
    50                  55                  60

Arg Gln Leu Val Phe Asn Glu Ile Leu Gln Ala Ala Tyr Gln Leu Met
65                  70                  75                  80

Val Asp Val Phe Gly Asn Tyr Val Ile Gln Lys Phe Phe Glu Phe Gly
                    85                  90                  95

Ser Leu Glu Gln Lys Leu Ala Leu Ala Glu Arg Ile Arg Gly His Val
                100                 105                 110

Leu Ser Leu Ala Leu Gln Met Tyr Gly Cys Arg Val Ile Gln Lys Ala
            115                 120                 125

Leu Glu Phe Ile Pro Ser Asp Gln Gln Asn Glu Met Val Arg Glu Leu
    130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
                    165                 170                 175

Ile Asp Ala Phe Lys Gly Gln Val Phe Ala Leu Ser Thr His Pro Tyr
                180                 185                 190

Gly Cys Arg Val Ile Gln Arg Ile Leu Glu His Cys Leu Pro Asp Gln
            195                 200                 205

Thr Leu Pro Ile Leu Glu Glu Leu His Gln His Thr Glu Gln Leu Val
    210                 215                 220

Gln Asp Gln Tyr Gly Ser Tyr Val Ile Glu His Val Leu Glu His Gly
225                 230                 235                 240

Arg Pro Glu Asp Lys Ser Lys Ile Val Ala Glu Ile Arg Gly Asn Val
                    245                 250                 255

Leu Val Leu Ser Gln His Lys Phe Ala Asn Asn Val Val Gln Lys Cys
                260                 265                 270

Val Thr His Ala Ser Arg Thr Glu Arg Ala Val Leu Ile Asp Glu Val
            275                 280                 285

Cys Thr Met Asn Asp Gly Pro His Ser Ala Leu Tyr Thr Met Met Lys
    290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
                    325                 330                 335

Thr Leu Arg Lys Tyr Thr Tyr Gly Lys His Ile Leu Ala Lys Leu Glu
                340                 345                 350

Lys Tyr Tyr Met Lys Asn Gly Val Asp Leu Gly Gly Pro Ala Gly Gly
            355                 360                 365

Gly Gly Ser Gly Gly Gly Ser Gly Gly Gly Ser Gly Pro Lys
    370                 375                 380

Lys Lys Arg Lys Val Ala Ala Gly Ser Pro Ser Gly Gln Ile Ser
385                 390                 395                 400

Asn Gln Ala Leu Ala Leu Ala Pro Ser Ser Ala Pro Val Leu Ala Gln
                    405                 410                 415

Thr Met Val Pro Ser Ser Ala Met Val Pro Leu Ala Gln Pro Pro Ala
                420                 425                 430

Pro Ala Pro Val Leu Thr Pro Gly Pro Pro Gln Ser Leu Ser Ala Pro
            435                 440                 445

Val Pro Lys Ser Thr Gln Ala Gly Glu Gly Thr Leu Ser Glu Ala Leu
    450                 455                 460

Leu His Leu Gln Phe Asp Ala Asp Glu Asp Leu Gly Ala Leu Leu Gly
```

```
            465                 470                 475                 480
Asn Ser Thr Asp Pro Gly Val Phe Thr Asp Leu Ala Ser Val Asp Asn
                485                 490                 495

Ser Glu Phe Gln Gln Leu Leu Asn Gln Gly Val Ser Met Ser His Ser
                500                 505                 510

Thr Ala Glu Pro Met Leu Met Glu Tyr Pro Glu Ala Ile Thr Arg Leu
                515                 520                 525

Val Thr Gly Ser Gln Arg Pro Pro Asp Pro Ala Pro Thr Pro Leu Gly
                530                 535                 540

Thr Ser Gly Leu Pro Asn Gly Leu Ser Gly Asp Glu Asp Phe Ser Ser
545                 550                 555                 560

Ile Ala Asp Met Asp Phe Ser Ala Leu Leu Ser Gln Ile Ser Ser Ser
                565                 570                 575

Gly Gln Gly Gly Gly Gly Ser Gly Phe Ser Val Asp Thr Ser Ala Leu
                580                 585                 590

Leu Asp Leu Phe Ser Pro Ser Val Thr Val Pro Asp Met Ser Leu Pro
                595                 600                 605

Asp Leu Asp Ser Ser Leu Ala Ser Ile Gln Glu Leu Leu Ser Pro Gln
                610                 615                 620

Glu Pro Pro Arg Pro Pro Glu Ala Glu Asn Ser Ser Pro Asp Ser Gly
625                 630                 635                 640

Lys Gln Leu Val His Tyr Thr Ala Gln Pro Leu Phe Leu Leu Asp Pro
                645                 650                 655

Gly Ser Val Asp Thr Gly Ser Asn Asp Leu Pro Val Leu Phe Glu Leu
                660                 665                 670

Gly Glu Gly Ser Tyr Phe Ser Glu Gly Asp Gly Phe Ala Glu Asp Pro
                675                 680                 685

Thr Ile Ser Leu Leu Thr Gly Ser Glu Pro Pro Lys Ala Lys Asp Pro
                690                 695                 700

Thr Val Ser Ile Asp
705

<210> SEQ ID NO 172
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Met Gly Ser Pro Lys Lys Lys Arg Lys Val Glu Ala Ser Met Asp Ala
1               5                   10                  15

Lys Ser Leu Thr Ala Trp Ser Arg Thr Leu Val Thr Phe Lys Asp Val
                20                  25                  30

Phe Val Asp Phe Thr Arg Glu Glu Trp Lys Leu Leu Asp Thr Ala Gln
                35                  40                  45

Gln Ile Val Tyr Arg Asn Val Met Leu Glu Asn Tyr Lys Asn Leu Val
                50                  55                  60

Ser Leu Gly Tyr Gln Leu Thr Lys Pro Asp Val Ile Leu Arg Leu Glu
65                  70                  75                  80

Lys Gly Glu Glu Pro Trp Leu Val Ser Arg Gly Ser Ile Val Gly Ile
                85                  90                  95

Leu Pro Pro Lys Lys Lys Arg Lys Val Ser Arg Gly Arg Ser Arg Leu
                100                 105                 110
```

```
Leu Glu Asp Phe Arg Asn Asn Arg Tyr Pro Asn Leu Gln Leu Arg Glu
        115                 120                 125

Ile Ala Gly His Ile Met Glu Phe Ser Gln Asp Gln His Gly Ser Arg
    130                 135                 140

Phe Ile Gln Leu Lys Leu Glu Arg Ala Thr Pro Ala Glu Arg Gln Leu
145                 150                 155                 160

Val Phe Asn Glu Ile Leu Gln Ala Ala Tyr Gln Leu Met Val Asp Val
                165                 170                 175

Phe Gly Asn Tyr Val Ile Gln Lys Phe Phe Glu Phe Gly Ser Leu Glu
                180                 185                 190

Gln Lys Leu Ala Leu Ala Glu Arg Ile Arg Gly His Val Leu Ser Leu
            195                 200                 205

Ala Leu Gln Met Tyr Gly Cys Arg Val Ile Gln Lys Ala Leu Glu Phe
        210                 215                 220

Ile Pro Ser Asp Gln Gln Asn Glu Met Val Arg Glu Leu Asp Gly His
225                 230                 235                 240

Val Leu Lys Cys Val Lys Asp Gln Asn Gly Asn His Val Val Gln Lys
                245                 250                 255

Cys Ile Glu Cys Val Gln Pro Gln Ser Leu Gln Phe Ile Ile Asp Ala
            260                 265                 270

Phe Lys Gly Gln Val Phe Ala Leu Ser Thr His Pro Tyr Gly Cys Arg
        275                 280                 285

Val Ile Gln Arg Ile Leu Glu His Cys Leu Pro Asp Gln Thr Leu Pro
    290                 295                 300

Ile Leu Glu Glu Leu His Gln His Thr Glu Gln Leu Val Gln Asp Gln
305                 310                 315                 320

Tyr Gly Ser Tyr Val Ile Glu His Val Leu Glu His Gly Arg Pro Glu
                325                 330                 335

Asp Lys Ser Lys Ile Val Ala Glu Ile Arg Gly Asn Val Leu Val Leu
                340                 345                 350

Ser Gln His Lys Phe Ala Asn Asn Val Val Gln Lys Cys Val Thr His
            355                 360                 365

Ala Ser Arg Thr Glu Arg Ala Val Leu Ile Asp Glu Val Cys Thr Met
        370                 375                 380

Asn Asp Gly Pro His Ser Ala Leu Tyr Thr Met Met Lys Asp Gln Tyr
385                 390                 395                 400

Ala Asn Tyr Val Val Gln Lys Met Ile Asp Val Ala Glu Pro Gly Gln
                405                 410                 415

Arg Lys Ile Val Met His Lys Ile Arg Pro His Ile Ala Thr Leu Arg
            420                 425                 430

Lys Tyr Thr Tyr Gly Lys His Ile Leu Ala Lys Leu Glu Lys Tyr Tyr
        435                 440                 445

Met Lys Asn Gly Val Asp Leu Gly
        450                 455

<210> SEQ ID NO 173
<211> LENGTH: 10
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 173
gccagatgcc                                                              10
```

THREE-COMPONENT CRISPR/CAS COMPLEX SYSTEM AND USES THEREOF

REFERENCE TO RELATED APPLICATIONS

This is a continuation application of International Patent Application No. PCT/US2016/021491, filed on Mar. 9, 2016 and published as WO2016/148994, which claims priority to U.S. Provisional Application No. 62/132,644, filed on Mar. 13, 2015, and 62/221,249, filed on Sep. 21, 2015, the entire contents of each of the applications (including sequence listing and drawings) are incorporated herein by reference in their entirety.

SEQUENCE LISTING

The instant application contains a Sequence Listing which has been submitted electronically in International Patent Application No. PCT/US2016/021491, filed on Mar. 9, 2016, in ASCII format and is hereby incorporated by reference in its entirety. Said ASCII copy, created on May 13, 2016, is named 122854-00620_SL.txt and is 17,305 bytes in size.

BACKGROUND OF THE INVENTION

In the CRISPR/Cas system, Cas9 protein and sgRNA (single guide RNA) constitute a sufficient two-component DNA endonuclease whose specificity is provided by target-matching sequence on sgRNA while endonuclease activity resides on the Cas9 protein.

Nuclease-defective or nuclease-deficient Cas9 protein (e.g., dCas9) with mutations on its nuclease domains retains DNA binding activity when complexed with sgRNA. dCas9 protein can tether and localize effector domains or protein tags by means of protein fusions to sites matched by sgRNA, thus constituting an RNA-guided DNA binding enzyme. dCas9 can be fused to transcriptional activation domain (e.g., VP64) or repressor domain (e.g., KRAB), and be guided by sgRNA to activate or repress target genes, respectively. dCas9 can also be fused with fluorescent proteins and achieve live-cell fluorescent labeling of chromosomal regions. However, in such systems, only one Cas9-effector fusion is possible because sgRNA:Cas9 pairing is exclusive. Also, in cases where multiple copies of protein tags or effector fusions are necessary to achieve some biological threshold or signal detection threshold, multimerization of effector or protein tags by direct fusion with dCas9 protein is technically limited, by constraints such as difficulty in delivering the large DNA encoding such fusions, or difficulty in translating or translocating such large proteins into the nucleus due to protein size.

SUMMARY OF THE INVENTION

The invention described herein enables multiplexity and polymerization of effector or protein tags, by providing a three-component CRISPR/Cas complex/system comprising a Cas9 protein (e.g., a wildtype (wt) Cas9, a Cas9 Nickase, or a dCas9 protein), a modified sgRNA as a subject polynucleotide (e.g., "sgRNA-PBS"), and one or more fusion proteins of PUF domain(s) with effector domains or protein tags ("PUF domain-fusion[s]"). sgRNA-PBS can be derived by inserting multiple copies of short PUF (e.g., 8-mer) recognition sequences downstream of the sgRNA stem loops or upstream of the target-matching region. PUF domains of each PUF domain-effector fusion can be programmed to recognize the 8-mer recognition sequence on the subject polynucleotide, thus bringing the one or more effector domains fused to the PUF domains to specific regions of a target DNA recognized by the target-matching sgRNA.

The three-component CRISPR/Cas complexes/systems of the invention are advantageous in terms of multiplicity, since different three-component CRISPR/Cas complexes/systems can be simultaneously delivered into a cell or animal, and each can operate at the defined target sites with orthogonality (i.e., without interference with other three-component CRISPR/Cas complexes/systems and their target sites). Since PUF domains can be easily programmed to recognize any 8-mer RNA recognition sequences, this system expands the multiplexibility to a theoretical maximum of $4^8$ (65536) when the RNA recognition sequence is only 8-mer (and potentially much more when the RNA recognition sequence is longer).

The three-component CRISPR/Cas complexes/systems of the invention are also advantageous in terms of polymerizability: the simplicity of the linear 8-mer sequence allows extensive polymerization without hindering Cas9:sgRNA DNA binding activity. Such feature allows multiple molecules of PUF-fusions to be assembled on the modified sgRNA, thus allowing local concentration of effector or protein tags. Such feature is particularly beneficial in applications such as fluorescent imaging or transcriptional regulation, where proximity synergism allows maximal effective regulation or signal-to-noise ratio.

A further advantage of the invention relates to stoichiometric complex formation. Different 8-mer sequences can be orderly inserted onto the sgRNA-PBS construct to allow complex formation with defined stoichiometry and ordering of the PUF-fusions on the sgRNA-PBS.

Thus one aspect of the invention provides a polynucleotide comprising: (1) a DNA-targeting sequence that is complementary to a target polynucleotide sequence; (2) a Cas9-binding sequence; and, (3) one or more copies of a PUF domain-Binding Sequence (PBS), wherein each of said one or more copies of the PBS binds to the same or a different PUF domain; wherein a Cas9 protein (e.g., a wildtype (wt) Cas9, a Cas9 Nickase, or a dCas9 protein) is capable of forming a complex with the polynucleotide by binding to the Cas9-binding sequence.

As used herein, "Cas9 protein" include a wildtype Cas9 protein, a Cas9 nickase in which one of the two catalytic sites for endonuclease activity (RuvC and HNH) is defective or lacks activity, and a dCas9 protein in which both catalytic sites for endonuclease activity are defective or lack activity. In certain embodiments, the Cas9 protein is a wt Cas9. In certain embodiments, the Cas9 protein lacks nuclease activity or is nuclease deficient. In certain embodiments, the Cas9 protein is a nickase (e.g., for example, the nickase can be a Cas9 Nickase with a mutation at a position corresponding to D10A of *S. pyogenes* Cas9; or the nickase can be a Cas9 Nickase with a mutation at a position corresponding to H840A of *S. pyogenes* Cas9). In certain embodiments, the Cas9 protein is a dCas9 (e.g., a dCas9 with mutations at positions corresponding to D10A and H840A of *S. pyogenes* Cas9). In certain embodiments, the Cas9 protein is not wt Cas9. In certain embodiments, the Cas9 protein is not nickase. In certain embodiments, the Cas9 protein is not dCas9.

In certain embodiments, a "modified Cas9 protein" refers to a Cas9 that is not a wt Cas9 protein, such as a dCas9 or Cas9 nickase.

In certain embodiments, the dCas9 protein is nuclease-deficient but retains DNA-binding ability when complexed with the polynucleotide.

In certain embodiments, the DNA-targeting sequence base-pairs with the target polynucleotide sequence when the Cas9 protein (e.g., wt, nickase, or dCas9 protein) is complexed with the polynucleotide.

In certain embodiments, the target polynucleotide sequence comprises or is adjacent to a transcription regulatory element. For example, the transcription regulatory element may comprise one or more of: core promoter, proximal promoter element, enhancer, silencer, insulator, and locus control region.

In certain embodiments, the target polynucleotide sequence comprises or is adjacent to a telomere sequence, a centromere, or a repetitive genomic sequence.

In certain embodiments, the target polynucleotide sequence comprises or is adjacent to a genomic marker sequence (or a genomic locus of interest).

In certain embodiments, the target polynucleotide sequence is immediately 3' to a PAM (protospacer adjacent motif) sequence of the complementary strand, which can be 5'-CCN-3' wherein N is any DNA nucleotide.

In certain embodiments, the DNA-targeting sequence is complementary to the target polynucleotide sequence over about 12-22 nucleotides (nts), about 14-20 nts, about 16-20 nts, about 18-20 nts, or about 12, 14, 16, 18, or 20 nts (preferably, the complementary region comprises a continuous stretch of 12-22 nts, preferably at the 3' end of the DNA-binding sequence). For example, the DNA-binding sequence can be 50, 60, 70, 80, 90, or 95-100% complementary to the target polynucleotide sequence.

In certain embodiments, the DNA-binding sequence has a 5' end nucleotide G.

In certain embodiments, the polynucleotide further comprises a linker sequence linking the DNA-targeting sequence to the Cas9-binding sequence.

In certain embodiments, the Cas9-binding sequence forms a hairpin structure.

In certain embodiments, the Cas9-binding sequence is about 37-47 nt, or about 42 nt.

In certain embodiments, the Cas9 nickase protein lacks endonuclease activity due to point mutations at one endonuclease catalytic sites (RuvC and HNH) of wild type Cas9. The point mutations can be D10A or H840A.

In certain embodiments, the dCas9 protein lacks endonuclease activity due to point mutations at both endonuclease catalytic sites (RuvC and HNH) of wild type Cas9. The point mutations can be D10A and H840A.

In certain embodiments, each of the one or more copies of the PBS has about 8 nucleotides.

In certain embodiments, the polynucleotide comprises 1, 2, 3, 4, 5, 10, 15, 20, 25, 30, 35, 40, 45, 46, 47, 48, 49, or 50 copies, or 1-50, 2-45, 3-40, 5-35, 5-10, 10-20 copies of identical or different PBS.

In certain embodiments, the polynucleotide comprises a PBS of the sequence 5'-UGUAUGUA-3' that can be bound by the PUF domain PUF(3-2).

In certain embodiments, the polynucleotide comprises a PBS of the sequence 5'-UUGAUAUA-3' that can be bound by the PUF domain PUF(6-2/7-2).

Another aspect of the invention provides a vector encoding any one of the subject polynucleotide.

In certain embodiments, transcription of the polynucleotide is under the control of a constitutive promoter, or an inducible promoter.

In certain embodiments, the vector is active in a cell from a mammal (a human; a non-human primate; a non-human mammal; a rodent such as a mouse, a rat, a hamster, a Guinea pig; a livestock mammal such as a pig, a sheep, a goat, a horse, a camel, cattle; or a pet mammal such as a cat or a dog); a bird, a fish, an insect, a worm, a yeast, or a bacterium.

In a related aspect, the invention provides a plurality of any one of the subject vectors, wherein two of the vectors differ in the encoded polynucleotides in their respective DNA-targeting sequences, Cas9-binding sequences, and/or the copy number, identity, or relative order of the PBS.

Another aspect of the invention provides a complex comprising any one of the subject polynucleotide, and the Cas9 protein (e.g., wt, nickase, or dCas9 protein).

In certain embodiments, the complex further comprises one or more PUF domain(s) bound to said one or more PBS(s).

In certain embodiments, each of the PUF domains is fused to an effector domain.

In certain embodiments, the effector domain is independently a transcription repressor, a transcription activator, a fluorescent protein, an enzyme, or a chromatin remodeling protein (HDAC/HAT).

In certain embodiments, at least two of the PUF domains are fused to different effector domains.

In certain embodiments, the Cas9 protein (e.g., wt, nickase, or dCas9 protein), the PUF domain, and/or the effector domain further comprises a nuclear localization sequence (NLS).

In certain embodiments, the complex is bound to the target polynucleotide sequence through the DNA-targeting sequence.

Another aspect of the invention provides a host cell comprising any one of the subject vector, or the plurality of the subject vectors.

In certain embodiments, the host cell further comprises a second vector encoding the Cas9 protein (e.g., wt, nickase, or dCas9 protein).

In certain embodiments, the second vector further encodes an effector domain fused to the Cas9 protein (e.g., wt, nickase, or dCas9 protein).

In certain embodiments, expression of the Cas9 protein (e.g., wt, nickase, or dCas9 protein) is under the control of a constitutive promoter or an inducible promoter.

In certain embodiments, the host cell further comprises a third vector encoding said one or more PUF domains, each fused to an effector domain.

In certain embodiments, expression of the one or more PUF domains is independently under the control of a constitutive promoter or an inducible promoter.

In certain embodiments, the effector domain is a transcription repressor, a transcription activator, a fluorescent protein, an enzyme, or a chromatin remodeling protein (HDAC/HAT).

In certain embodiments, the second vector further encodes a nuclear localization signal fused to the Cas9 protein (e.g., wt, nickase, or dCas9 protein) or the effector domain, and/or the third vector further encodes a nuclear localization signal fused to the PUF domain or the effector domain.

In certain embodiments, the second vector is the same as the vector, and/or wherein the third vector is the same as the vector or the second vector.

In certain embodiments, the host cell is in a live animal.

In certain embodiments, the host cell is a cultured cell.

Another aspect of the invention provides a method of assembling the complex of the invention at the target polynucleotide sequence, the method comprising contacting or bringing to the vicinity of the target polynucleotide sequence: (1) any one of the subject polynucleotide, or any one of the subject vector, or the subject plurality of vectors; (2) the Cas9 protein (e.g., wt, nickase, or dCas9 protein), or any one of the subject second vector; and, (3) one or more of the PUF domains, each fused to an effector domain, or any one of the subject third vector.

In certain embodiments, the complex is assembled inside a cell, the target polynucleotide sequence is a part of the genomic DNA of the cell, and wherein the subject vector, the subject second vector, and the subject third vector are introduced into the cell.

In certain embodiments, the target polynucleotide sequence is at or near a genomic locus rich in heterochromatin, and wherein the effector domain is a detectable marker (e.g., a fluorescent protein).

In certain embodiments, the target polynucleotide sequence is at or near a transcription regulatory element of a target gene, and wherein the effector domain is a transcription modulator (e.g., activator, suppressor).

In certain embodiments, transcription of the target gene affects cell fate determination, cell differentiation, metabolic flux, or a biologically or biochemically determinable outcome.

Another aspect of the invention provides a method of modulating transcription of a plurality of target genes in a cell, the method comprising: introducing into the cell the subject plurality of the vectors, a coding sequence for a Cas9 protein (e.g., wt, nickase, or dCas9 protein), and a coding sequence for one or more PUF domains, wherein each of said target genes comprises a target polynucleotide sequence that permits (1) the assembly, at the target polynucleotide sequence, of a tripartite complex of a polynucleotide encoded by one of said plurality of the vector, the Cas9 protein (e.g., wt, nickase, or dCas9 protein), and a PUF domain; and (2) transcription modulation of the target gene comprising the target polynucleotide sequence. In certain embodiments, the Cas9 protein is a dCas9 protein.

In certain embodiments, the transcription of at least one target gene is enhanced/stimulated, while the transcription of at least another target gene is inhibited.

In a related aspect, the invention also provides a method of epigenotic modulation (e.g., modulating the epigenetic states of chromatin not directly related to transcriptional activity), at a plurality of target genes in a cell, the method comprising: introducing into the cell the subject plurality of the vectors, a coding sequence for a wt Cas9 protein or a Cas9 nickase, and a coding sequence for one or more PUF domain fusions, wherein each of the target genes comprises a target polynucleotide sequence that permits (1) the assembly, at the target polynucleotide sequence, of a tripartite complex of a polynucleotide encoded by one of the plurality of the vector, the wt/nickase Cas9 protein, and a PUF domain fusion; and (2) epigenotic modulation of the target gene comprising the target polynucleotide sequence. The method can be useful, for example, to change epigenetic state (e.g., opening up the chromatin) at the same time to gain access/stability of Cas9 binding to closed chromatin sites (e.g., to increase cut and genome editing at those sites).

Another aspect of the invention provides a kit comprising: (1) a subject polynucleotide, or a subject vector; (2) a subject second vector encoding the Cas9 protein (e.g., wt, nickase, or dCas9 protein); and (3) a subject third vector encoding one or more PUF domains, each fused to an effector domain.

In certain embodiments, the kit further comprises transformation, transfection, or infection reagents to facilitate the introduction of said vectors into a cell.

It should be understood that any embodiments described herein, including those only described in the Example section or only under one aspect of the invention, can be combined with any one or more other embodiments, unless specifically disclaimed or otherwise improper.

BRIEF DESCRIPTION OF THE DRAWINGS

FIG. 1A is a schematic drawing showing the subject 3-component CRISPR/Cas complex/system, which improves the conventional two-hybrid dCas9 fusion design by splitting it into a three-hybrid system, in which sgRNA-PBS bridges the DNA binding activity of dCas9/sgRNA with the effector function provided by a PUF fusion. The middle panels represent the structure of a representative PUF domain, showing the 8 repeats in the C to N direction and the corresponding interaction with the 8-mer target RNA in the 5' to 3' direction. PUF RNA recognition code table shows exemplary di-residues and the corresponding RNA base recognized. In the lower panel, a table of notation adopted for simplicity to describe the 4 PUF isotypes and the corresponding pumilio binding sites (PBS) and their sequences. FIG. 1B, upper panel, is a schematic for the experiment to test the ability of dCas9-VP64 to bind and activate a tdTomato transgene after inserting varying number of PBS at the 3' end of the sgRNA, e.g., experimental set up for testing the effect of sgRNA-PBS (with 0, 5, 15, 25, or 47 PBS) on the ability of the dCas9::VP64 construct to activate a TetO::tdTomato transgene. The lower panel is column plot showing the mean fold changes (±S.E.M.) in tdTomato fluorescence (relative to the dCas9-VP64/sgCtl-0×PBSa control), as measured by fluorescence activated cell sorting (FACS), of cells transfected with the different constructs indicated in the legend below the plot. The legend describes the sgRNA used in three parameters: sgRNA match refers to the DNA target recognized by the sgRNA; #PBS and PBS Type indicate the number and the types of PBS, respectively, appended to the end of the sgRNA. In FIG. 1C, upper panel, is a schematic describing the experiment to test activation of a TetO::tdTomato transgene by the subject activator with different numbers of appended PBS. The lower panel is a column plot showing the fold changes (±S.E.M.) of tdTomato fluorescence (relative to control dCas9/PUFb-VP64/sgCtl-0×PBSb) of cells transfected with the different constructs indicated in the legend blow the plot. The legend describes the PUF isotype (PUF-VP64) used and the sgRNA-PBS used in terms of the number and type of PBS as well as the DNA target recognized by sgRNA indicated by shaded boxes. In FIG. 1D, upper panel, is a schematic illustrating the experiment to test the independency of the subject activator isotypes in activating a TetO::tdTomato transgene. The lower panel is a column plot showing the mean fold changes (±S.E.M.) of tdTomato fluorescence (relative to the respective controls dCas9/PUFx-VP64/sgCtl-5×PBSx for PUF/PBS isotype x) of cells transfected with the different constructs indicated in the legend below the plot. The legends indicate the PUF isotype used (PUF-VP64), the PBS isotype (5×PBS; "-" indicates sgRNA without PBS) and DNA target indicated by shaded boxes (sgRNA Match). All plots show results of three replicate measurements.

FIG. 2A is a schematic of the experiment testing the assembly of PUF(3-2)::VP64 and PUF(6-2/7-2)::P65-HSF1 via recruitment by sgRNA containing both PBS32 and PBS6272. The activity was measured by the tdTomato fluorescent reporter activity. FIG. 2B is a column chart showing the relative mean tdTomato fluorescence resulting from transfecting the activator protein(s) with non-targeting (sgControl) and Tet-targeting (sgTetO) sgRNAs with 4×[PBS32-PBS6272] heterodimer sites.

FIG. 3A, upper panel: a gene model showing the relative match positions (Strokes labeled 1~4) of sgRNA-PBS used to activate OCT4 gene. Lower panel: Mean fold changes (with 95% C.I.) measured by qRT-PCR (compared to the Control sample) for activation of OCT4 expression using dCas9/PUFa-p65HSF1 3-component system activator module, or dCas9-p65HSF1 activator with the indicated cocktail of OCT4 targeting sgRNA-5×PBSa or control sgRNAs-5×PBSa. The shaded boxes in the legend indicate the use of single sgRNA-5×PBSa with a control (Ctl) sequence, the individual OCT4-targeting sgRNA-5×PBSa corresponding to numbered strokes in the gene model, or a cocktail of the 4 OCT4-targeting sgRNA-5×PBSa. FIG. 3B, upper panel: a gene model showing the relative match positions (Strokes labeled 1-4) of sgRNA-PBS used to activate SOX2 gene. Mean fold changes (with 95% C.I.) measured by qRT-PCR (compared to the Ctl sample) for activation of SOX2 expression using dCas9/PUFa-p65HSF1 activator or dCas9-p65HSF1 activator with the indicated cocktail of SOX2 targeting sgRNA-5×PBSa or control sgRNA-5×PBSa. The shaded boxes in the legend indicate the use of single sgRNA-5×PBSa with a control (Ctl) sequence, the individual SOX2-targeting sgRNA-5×PBSa corresponding to the numbered strokes in the gene model, or a cocktail of 4 SOX2-targeting sgRNA-5×PBSa. FIG. 3C shows Mean fold changes (with 95% C.I.) of OCT4 expression with the indicated single or cocktails of OCT4-targeting sgRNA-PBSa with 1, 5, 15, or 25 copies of PBSa. FIG. 3D shows Mean fold changes (with 95% C.I.) of SOX2 expression with the indicated single or cocktails of SOX2-targeting sgRNA-PBSa with 1, 5, 15, or 25 copies of PBSa.

FIG. 4A is a schematic showing an experiment to simultaneously activate a TetO::tdTomato transgene with dCas9/sgTetO-PBS32/PUF(3-2)::VP64 and repress a SV40::EGFP transgene with dCas9/sgSV40-PBS6272/KRAB::PUF(6-2/7-2). FIG. 4B is a column chart showing relative mean EGFP and tdTomato fluorescence for the samples transfected with the constructs indicated in the table.

FIG. 4C, left panel: schematic diagram illustrating the experiment to achieve simultaneous activation and repression of TetO::tdTomato and SV40::EGFP by PUFc-p65HSF1 and KRAB-PUFa, respectively. Right panel: Top column plot shows mean fold changes (with S.E.M.) of tdTomato fluorescence; Bottom column plot shows mean fold changes (with S.E.M.) of EGFP fluorescence of cells transfected with constructs indicated in the central legend. The central legend indicates the inclusion by shading the transfection of PUFc-p65HSF1 and KRAB-PUFa, as well as the DNA match to either Ctl, TetO or SV40P1 of the sgRNA-PBSc and sgRNA-PBSa by the black shaded boxes. FIG. 4D, left panel: schematic diagram illustrating the experiment to simultaneously activate and repress OCT4 and SOX2, respectively by PUFb-p65HSF1 and BFPKRAB-PUFa. Right panel: Top column plot shows mean fold changes (with 95% C.I.) of gene expression of OCT4; Bottom column plot shows mean fold changes (with 95% C.I.) of gene expression of SOX2 of cells transfected with constructed indicated in the central legend. The central legend indicates the DNA match for the sgRNA-5×PBSb and sgRNA-5×PBSa to control (Ctl), OCT4 promoters (OCT4pp) or SOX2 promoters (SOX2pp) by the black shaded boxes. The PUFb-p65HSF1+BFPKRAB-PUFa row indicates the inclusion of the activator-repressor models in samples with the yellow-highlighted boxes. These experiments used cocktails of 4 sgRNA-5×PBS for both OCT4 and SOX2 genes.

FIG. 5A is a schematics of enhancer activation experiment using dCas9-CBPHAT direct fusion or 3-component module dCas9/CBPHAT-PUFa or dCas9/PUFa-CBPHAT to target Proximal Promoter (PP), Proximal Enhancer (PE) or Distal Enhancer (DE) of OCT4. The 4 guides targeting each of these regions are shown with the number above the red strokes indicating the locations of match. FIG. 5B shows Mean fold changes (with 95% C.I.) of OCT4 expression (relative to the corresponding sgCtl targeting experiments) of cells transfected with plasmids expressing dCas9-CBPHAT, dCas9/CBPHAT-PUFa or dCas9/PUFa-CBPHAT and cocktail of 4 sgRNA-5×PBSa targeting each of PP, PE or Distal Enhancer DE. FIG. 5C shows Mean fold changes (with 95% C.I.) of OCT4 expression (relative to the sgCtl experiment) after transfection of dCas9/CBPHAT-PUFa and single or cocktails of sgRNAs targeting PP, PE, DE of OCT4. The legend indicates the inclusion of the individual guides targeting each of the region or a cocktail of guides with the shaded boxes.

FIGS. 6A-6G show that the subject 3-component CRISPR/Cas complex/system allows multimerization of fluorescent proteins and simultaneous labeling of telomeres and centromeres (Scale bars: 5 µm). FIG. 6A is a schematic showing the use of dCas9/sgTelomere-PBS32/Clover::PUF(3-2) (or PUFa) to label telomeric repeats with green fluorescence. FIG. 6B shows confocal fluorescent microscopy images showing labeling of telomeres by Clover-PUFa and sgTelomere equipped with, from left to right, increasing number (0, 5, 15, 25) of PBSa. FIG. 6C shows anti-TRF2 immunostaining confirmation of labeling of telomeres by dCas9/Clover-PUFa/sgTelomere-25×PBSa. FIG. 6D shows quantification of the number of fluorescent foci in HEK293T cells transfected with dCas9/PUFa::Clover and a telomere-targeting sgRNA with 0, 5, 15 or 25 PBSa sites. (n=20; Mann-Whitney statistics: *=p<0.0005, =p<0.0001). FIG. 6E shows quantification of signal-to-noise ratio as a proportion of total signal at foci over the total nuclear signal by the subject 3-component system with 5, 15, or 25×PBSa on the sgRNA targeting telomeres. (n=20; Mann-Whitney statistics: **=p<0.0001). FIG. 6F shows anti-CREST confirmation of labeling of centromeres by Clover-PUFc/sgCentromere-20×PBSc. FIG. 6G is a representative confocal fluorescent microscopy image showing the co-labeling of centromeres and telomeres by Clover-PUFc/sgCentromere-20×PBSc and mRuby2-PUFa/sgTelomere-25×PBSa, respectively.

FIG. 8A illustrates multiplexing: sgRNA with different PBS isotypes can recruit the effectors tethered by the cognate PUF isotypes, providing the mechanism for multiplexing dCas9 for localizing different effector functions or proteins tags at separate chromosomal loci. FIG. 8B illustrates multimerization: the short and linear feature of PBS allow sgRNA to be equipped with many copies of PBS, thus allowing recruitment of many molecules of PUF-fusions at target loci. FIG. 8C illustrates complex formation: sgRNA equipped with different combinations, orders and numbers of PBS can potentially act as a scaffold to direct assembly of protein complexes with desired stoichiometry and configurations.

DETAILED DESCRIPTION OF THE INVENTION

1. Overview

Figure 1A:
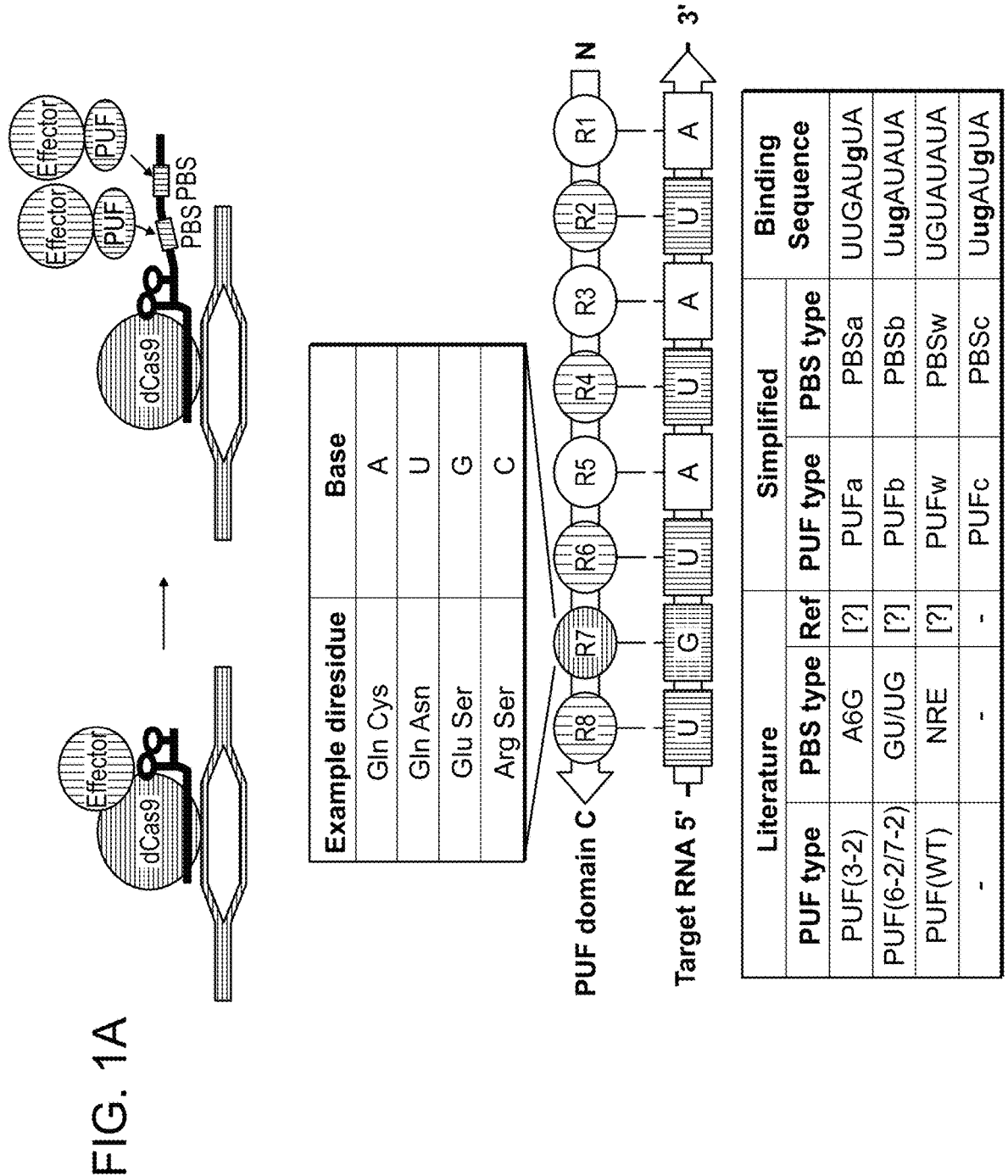
FIGS. 1A-1D show that insertion of PUF domain-binding sequences (PBS) to sgRNA 3'-end did not substantially impact dCas9/sgRNA function, and that independent recruitment and multimerization of activators can be achieved using the subject 3-component CRISPR/Cas complex/system.

The invention described herein provides a polynucleotide comprising three functional sequences, for binding to a target polynucleotide sequence (e.g., the DNA-targeting sequence); for binding to either a wildtype (wt) Cas9 protein, or a modified Cas9 protein (e.g., Cas9 nickase or dCas9) with reduced or deficient nuclease activity (e.g., Cas9-binding sequence); and for binding to one or more PUF domain(s), each fused to a functional or effector domain. The polynucleotide of the invention, together with the wt or modified Cas9 protein and the one or more PUF domain fusion proteins, may form a 3-component complex (the subject 3-component CRISPR/Cas complex/system) at a specific target DNA sequence to effect one or more biological effects at the specific target DNA sequence.

The invention also provides a vector encoding such a polynucleotide, and a complex formed by the polynucleotide, the Cas9 protein (e.g., wt, nickase, or dCas9 protein), and at least one of the PUF domain fusion proteins. The invention further provides host cells comprising the vector or the polynucleotide.

The subject 3-component CRISPR/Cas complex/system can bring about a variety of biological functions at the target DNA sequence, including but are not limited to: enhanced homologous recombination to increase efficiency of knock-in, simultaneous transcription activation and/or repression at multiple genomic loci; detection of specific sequences at genomic loci by fluorescent imaging or other detectable signal; and affecting cell fate determination, cell differentiation, metabolic flux, or a biologically or biochemically determinable outcome, etc.

The invention further provides kits and reagents for carrying out the methods of the invention.

Thus in one aspect, the invention provides a polynucleotide comprising: (1) a DNA-targeting sequence that is complementary to a target polynucleotide sequence; (2) a Cas9-binding sequence; and, (3) one or more copies of a PUF domain-Binding Sequence (PBS), wherein each of the one or more copies of the PBS binds to the same or a different PUF domain; wherein a Cas9 protein (e.g., wt, nickase, or dCas9 protein) is capable of forming a complex with the polynucleotide by binding to the Cas9-binding sequence. In certain embodiments, the dCas9 protein has reduced nuclease activity, or lacks nuclease activity (e.g., is nuclease-deficient), but retains DNA-binding ability when complexed with the subject polynucleotide. In certain embodiments, (1) -(3) are arranged from 5' to 3', in that order. In other embodiments, one or more of the PBS may be 5' to the DNA-targeting sequence, and/or 5' to the Cas9-binding sequence.

The target polynucleotide sequence can be any DNA sequence. In certain embodiments, the target polynucleotide sequence comprises, or is adjacent to, one or more transcription regulatory element(s). In certain embodiments, the transcription regulatory element(s) comprises one or more of: a core promoter, a proximal promoter element, an enhancer, a silencer, an insulator, and a locus control region. In another embodiment, the target polynucleotide sequence comprises, or is adjacent to, a centromere sequence, a telomere sequence, or a repetitive genomic sequence. The telomere sequence may be characterized by having 5-15 kb tracks of TTAGGG repeats. In yet another embodiment, the target polynucleotide sequence comprises, or is adjacent to, a genomic marker sequence or any genomic locus of interest.

In certain embodiments, the target polynucleotide sequence is immediately 3' to a PAM (protospacer adjacent motif) sequence of the complementary strand. For example, in certain embodiments, the PAM sequence of the complementary strand is 5'-CCN-3', wherein N is any DNA nucleotide.

In other embodiments, the PAM sequence of the complementary strand matches the specific Cas9 protein or homologs or orthologs to be used.

As is known in the art, for Cas9 to successfully bind to DNA, the target sequence in the genomic DNA must be complementary to the guide RNA sequence and must be immediately followed by the correct protospacer adjacent motif or PAM sequence. The PAM sequence is present in the DNA target sequence but not in the guide RNA sequence. Any DNA sequence with the correct target sequence followed by the PAM sequence will be bound by Cas9.

The PAM sequence varies by the species of the bacteria from which the Cas9 was derived. The most widely used Type II CRISPR system is derived from *S. pyogenes* and the PAM sequence is 5'-NGG-3' located on the immediate 3' end of the guide RNA recognition sequence (or 5'-CCN-3' on the complementary strand). The PAM sequences of other Type II CRISPR systems from different bacterial species are listed in the Table below.

| | |
|---|---|
| *Streptococcus pyogenes* (SP) | NGG |
| *Neisseria meningitidis* (NM) | NNNNGATT |

| | |
|---|---|
| *Streptococcus thermophilus* (ST) | NNAGAA |
| *Treponema denticola* (TD) | NAAAAC |

In certain embodiments, the DNA-targeting sequence base-pairs with the target polynucleotide sequence when the Cas9 protein (e.g., wt, nickase, or dCas9 protein) is complexed with the polynucleotide.

It should be noted that the DNA-targeting sequence may or may not be 100% complementary to the target polynucleotide sequence. In certain embodiments, the DNA-targeting sequence is complementary to the target polynucleotide sequence over about 8-25 nucleotides (nts), about 12-22 nucleotides, about 14-20 nts, about 16-20 nts, about 18-20 nts, or about 8, 9, 10, 11, 12, 13, 14, 15, 16, 17, 18, 19, 20, 21, 22, 23, 24, or 25 nts. In certain embodiments, the complementary region comprises a continuous stretch of about 12-22 nts, preferably at the 3' end of the DNA-targeting sequence. In certain embodiments, the 5' end of the DNA-targeting sequence has up to 8 nucleotide mismatches with the target polynucleotide sequence. In certain embodiments, the DNA-binding sequence is about 50, 55, 60, 65, 70, 75, 80, 85, 90, 95, or 100% complementary to the target polynucleotide sequence.

In a related embodiment, there is no more than 15-nucleotide match at the 3' end of the DNA-targeting sequence compared to the complementary target polynucleotide sequence, and the Cas9 protein in the complex is a wt Cas9 protein which, under the circumstance, binds but does not cut a target DNA.

In certain embodiments, the DNA-binding sequence has a 5' end nucleotide G.

In certain embodiments, the polynucleotide further comprises a linker sequence linking the DNA-targeting sequence to the Cas9-binding sequence.

In certain embodiments, the Cas9-binding sequence forms a hairpin structure. In certain embodiments, the Cas9-binding sequence is about 30-100 nt, about 35-50 nt, about 37-47 nt, or about 42 nt in length.

An exemplary Cas9-binding sequence is GTTT-TAGAGCTAGAAATAGCAAGTTAA AATAAGGCTA (SEQ ID NO: 1). Another exemplary Cas9-binding sequence is GTTTAAGAGCTATGC TG GAAACAGCAT-AGCAAGTTTAAATAAGGCTA (SEQ ID NO: 2).

The modified Cas9 protein (nickase or dCas9) may have reduced nuclease activity, or lacks nuclease activity at one or both endonuclease catalytic sites. In certain embodiments, the dCas9 protein lacks endonuclease activity due to point mutations at both endonuclease catalytic sites (RuvC and HNH) of wild type Cas9. For example, the point mutations may be D10A and H840A, respectively, in the *S. pyogenes* Cas9, or in the corresponding residues in species other than *S. pyogenes*. In certain embodiments, the modified Cas9 protein lacks endonuclease catalytic activity at one but not both sites of wt Cas9, and is able to create a nick on a dsDNA target (Cas9 nickase).

In certain embodiments, each of the one or more copies of the PBS has about 8 nucleotides. One exemplary PBS may have a sequence of 5'-UGUAUGUA-3', which can be bound by the PUF domain PUF(3-2). Another exemplary PBS may have a sequence of 5'-UUGAUAUA-3', which can be bound by the PUF domain PUF(6-2/7-2). Additional PBS and the corresponding PUF domains are described below.

The polynucleotide of the invention may have more than one copies of the PBS. In certain embodiments, the polynucleotide comprises 1, 2, 3, 4, 5, 10, 15, 20, 25, 30, 35, 40, 45, 46, 47, 48, 49, or 50 copies of PBS, such as 5, 6, 7, 8, 9, 10, 11, 12, 13, 14, or 15 copies of PBS. In certain embodiments, the range of the PBS copy number is L to H, wherein L is any one of 1, 2, 3, 4, 5, 6, 7, 8, 9, 10, 11, 12, 13, 14, 15, 20, 25, 30, 35, or 40, and wherein H is any one of 2, 3, 4, 5, 6, 7, 8, 9, 10, 11, 12, 13, 14, 15, 20, 25, 30, 35, 40, 45, 50, 55, 60, 65, 70, 80, 90, or 100, so long as H is greater than L. Each PBS may be the same or different.

In certain embodiments, the polynucleotide comprises about 5-15 copies of PBS, or about 5-14 copies, about 5-13 copies, about 5-12 copies, about 5-11 copies, about 5-10 copies, or about 5-9 copies of PBS.

In certain embodiments, the amount of the sgRNA-PBS and/or the amount of the PUF fusions transfected or expressed is adjusted to maximize PBS/PUF binding. For example, this can be achieved by increasing the expression of PUF-activator by a stronger promoter or using an inducible promoter, such as a Dox-inducible promoter.

In certain embodiments, the spacing between PBS sites and/or spacer sequences are optimized to improve system efficiency. For example, spacing optimization can be subject to particular PUF fusions, and can be different between PUF fusions that work as individual proteins and those PUF fusions that may need to be positioned close enough to function (e.g., protein complexes).

Another aspect of the invention provides a vector encoding any one of the subject polynucleotide. In certain embodiments, transcription of the polynucleotide is under the control of a constitutive promoter, or an inducible promoter. In certain embodiments, the vector is active in a cell from a mammal (a human; a non-human primate; a non-human mammal; a rodent such as a mouse, a rat, a hamster, a Guinea pig; a livestock mammal such as a pig, a sheep, a goat, a horse, a camel, cattle; or a pet mammal such as a cat or a dog); a bird, a fish, an insect, a worm, a yeast, or a bacterium.

In certain embodiments, the vector is a plasmid, a viral vector (such as adenoviral, retroviral, or lentiviral vector, or AAV vector), or a transposon (such as piggyBac transposon). The vector can be transiently transfected into a host cell, or be integrated into a host genome by infection or transposition.

A related aspect of the invention provides a plurality or a library of any one of the vectors of the invention, wherein two of the vectors differ in the encoded polynucleotides in their respective DNA-targeting sequences, Cas9-binding sequences, and/or the copy number, identity (sequence, binding specificity, etc.), or relative order of the PBS.

Another aspect of the invention provides a complex comprising any one of the polynucleotide of the invention, and the Cas9 protein (e.g., wt, nickase, or dCas9 protein). In certain embodiments, the complex comprises any one of the polynucleotide of the invention, and the Cas9 protein (e.g., wt, nickase, or dCas9 protein). In certain embodiments, the complex does not comprise the wt Cas9 protein. In certain embodiments, the complex comprises the wt Cas9.

In certain embodiments, the complex may further comprise one or more PUF domain or fusion thereof bound to the one or more PBS(s). In certain embodiments, each of the PUF domain is fused to an effector domain. Each effector domain can be independently (but is not limited to): a transcription repressor, a transcription activator, a fluorescent protein, an enzyme, or a chromatin remodeling protein (HDAC/HAT). In certain embodiments, at least two of the PUF domains are fused to different effector domains.

In certain embodiments, the Cas9 protein (e.g., wt, nickase, or dCas9 protein), the PUF domain, and/or the effector domain further comprises a nuclear localization signal (NLS).

In certain embodiments, the complex is bound to the target polynucleotide sequence through the DNA-targeting sequence of the polynucleotide.

Another aspect of the invention provides a host cell comprising any one of the subject vector, or the plurality of vectors.

In certain embodiments, the host cell further comprises a second vector encoding the Cas9 protein (e.g., wt, nickase, or dCas9 protein). In certain embodiments, the second vector further encodes an effector domain fused to the Cas9 protein (e.g., wt, nickase, or dCas9 protein). The expression of the Cas9 protein (e.g., wt, nickase, or dCas9 protein) can be under the control of a constitutive promoter or an inducible promoter.

In certain embodiments, the host cell may further comprise a third vector encoding the one or more PUF domains, each fused to an effector domain. The expression of the one or more PUF domains can be independently under the control of a constitutive promoter or an inducible promoter.

The effector domain can have any of many functions or biological effects. Merely to illustrate, the effector domain can be a protein involved in homologous recombination, a transcription repressor, a transcription activator, a fluorescent protein, an enzyme, or a chromatin remodeling protein (HDAC/HAT), etc.

In certain embodiments, the second vector may further encode a nuclear localization signal (NLS) fused to the Cas9 protein (e.g., wt, nickase, or dCas9 protein) or the effector domain, and/or the third vector may further encode a nuclear localization signal (NLS) fused to the PUF domain or the effector domain.

In certain embodiments, sequences that can be encoded by different vectors may be on the same vector. For example, in certain embodiments, the second vector may be the same as the vector, and/or the third vector may be the same as the vector or the second vector.

The host cell may be in a live animal, or may be a cultured cell.

In certain embodiments, the host cell may constitutively or inducibly express one or more components of the subject 3-component system (e.g., dCas9, PUF fusions).

Yet another aspect of the invention provides a method of assembling the complex of the invention at the target polynucleotide sequence, the method comprising contacting or bringing to the vicinity of the target polynucleotide sequence: (1) any one of the subject polynucleotide, or any one of the subject vector, or the plurality of vectors; (2) the Cas9 protein (e.g., wt, nickase, or dCas9 protein), or any one of the subject second vector encoding the Cas9 protein (e.g., wt, nickase, or dCas9 protein); and, (3) one or more of the PUF domains, each fused to an effector domain, or any one of the third vector encoding the PUF domain fusions.

In certain embodiments, the complex is assembled inside a cell, the target polynucleotide sequence is a part of the genomic DNA of the cell, and wherein the subject vector, second vector, and third vector are introduced into the cell.

In certain embodiments, the target polynucleotide sequence is at or near a genomic locus rich in heterochromatin, and wherein the effector domain is a detectable marker (e.g., a fluorescent protein). In another embodiment, the target polynucleotide sequence is at or near a transcription regulatory element of a target gene, and wherein the effector domain is a transcription modulator (e.g., activator, suppressor). The transcription of the target gene, for example, may affect cell fate determination, cell differentiation, metabolic flux, or a biologically or biochemically determinable outcome.

A related aspect of the invention provides a method of modulating transcription of a plurality of target genes in a cell, the method comprising: introducing into the cell the subject plurality of the vectors, a coding sequence for a dCas9 protein, and a coding sequence for one or more PUF domain fusions, wherein each of the target genes comprises a target polynucleotide sequence that permits (1) the assembly, at the target polynucleotide sequence, of a tripartite complex of a polynucleotide encoded by one of the plurality of the vector, the dCas9 protein, and a PUF domain fusion; and (2) transcription modulation of the target gene comprising the target polynucleotide sequence.

In a related aspect, the invention also provides a method of epigenetic modulation (e.g., modulating the epigenetic states of chromatin not directly related to transcriptional activity), at a plurality of target genes in a cell, the method comprising: introducing into the cell the subject plurality of the vectors, a coding sequence for a wt Cas9 protein or Cas9 nickase, and a coding sequence for one or more PUF domain fusions, wherein each of the target genes comprises a target polynucleotide sequence that permits (1) the assembly, at the target polynucleotide sequence, of a tripartite complex of a polynucleotide encoded by one of the plurality of the vector, the wt Cas9 protein or the Cas9 nickase, and a PUF domain fusion; and (2) epigenetic modulation of the target gene comprising the target polynucleotide sequence. The method can be useful, for example, to change epigenetic state (e.g., opening up the chromatin) at the same time to gain access/stability of Cas9 binding to closed chromatin sites (e.g., to increase cut and genome editing at those sites).

In certain embodiments, the transcription of at least one target gene is enhanced/stimulated, while the transcription of at least another target gene is inhibited.

The invention further provides a kit comprising: (1) a subject polynucleotide, or a vector encoding the same; (2) a second vector encoding the Cas9 protein (e.g., wt, nickase, or dCas9 protein); and (3) a third vector encoding one or more PUF domain(s), each fused to an effector domain. The kit may further comprise transformation, transfection, or infection reagents to facilitate the introduction of the vectors into a cell.

With the invention generally described above, various features of the invention will be further elaborated below. It should be understood that features of the invention, even when described in the context of separate embodiments, or even separate embodiments under different aspects of the invention, may be provided in combination in a single embodiment. Conversely, various features of the invention described in the context of a single embodiment, may also be provided separately or in any suitable subcombination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

2. The Polynucleotide of the Invention

The polynucleotide of the invention comprises three sequence segments: i) a first segment comprising a nucleotide sequence that is complementary to a target sequence; ii)

a second segment that interacts with a Cas9 protein (e.g., wt, nickase, or dCas9 protein with reduced nuclease activity or lacks nuclease activity) (e.g., the Cas9-binding sequence); and iii) one or more copies of a PUF domain-Binding Sequence (PBS).

In certain embodiments, the target sequence is an RNA. In certain embodiments, the target sequence is a DNA. In the description herein, the first segment is generally referred to as the "DNA-targeting sequence" when the target sequence is a DNA (such as a genomic DNA).

In related embodiments in which the target sequence is an RNA, the description herein below applies generally as well except that the reference to "DNA-targeting sequence" is replaced with "RNA-targeting sequence," in order to avoid redundancy. That is, the first segment comprises a nucleotide sequence complementary to the target polynucleotide sequence (DNA or RNA). In certain embodiments, the three segments i)-iii) are arranged, in that order, from 5' to 3'.

In certain embodiments, the polynucleotide of the invention can be a single RNA molecule (single RNA polynucleotide), which may include a "single-guide RNA," or "sgRNA." In another embodiment, the polynucleotide of the invention can comprise two RNA molecules (e.g., joined together via hybridization at the Cas9-binding sequence, see below). Thus the subject polynucleotide is inclusive, referring both to two-molecule polynucleotide and to single-molecule polynucleotide (e.g., sgRNAs).

a. DNA-Targeting Sequence

The DNA-targeting sequence is functionally similar or equivalent to the crRNA or guide RNA or gRNA of the CRISPR/Cas complex/system. However, in the context of the instant invention, the DNA-targeting sequence may not originate from any particular crRNA or gRNA, but can be arbitrarily designed based on the sequence of the target polynucleotide sequence.

The DNA-targeting sequence comprises a nucleotide sequence that is complementary to a specific sequence within a target DNA (or the complementary strand of the target DNA). In other words, the DNA-targeting sequence interacts with a target polynucleotide sequence of the target DNA in a sequence-specific manner via hybridization (i.e., base pairing). As such, the nucleotide sequence of the DNA-targeting sequence may vary, and it determines the location within the target DNA that the subject polynucleotide and the target DNA will interact. The DNA-targeting sequence can be modified or designed (e.g., by genetic engineering) to hybridize to any desired sequence within the target DNA. In certain embodiments, the target polynucleotide sequence is immediately 3' to a PAM (protospacer adjacent motif) sequence of the complementary strand, which can be 5'-CCN-3', wherein N is any DNA nucleotide. That is, in this embodiment, the complementary strand of the target polynucleotide sequence is immediately 5' to a PAM sequence that is 5'-NGG-3', wherein N is any DNA nucleotide. In related embodiments, the PAM sequence of the complementary strand matches the wt or dCas9. See above for the PAM sequences from species other than *S. pyogenes*.

The DNA-targeting sequence can have a length of from about 12 nucleotides to about 100 nucleotides. For example, the DNA-targeting sequence can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the DNA-targeting sequence can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting sequence that is complementary to a target polynucleotide sequence of the target DNA can have a length of at least about 12 nt. For example, the DNA-targeting sequence that is complementary to a target polynucleotide sequence of the target DNA can have a length at least about 12 nt, at least about 15 nt, at least about 18 nt, at least about 19 nt, at least about 20 nt, at least about 25 nt, at least about 30 nt, at least about 35 nt or at least about 40 nt. For example, the DNA-targeting sequence that is complementary to a target polynucleotide sequence of a target DNA can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. The nucleotide sequence of the DNA-targeting sequence that is complementary to the target polynucleotide sequence of the target DNA can have a length of at least about 12 nt.

In some cases, the DNA-targeting sequence that is complementary to a target polynucleotide sequence of the target DNA is 20 nucleotides in length. In some cases, the DNA-targeting sequence that is complementary to a target polynucleotide sequence of the target DNA is 19 nucleotides in length.

The percent complementarity between the DNA-targeting sequence and the target polynucleotide sequence of the target DNA can be at least 50% (e.g., at least 55%, at least 60%, at least 65%, at least 70%, at least 75%, at least 80%, at least 85%, at least 90%, at least 95%, at least 97%, at least 98%, at least 99%, or 100%). In some cases, the percent complementarity between the DNA-targeting sequence and the target polynucleotide sequence is 100% over the seven or eight contiguous 5'-most nucleotides of the target polynucleotide sequence. In some cases, the percent complementarity between the DNA-targeting sequence and the target polynucleotide sequence is at least 60% over about 20 contiguous nucleotides. In some cases, the percent complementarity between the DNA-targeting sequence and the target polynucleotide sequence is 100% over the 7, 8, 9, 10, 11, 12, 13, or 14 contiguous 5'-most nucleotides of the target polynucleotide sequence (i.e., the 7, 8, 9, 10, 11, 12, 13, or 14 contiguous 3'-most nucleotides of the DNA-targeting sequence), and as low as 0% over the remainder. In such a case, the DNA-targeting sequence can be considered to be 7, 8, 9, 10, 11, 12, 13, or 14 nucleotides in length, respectively.

b. Cas9-Binding Sequence

The protein-binding segment or protein-binding sequence of the subject polynucleotide binds to a wt Cas9, or a modified dCas9 protein (e.g., nickase or dCas9) with reduced endonuclease activity, or lacks endonuclease activity. For simplicity, the protein-binding sequence of the subject polynucleotide, which may bind to wt and/or modified Cas9 proteins, may simply be referred to as "Cas9-binding sequence" herein. However, it should be understood that when the Cas9-binding sequence of the invention binds to a dCas9, it is not prevented from binding to a wt Cas9 or a Cas9 nickase. In certain embodiments, the Cas9-binding sequence of the invention binds to dCas9 as well as wt Cas9 and/or Cas9 nickase.

The Cas9-binding sequence interacts with or bind to a Cas9 protein (e.g., wt, nickase, or dCas9 protein), and together they bind to the target polynucleotide sequence recognized by the DNA-targeting sequence. The Cas9-binding sequence comprises two complementary stretches of nucleotides that hybridize to one another to form a double stranded RNA duplex (a dsRNA duplex). These two complementary stretches of nucleotides may be covalently linked by intervening nucleotides known as linkers or linker nucleotides (e.g., in the case of a single-molecule polynucleotide), and hybridize to form the double stranded RNA duplex (dsRNA duplex, or "Cas9-binding hairpin") of the Cas9-binding sequence, thus resulting in a stem-loop structure. Alternatively, in some embodiment, the two complementary stretches of nucleotides may not be covalently linked, but instead are held together by hybridization between complementary sequences (e.g., in the case of a two-molecule polynucleotide of the invention).

The Cas9-binding sequence can have a length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the Cas9-binding sequence can have a length of from about 15 nucleotides (nt) to about 80 nt, from about 15 nt to about 50 nt, from about 15 nt to about 40 nt, from about 15 nt to about 30 nt, from about 37 nt to about 47 nt (e.g., 42 nt), or from about 15 nt to about 25 nt.

The dsRNA duplex of the Cas9-binding sequence can have a length from about 6 base pairs (bp) to about 50 bp. For example, the dsRNA duplex of the Cas9-binding sequence can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the Cas9-binding sequence can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp. In some embodiments, the dsRNA duplex of the Cas9-binding sequence has a length of 36 base pairs. The percent complementarity between the nucleotide sequences that hybridize to form the dsRNA duplex of the Cas9-binding sequence can be at least about 60%. For example, the percent complementarity between the nucleotide sequences that hybridize to form the dsRNA duplex of the Cas9-binding sequence can be at least about 65%, at least about 70%, at least about 75%, at least about 80%, at least about 85%, at least about 90%, at least about 95%, at least about 98%, or at least about 99%. In some cases, the percent complementarity between the nucleotide sequences that hybridize to form the dsRNA duplex of the Cas9-binding sequence is 100%.

The linker can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker is 4 nt.

Figure 8A:
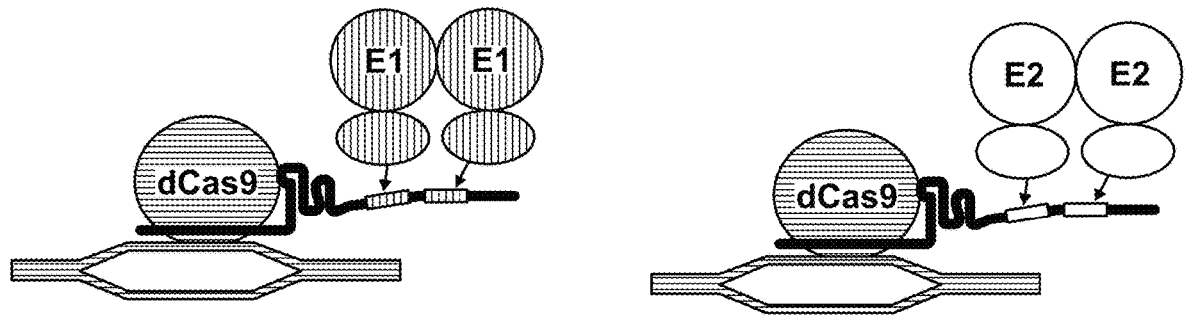
FIGS. 8A-8C is a cartoon illustration highlighting some features of the subject 3-component CRISPR/Cas complex/system.
Figure 8B:
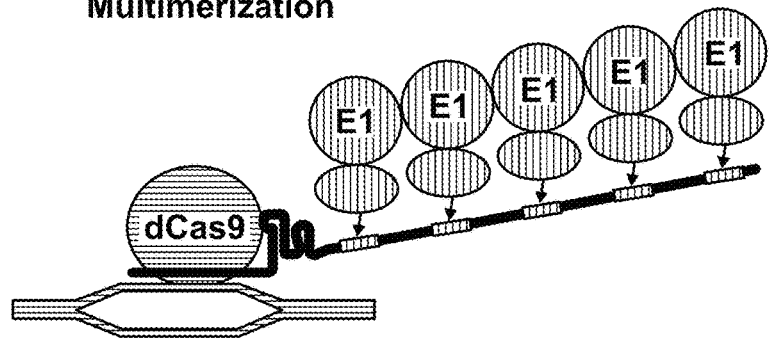
Figure 8C:
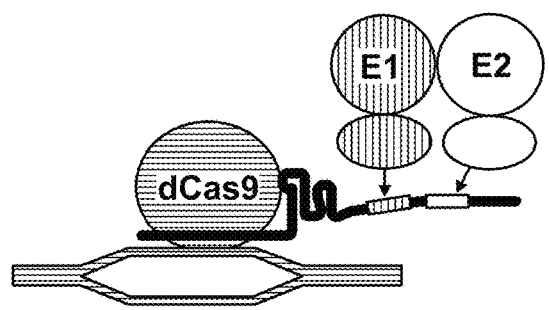

Non-limiting examples of nucleotide sequences that can be included in a suitable Cas9-binding sequence (i.e., Cas9 handle) are set forth in SEQ ID NOs: 563-682 of WO 2013/176772 (see, for examples, FIGS. 8 and 9 of WO 2013/176772), incorporated herein by reference.

In some cases, a suitable Cas9-binding sequence comprises a nucleotide sequence that differs by 1, 2, 3, 4, or 5 nucleotides from any one of the above-listed sequences.

c. PUF Domain-Binding Sequence (PBS)

The subject polynucleotide comprises one or more tandem sequences, each of which can be specifically recognized and bound by a specific PUF domain (infra). Since a PUF domain can be engineered to bind virtually any PBS based on the nucleotide-specific interaction between the individual PUF motifs of PUF domain and the single RNA nucleotide they recognize, the PBS sequences can be any designed sequence that bind their corresponding PUF domain.

In certain embodiments, a PBS of the invention has 8-mer. In other embodiments, a PBS of the invention has 5, 6, 7, 8, 9, 10, 11, 12, 13, 14, 15, 16 or more RNA nucleotides.

In certain embodiments, the PBS of the invention has the sequence 5'-UGUAUAUA-3', and binds the wt human Pumilio 1 PUF domain.

In certain embodiments, the PBS of the invention has the sequence 5'-UGUAUGUA-3', and binds the PUF domain PUF(3-2).

In certain embodiments, the PBS of the invention has the sequence 5'-UUGAUAUA-3', and binds the PUF domain PUF(6-2/7-2).

In certain embodiments, the PBS of the invention has the sequence 5'-UGGAUAUA-3', and binds the PUF domain PUF(6-2).

In certain embodiments, the PBS of the invention has the sequence 5'-UUUAUAUA-3', and binds the PUF domain PUF(7-2).

In certain embodiments, the PBS of the invention has the sequence 5'-UGUGUGUG-3', and binds the PUF domain PUF$^{531}$.

In certain embodiments, the PBS of the invention has the sequence 5'-UGUAUAUG-3', and binds the PUF domain PUF(1-1).

In certain embodiments, the PBS of the invention has the sequence 5'-UUUAUAUA-3' or 5'-UAUAUAUA-3', and binds the PUF domain PUF(7-1).

In certain embodiments, the PBS of the invention has the sequence 5'-UGUAUUUA-3', and binds the PUF domain PUF(3-1).

In certain embodiments, the PBS of the invention has the sequence 5'-UUUAUUUA-3', and binds the PUF domain PUF(7-2/3-1).

Applicant has created 65,536 8-mer PBS and their corresponding PUF domain sequences (see below) that can bind the specific PBS. Applicant has also created a python script to retrieve any of the 65,536 individual PUF domain sequences that binds a given 8-mer PBS. For example, for the 8-mer UUGAUGUA, one possible PUF domain sequence can be:

(SEQ ID NO: 3)
GRSRLLEDFRNNRYPNLQLREIAGHIMEFSQDQHGCRFIQLKLERATPAE

RQLVFNEILQAAYQLMVDVFGNYVIQKFFEFGSLEQKLALAERIRGHVLS

LALQMYGSRVIEKALEFIPSDQQNEMVRELDGHVLKCVKDQNGNHVVQKC

IECVQPQSLQFIIDAFKGQVFALSTHPYGCRVIQRILEHCLPDQTLPILE

ELHQHTEQLVQDQYGSYVIEHVLEHGRPEDKSKIVAEIRGNVLVLSQHKF

ANNVVQKCVTHASRTERAVLIDEVCTMNDGPHSALYTMMKDQYANYVVQK

MIDVAEPGQRKIVMHKIRPHIATLRKYTYGKHILAKLEKYYMKNGVDLG

In certain embodiments, one or more spacer region(s) separates two adjacent PBS sequences. The spacer regions may have a length of from about 3 nucleotides to about 100 nucleotides. For example, the spacer can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the spacer can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the spacer is 4 nt.

d. Optional Other Sequences

A stability control sequence (e.g., transcriptional terminator segment) influences the stability of an RNA (e.g., a subject polynucleotide). One example of a suitable stability control sequence is a transcriptional terminator segment (i.e., a transcription termination sequence). A transcriptional terminator segment of a subject polynucleotide can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

Non-limiting examples of nucleotide sequences that can be included in a stability control sequence (e.g., transcriptional termination segment, or in any segment of the DNA-targeting RNA to provide for increased stability) include sequences set forth in SEQ ID NO: 683-696 of WO 2013/176772 (incorporated herein by reference), see, for example, SEQ ID NO: 795 of WO 2013/176772, a Rho-independent transcription termination site.

The stability control sequence may be situated after the Cas9-binding sequence, for example, between the Cas9-binding sequence and the first PBS, between two adjacent PBS, or after the last PBS.

In some embodiments, the polynucleotide of the invention or parts thereof (e.g., the DNA-targeting sequence, the Cas9-binding sequence, and/or the one or more of the PBS), or a polynucleotide encoding the Cas9 protein (e.g., wt, nickase, or dCas9 protein), or a polynucleotide encoding one of the PUF domain fusions (infra), may comprise a modification or sequence that provides for an additional desirable feature, e.g., modified or regulated stability; subcellular targeting; tracking, e.g., a fluorescent label; a binding site for a protein or protein complex; etc.).

Non-limiting examples include: a 5' cap (e.g., a 7-methylguanylate cap ($m^7G$)); a 3' polyadenylated tail (i.e., a 3' poly(A) tail); a riboswitch sequence or an aptamer sequence (e.g., to allow for regulated stability and/or regulated accessibility by proteins and protein complexes); a terminator sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); a modification or sequence that provides for increased, decreased, and/or controllable stability; and combinations thereof.

3. The Cas9 Protein (Wt, Nickase, or dCas9)

The Cas9 protein (e.g., wt, nickase, or dCas9 protein) of the invention comprises: i) an RNA-binding portion that interacts with the Cas9-binding sequence of the subject polynucleotide, and ii) an activity portion that exhibits wt, reduced endonuclease (e.g., endodeoxyribonuclease) activity, or lacks endonuclease (e.g., endodeoxyribonuclease) activity, depending on the identity of the Cas9 protein.

The Cas9-binding sequence of the polynucleotide and the Cas9 protein (e.g., wt, nickase, or dCas9 protein) can form a complex that binds to a specific target polynucleotide sequence, based on the sequence complementarity between the DNA-targeting sequence and the target polynucleotide sequence. The DNA-targeting sequence of the subject polynucleotide provides target specificity to the complex via its sequence complementarity to the target polynucleotide sequence of a target DNA. If the target polynucleotide sequence is at or adjacent to a transcription regulatory element or an epigenetic modification site of a target gene, the complex, together with transcription regulators or effectors that modulate epigenetic modification fused to PBS-binding PUF domain, can selectively modulate transcription or epigenetic modulation of the target gene.

In certain embodiments, the modified Cas9 protein has reduced or lacks endonuclease (e.g., endodeoxyribonuclease) activity. For example, a modified Cas9 suitable for use in a method of the present invention may be a Cas9 nickase, or exhibits less than about 20%, less than about 15%, less than about 10%, less than about 5%, less than about 1%, or less than about 0.1%, of the endonuclease (e.g., endodeoxyribonuclease) activity of a wild-type Cas9 polypeptide, e.g., a wild-type Cas9 polypeptide comprising an amino acid sequence as depicted in FIG. 3 and SEQ ID NO: 8 of WO 2013/176772 (incorporated herein by reference). In some embodiments, the dCas9 has substantially no detectable endonuclease (e.g., endodeoxyribonuclease) activity. In some embodiments when a dCas9 has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the polypeptide can still bind to target DNA in a site-specific manner, because it is still guided to a target polynucleotide sequence by a DNA-targeting sequence of the subject polynucleotide, as long as it retains the ability to interact with the Cas9-binding sequence of the subject polynucleotide.

In some cases, a suitable Cas9 protein (e.g., wt, nickase, or dCas9 protein) comprises an amino acid sequence having at least about 75%, at least about 80%, at least about 85%, at least about 90%, at least about 95%, at least about 99% or 100% amino acid sequence identity to amino acids 7-166 or 731-1003 of the Cas9/Csn1 amino acid sequence (of *Streptococcus pyogenes*), as depicted in FIG. 3 and SEQ ID NO: 8 of WO 2013/176772 (incorporated by reference), or to the corresponding portions in any one of the amino acid sequences SEQ ID NOs: 1-256 and 795-1346 of WO 2013/176772 (incorporated by reference), preferably to the corresponding portions in any one of the amino acid sequences of the orthogonal Cas9 sequences from *S. pyogenes, N. meningitidis, S. thermophilus* and *T. denticola* (see, Esvelt et al., Nature Methods, 10(11): 1116-1121, 2013, incorporated by reference).

In some cases, the Cas9 nickase can cleave the complementary strand of the target DNA but has reduced ability to cleave the non-complementary strand of the target DNA. For example, the Cas9 nickase can have a mutation (amino acid substitution) that reduces the function of the RuvC domain. As a non-limiting example, in some cases, the Cas9 nickase is a D10A (aspartate to alanine) mutation of the amino acid sequence depicted in FIG. 3 of WO 2013/176772, or the corresponding mutation of any of the amino acid sequences set forth in SEQ ID NOs: 1-256 and 795-1346 of WO 2013/176772 (all such sequences incorporated by reference).

In some cases, the Cas9 nickase can cleave the non-complementary strand of the target DNA but has reduced ability to cleave the complementary strand of the target DNA. For example, the Cas9 nickase can have a mutation (amino acid substitution) that reduces the function of the HNH domain (RuvC/HNH/RuvC domain motifs). As a non-limiting example, in some cases, the Cas9 nickase is a H840A (histidine to alanine at amino acid position 840 of SEQ ID NO: 8 of WO 2013/176772, incorporated by reference) or the corresponding mutation of any of the amino acid sequences set forth in SEQ ID NOs: 1-256 and 795-1346 of WO 2013/176772 (all such sequences incorporated by reference).

In some cases, the dCas9 has a reduced ability to cleave both the complementary and the non-complementary strands of the target DNA. As a non-limiting example, in some cases, the dCas9 harbors both D10A and H840A mutations of the amino acid sequence depicted in FIG. 3 of WO 2013/176772 or the corresponding mutations of any of the amino acid sequences set forth in SEQ ID NOs: 1-256 and 795-1346 of WO 2013/176772 (all such sequences incorporated by reference).

Other residues can be mutated to achieve the same effect (i.e. inactivate one or the other nuclease portions). As non-limiting examples, residues D10, G12, G17, E762, H840, N854, N863, H982, H983, A984, D986, and/or A987 (or the corresponding mutations of any of the proteins set forth as SEQ ID NOs: 1-256 and 795-1346) can be altered (i.e., substituted) (see FIGS. 3, 5, 11A, and Table 1 of WO 2013/176772 (all incorporated by reference) for more information regarding the conservation of Cas9 amino acid residues). Also, mutations other than alanine substitutions are suitable.

In some cases, the Cas9 protein (e.g., wt, nickase, or dCas9 protein) is optionally a fusion polypeptide comprising: i) a Cas9 protein (e.g., wt, nickase, or dCas9 protein); and b) a covalently linked heterologous polypeptide (also referred to as a "fusion partner"), which can be the same or different from the fusion partner fused to the PUF domains (infra).

4. PUF Domain (and the Optional Cas9) Fusion Proteins

PUF proteins (named after *Drosophila* Pumilio and *C. elegans* fem-3 binding factor) are known to be involve in mediating mRNA stability and translation. These protein contain a unique RNA-binding domain known as the PUF domain. The RNA-binding PUF domain, such as that of the human Pumilio 1 protein (referred here also as PUM), contains 8 repeats (each repeat called a PUF motif or a PUF repeat) that bind consecutive bases in an anti-parallel fashion, with each repeat recognizing a single base—i.e., PUF repeats R1 to R8 recognize nucleotides N8 to N1, respectively. For example, PUM is composed of eight tandem repeats, each repeat consisting of 34 amino acids that folds into tightly packed domains composed of alpha helices.

Each PUF repeat uses two conserved amino acids from the center of each repeat to specifically recognize the edge of one individual base within the RNA recognition sequence, and a third amino acid (Tyr, His or Arg) to stack between adjacent bases, causing a very specific binding between a PUF domain and an 8-mer RNA. For example, the code to recognize base U is the amino acid sequence "NYxxQ", whereas "(C/S)RxxQ" recognizes A and "SNxxE" recognizes G. These amino acids correspond to positions 12, 13, and 16 in the human Pumilio 1 PUF motif. The two recognition amino acid side chains at positions 12 and 16 in each PUF α-α-α repeat recognize the Watson-Crick edge of the corresponding base and largely determine the specificity of that repeat.

Therefore, the sequence specificity of the PUF domains can be altered precisely by changing the conserved amino acid (e.g., by site-directed mutagenesis) involved in base recognition within the RNA recognition sequence. By changing two amino acids in each repeat, a PUF domain can be modified to bind almost any 8-nt RNA sequence. This unique binding mode makes PUF and its derivatives a programmable RNA-binding domain that can be used in the instant invention, as part of a PUF domain-fusion that brings any effector domain to a specific PBS on the subject polynucleotide.

As used herein, "PUF domain" refers to a wildtype or naturally existing PUF domain, as well as a PUF homologue domain that is based on/derived from a natural or existing PUF domain, such as the prototype human Pumilio 1 PUF domain. The PUF domain of the invention specifically binds to an RNA sequence (e.g., an 8-mer RNA sequence), wherein the overall binding specificity between the PUF domain and the RNA sequence is defined by sequence specific binding between each PUF motif/PUF repeat within the PUF domain and the corresponding single RNA nucleotide.

In certain embodiments, the PUF domain comprises or consists essentially of 8 PUF motifs, each specifically recognizes and binds to one RNA nucleotide (e.g., A, U, G, or C).

Applicant has created 65,536 8-mer PBS and their corresponding PUF domain sequences (each about 350 amino acids long) that can bind the specific PBS. Applicant has also created a python script to retrieve any of the 65,536 individual PUF domain sequences that binds a given 8-mer PBS.

In certain embodiments, the PUF domain has more or less than 8 PUF motifs/repeats, e.g., the PUF domain comprises or consists essentially of 5, 6, 7, 8, 9, 10, 11, 12, 13, 14, 15, 16, or more PUF repeats/motifs, each specifically recognizes and binds to one RNA nucleotide (e.g., A, U, G, or C), so long as the PUF domain binds the RNA of 5, 6, 7, 8, 9, 10, 11, 12, 13, 14, 15, 16 or more nucleotides. By increasing or decreasing the number of PUF motifs, the length of the recognized RNA will be correspondingly increased or decreased. Since each PUF motif recognizes one RNA base, decreasing the domain by one motif decreases the length of the RNA recognized by one base; while increasing the domain by one motif increases the length of the RNA recognized by one base. Any number of motifs may be present. Therefore, in such embodiments, the specificity of the PUF domain-fusions of the invention may be altered due to changes in PUF domain length. In certain embodiments, the additional PUF motifs are inserted between two of the original PUF motifs, e.g., before the $1^{st}$, between the $1^{st}$ and the $2^{nd}$, the $2^{nd}$ and the $3^{rd}$, the $3^{rd}$ and the $4^{th}$, the $4^{th}$ and the $5^{th}$, the $5^{th}$ and the $6^{th}$, the $6^{th}$ and the $7^{th}$, the $7^{th}$ and the $8^{th}$, or after the $8^{th}$. In certain embodiments, there are 1, 2, 3, 4, 5, 6, 7, 8, or more inserted PUF motifs between any of the insertion points above. For example, in certain embodiments, there are 1, 2, 3, 4, 5, 6, 7, 8, or more inserted PUF motifs between the $5^{th}$ and the $6^{th}$ original PUF motif. Filipovska et al. (*Nature Chemical Biology* doi: 10.1038/NChemBio.577, published online: 15 may 2011) have reported an engineered PUF domain with 16 PUF motifs, including 8 additional PUF motifs inserted between the $5^{th}$ and $6^{th}$ original PUF motifs.

In certain embodiments, the PUF domain comprises PUF motifs from different PUF domains from different proteins. For example, a PUF domain of the invention may be constructed with PUF motifs from the human Pumilio 1 protein and one or more other PUF motifs from one or more other PUF proteins, such as PuDp or FBF. The RNA binding pockets of PUF domains have natural concave curvatures. Since different PUF proteins may have different curvatures, different PUF motifs in a PUF domain may be used to alter the curvature of the PUF domain. Altering the curvature is another method for altering the specificity and/or binding affinity of the PUF domain since flatter curvatures may allow for the recognition of more RNA bases.

Also included in the scope of the invention are functional variants of the subject PUF domains or fusions thereof. The term "functional variant" as used herein refers to a PUF domain having substantial or significant sequence identity or similarity to a parent PUF domain, which functional variant retains the biological activity of the PUF domain of which it is a variant—e.g., one that retains the ability to recognize target RNA to a similar extent, the same extent, or to a higher extent in terms of binding affinity, and/or with substantially the same or identical binding specificity, as the parent PUF domain. The functional variant PUF domain can, for instance, be at least about 30%, 50%, 75%, 80%, 90%, 98% or more identical in amino acid sequence to the parent PUF domain. The functional variant can, for example, comprise the amino acid sequence of the parent PUF domain with at least one conservative amino acid substitution, for example, conservative amino acid substitutions in the scaffold of the PUF domain (i.e., amino acids that do not interact with the RNA). Alternatively or additionally, the functional variants can comprise the amino acid sequence of the parent PUF domain with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent PUF domain, or may alter the stability of the PUF domain to a desired level (e.g., due to substitution of amino acids in the scaffold). The PUF domain can consist essentially of the specified amino acid sequence or sequences described herein, such that other components, e.g., other amino acids, do not materially change the biological activity of the functional variant.

In certain embodiments, the PUF domain is a Pumilio homology domain (PU-HUD). In a particular embodiment, the PU-HUD is a human Pumilio 1 domain. The sequence of the human PUM is known in the art and is reproduced below:

(SEQ ID NO: 4)

Gly Arg Ser Arg Leu Leu Glu Asp Phe Arg Asn Asn Arg Tyr Pro Asn

Leu Gln Leu Arg Glu Ile Ala Gly His Ile Met Glu Phe Ser Gln Asp

Gln His Gly Ser Arg Phe Ile Gln Leu Lys Leu Glu Arg Ala Thr Pro

Ala Glu Arg Gln Leu Val Phe Asn Glu Ile Leu Gln Ala Ala Tyr Gln

Leu Met Val Asp Val Phe Gly Asn Tyr Val Ile Gln Lys Phe Phe Glu

Phe Gly Ser Leu Glu Gln Lys Leu Ala Leu Ala Glu Arg Ile Arg Gly

-continued

```
His Val Leu Ser Leu Ala Leu Gln Met Tyr Gly Cys Arg Val Ile Gln

Lys Ala Leu Glu Phe Ile Pro Ser Asp Gln Gln Asn Glu Met Val Arg

Glu Leu Asp Gly His Val Leu Lys Cys Val Lys Asp Gln Asn Gly Asn

His Val Val Gln Lys Cys Ile Glu Cys Val Gln Pro Gln Ser Leu Gln

Phe Ile Ile Asp Ala Phe Lys Gly Gln Val Phe Ala Leu Ser Thr His

Pro Tyr Gly Cys Arg Val Ile Gln Arg Ile Leu Glu His Cys Leu Pro

Asp Gln Thr Leu Pro Ile Leu Glu Glu Leu His Gln His Thr Glu Gln

Leu Val Gln Asp Gln Tyr Gly Asn Tyr Val Ile Gln His Val Leu Glu

His Gly Arg Pro Glu Asp Lys Ser Lys Ile Val Ala Glu Ile Arg Gly

Asn Val Leu Val Leu Ser Gln His Lys Phe Ala Ser Asn Val Val Glu

Lys Cys Val Thr His Ala Ser Arg Thr Glu Arg Ala Val Leu Ile Asp

Glu Val Cys Thr Met Asn Asp Gly Pro His Ser Ala Leu Tyr Thr Met

Met Lys Asp Gln Tyr Ala Asn Tyr Val Val Gln Lys Met Ile Asp Val

Ala Glu Pro Gly Gln Arg Lys Ile Val Met His Lys Ile Arg Pro His

Ile Ala Thr Leu Arg Lys Tyr Thr Tyr Gly Lys His Ile Leu Ala Lys

Leu Glu Lys Tyr Tyr Met Lys Asn Gly Val Asp Leu Gly
```

The wt human PUM specifically binds the Nanos Response Element (NRE) RNA, bearing a core 8-nt sequence 5'-UGUAUAUA-3'.

In certain embodiments, the PUF domain of the invention is any PUF protein family member with a Pum-HD domain. Non-limiting examples of a PUF family member include FBF in *C. elegans*, Ds pum in *Drosophila*, and PUF proteins in plants such as *Arabidopsis* and rice. A phylogenetic tree of the PUM-HDs of *Arabidopsis*, rice and other plant and non-plant species is provided in Tam et al. ("The Puf family of RNA-binding proteins in plants: phylogeny, structural modeling, activity and subcellular localization." *BMC Plant Biol.* 10:44, 2010, the entire contents of which are incorporated by reference herein).

PUF family members are highly conserved from yeast to human, and all members of the family bind to RNA in a sequence specific manner with a predictable code. The accession number for the domain is PS50302 in the Prosite database (Swiss Institute of Bioinformatics) and a sequence alignment of some of the members of this family is shown in FIGS. 5 & 6 of WO 2011-160052 A2 (ClustalW multiple sequence alignment of human, mouse, rat Pumilio 1 (hpum1, Mpum1, Ratpum1) and human and mouse Pumilio 2 (hpum2, Mpum2), respectively.

The *Drosophila* Pumilio (PumDr) is very different in length from other mammalian Pumilio 1 homologues, thus only the C-terminal PUF HUD domain is shown in the sequence alignment with human PUM1 and PUM2 in FIG. 6 of WO 2011/160052A2. The N-terminal part of human and fly Pum proteins shows weak homology (40% similarity) and differs significantly in size and protein sequence. The C-terminal part shows a very high degree of homology and evolutionary conservation (78% identity, 86% similarity for PUM1 and 79% identity, 88% similarity for PUM2), with highly conserved protein sequence and structure of the Pum RNA-binding domain. In all three proteins PUM-HD is composed of the N-terminal conserved part of 20 amino acids, eight Pum repeats of 36 amino acids each, and the C-terminal conserved region. In human Pumilio proteins, the C-conserved part is 44 amino acids long, whereas *Drosophila* protein has an insert of additional 85 amino acids in the C-conserved region. The nucleotide and amino acid sequences can be found in the DDBJ/EMBL/GENBANK® databases under accession nos. AF315592 (PUM1) and AF315591 (PUM2) (Spassov & Jurecic, "Cloning and comparative sequence analysis of PUM1 and PUM2 genes, human members of the Pumilio family of RNA-binding proteins," *Gene*, 299:195-204, October 2002, the entire contents of each of which (publication and sequences) are incorporated by reference herein).

In addition, all aligned sequences, i.e., SEQ ID NOs:55-60 of WO 2011/160052A2, are incorporated herein by reference.

In some embodiments, the PUF domain of the invention can be made up of eight 36 mers, in which 33 of the amino acids are conserved and the $34^{th}$, $35^{th}$ and $36^{th}$ amino acids can vary, imparting specificity for a particular base in an RNA sequence. In particular embodiments, the RNA binding domain is about 300 (e.g., 310, 309, 308, 307, 306, 305, 304, 303, 302, 301, 300, 299, 298, 297, 296, 295, 294, 293, 292, 291, 290, etc.) amino acids in length. In some embodiments, the PUF domain of this invention is designed to bind to a specific RNA sequence of about 8 nucleotides (e.g., 8-16 contiguous RNA bases). In particular embodiments, the fifth nucleotide of the 8-nt sequence is a U or C, while the other 7 nucleotides can vary.

In some embodiments, the PUF domain is modified from a wt PUF domain to bind an RNA sequence that is different from the RNA sequence bound by the unmodified (i.e., wild type) RNA binding PUF domain. The RNA sequence can be about an 8mer (e.g., an 8mer, 9 mer, 10mer, 11mer, 12mer, 13mer, 14mer, 15mer, 16mer, etc.). The ability to introduce modifications into the amino acid sequence of the RNA binding domain to alter its specificity for a target RNA sequence is based on the known interactions of bases with the different amino acid side chains of the RNA binding domain (e.g., PUF proteins). The RNA recognition code of the PUF domain is shown below, which can be generally written as:

SerXXXGlu for G (guanine), such as SNxxE;
CysXXXGln, such as CysArgXXGln or SerArgXXGln (i.e., (C/S)RxxQ) for A (adenine);
AsnXXXGln for U (uracil), such as NYxxQ, and,
SnXXXArg for C (cytosine), such as SerTyrXXArg.
where X is any amino acid, and Sn represents a small or nucleophilic residue such as Gly, Ala, Ser, Thr, or Cys.

Based on the guidelines above, at least one PUF domain can be constructed based on any given 8-mer sequences. Specifically, a PUF domain binding to an 8-mer RNA sequence of 5'-$N_1N_2N_3N_4N_5N_6N_7N_8$-3' can have the following sequence formula, in which R1-R8 each represents a PUF motif peptide sequence listed in the tables below, depending on the specific identity of the ribonucleotide (i.e., A, U, C, or G) at any of the $N_1$-$N_8$ locations. Note that R1 binds $N_8$, R2 binds $N_7$, etc.

```
GlyArgSerArgLeuLeuGluAspPheArgAsnAsnArgTyrProAsnLeuGlnLeuArgGluIle

AlaGlyHisIleMetGluPheSerGlnAsp[R1]ThrProAlaGluArgGlnLeuValPheAsn

GluIleLeuGlnAlaAlaTyrGlnLeuMetValAsp[R2]SerLeuGluGlnLysLeuAlaLeu

AlaGluArgIleArgGlyHisValLeuSerLeuAlaLeuGln[R3]ProSerAspGlnGlnAsn

GluMetValArgGluLeuAspGlyHisValLeuLysCysValLysAsp[R4]GlnProGlnSer

LeuGlnPheIleIleAspAlaPheLysGlyGlnValPheAlaLeuSerThrHis[R5]LeuPro

AspGlnThrLeuProIleLeuGluGluLeuHisGlnHisThrGluGlnLeuValGlnAsp[R6]

ArgProGluAspLysSerLysIleValAlaGluIleArgGlyAsnValLeuValLeuSerGln

His[R7]SerArgThrGluArgAlaValLeuIleAspGluValCysThrMetAsnAspGlyPro

HisSerAlaLeuTyrThrMetMetLysAsp[R8]GluProGlyGlnArgLysIleValMetHis

LysIleArgProHisIleAlaThrLeuArgLysTyrThrTyrGlyLysHisIleLeuAlaLys

LeuGluLysTyrTyrMetLysAsnGlyValAspLeuGly (SEQ ID NO: 5)
```

| $N_8$ nucleotide | R1 peptide sequence(s) | |
|---|---|---|
| A | GlnHisGlyCysArgPheIleGlnLeuLysLeuGluArgAla | (SEQ ID NO: 6) |
|   | GlnHisGlySerArgPheIleGlnLeuLysLeuGluArgAla | (SEQ ID NO: 7) |
| C | GlnHisGlySerArgPheIleArgLeuLysLeuGluArgAla | (SEQ ID NO: 8) |
|   | GlnHisGlyGlyArgPheIleArgLeuLysLeuGluArgAla | (SEQ ID NO: 9) |
|   | GlnHisGlyAlaArgPheIleArgLeuLysLeuGluArgAla | (SEQ ID NO: 10) |
|   | GlnHisGlyThrArgPheIleArgLeuLysLeuGluArgAla | (SEQ ID NO: 11) |
|   | GlnHisGlyCysArgPheIleArgLeuLysLeuGluArgAla | (SEQ ID NO: 12) |
| G | GlnHisGlySerArgPheIleGluLeuLysLeuGluArgAla | (SEQ ID NO: 13) |
| U | GlnHisGlyAsnArgPheIleGlnLeuLysLeuGluArgAla | (SEQ ID NO: 14) |

| $N_7$ nucleotide | R2 peptide sequence(s) | |
|---|---|---|
| A | ValPheGlyCysArgValIleGlnLysPhePheGluPheGly | (SEQ ID NO: 15) |
|   | ValPheGlySerArgValIleGlnLysPhePheGluPheGly | (SEQ ID NO: 16) |
|   | ValPheGlyCysTyrValIleGlnLysPhePheGluPheGly | (SEQ ID NO: 17) |
|   | ValPheGlySerTyrValIleGlnLysPhePheGluPheGly | (SEQ ID NO: 18) |
| C | ValPheGlySerTyrValIleArgLysPhePheGluPheGly | (SEQ ID NO: 19) |
|   | ValPheGlyGlyTyrValIleArgLysPhePheGluPheGly | (SEQ ID NO: 20) |
|   | ValPheGlyAlaTyrValIleArgLysPhePheGluPheGly | (SEQ ID NO: 21) |
|   | ValPheGlyThrTyrValIleArgLysPhePheGluPheGly | (SEQ ID NO: 22) |
|   | ValPheGlyCysTyrValIleArgLysPhePheGluPheGly | (SEQ ID NO: 23) |
| G | ValPheGlySerTyrValIleGluLysPhePheGluPheGly | (SEQ ID NO: 24) |
| U | ValPheGlyAsnTyrValIleGlnLysPhePheGluPheGly | (SEQ ID NO: 25) |

| $N_6$ nucleotide | R3 peptide sequence(s) | |
|---|---|---|
| A | MetTyrGlyCysArgValIleGlnLysAlaLeuGluPheIle | (SEQ ID NO: 26) |
|   | MetTyrGlySerArgValIleGlnLysAlaLeuGluPheIle | (SEQ ID NO: 27) |
| C | MetTyrGlySerArgValIleArgLysAlaLeuGluPheIle | (SEQ ID NO: 28) |
|   | MetTyrGlyGlyArgValIleArgLysAlaLeuGluPheIle | (SEQ ID NO: 29) |
|   | MetTyrGlyAlaArgValIleArgLysAlaLeuGluPheIle | (SEQ ID NO: 30) |
|   | MetTyrGlyThrArgValIleArgLysAlaLeuGluPheIle | (SEQ ID NO: 31) |
|   | MetTyrGlyCysArgValIleArgLysAlaLeuGluPheIle | (SEQ ID NO: 32) |

| | |
|---|---|
| G | MetTyrGlySerArgValIleGluLysAlaLeuGluPheIle (SEQ ID NO: 33) |
| U | MetTyrGlyAsnArgValIleGlnLysAlaLeuGluPheIle (SEQ ID NO: 34) |

| $N_5$ nucleotide | R4 peptide sequence(s) |
|---|---|
| A | GlnAsnGlyCysArgValValGlnLysCysIleGluCysVal (SEQ ID NO: 35)<br>GlnAsnGlySerArgValValGlnLysCysIleGluCysVal (SEQ ID NO: 36)<br>GlnAsnGlyCysHisValValGlnLysCysIleGluCysVal (SEQ ID NO: 37)<br>GlnAsnGlySerHisValValGlnLysCysIleGluCysVal (SEQ ID NO: 38) |
| C | GlnAsnGlySerHisValValArgLysCysIleGluCysVal (SEQ ID NO: 39)<br>GlnAsnGlyGlyHisValValArgLysCysIleGluCysVal (SEQ ID NO: 40)<br>GlnAsnGlyAlaHisValValArgLysCysIleGluCysVal (SEQ ID NO: 41)<br>GlnAsnGlyThrHisValValArgLysCysIleGluCysVal (SEQ ID NO: 42)<br>GlnAsnGlyCysHisValValArgLysCysIleGluCysVal (SEQ ID NO: 43) |
| G | GlnAsnGlySerHisValValGluLysCysIleGluCysVal (SEQ ID NO: 44) |
| U | GlnAsnGlyAsnHisValValGlnLysCysIleGluCysVal (SEQ ID NO: 45) |

| $N_4$ nucleotide | R5 peptide sequence(s) |
|---|---|
| A | ProTyrGlyCysArgValIleGlnArgIleLeuGluHisCys (SEQ ID NO: 46)<br>ProTyrGlySerArgValIleGlnArgIleLeuGluHisCys (SEQ ID NO: 47) |
| C | ProTyrGlySerArgValIleArgArgIleLeuGluHisCys (SEQ ID NO: 48)<br>ProTyrGlyGlyArgValIleArgArgIleLeuGluHisCys (SEQ ID NO: 49)<br>ProTyrGlyAlaArgValIleArgArgIleLeuGluHisCys (SEQ ID NO: 50)<br>ProTyrGlyThrArgValIleArgArgIleLeuGluHisCys (SEQ ID NO: 51)<br>ProTyrGlyCysArgValIleArgArgIleLeuGluHisCys (SEQ ID NO: 52) |
| G | ProTyrGlySerArgValIleGluArgIleLeuGluHisCys (SEQ ID NO: 53) |
| U | ProTyrGlyAsnArgValIleGlnArgIleLeuGluHisCys (SEQ ID NO: 54) |

| $N_3$ nucleotide | R6 peptide sequence(s) |
|---|---|
| A | GlnTyrGlyCysArgValIleGlnHisValLeuGluHisGly (SEQ ID NO: 55)<br>GlnTyrGlySerArgValIleGlnHisValLeuGluHisGly (SEQ ID NO: 56)<br>GlnTyrGlyCysTyrValIleGlnHisValLeuGluHisGly (SEQ ID NO: 57)<br>GlnTyrGlySerTyrValIleGlnHisValLeuGluHisGly (SEQ ID NO: 58) |
| C | GlnTyrGlySerTyrValIleArgHisValLeuGluHisGly (SEQ ID NO: 59)<br>GlnTyrGlyGlyTyrValIleArgHisValLeuGluHisGly (SEQ ID NO: 60)<br>GlnTyrGlyAlaTyrValIleArgHisValLeuGluHisGly (SEQ ID NO: 61)<br>GlnTyrGlyThrTyrValIleArgHisValLeuGluHisGly (SEQ ID NO: 62)<br>GlnTyrGlyCysTyrValIleArgHisValLeuGluHisGly (SEQ ID NO: 63) |
| G | GlnTyrGlySerTyrValIleGluHisValLeuGluHisGly (SEQ ID NO: 64) |
| U | GlnTyrGlyAsnTyrValIleGlnHisValLeuGluHisGly (SEQ ID NO: 65) |

| $N_2$ nucleotide | R7 peptide sequence(s) |
|---|---|
| A | LysPheAlaCysArgValValGlnLysCysValThrHisAla (SEQ ID NO: 66)<br>LysPheAlaSerArgValValGlnLysCysValThrHisAla (SEQ ID NO: 67)<br>LysPheAlaCysAsnValValGlnLysCysValThrHisAla (SEQ ID NO: 68)<br>LysPheAlaSerAsnValValGlnLysCysValThrHisAla (SEQ ID NO: 69) |
| C | LysPheAlaSerAsnValValArgLysCysValThrHisAla (SEQ ID NO: 70)<br>LysPheAlaGlyAsnValValArgLysCysValThrHisAla (SEQ ID NO: 71)<br>LysPheAlaAlaAsnValValArgLysCysValThrHisAla (SEQ ID NO: 72)<br>LysPheAlaThrAsnValValArgLysCysValThrHisAla (SEQ ID NO: 73)<br>LysPheAlaCysAsnValValArgLysCysValThrHisAla (SEQ ID NO: 74) |
| G | LysPheAlaSerAsnValValGluLysCysValThrHisAla (SEQ ID NO: 75) |
| U | LysPheAlaAsnAsnValValGlnLysCysValThrHisAla (SEQ ID NO: 76) |

-continued

| $N_1$ nucleotide | R8 peptide sequence(s) |
|---|---|
| A | GlnTyrAlaCysArgValValGlnLysMetIleAspValAla (SEQ ID NO: 77)<br>GlnTyrAlaSerArgValValGlnLysMetIleAspValAla (SEQ ID NO: 78)<br>GlnTyrAlaCysTyrValValGlnLysMetIleAspValAla (SEQ ID NO: 79)<br>GlnTyrAlaSerTyrValValGlnLysMetIleAspValAla (SEQ ID NO: 80) |
| C | GlnTyrAlaSerTyrValValArgLysMetIleAspValAla (SEQ ID NO: 81)<br>GlnTyrAlaGlyTyrValValArgLysMetIleAspValAla (SEQ ID NO: 82)<br>GlnTyrAlaAlaTyrValValArgLysMetIleAspValAla (SEQ ID NO: 83)<br>GlnTyrAlaThrTyrValValArgLysMetIleAspValAla (SEQ ID NO: 84)<br>GlnTyrAlaCysTyrValValArgLysMetIleAspValAla (SEQ ID NO: 85) |
| G | GlnTyrAlaSerTyrValValGluLysMetIleAspValAla (SEQ ID NO: 86) |
| U | GlnTyrAlaAsnTyrValValGlnLysMetIleAspValAla (SEQ ID NO: 87) |

Several exemplary PUF domains with modified RNA binding specificity, constructed based on the above RNA recognition code, are provided below, each can be used to construct PUF domain-fusions of the invention.

PUF (3-2)
(SEQ ID NO: 88)
Gly Arg Ser Arg Leu Leu Glu Asp Phe Arg Asn Asn Arg Tyr Pro Asn
Leu Gln Leu Arg Glu Ile Ala Gly His Ile Met Glu Phe Ser Gln Asp
Gln His Gly Ser Arg Phe Ile Gln Leu Lys Leu Glu Arg Ala Thr Pro
Ala Glu Arg Gln Leu Val Phe Asn Glu Ile Leu Gln Ala Ala Tyr Gln
Leu Met Val Asp Val Phe Gly Asn Tyr Val Ile Gln Lys Phe Phe Glu
Phe Gly Ser Leu Glu Gln Lys Leu Ala Leu Ala Glu Arg Ile Arg Gly
His Val Leu Ser Leu Ala Leu Gln Met Tyr Gly Ser Arg Val Ile Glu
Lys Ala Leu Glu Phe Ile Pro Ser Asp Gln Gln Asn Glu Met Val Arg
Glu Leu Asp Gly His Val Leu Lys Cys Val Lys Asp Gln Asn Gly Asn
His Val Val Gln Lys Cys Ile Glu Cys Val Gln Pro Gln Ser Leu Gln
Phe Ile Ile Asp Ala Phe Lys Gly Gln Val Phe Ala Leu Ser Thr His
Pro Tyr Gly Cys Arg Val Ile Gln Arg Ile Leu Glu His Cys Leu Pro
Asp Gln Thr Leu Pro Ile Leu Glu Glu Leu His Gln His Thr Glu Gln
Leu Val Gln Asp Gln Tyr Gly Asn Tyr Val Ile Gln His Val Leu Glu
His Gly Arg Pro Glu Asp Lys Ser Lys Ile Val Ala Glu Ile Arg Gly
Asn Val Leu Val Leu Ser Gln His Lys Phe Ala Ser Asn Val Val Glu
Lys Cys Val Thr His Ala Ser Arg Thr Glu Arg Ala Val Leu Ile Asp
Glu Val Cys Thr Met Asn Asp Gly Pro His Ser Ala Leu Tyr Thr Met
Met Lys Asp Gln Tyr Ala Asn Tyr Val Val Gln Lys Met Ile Asp Val
Ala Glu Pro Gly Gln Arg Lys Ile Val Met His Lys Ile Arg Pro His
Ile Ala Thr Leu Arg Lys Tyr Thr Tyr Gly Lys His Ile Leu Ala Lys
Leu Glu Lys Tyr Tyr Met Lys Asn Gly Val Asp Leu Gly

PUF(3-2) has two point mutations (C935S/Q939E) in the PUF repeat 3, and recognizes a cognate RNA with a mutation at position 6 of the NRE (A6G; 5'-UGUAUGUA-3').

```
PUF (6-2/7-2)
                                                         (SEQ ID NO: 89)
Gly Arg Ser Arg Leu Leu Glu Asp Phe Arg Asn Asn Arg Tyr Pro Asn

Leu Gln Leu Arg Glu Ile Ala Gly His Ile Met Glu Phe Ser Gln Asp

Gln His Gly Ser Arg Phe Ile Gln Leu Lys Leu Glu Arg Ala Thr Pro

Ala Glu Arg Gln Leu Val Phe Asn Glu Ile Leu Gln Ala Ala Tyr Gln

Leu Met Val Asp Val Phe Gly Asn Tyr Val Ile Gln Lys Phe Phe Glu

Phe Gly Ser Leu Glu Gln Lys Leu Ala Leu Ala Glu Arg Ile Arg Gly

His Val Leu Ser Leu Ala Leu Gln Met Tyr Gly Cys Arg Val Ile Gln

Lys Ala Leu Glu Phe Ile Pro Ser Asp Gln Gln Asn Glu Met Val Arg

Glu Leu Asp Gly His Val Leu Lys Cys Val Lys Asp Gln Asn Gly Asn

His Val Val Gln Lys Cys Ile Glu Cys Val Gln Pro Gln Ser Leu Gln

Phe Ile Ile Asp Ala Phe Lys Gly Gln Val Phe Ala Leu Ser Thr His

Pro Tyr Gly Cys Arg Val Ile Gln Arg Ile Leu Glu His Cys Leu Pro

Asp Gln Thr Leu Pro Ile Leu Glu Glu Leu His Gln His Thr Glu Gln

Leu Val Gln Asp Gln Tyr Gly Ser Tyr Val Ile Glu His Val Leu Glu

His Gly Arg Pro Glu Asp Lys Ser Lys Ile Val Ala Glu Ile Arg Gly

Asn Val Leu Val Leu Ser Gln His Lys Phe Ala Asn Asn Val Val Gln

Lys Cys Val Thr His Ala Ser Arg Thr Glu Arg Ala Val Leu Ile Asp

Glu Val Cys Thr Met Asn Asp Gly Pro His Ser Ala Leu Tyr Thr Met

Met Lys Asp Gln Tyr Ala Asn Tyr Val Val Gln Lys Met Ile Asp Val

Ala Glu Pro Gly Gln Arg Lys Ile Val Met His Lys Ile Arg Pro His

Ile Ala Thr Leu Arg Lys Tyr Thr Tyr Gly Lys His Ile Leu Ala Lys

Leu Glu Lys Tyr Tyr Met Lys Asn Gly Val Asp Leu Gly
```

PUF (6-2/7-2) has double point mutations (N1043S/Q1047E and S1079N/E1083Q) in repeats 6 and 7, respectively, and recognizes a cognate RNA sequence with two mutations at positions 2 and 3 of the NRE (GU/UG; 5'-UUGAUAUA-3').

A related PUF (6-2) has point mutations (N1043S/Q1047E) in repeats 6, and recognizes a cognate RNA sequence with a mutation at position 3 of the NRE (5'-UGGAUAUA-3').

Another related PUF (7-2) has point mutations (S1079N/E1083Q) in repeats 7, and recognizes a cognate RNA sequence with a mutation at position 2 of the NRE (5'-UUUAUAUA-3').

```
PUF531
                                                         (SEQ ID NO: 90)
Gly Arg Ser Arg Leu Leu Glu Asp Phe Arg Asn Asn Arg Tyr Pro Asn

Leu Gln Leu Arg Glu Ile Ala Gly His Ile Met Glu Phe Ser Gln Asp

Gln His Gly Ser Arg Phe Ile Glu Leu Lys Leu Glu Arg Ala Thr Pro

Ala Glu Arg Gln Leu Val Phe Asn Glu Ile Leu Gln Ala Ala Tyr Gln

Leu Met Val Asp Val Phe Gly Asn Tyr Val Ile Gln Lys Phe Phe Glu

Phe Gly Ser Leu Glu Gln Lys Leu Ala Leu Ala Glu Arg Ile Arg Gly

His Val Leu Ser Leu Ala Leu Gln Met Tyr Gly Ser Arg Val Ile Glu

Lys Ala Leu Glu Phe Ile Pro Ser Asp Gln Gln Asn Glu Met Val Arg
```

```
Glu Leu Asp Gly His Val Leu Lys Cys Val Lys Asp Gln Asn Gly Asn

His Val Val Gln Lys Cys Ile Glu Cys Val Gln Pro Gln Ser Leu Gln

Phe Ile Ile Asp Ala Phe Lys Gly Gln Val Phe Ala Leu Ser Thr His

Pro Tyr Gly Ser Arg Val Ile Glu Arg Ile Leu Glu His Cys Leu Pro

Asp Gln Thr Leu Pro Ile Leu Glu Glu Leu His Gln His Thr Glu Gln

Leu Val Gln Asp Gln Tyr Gly Asn Tyr Val Ile Gln His Val Leu Glu

His Gly Arg Pro Glu Asp Lys Ser Lys Ile Val Ala Glu Ile Arg Gly

Asn Val Leu Val Leu Ser Gln His Lys Phe Ala Ser Asn Val Val Glu

Lys Cys Val Thr His Ala Ser Arg Thr Glu Arg Ala Val Leu Ile Asp

Glu Val Cys Thr Met Asn Asp Gly Pro His Ser Ala Leu Tyr Thr Met

Met Lys Asp Gln Tyr Ala Asn Tyr Val Val Gln Lys Met Ile Asp Val

Ala Glu Pro Gly Gln Arg Lys Ile Val Met His Lys Ile Arg Pro His

Ile Ala Thr Leu Arg Lys Tyr Thr Tyr Gly Lys His Ile Leu Ala Lys

Leu Glu Lys Tyr Tyr Met Lys Asn Gly Val Asp Leu Gly
```

The PUF domain PUF[531] has mutations (Q867E/Q939E/C935S/Q1011E/C1007S) in wild type PUF repeats 1, 3 and 5, and recognizes the sequence 5'-UGUGUGUG-3'. The PUF[531] can recognize its new target sequence with very high affinity, compared to the wild type PUF RNA.

Another modified PUF domain PUF(1-1) has one point mutation (Q867E) in the PUF repeat 1, and recognizes a cognate RNA with a mutation at position 8 of the NRE (A8G; 5'-UGUAUAUG-3').

Yet another modified PUF domain PUF(7-1) has one point mutation (E1083Q) in the PUF repeat 7, and recognizes a cognate RNA with a mutation at position 2 of the NRE (G2U; 5'-UUUAUAUA-3'; or G2A; 5'-UAUAUAUA-3').

Still another modified PUF domain PUF(3-1) has one point mutation (C935N) in the PUF repeat 3, and recognizes a cognate RNA with a mutation at position 6 of the NRE (A6U; 5'-UGUAUUUA-3').

A further modified PUF (7-2/3-1) has point mutations (C935N/51079N/E1083Q) in repeats 7 and 3, and recognizes a cognate RNA sequence with mutations at positions 2 and 6 of the NRE (5'-UUUAUUUA-3').

The sequences of certain modified PUF domains are represented below.

```
                                              (SEQ ID NO: 91)
Gly Arg Ser Arg Leu Leu Glu Asp Phe Arg Asn Asn Arg Tyr Pro Asn

Leu Gln Leu Arg Glu Ile Ala Gly His Ile Met Glu Phe Ser Gln Asp

Gln His Gly Ser Arg Phe Ile Glu Leu Lys Leu Glu Arg Ala Thr Pro

Ala Glu Arg Gln Leu Val Phe Asn Glu Ile Leu Gln Ala Ala Tyr Gln

Leu Met Val Asp Val Phe Gly Cys Arg Val Ile Gln Lys Phe Phe Glu

Phe Gly Ser Leu Glu Gln Lys Leu Ala Leu Ala Glu Arg Ile Arg Gly

His Val Leu Ser Leu Ala Leu Gln Met Tyr Gly Cys Arg Val Ile Gln

Lys Ala Leu Glu Phe Ile Pro Ser Asp Gln Gln Asn Glu Met Val Arg

Glu Leu Asp Gly His Val Leu Lys Cys Val Lys Asp Gln Asn Gly Asn

His Val Val Gln Lys Cys Ile Glu Cys Val Gln Pro Gln Ser Leu Gln

Phe Ile Ile Asp Ala Phe Lys Gly Gln Val Phe Ala Leu Ser Thr His

Pro Tyr Gly Cys Arg Val Ile Gln Arg Ile Leu Glu His Cys Leu Pro

Asp Gln Thr Leu Pro Ile Leu Glu Glu Leu His Gln His Thr Glu Gln

Leu Val Gln Asp Gln Tyr Gly Ser Tyr Val Ile Glu His Val Leu Glu

His Gly Arg Pro Glu Asp Lys Ser Lys Ile Val Ala Glu Ile Arg Gly

Asn Val Leu Val Leu Ser Gln His Lys Phe Ala Asn Asn Val Val Gln

Lys Cys Val Thr His Ala Ser Arg Thr Glu Arg Ala Val Leu Ile Asp
```

```
Glu Val Cys Thr Met Asn Asp Gly Pro His Ser Ala Leu Tyr Thr Met

Met Lys Asp Gln Tyr Ala Ser Tyr Val Val Glu Lys Met Ile Asp Val

Ala Glu Pro Gly Gln Arg Lys Ile Val Met His Lys Ile Arg Pro His

Ile Ala Thr Leu Arg Lys Tyr Thr Tyr Gly Lys His Ile Leu Ala Lys

Leu Glu Lys Tyr Tyr (SEQ ID NO: 92)
Gly Arg Ser Arg Leu Leu Glu Asp Phe Arg Asn Asn Arg Tyr Pro Asn

Leu Gln Leu Arg Glu Ile Ala Gly His Ile Met Glu Phe Ser Gln Asp

Gln His Gly Asn Arg Phe Ile Gln Leu Lys Leu Glu Arg Ala Thr Pro

Ala Glu Arg Gln Leu Val Phe Asn Glu Ile Leu Gln Ala Ala Tyr Gln

Leu Met Val Asp Val Phe Gly Ser Tyr Val Ile Glu Lys Phe Phe Glu

Phe Gly Ser Leu Glu Gln Lys Leu Ala Leu Ala Glu Arg Ile Arg Gly

His Val Leu Ser Leu Ala Leu Gln Met Tyr Gly Ser Arg Val Ile Glu

Lys Ala Leu Glu Phe Ile Pro Ser Asp Gln Gln Asn Glu Met Val Arg

Glu Leu Asp Gly His Val Leu Lys Cys Val Lys Asp Gln Asn Gly Asn

His Val Val Gln Lys Cys Ile Glu Cys Val Gln Pro Gln Ser Leu Gln

Phe Ile Ile Asp Ala Phe Lys Gly Gln Val Phe Ala Leu Ser Thr His

Pro Tyr Gly Ser Arg Val Ile Glu Arg Ile Leu Glu His Cys Leu Pro

Asp Gln Thr Leu Pro Ile Leu Glu Glu Leu His Gln His Thr Glu Gln

Leu Val Gln Asp Gln Tyr Gly Ser Tyr Val Ile Glu His Val Leu Glu

His Gly Arg Pro Glu Asp Lys Ser Lys Ile Val Ala Glu Ile Arg Gly

Asn Val Leu Val Leu Ser Gln His Lys Phe Ala Cys Asn Val Val Gln

Lys Cys Val Thr His Ala Ser Arg Thr Glu Arg Ala Val Leu Ile Asp

Glu Cys Val Thr Met Asn Asp Gly Pro His Ser Ala Leu Tyr Thr Met

Met Lys Asp Gln Tyr Ala Ser Tyr Val Val Glu Lys Met Ile Asp Val

Ala Glu Pro Gly Gln Arg Lys Ile Val Met His Lys Ile Arg Pro His

Ile Ala Thr Leu Arg Lys Tyr Thr Tyr Gly Lys His Ile Leu Ala Lys

Leu Glu Lys Tyr Tyr (SEQ ID NO: 93)
Gly Arg Ser Arg Leu Leu Glu Asp Phe Arg Asn Asn Arg Tyr Pro Asn

Leu Gln Leu Arg Glu Ile Ala Gly His Ile Met Glu Phe Ser Gln Asp

Gln His Gly Cys Arg Phe Ile Gln Leu Lys Leu Glu Arg Ala Thr Pro

Ala Glu Arg Gln Leu Val Phe Asn Glu Ile Leu Gln Ala Ala Tyr Gln

Leu Met Val Asp Val Phe Gly Ser Tyr Val Ile Glu Lys Phe Phe Glu

Phe Gly Ser Leu Glu Gln Lys Leu Ala Leu Ala Glu Arg Ile Arg Gly

His Val Leu Ser Leu Ala Leu Gln Met Tyr Gly Asn Arg Val Ile Gln

Lys Ala Leu Glu Phe Ile Pro Ser Asp Gln Gln Asn Glu Met Val Arg

Glu Leu Asp Gly His Val Leu Lys Cys Val Lys Asp Gln Asn Gly Asn

His Val Val Gln Lys Cys Ile Glu Cys Val Gln Pro Gln Ser Leu Gln

Phe Ile Ile Asp Ala Phe Lys Gly Gln Val Phe Ala Leu Ser Thr His

Pro Tyr Gly Cys Arg Val Ile Gln Arg Ile Leu Glu His Cys Leu Pro
```

-continued

```
Asp Gln Thr Leu Pro Ile Leu Glu Glu Leu His Gln His Thr Glu Gln

Leu Val Gln Asp Gln Tyr Gly Ser Tyr Val Ile Glu His Val Leu Glu

His Gly Arg Pro Glu Asp Lys Ser Lys Ile Val Ala Glu Ile Arg Gly

Asn Val Leu Val Leu Ser Gln His Lys Phe Ala Cys Asn Val Val Gln

Lys Cys Val Thr His Ala Ser Arg Thr Glu Arg Ala Val Leu Ile Asp

Glu Cys Val Thr Met Asn Asp Gly Pro His Ser Ala Leu Tyr Thr Met

Met Lys Asp Gln Tyr Ala Cys Tyr Val Val Gln Lys Met Ile Asp Val

Ala Glu Pro Gly Gln Arg Lys Ile Val Met His Lys Ile Arg Pro His

Ile Ala Thr Leu Arg Lys Tyr Thr Tyr Gly Lys His Ile Leu Ala Lys

Leu Glu Lys Tyr Tyr
```

According to the invention, heterologous polypeptide (also referred to as a "fusion partner") can be fused to the PUF domain of the invention that binds to at least one of the PBS on the subject polynucleotide. In addition, if desired, the same or different fusion partner can also optionally be fused to the Cas9 protein (e.g., wt, nickase, or dCas9 protein). Thus as described herein, unless specifically disclaimed, any of the fusion partners are intended to be fused to PUF domain, and optionally also fused to the Cas9 protein (e.g., wt, nickase, or dCas9 protein). The fusion partner fused to the PUF domain can be the same or different from the optional fusion partner fused to the Cas9 protein (e.g., wt, nickase, or dCas9 protein) (infra).

The fusion partner may exhibit an activity (e.g., enzymatic activity). Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying the DNA directly (e.g., methylation of DNA) or at modifying a DNA-associated polypeptide (e.g., a histone or DNA binding protein).

| Protein name | Function |
|---|---|
| Transcriptional Activators | |
| GAL4 | Transcription activation |
| VP16 | Transcription activation |
| VP64 | Transcription activation |
| p65 subdomain (NFkB) | Transcription activation |
| Transcriptional repressers | |
| KRAB | Transcription repression |
| Mad mSIN3 interaction domain (SID) | Transcription repression |
| the ERF repressor domain (ERD) | Transcription repression |
| Histone lysine methyltransferases (KMT) | |
| KMT1 family: SUV39H1, SUV39H2, G9A, ESET/SETDB1, and homologs (Clr4, Su(var)3-9) | Heterochromatin formation/ transcription repression |
| KMT2 family: hSET1A, hSET1B, MLL1 to 5, ASH1, and homologs (Trx, Trr, Ash1) | Transcription activation |
| KMT3 family: SYMD2, NSD1 | Transcription activation |
| KMT4: DOT1L and homologs | Transcription activation |
| KMT5 family: Pr-SET7/8, SUV4-20H1, and homologs (PR-set7, Suv4-20, Set9) | DNA damage response, transcription repression |
| KMT6: EZH2 | Polycomb silencing |
| KMT8: RIZ1 | Transcription repression |
| Histone lysine demethylates (KDM) | |
| KDM1: LSD1/BHC110 and homologs (SpLsd1/Swm1/Saf110, Su(var)3-3) | Transcription activation and repression, heterochromatin formation |
| KDM3 family: JHDM2a/b | Androgen receptor gene activation, spermatogenesis |
| KDM4 family: JMJD2A/JHDM3A, JMJD2B, JMJD2C/GASC1, JMJD2D, and homologs (Rph1) | Transcription elongation, transcription repression, heterochromatin formation, genome integrity |
| KDM5 family: JARID1A/RBP2, JARID1B/PLU-1, JARID1C/SMCX, JARID1D/SMCY, and homologs (Lid, Jhn2, Jmj2) | Transcription repression |
| KDM6 family: UTX, JMJD3 | Transcription activation |
| Histone lysine acetyltransferases (KAT) | |
| KAT2 family: hGCN5, PCAF, and homologs (dGCN5/PCAF, Gcn5) | Transcription activation, DNA repair |

| Protein name | Function |
| --- | --- |
| KAT3 family: CBP, p300, and homologs (dCBP/NEJ) | Transcription activation, DNA repair |
| KAT4: TAF1 and homologs (dTAF1) | Transcription activation |
| KAT5: TIP60/PLIP, and homologs | Transcription activation, DNA repair |
| KAT6: MOZ/MYST3, MORF/MYST4, and homologs (Mst2, Sas3, CG1894) | Transcription activation and elongation, DNA replication |
| KAT7: HBO1/MYST2, and homologs (CHM, Mst2) | Transcription, DNA replication |
| KAT8: HMOF/MYST1, and homologs (dMOF, CG1894, Sas2, Mst2) | Chromatin boundaries, dosage compensation, DNA repair |
| KAT13 family: SRC1, ACTR, P160, CLOCK, and homologs | Transcription activation |
| Histone lysine deacetylases | |
| Class I: HDAC1, HDAC2, HDAC3, HDAC8, and its homologs (Rpd3, Hos1, Cir6) | Transcription repression, heterochromatin formation |
| Class IIa: HDAC4, HDAC5, HDAC7, HDAC9, and its homologs (Hda1, Cir3 etc.) | Transcription repression, heterochromatin formation |
| Class III: SIRT1, SIRT2, and its homologs (Sir2, Hst1, Hst2, Hst3, Hst4) | Transcription repression, heterochromatin formation |
| Class IV: HDAC11 | Transcription repression |
| DNA methylases (adenosine or cytosine modification) | |
| Dam (*E. coli*) | Restriction system |
| Dcm (*E. coli*) | Restriction system |
| M. SssI (Spiroplasma sp) | Restriction system |
| DNMT1 | Transcription repression. imprinting, heterochromatin formation |
| DNMT3a/DNMT3b, METI, DRM3 (plants), and homologs | Transcription repression. imprinting, heterochromatin formation |
| Chromomethylases e.g. ZMET2, CMT1, CMT2 (plants) | Transcription repression. imprinting, heterochromatin formation |
| DNA demethylases | |
| AID/Apobec deaminase family: AID | Transcription activation, genome integrity |
| TET dioxygenase family: TET1 | Transcription activation, genome integrity |
| DEMETER glycosylase family: DME, DML1, DML2, ROS1 | Transcription activation, genome integrity |
| Boundary elements | |
| CTCF | Chromatin insulation, heterochromatin spreading suppression |
| Periphery recruitment elements | |
| Lamin A | Transcription repression |
| Lamin B | Transcription repression |
| Protein docking elements | |
| FKBP/FRB (*S. pombe*) | rapamycin dependent recruitment |
| Pil1/Aby1 (*E. coli*) | ABA dependent recruitment |

Additional fusion partners may include the various fluorescent protein, polypeptides, variants, or functional domains thereof, such as GFP, Superfolder GFP, EGFP, BFP, EBFP, EBFP2, Azurite, mKalamal, CFP, ECFP, Cerulean, CyPet, mTurquoise2, YFP, Citrine, Venus, Ypet, BFPms1, roGFP, and bilirubin-inducible fluorescent proteins such as UnaG, dsRed, eqFP611, Dronpa, TagRFPs, KFP, EosFP, Dendra, IrisFP, etc.

Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Additional non-limiting examples of fusion partners to accomplish increased or decreased transcription are listed below, and include transcription activator and transcription repressor domains (e.g., the Kruppel associated box (KRAB or SKD); the Mad mSIN3 interaction domain (SID); the ERF repressor domain (ERD), etc.).

In some embodiments, the heterologous sequence can be fused to the C-terminus of the PUF domain or Cas9 protein (e.g., wt, nickase, or dCas9 protein). In some embodiments, the heterologous sequence can be fused to the N-terminus of the PUF domain or Cas9 protein (e.g., wt, nickase, or dCas9 protein). In some embodiments, the heterologous sequence can be fused to an internal portion (i.e., a portion other than the N- or C-terminus) of the PUF domain or Cas9 protein (e.g., wt, nickase, or dCas9 protein).

In some embodiments, a PUF domain fusion is generated by fusing a PUF domain with a heterologous sequence that provides for subcellular localization (i.e., the heterologous sequence is a subcellular localization sequence, e.g., a nuclear localization signal (NLS, such as PPKKKRKV (SEQ ID NO: 94)) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag (SEQ ID NO: 95); a hemagglutinin (HA) tag; a FLAG tag; a Myc tag; and the like. In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target DNA (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a chimeric PUF domain or Cas9 protein (e.g., wt, nickase, or dCas9 protein) to bind to another protein of interest, e.g., a DNA or histone modifying protein, a transcription factor or transcription repressor, a recruiting protein, etc.).

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled at least in part by the degron sequence. In some cases, a suitable degron is constitutive such that the degron exerts its influence on protein stability independent of experimental control (i.e., the degron is not drug inducible, temperature inducible, etc.). In some cases, the degron provides the PUF domain or Cas9 protein (e.g., wt, nickase, or dCas9 protein) with controllable stability such that the PUF domain or Cas9 protein (e.g., wt, nickase, or dCas9 protein) can be turned "on" (i.e., stable) or "off" (i.e., unstable, degraded) depending on the desired conditions. For example, if the degron is a temperature sensitive degron, the PUF domain or Cas9 protein (e.g., wt, nickase, or dCas9 protein) may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non- functional (i.e., "off, degraded") above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., *Science*, 263(5151): 1273-1276, 1994: "Heat-inducible degron: a method for constructing temperature-sensitive mutants"; Schoeber et al., *Am. J. Physiol. Renal. Physiol.*, 296(1): F204-211, 2009: "Conditional fast expression and function of multimeric TRPV5 channels using Shield-1"; Chu et al., *Bioorg. Med. Chem. Lett.*, 18(22): 5941-4, 2008: "Recent progress with FKBP-derived destabilizing domains"; Kanemaki, *Pflugers Arch.*, 2012: "Frontiers of protein expression control with conditional degrons"; Yang et al., *Mol. Cell.*, 48(4):487-8, 2012: "Titivated for destruction: the methyl degron"; Barbour et al., *Biosci. Rep.*, 33(1), 2013: "Characterization of the bipartite degron that regulates ubiquitin-independent degradation of thymidylate synthase"; and Greussing et al., *J. Vis. Exp.*, (69), 2012: "Monitoring of ubiquitin-proteasome activity in living cells using a Degron (dgn)-destabilized green fluorescent protein (GFP)-based reporter protein"; all of which are incorporated in their entirety by reference).

Exemplary degron sequences have been well-characterized and tested in both cells and animals. Thus, fusing Cas9 protein (e.g., wt, nickase, or dCas9 protein) to a degron sequence produces a "tunable" and "inducible" PUF domain or Cas9 (e.g., wt, nickase, or dCas9 protein).

Any of the fusion partners described herein can be used in any desirable combination. As one non-limiting example to illustrate, each PUF domain can be independently fused to the same or different fusion partners, and they may bind in any order on the series of PBS of the subject polynucleotide. For example, one PUF domain can be fused to a YFP sequence for detection, a second PUF domain fused to a degron sequence for stability, and a third PUF domain fused to a transcription activator sequence to increase transcription of the target DNA. Any of these types of PUF domain fusions can have more than 1 binding sites or PBS on the subject polynucleotide, in any desired order. The number of fusion partners that can be used in the PUF domain fusions is largely unlimited (e.g., at least 2, 5, 10, 20, 30, 40, 50 or more).

In some embodiments, any PUF domain or Cas9 protein (e.g., wt, nickase, or dCas9 protein) fusion protein may comprises one or more (e.g. two or more, three or more, four or more, or five or more) heterologous sequences or fusion partners.

In some embodiments, any of the subject Cas9 protein (e.g., wt, nickase, or dCas9 protein) or PUF domain fusions can be codon-optimized. This type of optimization is known in the art and entails the mutation of foreign-derived DNA to mimic the codon preferences of the intended host organism or cell while encoding the same protein. Thus, the codons are changed, but the encoded protein remains unchanged. For example, if the intended target cell was a human cell, a human codon-optimized PUF domain or Cas9 protein (e.g., wt, nickase, or dCas9 protein) fusion would be a better suited PUF domain or Cas9 protein (e.g., wt, nickase, or dCas9 protein) fusion. As another non-limiting example, if the intended host cell were a mouse cell, than a mouse codon-optimized PUF domain fusion or Cas9 protein (e.g., wt, nickase, or dCas9 protein) would be a suitable PUF domain fusion or Cas9 protein (e.g., wt, nickase, or dCas9 protein). While codon optimization is not required, it is acceptable and may be preferable in certain cases.

Any of the subject PUF domain can be made using, for example, a Golden Gate Assembly kit (see Abil et al., *Journal of Biological Engineering* 8:7, 2014), which is available at Addgene (Kit #1000000051).

5. Modulation of Transcription

The PUF domain and/or Cas9 protein (e.g., wt, nickase, or dCas9 protein) fusion protein of the invention is targeted by the DNA-targeting sequence of the subject polynucleotide to a specific location (i.e., target polynucleotide sequence) in the target DNA, and exerts locus-specific regulation, such as blocking RNA polymerase binding to a promoter (which selectively inhibits transcription activator function), and/or modifying the local chromatin status (e.g., when a fusion sequence is used that modifies the target DNA or modifies a polypeptide associated with the target DNA). In some cases, the changes are transient (e.g., transcription repression or activation). In some cases, the changes are inheritable (e.g., when epigenetic modifications are made to the target DNA or to proteins associated with the target DNA, e.g., nucleosomal histones).

The biological effects of a method using a subject PUF domain or Cas9 protein (e.g., wt, nickase, or dCas9 protein) fusion protein can be detected by any convenient method (e.g., gene expression assays; chromatin-based assays, e.g., Chromatin immunoPrecipitation (ChIP), Chromatin in vivo Assay (CiA), etc.; and the like).

In some cases, a subject method involves using two or more different DNA-targeting sequences. For example, two different DNA-targeting sequences can be used in a single host cell, where the two different DNA-targeting sequences target two different target polynucleotide sequences in the same target nucleic acid. Thus, for example, a subject transcriptional modulation method can further comprise introducing into the host cell a second DNA-targeting sequence, or a nucleic acid comprising a nucleotide sequence encoding the second DNA-targeting sequence. In some cases, use of two different DNA-targeting sequences targeting two different targeting sequences in the same target nucleic acid provides for increased modulation (e.g., reduction or increase) in transcription of the target nucleic acid.

As another example, two different DNA-targeting sequences can be used in a single host cell, where the two different DNA-targeting sequences target two different target nucleic acids.

Thus, in certain embodiments, a transcription modulation method of the present invention provides for selective modulation (e.g., reduction or increase) of a target nucleic acid in a host cell. For example, "selective" reduction of transcription of a target nucleic acid reduces transcription of the target nucleic acid by at least about 10%, at least about 20%, at least about 30%, at least about 40%, at least about 50%, at least about 60%, at least about 70%, at least about 80%, at least about 90%, or greater than 90%, compared to the level of transcription of the target nucleic acid in the absence of a DNA-targeting sequence/modified Cas9 polypeptide/PUF domain-fusion complex. Selective reduction of transcription of a target nucleic acid reduces transcription of the target nucleic acid, but does not substantially reduce transcription of a non-target nucleic acid, e.g., transcription of a non-target nucleic acid is reduced, if at all, by less than 10% compared to the level of transcription of the non-target nucleic acid in the absence of the DNA-targeting sequence/modified Cas9 polypeptide/PUF domain-fusion complex.

On the other hand, "selective" increased transcription of a target DNA can increase transcription of the target DNA by at least about 1.1 fold (e.g., at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 12 fold, at least about 15 fold, or at least about 20-fold) compared to the level of transcription of the target DNA in the absence of the DNA-targeting sequence/modified Cas9 polypeptide/PUF domain-fusion complex. Selective increase of transcription of a target DNA increases transcription of the target DNA, but does not substantially increase transcription of a non-target DNA, e.g., transcription of a non-target DNA is increased, if at all, by less than about 5-fold (e.g., less than about 4-fold, less than about 3-fold, less than about 2-fold, less than about 1.8-fold, less than about 1.6-fold, less than about 1.4-fold, less than about 1.2-fold, or less than about 1.1-fold) compared to the level of transcription of the non-targeted DNA in the absence of the DNA-targeting sequence/modified Cas9 polypeptide/PUF domain-fusion complex.

As a non-limiting example, increased transcription can be achieved by fusing dCas9 to a heterologous sequence, and/or by fusing the heterologous sequence to one of the PUF domains that binds to a PBS of the subject polynucleotide. Suitable fusion partners include, but are not limited to, a polypeptide that provides an activity that indirectly increases transcription by acting directly on the target DNA or on a polypeptide (e.g., a histone or other DNA-binding protein) associated with the target DNA. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). See section entitled "PUF domain (and the optional dCas9) Fusion Proteins."

A non-limiting example of a subject method using a dCas9 fusion protein and/or a PUF domain-fusion protein to increase transcription in a prokaryote includes a modification of the bacterial one-hybrid (B1H) or two-hybrid (B2H) system. In the B1H system, a DNA binding domain (BD) is fused to a bacterial transcription activation domain (AD, e.g., the alpha subunit of the E. coli RNA polymerase (RNAPα)). Thus, a subject dCas9 or PUF domain can be fused to a heterologous sequence comprising an AD. When the subject dCas9 or PUF domain fusion protein arrives at the upstream region of a promoter (targeted there by the DNA-targeting sequence) the AD (e.g., RNAPα) of the dCas9 or PUF domain fusion protein recruits the RNAP holoenzyme, leading to transcription activation. In the B2H system, the BD is not directly fused to the AD; instead, their interaction is mediated by a protein-protein interaction (e.g., GAL11P-GAL4 interaction). To modify such a system for use in the subject methods, dCas9 or PUF domain can be fused to a first protein sequence that provides for protein-protein interaction (e.g., the yeast GAL11P and/or GAL4 protein) and RNAPα can be fused to a second protein sequence that completes the protein-protein interaction (e.g., GAL4 if GAL11P is fused to dCas9 or PUF domain, GAL11P if GAL4 is fused to dCas9 or PUF domain, etc.). The binding affinity between GAL11P and GAL4 increases the efficiency of binding and transcription rate.

A non-limiting example of a subject method using a dCas9 and/or PUF domain fusion protein to increase transcription in a eukaryotes includes fusion of dCas9 and/or PUF domain to an activation domain (AD) (e.g., GAL4, herpesvirus activation protein VP16 or VP64, human nuclear factor NF-κB p65 subunit, etc.). To render the system inducible, expression of the dCas9/PUF domain fusion protein can be controlled by an inducible promoter (e.g., Tet-ON, Tet-OFF, etc.). The DNA-targeting sequence can be designed to target known transcription response elements (e.g., promoters, enhancers, etc.), known upstream activating sequences (UAS), sequences of unknown or known function that are suspected of being able to control expression of the target DNA, etc.

In some embodiments, multiple subject polynucleotides are used simultaneously in the same cell to simultaneously modulate transcription at different locations on the same target DNA or on different target DNAs. In some embodiments, two or more subject polynucleotides target the same gene or transcript or locus. In some embodiments, two or more subject polynucleotides target different unrelated loci. In some embodiments, two or more subject polynucleotides target different, but related loci.

Because the subject polynucleotides are small and robust, they can be simultaneously present on the same expression vector and can even be under the same transcriptional control if so desired. In some embodiments, two or more (e.g., 3 or more, 4 or more, 5 or more, 10 or more, 15 or more, 20 or more, 25 or more, 30 or more, 35 or more, 40 or more, 45 or more, or 50 or more) subject polynucleotides are simultaneously expressed in a target cell, from the same or different vectors. The expressed subject polynucleotides can be differently recognized by orthogonal dCas9 proteins from different bacteria, such as S. pyogenes, S. thermophilus, L. innocua, and N. meningitidis.

To express multiple subject polynucleotides, an artificial RNA processing system mediated by the Csy4 endoribonuclease can be used. Multiple subject polynucleotides can be concatenated into a tandem array on a precursor transcript (e.g., expressed from a U6 promoter), and separated by Csy4-specific RNA sequence. Co-expressed Csy4 protein cleaves the precursor transcript into multiple subject polynucleotides. Advantages for using an RNA processing system include: first, there is no need to use multiple promoters or vectors; second, since all subject polynucleotides are processed from a precursor transcript, their concentrations are normalized for similar wt Cas9/Cas9 nickase/dCas9-binding.

Csy4 is a small endoribonuclease (RNase) protein derived from bacteria *Pseudomonas aeruginosa*. Csy4 specifically recognizes a minimal 17-bp RNA hairpin, and exhibits rapid (<1 min) and highly efficient (>99.9) RNA cleavage. Unlike most RNases, the cleaved RNA fragment remains stable and functionally active. The Csy4-based RNA cleavage can be repurposed into an artificial RNA processing system. In this system, the 17-bp RNA hairpins are inserted between multiple RNA fragments that are transcribed as a precursor transcript from a single promoter. Co-expression of Csy4 is effective in generating individual RNA fragments.

6. Host Cells

A method of the present invention to modulate transcription may be employed to induce transcriptional modulation in mitotic or post-mitotic cells in vivo and/or ex vivo and/or in vitro. Because the subject polynucleotide provides specificity by hybridizing to target polynucleotide sequence of a target DNA, a mitotic and/or post-mitotic cell can be any of a variety of host cell, where suitable host cells include, but are not limited to, a bacterial cell; an archaeal cell; a single-celled eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell; an animal cell; a cell from an invertebrate animal (e.g., an insect, a cnidarian, an echinoderm, a nematode, etc.); a eukaryotic parasite (e.g., a malarial parasite, e.g., *Plasmodium falciparum*; a helminth; etc.); a cell from a vertebrate animal (e.g., fish, amphibian, reptile, bird, mammal); a mammalian cell, e.g., a rodent cell, a human cell, a non-human primate cell, etc. Suitable host cells include naturally-occurring cells; genetically modified cells (e.g., cells genetically modified in a laboratory, e.g., by the "hand of man"); and cells manipulated in vitro in any way. In some cases, a host cell is isolated or cultured.

Any type of cell may be of interest (e.g., a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells," "primary cell lines," and "primary cultures" are used interchangeably herein to refer to cells and cells cultures that have been derived from a subject and allowed to grow in vitro for a limited number of passages, i.e. splittings, of the culture. For example, primary cultures include cultures that may have been passaged 0 times, 1 time, 2 times, 4 times, 5 times, 10 times, or 15 times, but not enough times go through the crisis stage. Primary cell lines can be are maintained for fewer than 10 passages in vitro. Target cells are in many embodiments unicellular organisms, or are grown in culture.

If the cells are primary cells, such cells may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% dimethyl sulfoxide (DMSO), 50% serum, 40% buffered medium, or other solutions commonly used in the art to preserve cells at such freezing temperatures, and thawed in a manner as commonly known in the art for thawing frozen cultured cells.

7. Introducing Nucleic Acid into a Host Cell

A subject polynucleotide, a nucleic acid comprising a nucleotide sequence encoding same, or a nucleic acid comprising a nucleotide sequence encoding the subject Cas9 protein (e.g., wt, nickase, or dCas9 protein) or PUF domain fusion, can be introduced into a host cell by any of a variety of well-known methods.

Methods of introducing a nucleic acid into a host cell are known in the art, and any known method can be used to introduce a nucleic acid (e.g., vector or expression construct) into a stem cell or progenitor cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., *Adv. Drug Deliv. Rev.*, pii: 50169-409X(12) 00283-9.doi:10.1016/j.addr.2012.09.023), and the like.

Thus the present invention also provides an isolated nucleic acid comprising a nucleotide sequence encoding a subject polynucleotide. In some cases, a subject nucleic acid also comprises a nucleotide sequence encoding a subject Cas9 protein (e.g., wt, nickase, or dCas9 protein) and/or a subject PUF domain fusion.

In some embodiments, a subject method involves introducing into a host cell (or a population of host cells) one or more nucleic acids (e.g., vectors) comprising nucleotide sequences encoding a subject polynucleotide and/or a subject Cas9 protein (e.g., wt, nickase, or dCas9 protein) and/or a subject PUF domain fusion. In some embodiments a host cell comprising a target DNA is in vitro. In some embodiments a host cell comprising a target DNA is in vivo. Suitable nucleic acids comprising nucleotide sequences encoding a subject polynucleotide and/or a subject Cas9 protein (e.g., wt, nickase, or dCas9 protein) and/or a subject PUF domain fusion include expression vectors, where the expression vectors may be recombinant expression vector.

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., *Invest Opthalmol. Vis. Sci.,* 35:2543-2549, 1994; Borras et al., *Gene Ther.,* 6:515-524, 1999; Li and Davidson, *Proc. Natl. Acad. Sci. USA,* 92:7700-7704, 1995; Sakamoto et al., *Hum. Gene Ther.,* 5:1088-1097, 1999; WO 94/12649, WO 93/03769; WO 93/19191; WO 94/28938; WO 95/11984 and WO 95/00655); adeno-associated virus (see, e.g., Ali et al., *Hum. Gene Ther.,* 9:81-86, 1998, Flannery et al., *Proc. Natl. Acad. Sci. USA,* 94:6916-6921, 1997; Bennett et al., *Invest Opthalmol Vis Sci* 38:2857-2863, 1997; Jomary et al., *Gene Ther.,* 4:683-690, 1997, Rolling et al., *Hum. Gene Ther.,* 10:641-648, 1999; Ali et al., *Hum. Mol. Genet.,* 5:591-594, 1996; Srivastava in WO 93/09239, Samulski et al., *J. Vir.,* 63:3822-3828, 1989; Mendelson et al., *Virol.,* 166: 154-165, 1988; and Flotte et al., *Proc. Natl. Acad. Sci. USA,* 90: 10613-10617, 1993); SV40; herpes simplex virus; human immunodeficiency virus (see, e.g., Miyoshi et al., *Proc. Natl. Acad. Sci. USA,* 94: 10319-23, 1997; Takahashi et al., *J. Virol.,* 73:7812-7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, HIV virus, myeloproliferative sarcoma virus, and mammary tumor virus); and the like.

Numerous suitable expression vectors are known to those skilled in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al., *Methods in Enzymology,* 153:516-544, 1987).

In some embodiments, a nucleotide sequence encoding a subject polynucleotide and/or a subject Cas9 protein (e.g., wt, nickase, or dCas9 protein) and/or a subject PUF domain fusion is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a subject polynucleotide and/ or a subject Cas9 protein (e.g., wt, nickase, or dCas9 protein) and/or a subject PUF domain fusion is operably linked to multiple control elements that allow expression of the nucleotide sequence encoding the subject polynucleotide and/or a subject Cas9 protein (e.g., wt, nickase, or dCas9 protein) and/or a subject PUF domain fusion in both prokaryotic and eukaryotic cells.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.) (e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., *Nature Biotech.,* 20:497-500, 2002), an enhanced U6 promoter (e.g., Xia et al., *Nucleic Acids Res.,* 31(17):e100, 2003), a human HI promoter (HI), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g., Tet-ON, Tet-OFF, etc.), Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject Cas9 protein (e.g., wt, nickase, or dCas9 protein) or PUF domain fusion in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSEN02, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al., *Cell,* 51:7-19, 1987; and Llewellyn et al., *Nat. Med.,* 16(10): 1161-1166, 2010); a serotonin receptor promoter (see, e.g., GenBank S62283); a tyrosine hydroxylase promoter (TH) (see, e.g., Oh et al., *Gene Ther.,* 16:437, 2009; Sasaoka et al., *Mol. Brain Res.,* 16:274, 1992; Boundy et al., *Neurosci.,* 18:9989, 1998; and Kaneda et al., *Neuron,* 6:583-594, 1991); a GnRH promoter (see, e.g., Radovick et al., *Proc. Natl. Acad. Sci. USA,* 88:3402-3406, 1991); an L7 promoter (see, e.g., Oberdick et al., *Science,* 248:223-226, 1990); a DNMT promoter (see, e.g., Bartge et al., *Proc. Natl. Acad. Sci. USA,* 85:3648-3652, 1988); an enkephalin promoter (see, e.g., Comb et al., *EMBO J.,* 17:3793-3805, 1988); a myelin basic protein (MBP) promoter; a $Ca^{2+}$-calmodulin-dependent protein kinase II-alpha (CamKIIa) promoter (see, e.g., Mayford et al., *Proc. Natl. Acad. Sci. USA,* 93: 13250, 1996; and Casanova et al., *Genesis,* 31:37, 2001); a CMV enhancer/platelet-derived growth factor-β promoter (see, e.g., Liu et al., *Gene Therapy,* 11:52-60, 2004); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al., *Endocrinol.* 138: 1604, 1997; Ross et al., *Proc. Natl. Acad. Sci. USA,* 87:9590, 1990; and Pavjani et al., *Nat. Med.,* 11:797, 2005); a glucose transporter-4 (GLUT4) promoter (see, e.g., Knight et al., *Proc. Natl. Acad. Sci. USA,* 100: 14725, 2003); a fatty acid translocase (FAT/CD36) promoter (see, e.g., Kuriki et al., *Biol. Pharm. Bull.,* 25: 1476, 2002; and Sato et al., *Biol. Chem.* 277: 15703, 2002); a stearoyl-CoA desaturase-1 (SCD1) promoter (Tabor et al., *Biol. Chem.* 274:20603, 1999); a leptin promoter (see, e.g., Mason et al., *Endocrinol.* 139: 1013, 1998; and Chen et al., *Biochem. Biophys. Res. Comm.,* 262: 187, 1999); an adiponectin promoter (see, e.g., Kita et al., *Biochem. Biophys. Res. Comm.,* 331:484, 2005; and Chakrabarti, *Endocrinol.* 151:2408, 2010); an adipsin promoter (see, e.g., Piatt et al., *Proc. Natl. Acad. Sci. USA,* 86:7490, 1989); a resistin promoter (see, e.g., Seo et al., *Molec. Endocrinol.,* 17: 1522, 2003); and the like.

Cardiomyocyte-specific spatially restricted promoters include, but are not limited to control sequences derived from the following genes: myosin light chain-2, a-myosin heavy chain, AE3, cardiac troponin C, cardiac actin, and the like. Franz et al., *Cardiovasc. Res.,* 35:560-566, 1997; Robbins et al., *Ann. N.Y. Acad. Sci.,* 752:492-505, 1995; Linn et al., *Circ. Res.,* 76:584-591, 1995; Parmacek et al., *Mol. Cell. Biol.,* 14:1870-1885, 1994; Hunter et al., *Hypertension,* 22:608-617, 1993; and Sartorelli et al., *Proc. Natl. Acad. Sci.,* 89:4047-4051, 1992.

Smooth muscle-specific spatially restricted promoters include, but are not limited to an SM22a promoter (see, e.g., Akyurek et al., *Mol. Med.,* 6:983, 2000; and U.S. Pat. No. 7,169,874); a smoothelin promoter (see, e.g., WO 2001/018048); an a-smooth muscle actin promoter; and the like. For example, a 0.4 kb region of the SM22a promoter, within which lie two CArG elements, has been shown to mediate vascular smooth muscle cell-specific expression (see, e.g., Kim et al., *Mol. Cell. Biol.,* 17:2266-2278, 1997; Li et al., *J. Cell Biol.,* 132:849-859, 1996; and Moessler et al., *Development,* 122:2415-2425, 1996).

Photoreceptor-specific spatially restricted promoters include, but are not limited to, a rhodopsin promoter; a rhodopsin kinase promoter (Young et al., *Ophthalmol. Vis. Sci.,* 44:4076, 2003); a beta phosphodiesterase gene promoter (Nicoud et al., *Gene Med.,* 9: 1015, 2007); a retinitis pigmentosa gene promoter (Nicoud et al., 2007, supra); an interphotoreceptor retinoid-binding protein (IRBP) gene enhancer (Nicoud et al. (2007) supra); an IRBP gene promoter (Yokoyama et al., *Exp. Eye Res.,* 55:225, 1992); and the like.

8. Libraries

The present invention also provides a plurality or library of the subject polynucleotide sequences, or a plurality or library of the vectors encoding the same. The latter may comprise a library of recombinant expression vectors comprising nucleotides encoding the subject polynucleotides.

A subject library can comprise from about 10 individual members to about $10^{12}$ individual members; e.g., a subject library can comprise from about 10 individual members to about $10^2$ individual members, from about $10^2$ individual members to about $10^3$ individual members, from about $10^3$ individual members to about $10^5$ individual members, from about $10^5$ individual members to about $10^7$ individual members, from about $10^7$ individual members to about $10^9$ individual members, or from about $10^9$ individual members to about $10^{12}$ individual members.

In certain embodiments, two of the vectors differ in the encoded polynucleotides in their respective DNA-targeting sequences, Cas9-binding sequences, and/or the copy number, identity (e.g., sequence, or binding specificity), or relative order of the PBS.

For example, in certain embodiments, an "individual member" of a subject library differs from other members of the library in the nucleotide sequence of the DNA-targeting sequence of the subject polynucleotide. Thus, e.g., each individual member of a subject library can comprise the same or substantially the same nucleotide sequence of the Cas9-binding sequence as all other members of the library; and can comprise the same or substantially the same nucleotide sequence of the PBS as all other members of the library; but differs from other members of the library in the nucleotide sequence of the DNA-targeting sequence of the subject polynucleotide. In this way, the library can comprise members that bind to different target polynucleotide sequences that are either on the same target gene or on different target genes.

In a related embodiment, members of the library may differ such that different DNA-targeting sequences are associated with different PBS, such that different target DNA can be independently regulated—e.g., some target genes are transcriptionally activated (and optionally labeled by a first fluorescent color), while others are transcriptionally repressed (and optionally labeled by a second fluorescent color).

In certain other embodiments, an individual member of a subject library differs from other members of the library in the nucleotide sequence of the Cas9-binding sequence of the subject polynucleotide. Thus, e.g., each individual member of a subject library can comprise the same or substantially the same nucleotide sequence of the DNA-targeting sequence as all other members of the library; and can comprise the same or substantially the same nucleotide sequence of the PBS as all other members of the library; but differs from other members of the library in the nucleotide sequence of the Cas9-binding sequence of the subject polynucleotide. In this way, the library can comprise members that bind to different orthogonal Cas9 protein (e.g., wt, nickase, or dCas9 protein) from different species, allowing separately and parallelly regulatable systems in the same host cell.

In certain other embodiments, an individual member of a subject library differs from other members of the library in the nucleotide sequence of the PBS of the subject polynucleotide. Thus, e.g., each individual member of a subject library can comprise the same or substantially the same nucleotide sequence of the DNA-targeting sequence as all other members of the library; and can comprise the same or substantially the same nucleotide sequence of the Cas9-binding sequence as all other members of the library; but differs from other members of the library in the nucleotide sequence of the PBS of the subject polynucleotide.

9. Exemplary Utilities

A method for modulating transcription according to the present invention finds use in a variety of applications, including research applications; diagnostic applications; industrial applications; and treatment applications.

Research applications may include, e.g., determining the effect of reducing or increasing transcription of a target nucleic acid on, e.g., development, metabolism, expression of a downstream gene, and the like.

High through-put genomic analysis can be carried out using a subject transcription modulation method, in which only the DNA-targeting sequence of the subject polynucleotide needs to be varied, while the Cas9-binding sequence and the PBS can (in some cases) be held constant. A library (e.g., a subject library) comprising a plurality of nucleic acids used in the genomic analysis would include: a promoter operably linked to a subject polynucleotide-encoding nucleotide sequence, where each nucleic acid would include a different DNA-targeting sequence, a common Cas9-binding sequence, and a common PBS. A chip could contain over $5 \times 10^4$ unique polynucleotide of the invention.

Applications would include large-scale phenotyping, gene-to-function mapping, and meta-genomic analysis.

The subject methods disclosed herein can also find use in the field of metabolic engineering. Because transcription levels can be efficiently and predictably controlled by designing an appropriate DNA-targeting RNA, as disclosed herein, the activity of metabolic pathways (e.g., biosynthetic pathways) can be precisely controlled and tuned by controlling the level of specific enzymes (e.g., via increased or decreased transcription) within a metabolic pathway of interest. Metabolic pathways of interest include those used for chemical (fine chemicals, fuel, antibiotics, toxins, agonists, antagonists, etc.) and/or drug production.

Biosynthetic pathways of interest include but are not limited to (1) the mevalonate pathway (e.g., HMG-CoA reductase pathway) (converts acetyl-CoA to dimethylallyl pyrophosphate (DMAPP) and isopentenyl pyrophosphate (IPP), which are used for the biosynthesis of a wide variety of biomolecules including terpenoids/isoprenoids), (2) the non-mevalonate pathway (i.e., the "2-C-methyl-D-erythritol 4-phosphate/1-deoxy-D-xylulose 5-phosphate pathway" or "MEP/DOXP pathway" or "DXP pathway") (also produces DMAPP and IPP, instead by converting pyruvate and glyceraldehyde 3-phosphate into DMAPP and IPP via an alternative pathway to the mevalonate pathway), (3) the polyketide synthesis pathway (produces a variety of polyketides via a variety of polyketide synthase enzymes. Polyketides include naturally occurring small molecules used for chemotherapy (e. g., tetracyclin, and macrolides) and industrially important polyketides include rapamycin (immunosuppressant), erythromycin (antibiotic), lovastatin (anticholesterol drug), and epothilone B (anticancer drug)), (4) fatty acid synthesis pathways, (5) the DAHP (3-deoxy-D-arabino-heptulosonate 7-phosphate) synthesis pathway, (6) pathways that produce potential biofuels (such as short-chain alcohols and alkane, fatty acid methyl esters and fatty alcohols, isoprenoids, etc.), etc.

The methods disclosed herein can also be used to design integrated networks (i.e., a cascade or cascades) of control. For example, a subject polynucleotide/Cas9 protein (e.g., wt, nickase, or dCas9 protein)/PUF domain fusion may be used to control (i.e., modulate, e.g., increase, decrease) the expression of another polynucleotide/Cas9 protein (e.g., wt, nickase, or dCas9 protein)/PUF domain fusion. For example, a first subject polynucleotide may be designed to target the modulation of transcription of a second Cas9 protein (e.g., wt, nickase, or dCas9 protein) or PUF domain fusion with a function that is different than the first PUF domain fusion (e.g., methyltransferase activity, demethylase activity, acetyltansferase activity, deacetylase activity, etc.). In addition, because different Cas9 proteins (e.g., wt, nickase, or dCas9 protein) (e.g., derived from different species) may require a different Cas9 handle (i.e., Cas9-binding sequence), the second Cas9 protein (e.g., wt, nickase, or dCas9 protein) can be derived from a different species than the first Cas9 protein (e.g., wt, nickase, or dCas9 protein) above. Thus, in some cases, the second Cas9 protein (e.g., wt, nickase, or dCas9 protein) can be selected such that it may not interact with the first subject polynucleotide. In other cases, the second Cas9 protein (e.g., wt, nickase, or dCas9 protein) can be selected such that it does interact with the first subject polynucleotide. In some such cases, the activities of the two (or more) Cas9 proteins (e.g., wt, nickase, or dCas9 protein)/PUF domain fusions may compete (e.g., if the polypeptides have opposing activities) or may synergize (e.g., if the polypeptides have similar or synergistic activities). Likewise, as noted above, any of the complexes (i.e., polynucleotide/Cas9 protein (e.g., wt, nickase, or dCas9 protein)/PUF domain fusion) in the network can be designed to control other polynucleotide/Cas9 protein (e.g., wt, nickase, or dCas9 protein)/PUF domain fusion. Because a subject polynucleotide/Cas9 protein (e.g., wt, nickase, or dCas9 protein)/PUF domain fusion can be targeted to any desired DNA sequence, the methods described herein can be used to control and regulate the expression of any desired target. The integrated networks (i.e., cascades of interactions) that can be designed range from very simple to very complex, and are without limit.

In a network wherein two or more components (e.g., polynucleotide/Cas9 protein (e.g., wt, nickase, or dCas9 protein)/PUF domain fusion) are each under regulatory control of another polynucleotide/Cas9 protein (e.g., wt, nickase, or dCas9 protein)/PUF domain fusion complex, the level of expression of one component of the network may affect the level of expression (e.g., may increase or decrease the expression) of another component of the network.

Through this mechanism, the expression of one component may affect the expression of a different component in the same network, and the network may include a mix of components that increase the expression of other components, as well as components that decrease the expression of other components. As would be readily understood by one of skill in the art, the above examples whereby the level of expression of one component may affect the level of expression of one or more different component(s) are for illustrative purposes, and are not limiting. An additional layer of complexity may be optionally introduced into a network when one or more components are modified (as described above) to be manipulatable (i.e., under experimental control, e.g., temperature control; drug control, i.e., drug inducible control; light control; etc.).

As one non-limiting example, a first subject polynucleotide can bind to the promoter of a second subject polynucleotide, which controls the expression of a target therapeutic/metabolic gene. In such a case, conditional expression of the first subject polynucleotide indirectly activates the therapeutic/metabolic gene. RNA cascades of this type are useful, for example, for easily converting a repressor into an activator, and can be used to control the logics or dynamics of expression of a target gene.

A subject transcription modulation method can also be used for drug discovery and target validation.

10. Kits

The present invention also provides a kit for carrying out a subject method. A subject kit may comprise: a) a polynucleotide of the present invention, or a nucleic acid (e.g., vector) comprising a nucleotide sequence encoding the same; optionally, b) a subject Cas9 protein (e.g., wt, nickase, or dCas9 protein), or a vector encoding the same (including an expressible mRNA encoding the same); and optionally, c) one or more subject PUF domain fusion each comprising a PUF domain fused to an effector domain that may be the same or different among the different PUF domain fusions, or a vector encoding the same (including an expressible mRNA encoding the same).

In certain embodiments, one or more of a)-c) may be encoded by the same vector.

In certain embodiments, the kit also comprises one or more buffers or reagents that facilitate the introduction of any one of a)-c) into a host cell, such as reagents for transformation, transfection, or infection.

For example, a subject kit can further include one or more additional reagents, where such additional reagents can be selected from: a buffer; a wash buffer; a control reagent; a control expression vector or RNA polynucleotide; a reagent for in vitro production of the wt or dCas9 or PUF domain fusion from DNA; and the like.

Components of a subject kit can be in separate containers; or can be combined in a single container.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example 1 sgRNA Scaffold Remains Functional with Insertion of 47 Copies of Engineered Pumilio Binding Sites This example demonstrates that the subject 3-component CRISPR/Cas complex/system can have at least 47 copies of the engineered 8-mer Pumilio homologue domain-binding sequences (PBSs) at the 3' end of sgRNA, without substantially affecting the function of the dCas9/sgRNA complex.

In particular, to test whether appending PBS to the 3' end of sgRNA affects sgRNA function, a series of modified Tet-targeting (sgTetO) or non-targeting control (sgControl) sgRNA were generated, with 0 copy, 5 copies, 15 copies, 25 copies, and 47 copies of the 8-mer Pumilio homologue domain-binding sequence (PBS) for PUF (3-2) (also simply referred to as PUFa) [PBS32 or PBSa: 5'-UGUAUgUA-3'], PUF(6-2/7-2) (also simply referred to as PUFb) [PBS6272 or PBSb: 5'-UugAUAUA-3']. See FIG. 1A. The ability of these constructs to direct the dCas9-VP64 transcriptional activator to activate tdTomato expression in a HEK293T/TetO::tdTomato cell line was tested.

Figure 1B:
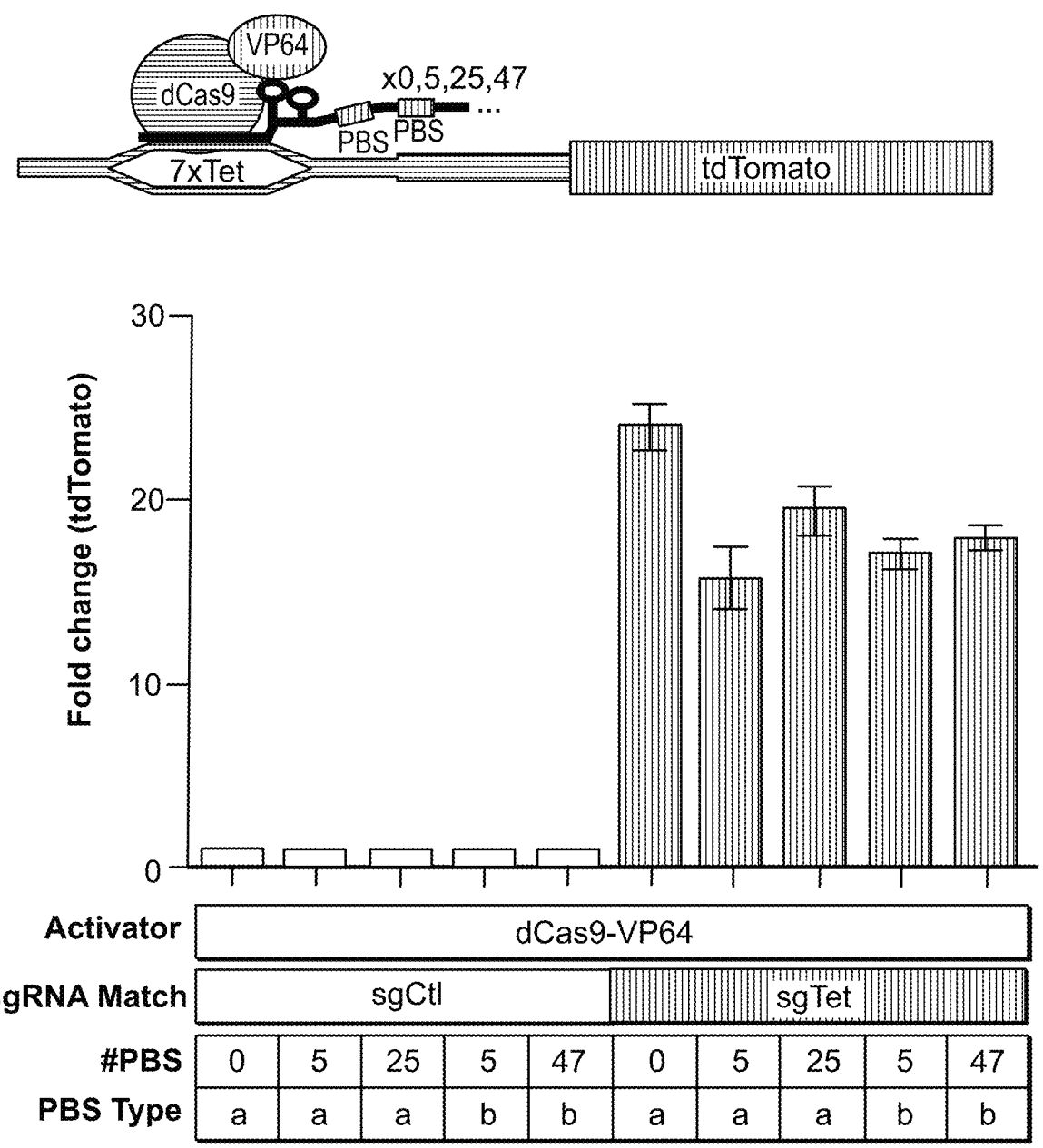
Figure 1C:
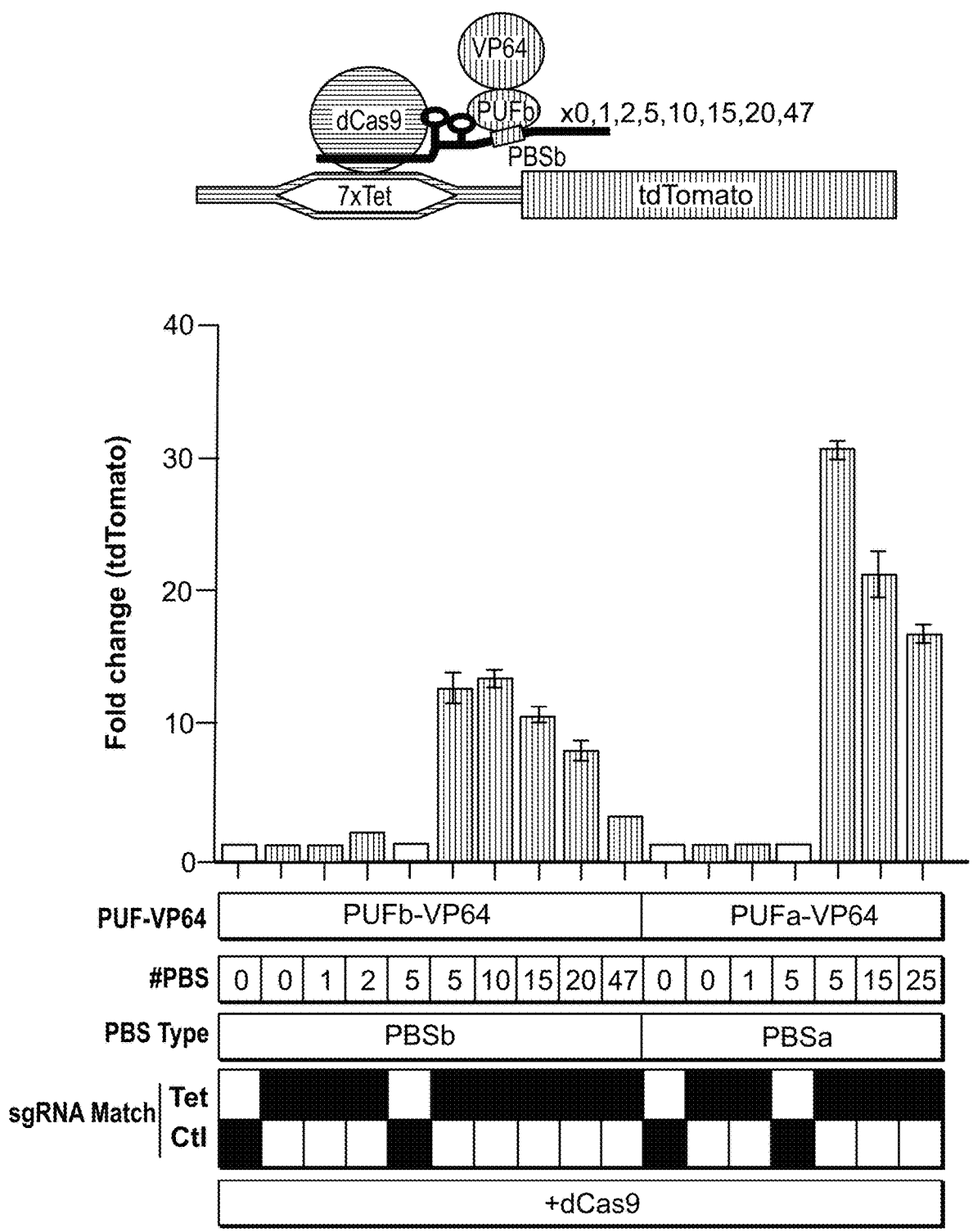

Cells were transfected with dCas9-VP64 with the different sgRNA scaffolds, and were analyzed by fluorescent-activated cell sorting (FACS) two days after transfection (FIG. 1B). All the control non-targeting sgRNAs did not activate tdTomato expression. Meanwhile, all the Tet-targeting sgRNAs with different number of PBS could direct dCas9-VP64 to activate tdTomato expression, showing that insertion of at least 47 copies of 8-mer sites do not substantially impact the activity of sgRNA in directing dCas9-VP64 to its targets (FIG. 1C).

Under the test condition, and for both PUFa-VP64/PBSa and PUFb-VP64/PBSb, 5-10 copies of PBS appended to the sgRNA were best able to activate the target transgene. Meanwhile, 15, 20, and 47 copies of PBS led to slightly lower, albeit still substantial transgene activation (FIG. 1C).

Example 2 the Subject 3-Component CRISPR/Cas Complexes/Systems are Orthogonal to Each Other Due to the Specificity of the Engineered Pumilio with the Cognate 8-Mer Binding Sites This example demonstrates that specificity between the differently programmed PUF domains and their corresponding sgRNA with their cognate 8-mer motifs provide independence or orthogonality between each of the subject 3-component CRISPR/Cas complex/system.

Fusions of PUF(3-2)::VP64 and PUF(6-2/7-2)::VP64, which interacts with sgRNA (sgRNA-PBS32) with 5'-UGUAUgUA-3' binding sites and sgRNA-PBS6272 with 5'-UugAUAUA-3' binding sites, respectively, were created, and their activity to turn on tdTomato expression in conjunction with dCas9 was tested. In addition, two additional pairs, PUFw-VP64 recognizing PBSw (5'-UGUAUAUA-3') and PUFc-VP64 recognizing PBSc (5'-UugAUgUA-3'), were also constructed to test their ability to activate the same TetO::tdTomato expression in conjunction with dCas9 (FIG. 1D).

Figure 1D:
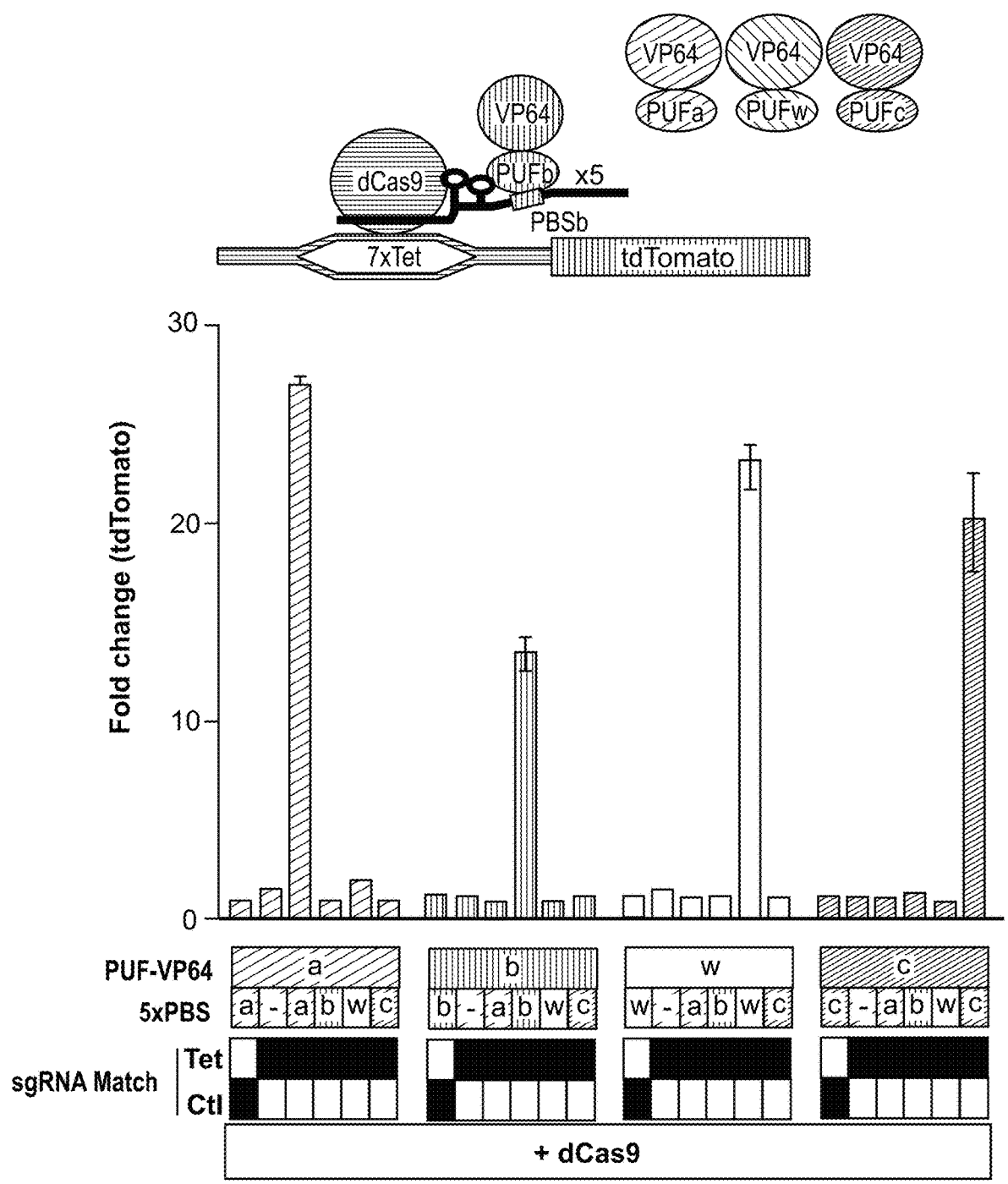

As shown in FIG. 1D, PUF::VP64 can activate tdTomato expression only when the sgRNA with the cognate binding sites were provided. This demonstrates that the subject 3-component CRISPR/Cas complex/system provides independence or orthogonality of effector function based on the pairing of PUF domains and their 8-mer binding sites on the sgRNA-PBS. Impressively, although PBSa and PBSw binding sites only differ by one nucleotide, their gene activation remains target-specific, demonstrating the high specificity of the subject 3-component CRISPR/Cas complex/system.

Example 3 the Subject 3-Component CRISPR/Cas Complex/System Allows Assembly of Protein Complex at Target Loci This example demonstrates that protein complexes with two or more different protein components can be assembled on sgRNA and operate at defined loci using the subject system.

Figure 2A:
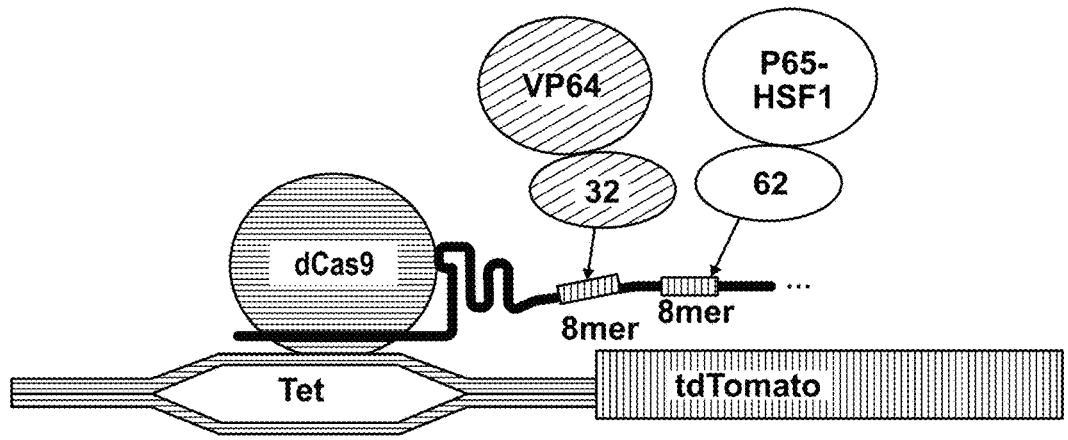
FIGS. 2A and 2B relate to the assembly of the subject 3-component CRISPR/Cas complex/system comprising VP64 and P65-HSF1.
Figure 2B:
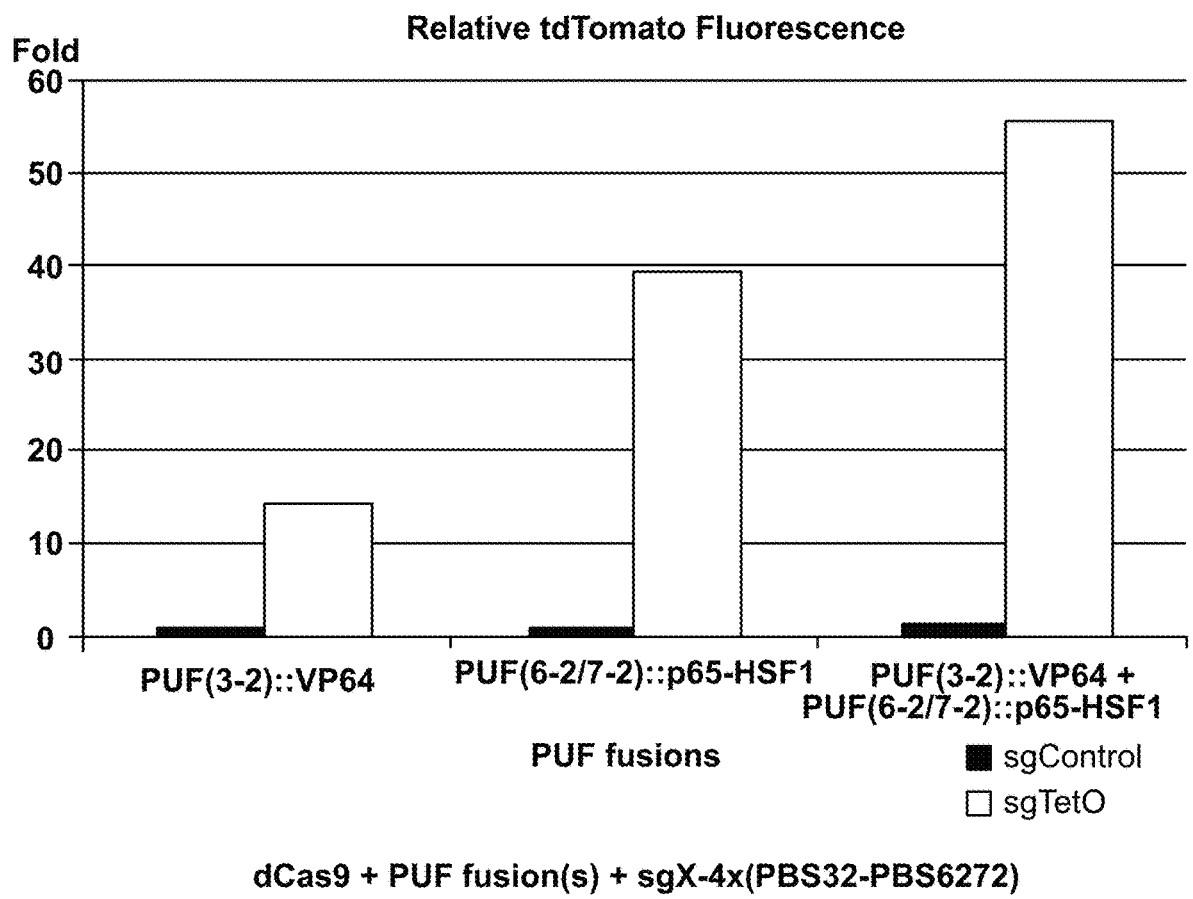

Specifically, p65-HSF1 has recently been shown to be a potent activator domain. An sgRNA with both PBS32 and PBS6272 positioned next to each other, and PUF(3-2)::VP64 and PUF(6-2/7-2)::p65-HSF1 fusions that would occupy the two different sites, were generated (FIG. 2A). Co-transfection of both PUF(3-2)::VP64 and PUF(6-2/7-2)::p65-HSF1 induced a tdTomato fluorescence, with an intensity about the sum of the fluorescent intensity resulting from transfecting the single activators alone. This indicates that sgRNA with binding sites for both PUF(3-2) and PUF(6-2/7-2) allows both fusion proteins of both types to assemble on the targeted genomic locus.

Figure 2C:
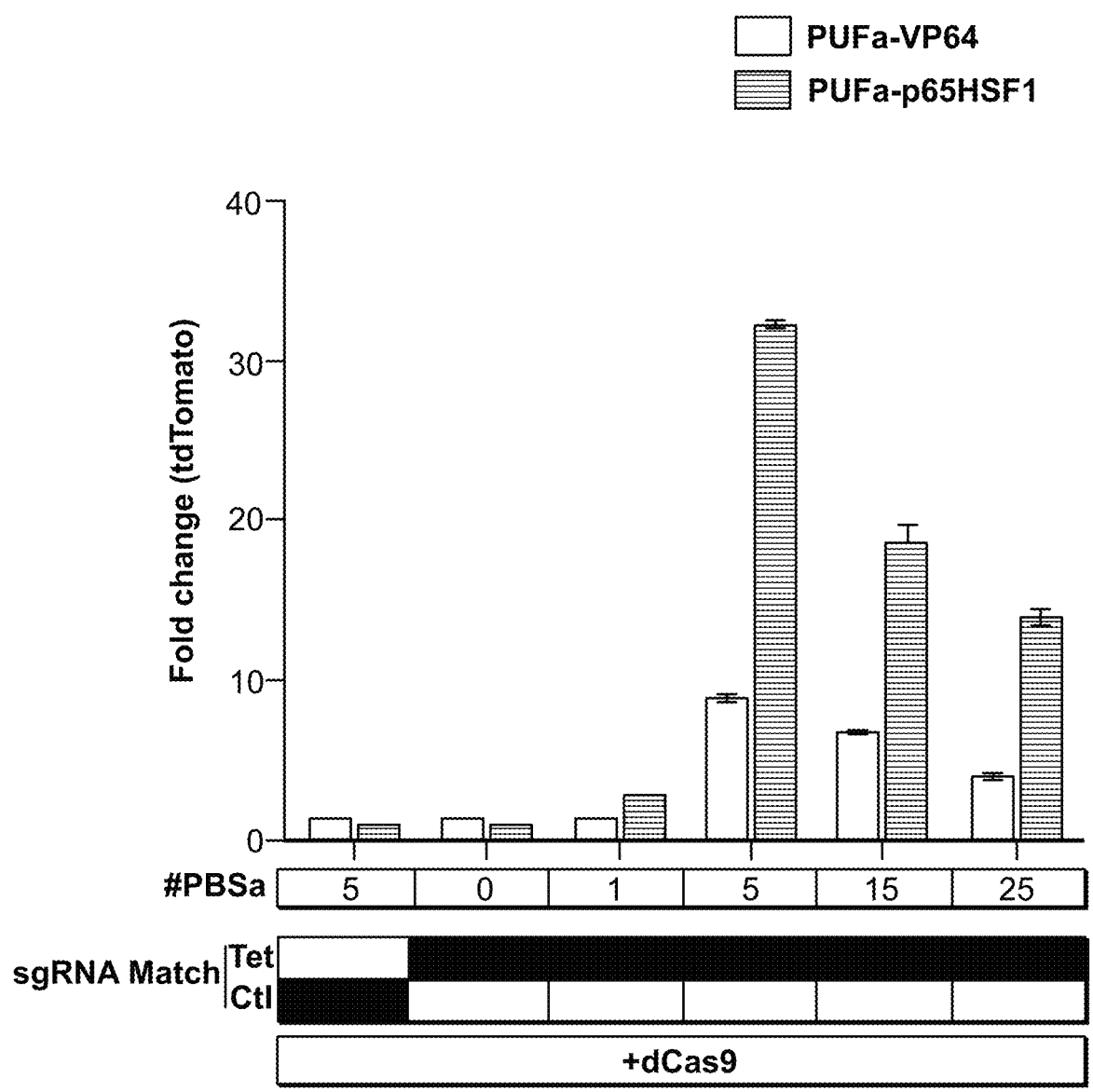
FIG. 2C shows comparison of the subject 3-component system activator using VP64 (PUFa::VP64; red columns) versus p65HSF1 (PUFa::p65HSF1; blue columns) as the activation domain in conjunction with Control sgRNA with 5×PBSa or TetO-targeting sgRNA with 0, 1, 5, 15, or 25 copies of PBSa. Columns show mean fold change (with S.E.M.; n=3) of tdTomato fluorescence relative to experiments using control sgRNA (sgCtl). The legend indicates the number of PBSa (#PBSa) on the sgRNA-PBS as well as the DNA match indicated by the shaded boxes.

A recent paper has tested both VP64 and p65HSF1 as transcriptional activation domains, and found p65HSF1 to be a more potent activator. To directly compare these two transcriptional activation domains, p65HSF1 PUF fusion (PUFa-p65HSF1) and VP64 PUF fusion (PUFa-VP64) were used to activate the TetO::tdTomato transgene using sgRNA with different number of PBSa (FIG. 2C). PUFa-p65HSF1 provided up to 3 times more activation as did PUFa-VP64. Activation was observed even with only one PBSa (previously not observed with PUFa-VP64 module). Thus p65HSF1 is confirmed to be a more potent transcriptional activation domain than VP64.

Example 4 the Subject 3-Component CRISPR/Cas Complex/System can Activate Endogenous Genes More Efficiently than dCas9 Direct Fusion with Activator We previously used a cocktail of 3-4 sgRNAs per gene to achieve robust endogenous gene activation of OCT4 and SOX2 using a dCas9-VP160 direct fusion while single sgRNAs failed to induce much activation (data not shown).

This example demonstrates that recruitment of multiple molecules of activator domains via multiple PBS on the sgRNA-PBS in the subject system increases transactivation activity, thus allowing the use of fewer sgRNAs to achieve endogenous gene activation.

Figure 3A:
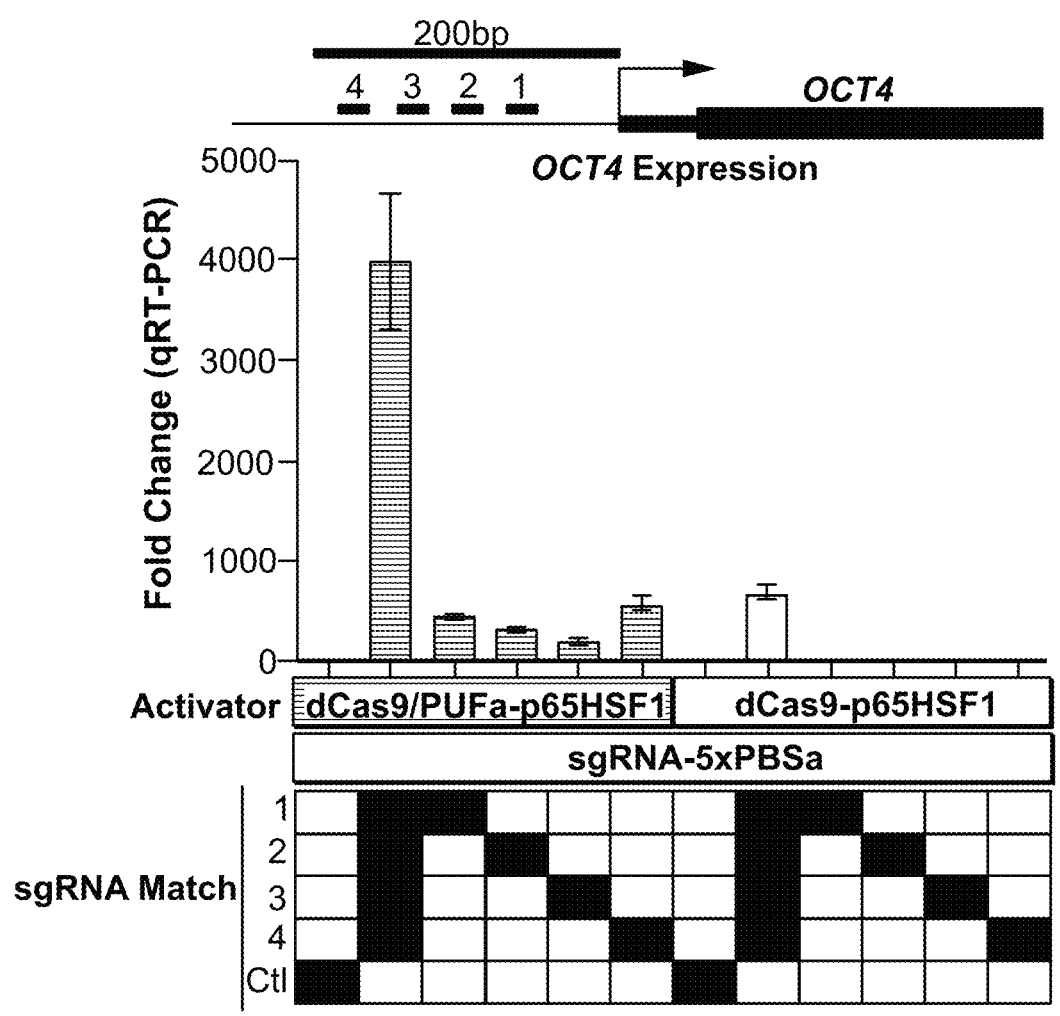
FIGS. 3A-3D show that the subject system allows for multimerization of activator to achieve robust endogenous gene activation.
Figure 3B:
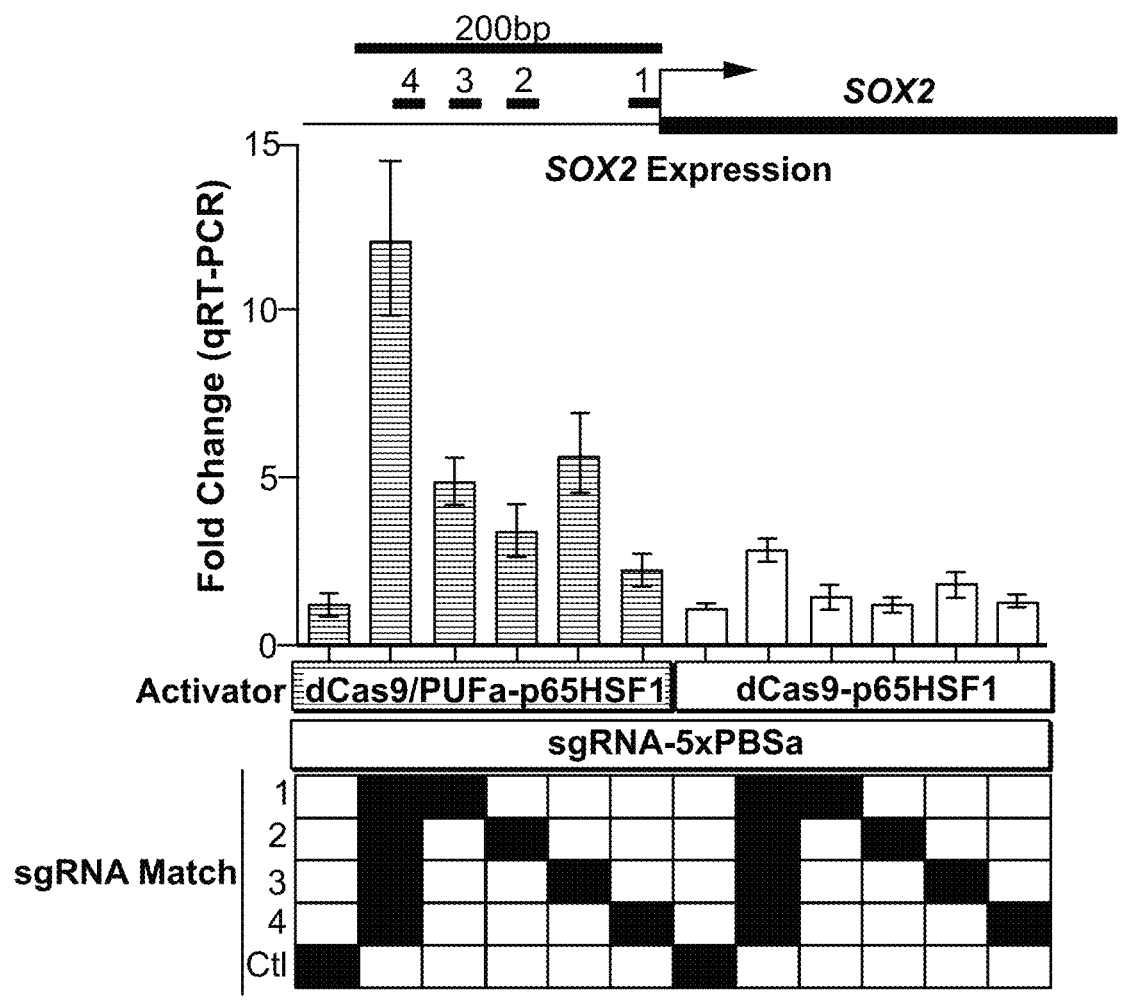
Figure 3C:
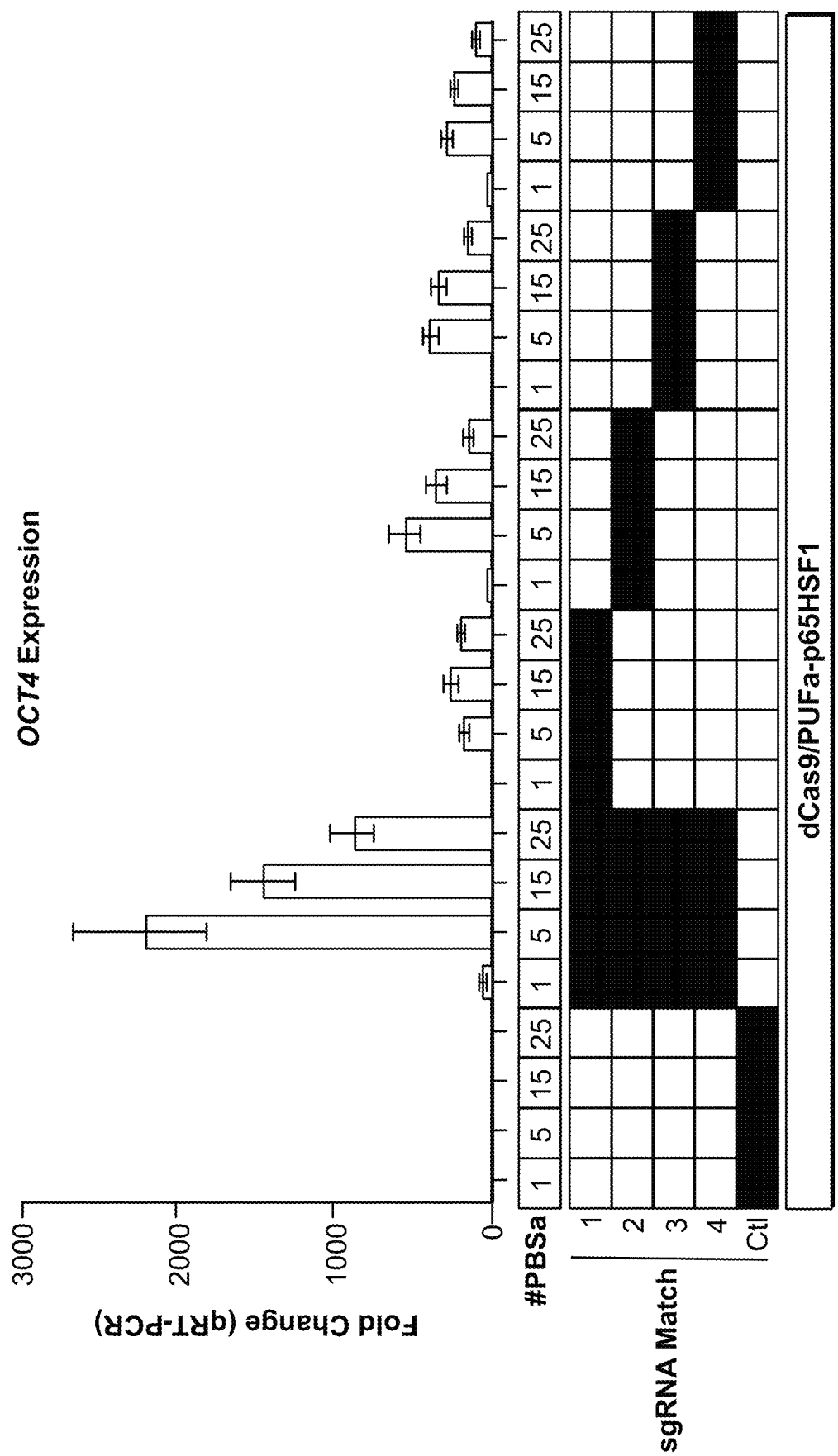

Specifically, activation of endogenous genes OCT4 and SOX2 in HEK293T were compared using the subject system with a direct dCas9-p65HSF1 activator using either a cocktail of four sgRNA-PBS per gene, or individual sgRNA-PBS (FIGS. 3A and 3B). Higher activation was observed using the subject 3-Component CRISPR/Cas Complex/System compared to direct fusion in the mixed sgRNA-PBS cocktail, as well as in single guide experiments in both OCT4 and SOX2 activation experiments (FIGS. 3A and 3B). Little to no activation by single guide targeting of direct fusion dCas9-p65HSF1 to OCT4 and SOX2 was observed, while robust activation was observed in the corresponding 3-component system experiments, showing the superior activity of the subject 3-Component CRISPR/Cas Complex/System activator over the direct fusion.

Figure 3D:
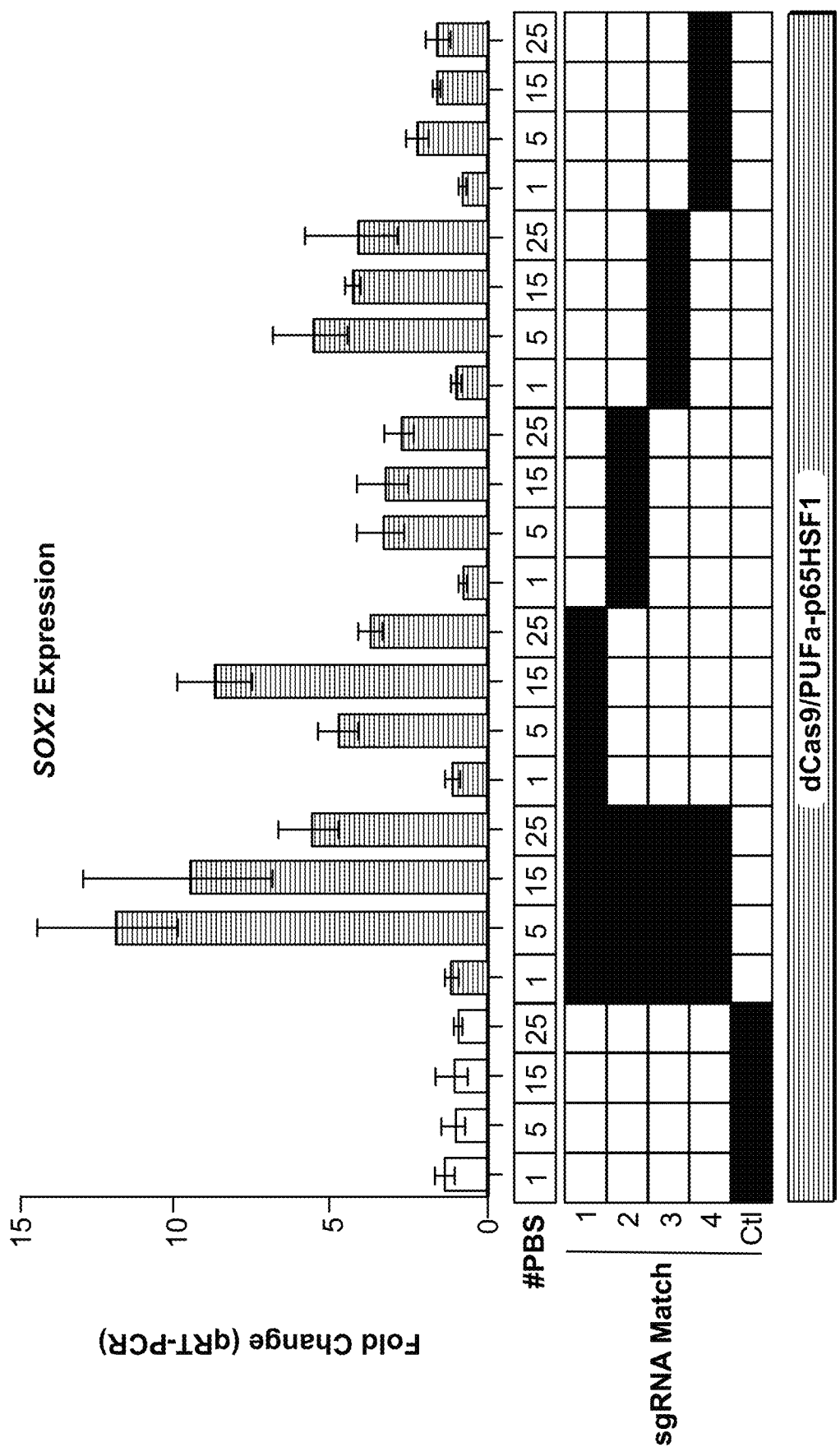

To determine the optimal number of PBSa sites on the sgRNA for OCT4 and SOX2 activation, sgRNA-PBS targeting either OCT4 or SOX2 proximal promoter with 1, 5, 15 or 25 copies of PBSa were constructed. In both OCT4 and SOX2 experiments, we observed highest activation using 5×PBSa, in either sgRNA-5×PBSa cocktail experiments and single sgRNA-5×PBSa experiments, recapitulating the finding in the TetO::tdTomato reporter experiments (FIGS. 3D and 3E).

Example 5 The Subject 3-Component CRISPR/Cas Complex/System Allows Simultaneous Activation and Repression of Target Genes This example demonstrates that different effector functions can be assigned to each of the subject 3-component CRISPR/Cas complex/system.

Figure 4A:
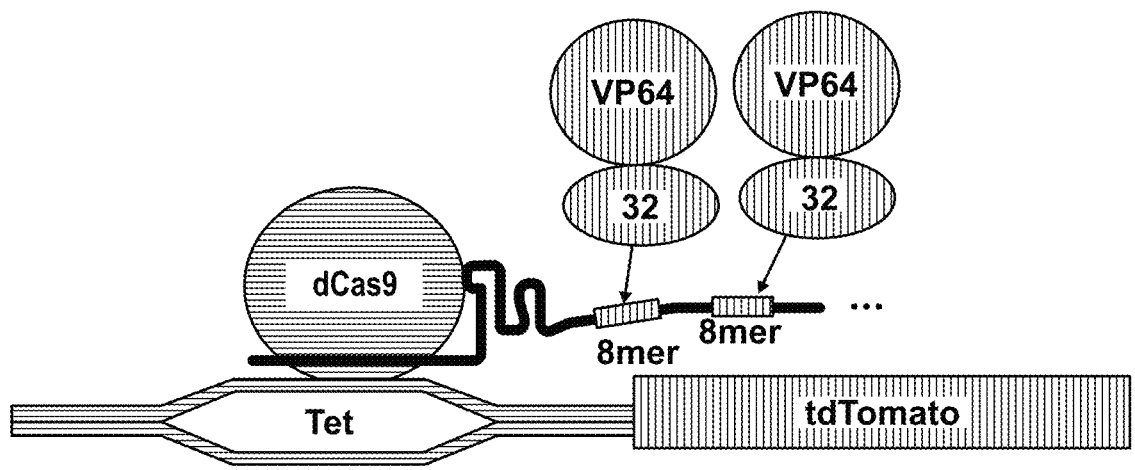
FIGS. 4A and 4B show that the subject 3-component CRISPR/Cas complex/system allows simultaneous activation and repression of two different target reporter genes.
Figure 4A:
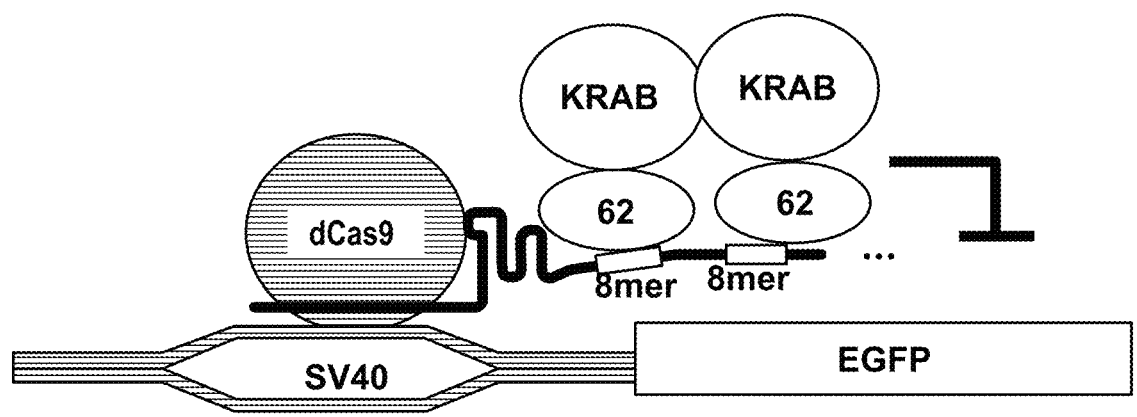
Figure 4B:
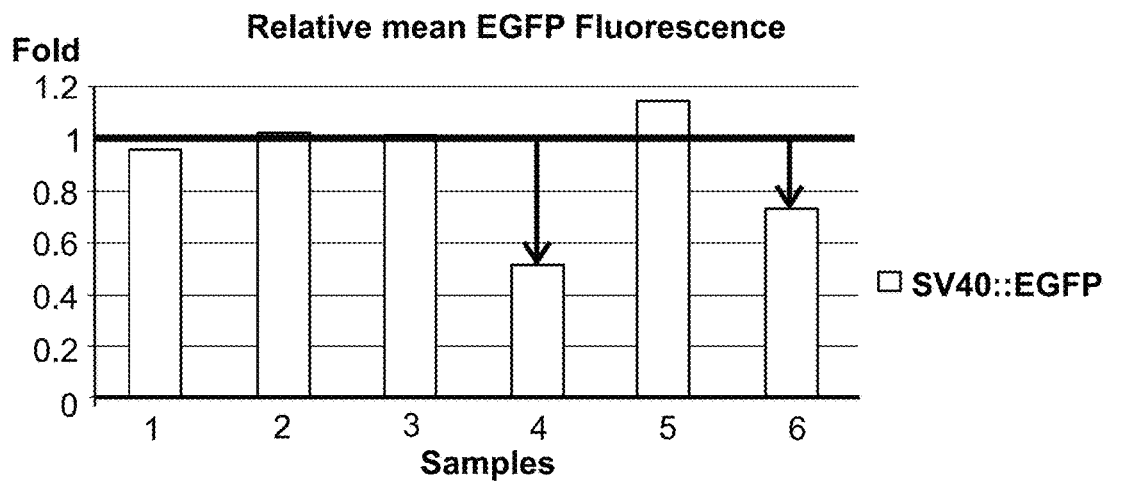
Figure 4B:
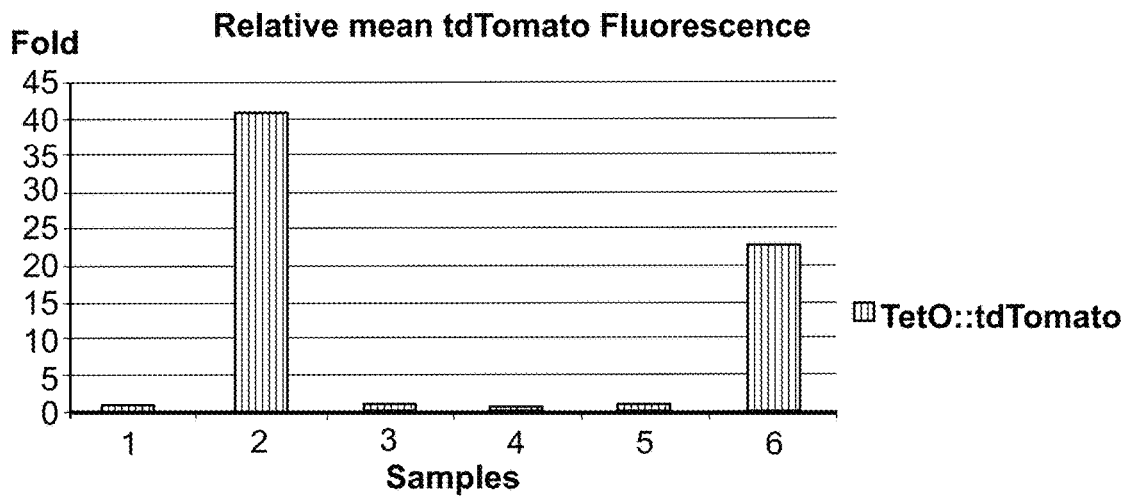

The KRAB::PUF(6-2/7-2) repression fusion and the sgRNA targeting SV40 promoter were first generated. A HEK293T reporter cell line having a tdTomato reporter under the control of the TetO promoter, and an EGFP reporter under the control of the SV40 promoter (HEK293T/TetO::tdTomato/SV40::EGFP) was then used to test simultaneous (1) activation of tdTomato via dCas9/sgTetO-PBS32/PUF(3-2)::VP64 binding to TetO promoter, and (2) repression of EGFP expression via binding of dCas9/sgSV40-PBS6272/KRAB::PUF(6-2/7-2) at the SV40 promoter (FIG. 4A). Expression of the 3-component CRISPR/Cas activator complex consisting of dCas9, sgTetO-5×PBS32 and PUF(3-2)::VP64 activated tdTomato fluorescence (FIG. 4B; sample 2) while expression of the 3-component CRISPR/Cas repressor complex consisting of dCas9, sgSV40-5×PBS6272 reduced EGFP fluorescence (FIG. 4B; sample 4). Co-expression of both activator and repressor complexes induced simultaneous activation of the tdTomato and repression of the EGFP transgene, respectively (FIG. 4B, sample 6), demonstrating that the subject 3-component CRISPR/Cas complexes with different effector functions can operate within the same cell and produce different output at their targets.

Figure 4C:
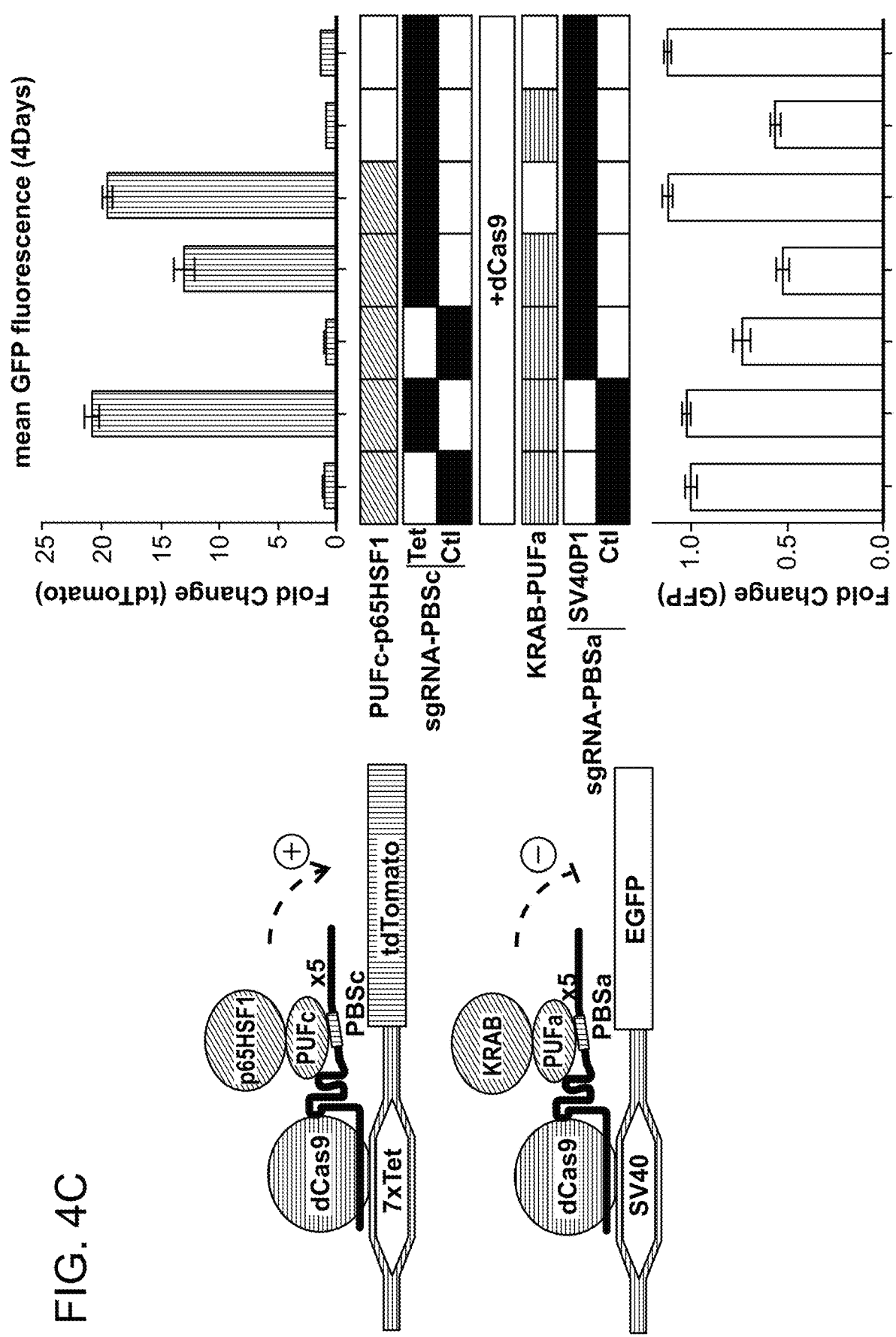
FIGS. 4C and 4D further demonstrate that the subject 3-component CRISPR/Cas complex/system can activate and repress different genes simultaneously.

To further confirm the versatility of the subject system in recruiting various effectors, a KRAB-PUFa repressor fusion and as well as a PUFc-p65HSF1 activator fusion were constructed. In a reporter cell line HEK293T/TetO::tdTomato/SV40::EGFP, the TetO::tdTomato reporter gene can be efficiently activated by dCas9/PUFc-p65HSF1/sgTetO-PBSc, while SV40::EGFP expression is significantly repressed by dCas9/KRAB-PUFa/sgSV40-PBSa (FIG. 4C). When both systems were applied, simultaneous activation of TetO::tdTomato and repression of SV40::EGFP expression were achieved (FIG. 4C). When non-targeting (sgCtl) sgRNA were used, or when the PUF fusions were omitted, the fluorescent levels of the respective reporters were not affected, showing that the effects on the reporters are specific and are due to the action of the effectors recruited by the cognate dCas9/sgRNA-PBS at the targets.

Figure 4D:
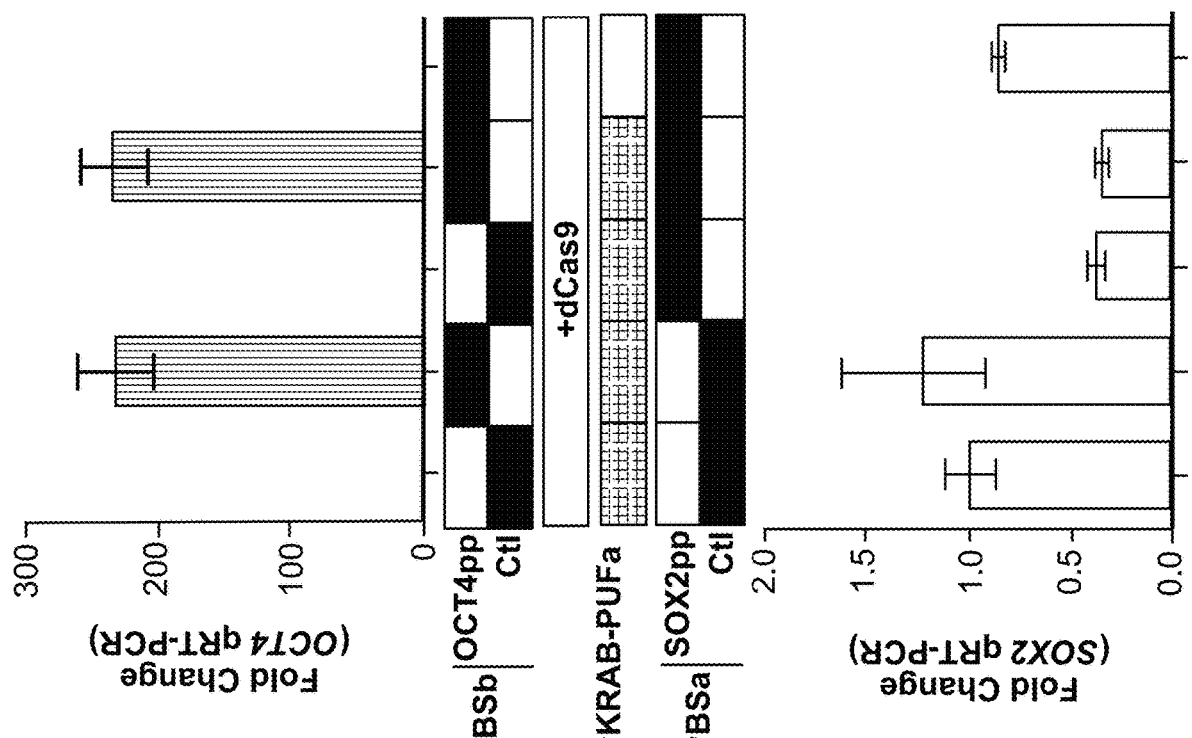
Figure 4D:
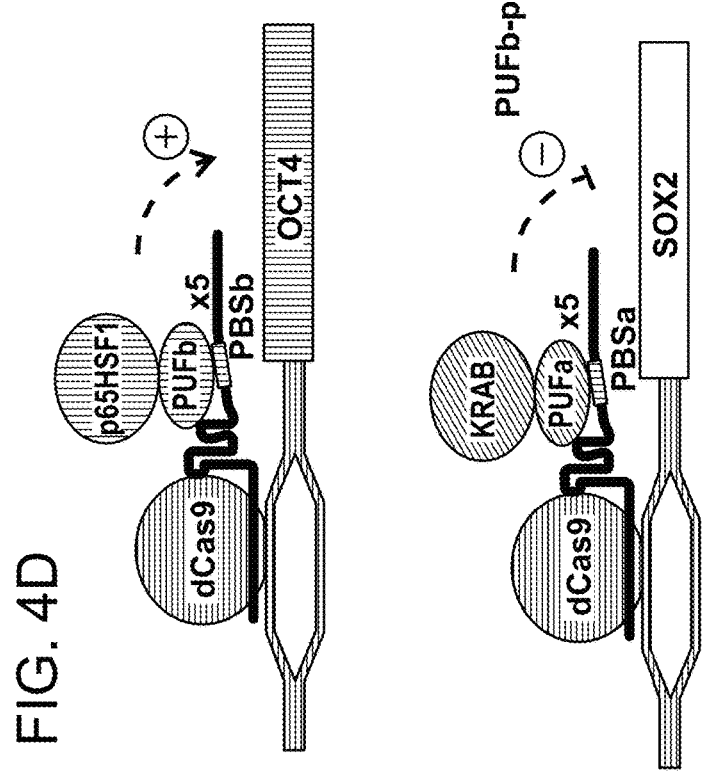

Next, it was tested whether the expression of multiple endogenous genes can be independently regulated using this strategy. The subject 3-component modules were directed to endogenous target genes by changing the targeting sequence of sgRNA-PBSb and sgRNA-PBSa so that PUFb-p65HSF1 was recruited to the OCT4 promoter and BFPKRAB-PUFa to the SOX2 promoter. Similar to the results from reporter gene experiments, effector-mediated simultaneous as well as independent activation of OCT4 and repression of SOX2 were achieved (FIG. 4D).

Example 6 Recruitment of Histone Acetyltransferase (HAT) Domain by the Subject 3-Component CRISPR/Cas Complex/System Achieves Enhancer Activation Artificial transcription factor systems can be used to recruit epigenetic modifiers to activate or repress genes. Recent experiments have used histone acetyltransferase (HAT) to activate enhancers. To demonstrate that the subject 3-component system can recruit multiple molecules of HAT domain to increase the efficiency of epigenetic editing, OCT4 was used as a model gene since its enhancers and the promoter are well defined, and the choice of enhancer usage is of biological significance corresponding to the embryonic stem cell states.

Figure 5A:
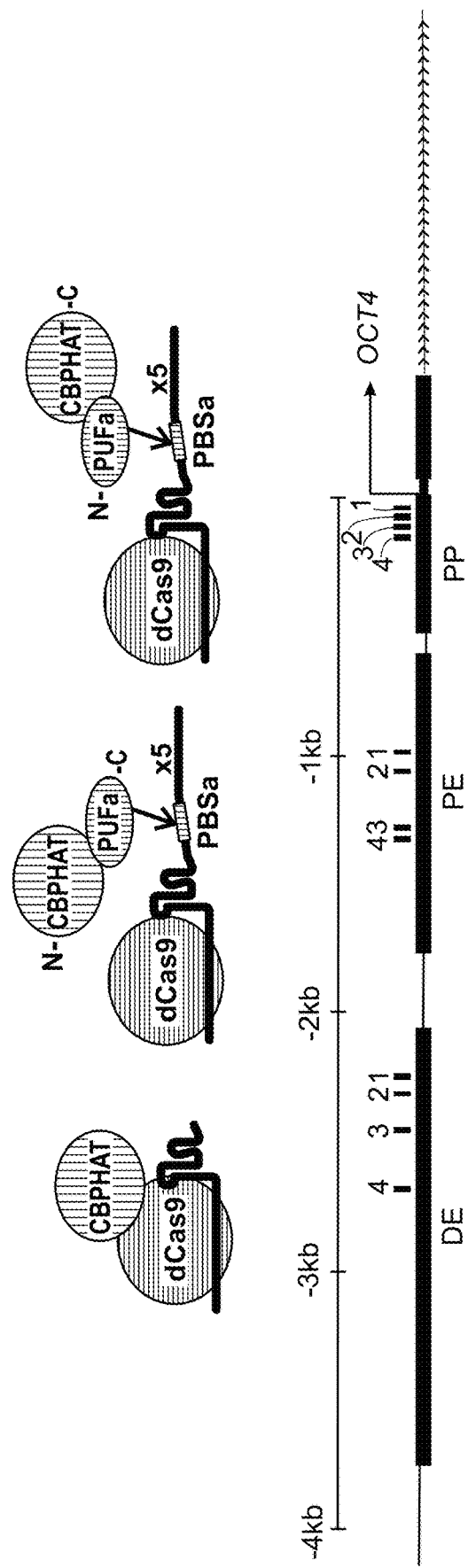
FIG. 5A-5C show that the subject 3-Component CRISPR/Cas Complex/System can be used to recruit histone acetyltransferase (HAT) domain of CREB-binding protein (CBP) at enhancers to activate target gene expression.

In this experiment, the Proximal Promoter (PP), Proximal Enhancer (PE) and Distal Enhancer (DE) were targeted, each with four different sgRNA-PBS (FIG. 5A). Direct fusion between HAT from CREB-binding protein (CBP) and the C-terminus of dCas9 (dCas9::CBPHAT) was constructed, so were an N-terminal fusion module CBPHAT::PUFa, and a C-terminal fusion module PUFa::CBPHAT. Their activity in activating OCT4 expression via binding to PP, PE and DE were then tested.

Figure 5B:
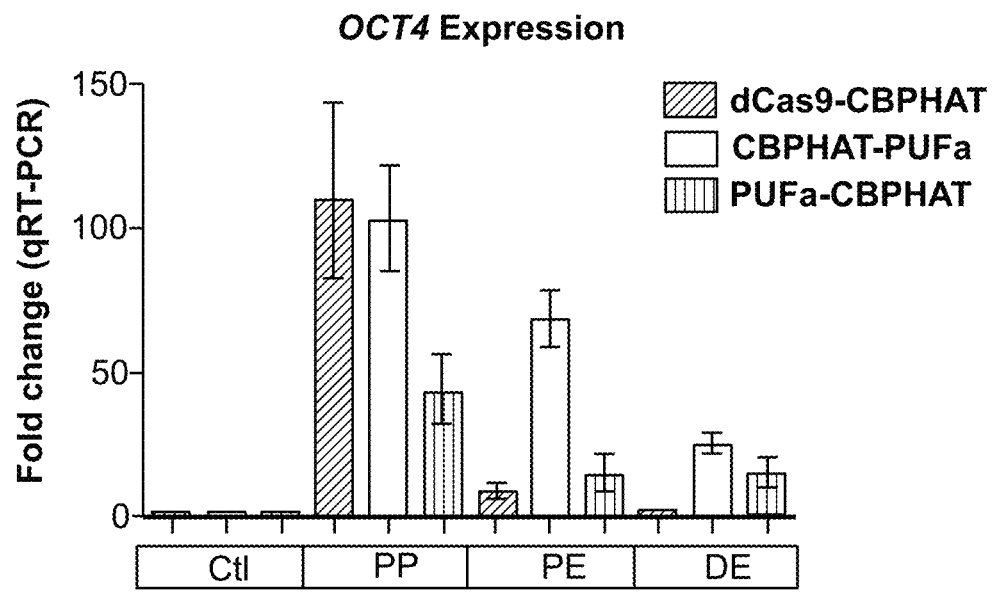
Figure 5C:
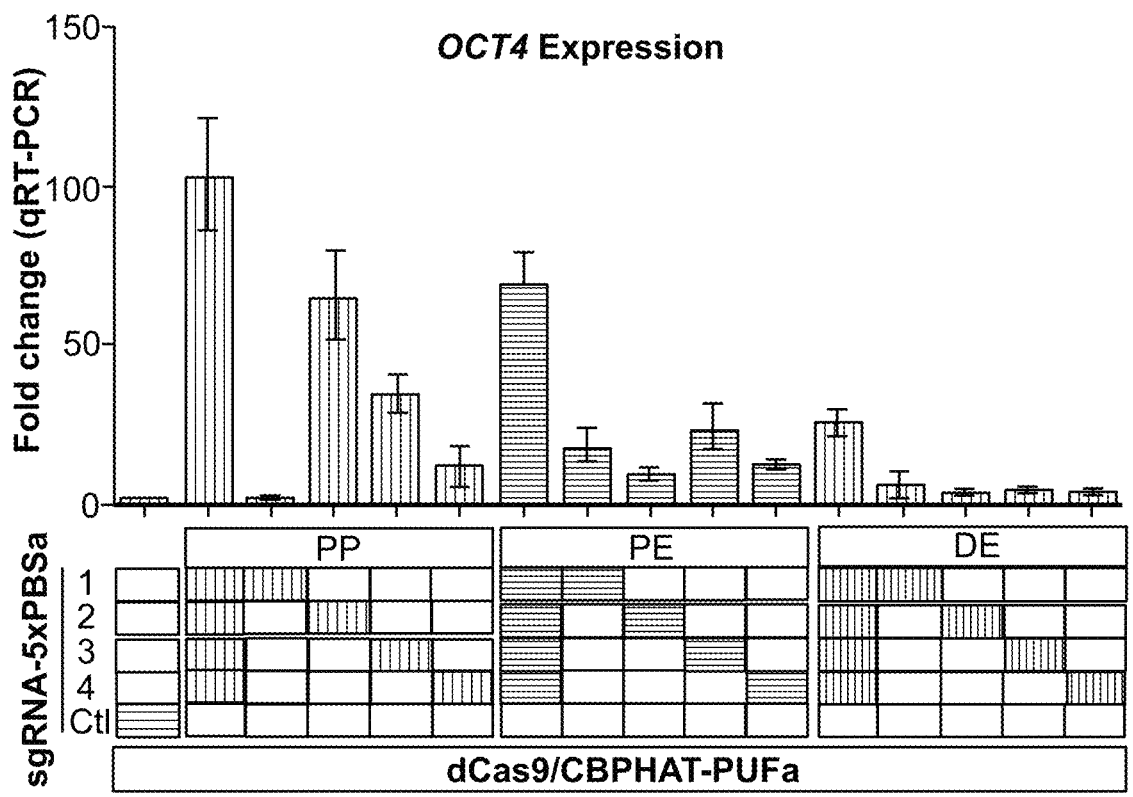

As shown in FIG. 5B, dCas9::CBPHAT and CBPHAT::PUFa have similar activity at proximal promoter (PP). Interestingly, when coupled with sgRNA with 5×PBSa, the subject 3-component modules have higher efficiency activating OCT4 gene via both enhancers PE and DE, with N-terminal fusion CBPHAT::PUFa giving the highest activation. Next, it was analyzed the activity of CBPHAT::PUFa directed by single sgRNA-5×PBSa to PP, PE and DE by sgRNA-5×PBSa (FIG. 5C). Although with smaller fold changes than using cocktails of 4 sgRNA-5×PBSa, single sgRNA-5×PBSa were able to activate the expression of OCT4 gene through targeting of these elements (FIG. 5C).

Example 7 The Subject 3-Component CRISPR/Cas Complex/System Allows Fluorescent Tagging of Telomeres In addition to transcriptional regulation, another important application of dCas9-effector is to label genomic loci for live cell imaging. This example demonstrates that the subject 3-component CRISPR/Cas complex/system can be used for fluorescent tagging of chromosomal loci, such as labeling of telomeres.

Figure 6A:
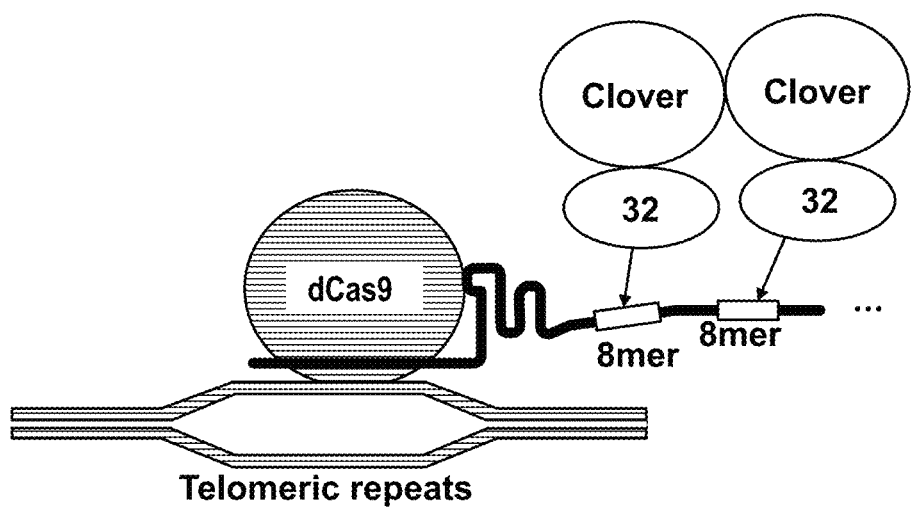
Figure 6D:
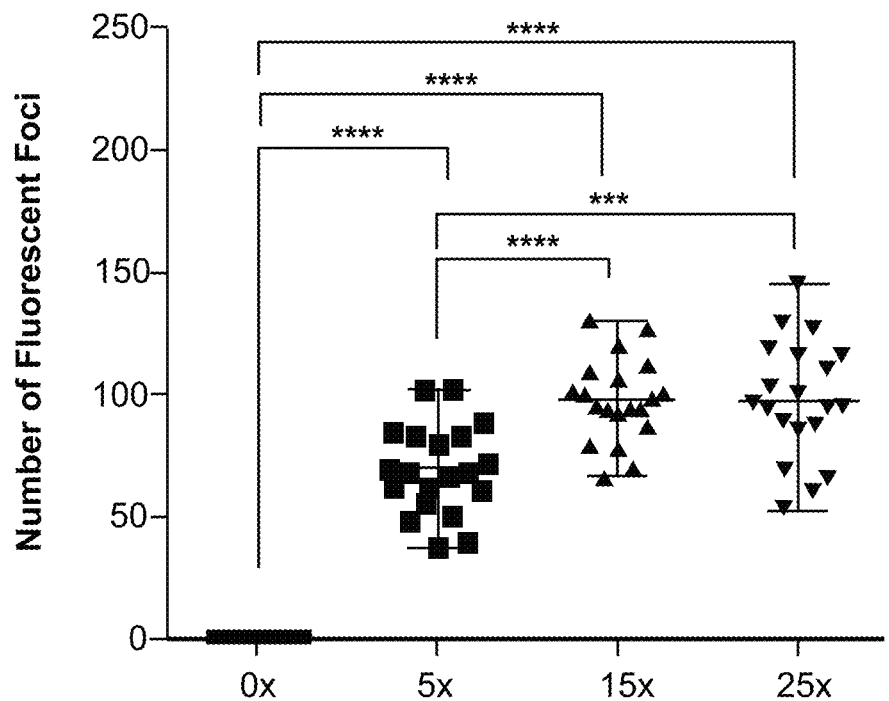
Figure 6E:
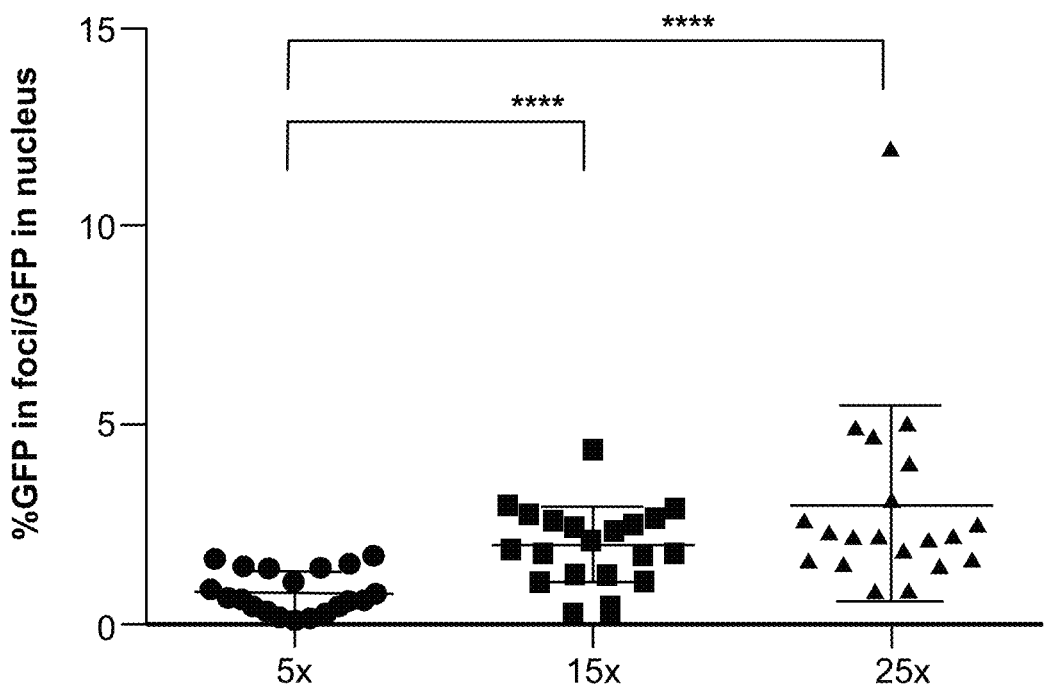

We appended sgRNA designed to target telomeres (sgTelomere) with 0, 5, 15, or 25 copies of PBSa to recruit fluorescent proteins fused to a PUFa domain (FIG. 6A). While expression of sgTelomere-5×PBSa, 15×PBSa and 25×PBSa with dCas9 and Clover::PUFa produced green fluorescent foci consistent with telomere labeling, expression of sgRNA harboring no PBSa site did not produce any foci (FIG. 6B). To confirm that subject 3-component system-directed fluorescent signal is indeed localized at telomeres, co-labeling experiment with antibody against telomeric repeat binding factor TRF2 was performed. The 3-component system telomere signals largely overlapped with the TRF labeling (FIG. 6C), indicating highly specific labeling of telomeres by sgRNA appended with PBSa sites that recruit Clover-PUFa.

Interestingly, the strength of telomere labeling increased as more copies of PBS were appended to the Telomere-sgRNAs (FIG. 6B). Quantification of foci number and signal-to-noise (% GFP in foci/total GFP in nucleus) showed progressive increase from experiment using sgRNA with 5, 15 to 25×PBSa (FIGS. 6D and 6E), indicating the multimerization feature of the subject 3-component system allows for titration of labeling intensity at target loci.

Example 8 The Subject 3-Component CRISPR/Cas Complex/System Allows Simultaneous Fluorescent Tagging of Telomeres and Centromeres This example demonstrates that the subject 3-component CRISPR/Cas complex/system can label more than one (e.g., two) genomic loci simultaneously in the same cells by using the multiplexing feature.

Figure 6F:
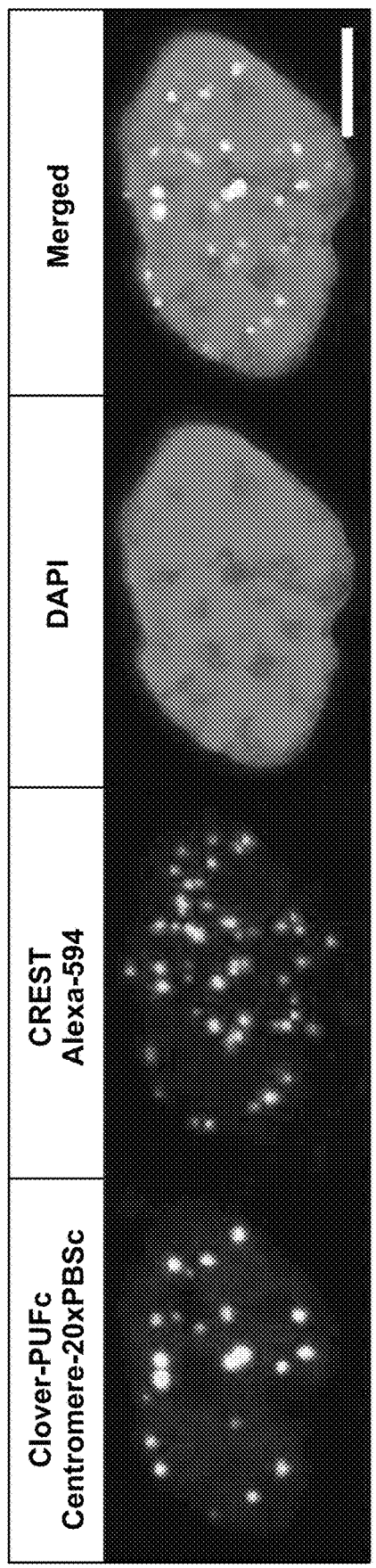
Figure 6G:
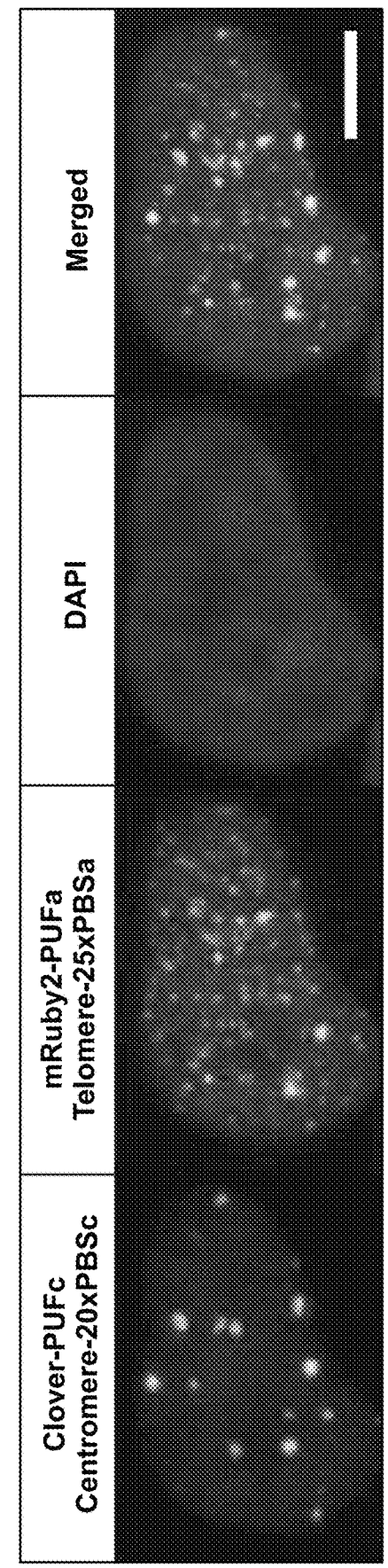

To further demonstrate the ability of the subject 3-component system to label two genomic loci simultaneously, an sgRNA was designed to target centromeres with appended binding sites for PUFc (sgCentromere-20×PBSc). Labeling of centromeres by the subject 3-component system and immunostaining using anti-CREST antibody were observed and confirmed (FIG. 6F). When Clover-PUFb/sgCentromere-20×PBSc, Ruby-PUFa/sgTelomere-25×PBSa and dCas9 were co-introduced into HEK293T cells, independent labeling of both centromeres and telomeres in the same cells were observed (FIG. 6G), demonstrating that the subject 3-component system can be used to independently label multiple genomic loci.

Example 9 The Subject 3-Component CRISPR/Cas Complex/System Allows Fluorescent Tagging of Non-repeat Chromosomal Loci A previous study using dCas9::GFP to label non-repetitive DNA reported the requirement of >32 targeting events to concentrate enough signal to label such non-repeat regions. This example demonstrates that, by incorporating multiple binding sites for PUF-fluorescent protein fusions, fluorescent signals can be concentrated at a target site, thus reducing the amount of targeting sites needed for detection of non-repeat DNA.

Figure 7:
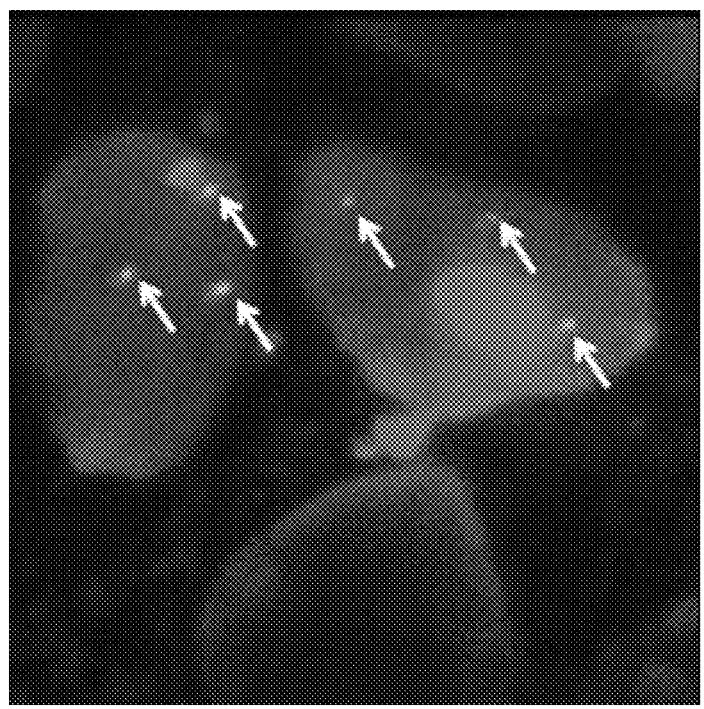
FIG. 7 is a representative confocal microscopy image of the MUC4 labeling, showing that the subject 3-component CRISPR/Cas complex/system allows labeling of non-repeat region with 7 sgRNA-15×PBS32 targeting MUC4 locus.

The non-repeat region at the MUC4 locus was tested in this example. Seven (7) sgRNAs each harboring 15×PBS32, Clover::PUF(3-2) and dCas9, labeling pattern reminiscent of that of MUC4 labeling was successfully detected (FIG. 7). This demonstrates that the subject 3-component CRISPR/Cas complex/system can be used to "polymerize" proteins at defined genomic loci, which enables and greatly expands the application of the subject 3-component CRISPR/Cas complex/system in the field of imaging.

The above examples demonstrate the ability of the subject 3-component CRISPR/Cas complex/system to achieve multiplexing (FIG. 8A), complex formation (FIG. 8C), and polymerization of proteins (FIG. 8B), including transcriptional regulators, epigenetic modifiers, and fluorescent proteins, and the system can independently direct them to defined genomic loci. This enables construction of complex molecular behavior at multiple loci, and allows studying and reconstitution of protein complexes with defined stoichiometry. The polymerization feature of the subject 3-component CRISPR/Cas complex/system allows concentration of enzymatic activity or other proteins to defined genomic loci, to increase the effect of the enzymatic activity or to concentrate signal enrichment for applications like chromosomal imaging.

More specifically, some main advantages of the subject 3-component system include: (A) Multiplexing. Different modules of the subject 3-component system can be simultaneously delivered into a cell and each can operate at their defined target sites with independence (i.e., without interference with other modules and their target sites). Since PUF domains can be easily programmed to recognize any 8-mer RNA motifs, this expands the potential number of independent modules to a theoretical maximum of $4^8$ (65536). By inserting a PUF array within another, the recognition site can be programmed to a 16-mer RNA motif, with a sequence space of $4^{16}$ (4.29 billion). (B) Multimerization: Simplicity of the linear 8-mer PBS motif allows extensive multimerization of PUF fusions on sgRNA-PBS without hindering sgRNA transcription or Cas9/sgRNA DNA binding activity. This feature allows multiple molecules of PUF fusions to be assembled on the sgRNA, allowing for localized concentration of effectors or protein tags. This is particularly beneficial for fluorescent imaging or transcriptional regulation. As shown with the above experiments labeling repeat sequences such as telomeres, sgRNA-PBS with more PBS increases signal at the telomeric foci. This feature may facilitate labeling of non-repeat sequences where usually tiling of more than 30 sgRNAs were required. Higher efficiency of HAT-mediated enhancer activation using the subject system versus direct dCas9-HAT fusion was observed. It is contemplated that multimerization can facilitate spreading of the epigenetic modification directed by the artificial epigenetic factors useful for reprogramming of large epigenetic domains such as super-enhancers or imprinted loci. (C) Stoichiometrically defined Complex formation: although not directly tested here, it is contemplated that the sgRNA-PBS can act as RNA scaffold for PUF-directed assembly of Stoichiometrically defined protein complexes. Specifically, Varying numbers of PBS copies with varying specificities can be appended to the sgRNA to allow for multiprotein complex formation with defined stoichiometry, as well as with defined ordering along the sgRNA-PB S.

The materials and methods used in the examples above are compiled below.

Cloning

A list of vectors, links to their Addgene entries are provided in Table S1 below. Detailed description of cloning strategies and sequences are given below.

PUFa [PUF(3-2)] and PUFb [PUF(6-2/7-2)] with N-terminal NLS were amplified from constructs containing these coding sequences with primers containing SgrAI and PacI sites and were used to replace SgrAI-dCas9-FseI from pAC164:pmax-dCas9Master_VP64 to create pAC1355: pmax-NLSPUFa_VP64 and pAC1356:pmax-NLSPUFb_VP64. A fusion PCR with 5' fragment up to repeat 4 of NLSPUFb and 3' fragment from repeat 5 to the end of NLSPUFa was used to create pAC1357:pmax-NLSPUFw_VP64. A fusion PCR of 5' fragment of NLSPUFa with 3' fragment of NLSPUb was used to create pAC1358: pmax-NLSPUFc_VP64.

p65HSF1 activator ORF was amplified from M52-P65-HSF1_GFP (Addgene: 61423) with FseI PacI sites to replace VP64 fragment in pAC164 to create pAC1410:pmax-dCas9_p65HSF1, and replace VP64 in pAC1355 and pAC1358 to create pAC1393: pmax-NLSPUFa _p65HSF1 and pAC1411:pmax-NLSPUFc_p65HSF1, respectively.

Clover and mRuby2 were amplified from pcDNA3-Clover (Addgene #40259) and pcDNA3-mRuby2 (Addgene #40260) respectively with primers containing SgrAI and FseI cloning site, ligated with various FseI-PUF-PacI amplified from the above pAC1356-1358 and vector digested from pAC149:pCR8-dCas9VP160 (Addgene #48221) to create gateway donor vectors pAC1402, pAC1403 and pAC1404 containing ORFs of Clover_PUFa and Clover_PUFc, mRuby2_PUFa, respectively. These ORFs are then transferred to PB3-neo vector by recombining with pAC1119:PB3-neo(−)-pmaxDEST(+) by LR Clonase (Invitrogen) to create expression vectors pAC1360 (Clover_PUFa), pAC1381 (Clover_PUFc) and pAC1362 (mRuby2_PUFa).

NLSKRAB repressor domain was amplified from SOX2 TALE Repressor (KRAB 1-75) (Addgene #42945) with primers containing AgeI-ClaI sites and ligated with NLSPUFa amplified with primers containing AclI PacI and with pAC1360 digested with SgrAI-PacI as vector to create pAC1412: PB3-neo(−)-pmax-NLSKRAB_NLSPUFa.

The FseI-p65HSF1-PacI fragment was released from pAC1393 and ligated with SgrAI-NLSPUMb fragment released from pAC1356 and pAC1360 digested with SgrAI-PacI as vector to create pAC1413: PB3-neo(−)-pmax-NLSPUFb_p65HSF1. The BFPKRAB fragment was amplified from pHR-SFFV-dCas9-BFP-KRAB (Addgene #46911) and was used to replace Clover fragment from pAC1360 to create pAC1414: PB3-neo(−)-pmax-BFPKRAB_NLSPUFa. Then, an NheI-CAGGS-NLSPUFb_p65HSF1-NheI fragment was amplified from pAC1413 and inserted into pAC1414 digested with NheI to create a dual expression vector for BFPKRAB-NLSPUFa and NLSPUFb-p65HSF1 (pAC1414: PB3-NLSPUFb_p65HSF1(−)neo(−)-BFPKRAB2_NLSPUFa).

Four gateway donor vectors with improved linker sequences and three extra NLS on the N-terminal and one additional NLS on the C-terminal of PUF as well as cloning sites for N-terminal (SgrAI,ClaI) and C-terminal (FseI-PacI) insertions were created (pAC1404-1408). HAT sequence was amplified from mouse Crebbp gene using mouse cDNA with primers containing FseI-PacI site and inserted into pAC164 to create pAC1364: pmax-dCas9Master_CBPHAT and into pAC1405 to create pAC1415: pCR8-4×NLSPUFa_2×NLS_CBPHAT. HAT sequence was amplified with another pair of primers containing SgrAI-AclI site and cloned into SgrAI-ClaI site of pAC1405 to create pAC1416: pCR8-CBPHAT_4×NLSPUFa_2×NLS. pAC1415 and pAC1416 were recombined into pAC90:pmax-DEST (Addgene #48222) to create expression vectors pAC1417: pmax-4×NLSPUFa_2×NLS_CBPHAT and pAC1418: pmax-CBPHAT_4×NLSPUFa_2×NLS, respectively. FseI-mCherry-PacI fragment was amplified from a plasmid containing mCherry sequence and ligated with SgrAI-dCas9-FseI to PB3-neo(−)-pmax to generate pAC1419: PB3-neo(−)-pmax-dCas9Master_mCherry.

Expression vectors for sgRNA-PBS were constructed as follows: First, a sgRNA scaffold based on sgF+E with BbsI for oligo cloning of guide sequence and with 3' BsaI (right upstream of the terminator) for insertion of PBS were ordered as a gBlock (IDT), and were cloned into pX330 (Addgene #42230) replacing the AflIII-NotI region to create vector pAC1394: pX-sgFE-BsaI(AGAT). Then, oligos encoding 5×PBSa sites each separated by ggc-spacer flanked by 5'-AGAT-3' overhangs on one side and 5'-ATCT-3' on the other side were treated with T4PNK and annealed and ligated into pAC1394 digested with BsaI (to create compatible overhangs). Clones were then screened for 1 copy (5×PBS), 2 copies (10×PBS), etc of the oligo insertions for the different number of PBS. For 1×PBS and 2×PBS vectors, they were constructed using oligo containing one PBS site. Guide sequence for each target were then cloned onto the sgRNA-PBS expression vectors via BbsI site as previously described. For sgRNA expression vectors with GFP expression markers, they were constructed by transferring the sgRNA-PBS expression cassette from the pX vectors onto a PB-GFP vector via AscI site. The different sgRNA expression constructs are listed in Table 51.

Cell Culture for Experiments

HEK293T cells were cultivated in Dulbecco's modified Eagle's medium (DMEM)(Sigma) with 10% fetal bovine serum (FBS)(Lonza), 4% Glutamax (Gibco), 1% Sodium Pyruvate (Gibco) and penicillin-streptomycin (Gibco). Incubator conditions were 37° C. and 5% $CO_2$. For activation experiments, cells were seeded into 12-well plates at 100,000 cells per well the day before being transfected with 200 ng of dCas9 construct, 100 ng of modified sgRNA and 100 ng of PUF-fusion with Attractene transfection reagent (Qiagen). After transfection, cells were grown for 48 hrs and harvested for either RNA extraction or fluorescent-activated cell sorting (FACS). For dual activation-repression experiments, transfection remained the same, however cells were seeded into 12-well plates at 150,000 cells per well and were grown for 72 hrs before being harvested for FACS. For experiments with OCT4 and SOX2 dual activation-repression, cells were triple-sorted by BFP (for the activator-repressor module PUFb-p65HSF1/BFPKRAB-PUFa), mCherry (for dCas9mCherry) and GFP (for the sgRNA-PBS on vectors co-expressing EGFP) before RNA extraction. For imaging experiments, cells were seeded into 6-well plates with 22×22×1 microscope cover glass at 300,000 cells per well the day before being transfected with 50 ng of dCas9 construct, 500 ng of modified sgRNA, and 50 ng of a PUF-fluorescent fusion with Attractene transfection reagent. After transfection, cells were grown for 48 hrs then immunostained.

Quantitative RT-PCR Analysis

Cells were harvested with trypsin, washed with Dulbecco's phosphate-buffered saline (dPBS), centrifuged at 125 g for 5 mins and then RNA was extracted using RNeasy Plus Mini Kit (Qiagen). A cDNA library was made using Applied Biosystems High Capacity RNA-to-cDNA kit with 1 μg of RNA. TaqMan Gene expression assays (Applied Biosystems) were designed using GAPDH (Hs03929097, VIC) as endogenous control and OCT4 (Hs00999632, FAM) and SOX2 (Hs01053049, FAM) as targets. TaqMan Universal Master Mix II, with UNG (Applied Biosystems) was used for Quantitative PCR (qPCR), with 2 μl of 1:10 diluted cDNA used for each reaction. Activation was analyzed with the Applied Biosystems ViiA7 instrument. Gene expression levels were calculated by "delta delta Ct" algorithm and normalized to control samples.

Fluorescent-Activated Cell Sorting

Cells were trypisinized and fixed for 10 min with 2% paraformaldehyde. Afterwards, the cells were centrifuged at 125 g for 5 min and resuspended in dPBS. Samples were analyzed on a FACScalibur flow cytometer using CellQuest Pro software (BD Bioscience). thousands events were collected in each run.

Immunostaining and Microscopy

While adherent to a cover glass, cells were fixed in 2% paraformaldehyde, washed with 0.1% Triton X-100 in dPBS, permeabilized with 0.4% Triton X-100 in dPBS for 5 min at 4° C., blocked in 5% Blotting-grade blocking buffer (BIO-RAD) for 30 min, incubated with the primary antibody in blocking buffer at 4° C. overnight, washed three times with dPBS, then incubated in the dark with a respective Alexa Fluor-conjugated secondary antibody at room temperature for 3 hours, washed again, and stained with DAPI. The cover glass was mounted on a slide with glycerol before imaging. Immunostaining of telomeres was performed with a 1:100 dilution of an anti-TRF2 primary antibody (Novus Biologicals: NB110-57130) and a 1:500 dilution of an Alexa fluor 594-conjugated anti-Rabbit IgG secondary antibody (Invitrogen, A11037). A 1:100 dilution of CREST antibody (Antibodies Incorporated: 15-235-0001) was used in conjunction with a 1:500 dilution of an Alexa fluor 594-conjugated anti-Human IgG secondary antibody (Invitrogen, A11014) to detect centromeres.

Sequences of some of the constructs used in the examples above and the related sequences are listed herein below.

```
>NLSPUFa_VP64 Key: NLS PUFa VP64
                                          (SEQ ID NO: 96)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGSRVIEKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGNYVIQHVLEHGRPEDKSKIVA

EIRGNVLVLSQHKFASNVVEKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID
```

In the above sequence, the NLS sequence is residues 6-12, PUFa is residues 15-363, and VP64 is residues 371-421.

```
>NLSPUFb_VP64 Key: NLS PUFb VP64
                                          (SEQ ID NO: 97)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGCRVIQKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGSYVIEHVLEHGRPEDKSKIVA

EIRGNVLVLSQHKFANNVVQKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID
```

In the above sequence, the NLS sequence is residues 6-12, PUFb is residues 15-363, and VP64 is residues 371-421.

```
>NLSPUFw_VP64 Key: NLS PUFw VP64
                                          (SEQ ID NO: 98)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGCRVIQKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGNYVIQHVLEHGRPEDKSKIVA

EIRGNVLVLSQHKFASNVVEKCVTHASRTERAVLIDEVCTMNDGPHSALY
```

-continued

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID

In the above sequence, the NLS sequence is residues 6-12, PUFw is residues 15-363, and VP64 is residues 371-421.

>NLSPUFc_VP64 Key: NLS PUFc VP64
(SEQ ID NO: 99)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGSRVIEKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGSYVIEHVLEHGRPEDKSKIVA

EIRGNVLVLSQHKFANNVVQKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID

In the above sequence, the NLS sequence is residues 6-12, PUFc is residues 15-363, and VP64 is residues 371-421.

>Clover_NLSPUFa Key: Clover NLS PUFa
(SEQ ID NO: 100)
MVSKGEELFTGVVPILVELDGDVNGHKFSVRGEGEGDATNGKLTLKFICT

TGKLPVPWPTLVTTFGYGVACFSRYPDHMKQHDFFKSAMPEGYVQERTIS

FKDDGTYKTRAEVKFEGDTLVNRIELKGIDFKEDGNILGHKLEYNFNSHN

VYITADKQKNGIKANFKIRHNVEDGSVQLADHYQQNTPIGDGPVLLPDNH

YLSHQSALSKDPNEKRDHMVLLEFVTAAGITHGMDELYKSRGPYSIVSPK

CGGGGSGPAGILPPKKKRKVSRGRSRLLEDFRNNRYPNLQLREIAGHIME

FSQDQHGSRFIQLKLERATPAERQLVFNEILQAAYQLMVDVFGNYVIQKF

FEFGSLEQKLALAERIRGHVLSLALQMYGSRVIEKALEFIPSDQQNEMVR

ELDGHVLKCVKDQNGNHVVQKCIECVQPQSLQFIIDAFKGQVFALSTHPY

GCRVIQRILEHCLPDQTLPILEELHQHTEQLVQDQYGNYVIQHVLEHGRP

EDKSKIVAEIRGNVLVLSQHKFASNVVEKCVTHASRTERAVLIDEVCTMN

DGPHSALYTMMKDQYANYVVQKMIDVAEPGQRKIVMHKIRPHIATLRKYT

YGKHILAKLEKYYMKNGVDLG

In the above sequence, the NLS sequence is residues 264-270, PUFa is residues 273-621, and Clover is residues 1-251.

>Clover_NLSPUFc Key: Clover NLS PUFc
(SEQ ID NO: 101)
MVSKGEELFTGVVPILVELDGDVNGHKFSVRGEGEGDATNGKLTLKFICT

TGKLPVPWPTLVTTFGYGVACFSRYPDHMKQHDFFKSAMPEGYVQERTIS

FKDDGTYKTRAEVKFEGDTLVNRIELKGIDFKEDGNILGHKLEYNFNSHN

VYITADKQKNGIKANFKIRHNVEDGSVQLADHYQQNTPIGDGPVLLPDNH

YLSHQSALSKDPNEKRDHMVLLEFVTAAGITHGMDELYKSRGPYSIVSPK

CGGGGSGPAGILPPKKKRKVSRGRSRLLEDFRNNRYPNLQLREIAGHIME

FSQDQHGSRFIQLKLERATPAERQLVFNEILQAAYQLMVDVFGNYVIQKF

FEFGSLEQKLALAERIRGHVLSLALQMYGSRVIEKALEFIPSDQQNEMVR

ELDGHVLKCVKDQNGNHVVQKCIECVQPQSLQFIIDAFKGQVFALSTHPY

GCRVIQRILEHCLPDQTLPILEELHQHTEQLVQDQYGSYVIEHVLEHGRP

EDKSKIVAEIRGNVLVLSQHKFANNVVQKCVTHASRTERAVLIDEVCTMN

DGPHSALYTMMKDQYANYVVQKMIDVAEPGQRKIVMHKIRPHIATLRKYT

YGKHILAKLEKYYMKNGVDLG

In the above sequence, the NLS sequence is residues 264-270, PUFc is residues 273-621, and Clover is residues 1-251.

>mRuby2_NLSPUFa Key: 6xHis-mRuby2
("6xHis" disclosed as SEQ ID NO: 95)
NLS PUFa
(SEQ ID NO: 102)
MVRGSHHHHHHGMASMTGGQQMGRDLYDDDDKDPMVSKGEELIKENMRMK

VVMEGSVNGHQFKCTGEGEGNPYMGTQTMRIKVIEGGPLPFAFDILATSF

MYGSRTFIKYPKGIPDFFKQSFPEGFTWERVTRYEDGGVVTVMQDTSLED

GCLVYHVQVRGVNFPSNGPVMQKKTKGWEPNTEMMYPADGGLRGYTHMAL

KVDGGGHLSCSFVTTYRSKKTVGNIKMPGIHAVDHRLERLEESDNEMFVV

QREHAVAKFAGLGGGMDELYKGGGGSGPAGILPPKKKRKVSRGRSRLLED

FRNNRYPNLQLREIAGHIMEFSQDQHGSRFIQLKLERATPAERQLVFNEI

LQAAYQLMVDVFGNYVIQKFFEFGSLEQKLALAERIRGHVLSLALQMYGS

RVIEKALEFIPSDQQNEMVRELDGHVLKCVKDQNGNHVVQKCIECVQPQS

LQFIIDAFKGQVFALSTHPYGCRVIQRILEHCLPDQTLPILEELHQHTEQ

LVQDQYGNYVIQHVLEHGRPEDKSKIVAEIRGNVLVLSQHKFASNVVEKC

VTHASRTERAVLIDEVCTMNDGPHSALYTMMKDQYANYVVQKMIDVAEPG

QRKIVMHKIRPHIATLRKYTYGKHILAKLEKYYMKNGVDLG

In the above sequence, the NLS sequence is residues 284-290, PUFa is residues 293-641, and 6xHis-mRuby2 ("6xHis" disclosed as SEQ ID NO: 95) is residues 1-271, including the 6xHis tag ("6xHis" disclosed as SEQ ID NO: 95) at residues 6-11.

>NLSPUFa_p65HSF1 Key: PUFa NLS
p65HSF1
(SEQ ID NO: 103)
MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGSRVIEKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGNYVIQHVLEHGRPEDKSKIVA

EIRGNVLVLSQHKFASNVVEKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGGGGSGGGGSGGGGSGPKKKRKVAAAGSPSGQIS

NQALALAPSSAPVLAQTMVPSSAMVPLAQPPAPAPVLTPGPPQSLSAPVP

-continued

```
KSTQAGEGTLSEALLHLQFDADEDLGALLGNSTDPGVFTDLASVDNSEFQ

QLLNQGVSMSHSTAEPMLMEYPEAITRLVTGSQRPPDPAPTPLGTSGLPN

GLSGDEDFSSIADMDFSALLSQISSSGQGGGGSGFSVDTSALLDLFSPSV

TVPDMSLPDLDSSLASIQELLSPQEPPRPPEAENSSPDSGKQLVHYTAQP

LFLLDPGSVDTGSNDLPVLFELGEGSYFSEGDGFAEDPTISLLTGSEPPK

AKDPTVSID
```

In the above sequence, the NLS sequence is residues 6-12, PUFa is residues 15-363, p65 is residues 427-575, and HSF1 is residues 584-707.

>NLSKRAB_NLSPUFa Key: NLSKRAB
PUFa
(SEQ ID NO: 104)
```
MGSPKKKRKVEASMDAKSLTAWSRTLVTFKDVFVDFTREEWKLLDTAQQI

VYRNVMLENYKNLVSLGYQLTKPDVILRLEKGEEPWLVSRGSIVGILPPK

KKRKVSRGRSRLLEDFRNNRYPNLQLREIAGHIMEFSQDQHGSRFIQLKL

ERATPAERQLVFNEILQAAYQLMVDVFGNYVIQKFFEFGSLEQKLALAER

IRGHVLSLALQMYGSRVIEKALEFIPSDQQNEMVRELDGHVLKCVKDQNG

NHVVQKCIECVQPQSLQFIIDAFKGQVFALSTHPYGCRVIQRILEHCLPD

QTLPILEELHQHTEQLVQDQYGNYVIQHVLEHGRPEDKSKIVAEIRGNVL

VLSQHKFASNVVEKCVTHASRTERAVLIDEVCTMNDGPHSALYTMMKDQY

ANYVVQKMIDVAEPGQRKIVMHKIRPHIATLRKYTYGKHILAKLEKYYMK

NGVDLG
```

In the above sequence, the two NLS sequences are residues 4-10 and residues 99-105, PUFa is residues 108-456, and KRAB is residues 11-92.

>BFPKRAB_NLSPUFa Key: HA-2xNLS-
BFPKRAB NLS PUFa
(SEQ ID NO: 105)
```
MAYPYDVPDYASLGSGSPKKKRKVEDPKKKRKVDGIGSGSNGSSGSSELI

KENMHMKLYMEGTVDNHHFKCTSEGEGKPYEGTQTMRIKVVEGGPLPFAF

DILATSFLYGSKTFINHTQGIPDFFKQSFPEGFTWERVTTYEDGGVLTAT

QDTSLQDGCLIYNVKIRGVNFTSNGPVMQKKTLGWEAFTETLYPADGGLE

GRNDMALKLVGGSHLIANIKTTYRSKKPAKNLKMPGVYYVDYRLERIKEA

NNETYVEQHEVAVARYCDLPSKLGHKLNGGGGGMDAKSLTAWSRTLVTFK

DVFVDFTREEWKLLDTAQQIVYRNVMLENYKNLVSLGYQLTKPDVILRLE

KGEEPGGSGGGSGPAGILPPKKKRKVSRGRSRLLEDFRNNRYPNLQLREI

AGHIMEFSQDQHGSRFIQLKLERATPAERQLVFNEILQAAYQLMVDVFGN

YVIQKFFEFGSLEQKLALAERIRGHVLSLALQMYGSRVIEKALEFIPSDQ

QNEMVRELDGHVLKCVKDQNGNHVVQKCIECVQPQSLQFIIDAFKGQVFA

LSTHPYGCRVIQRILEHCLPDQTLPILEELHQHTEQLVQDQYGNYVIQHV

LEHGRPEDKSKIVAEIRGNVLVLSQHKFASNVVEKCVTHASRTERAVLID

EVCTMNDGPHSALYTMMKDQYANYVVQKMIDVAEPGQRKIVMHKIRPHIA

TLRKYTYGKHILAKLEKYYMKNGVDLG
```

In the above sequence, the NLS sequence is residues 370-376, PUFa is residues 379-727, and HA-2xNLS-BFPKRAB is residues 1-355, including the HA tag at residues 3-11.

>dCas9Master_mCherry HATag NLS
dCas9 mCherry
(SEQ ID NO: 106)
```
MIDGGGGSGGGGSGGGGSMYPYDVPDYASPKKKRKVEASDKKYSIGLAIG

TNSVGWAVITDEYKVPSKKFKVLGNTDRHSIKKNLIGALLFDSGETAEAT

RLKRTARRRYTRRKNRICYLQEIFSNEMAKVDDSFFHRLEESFLVEEDKK

HERHPIFGNIVDEVAYHEKYPTIYHLRKKLVDSTDKADLRLIYLALAHMI

KFRGHFLIEGDLNPDNSDVDKLFIQLVQTYNQLFEENPINASGVDAKAIL

SARLSKSRRLENLIAQLPGEKKNGLFGNLIALSLGLTPNFKSNFDLAEDA

KLQLSKDTYDDDLDNLLAQIGDQYADLFLAAKNLSDAILLSDILRVNTEI

TKAPLSASMIKRYDEHHQDLTLLKALVRQQLPEKYKEIFFDQSKNGYAGY

IDGGASQEEFYKFIKPILEKMDGTEELLVKLNREDLLRKQRTFDNGSIPH

QIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHS

LLYEYFTVYNELTKVKYVTEGMRKPAFLSGEQKKAIVDLLFKTNRKVTVK

QLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRL

SRKLINGIRDKQSGKTILDFLKSDGFANRNFMQLIHDDSLTFKEDIQKAQ

VSGQGDSLHEHIANLAGSPAIKKGILQTVKVVDELVKVMGRHKPENIVIE

MARENQTTQKGQKNSRERMKRIEEGIKELGSQILKEHPVENTQLQNEKLY

LYYLQNGRDMYVDQELDINRLSDYDVDAIVPQSFLKDDSIDNKVLTRSDK

NRGKSDNVPSEEVVKKMKNYWRQLLNAKLITQRKFDNLTKAERGGLSELD

KAGFIKRQLVETRQITKHVAQILDSRMNTKYDENDKLIREVKVITLKSKL

VSDFRKDFQFYKVREINNYHHAHDAYLNAVVGTALIKKYPKLESEFVYGD

YKVYDVRKMIAKSEQEIGKATAKYFFYSNIMNFFKTEITLANGEIRKRPL

IETNGETGEIVWDKGRDFATVRKVLSMPQVNIVKKTEVQTGGFSKESILP

KRNSDKLIARKKDWDPKKYGGFDSPTVAYSVLVVAKVEKGKSKKLKSVKE

LLGITIMERSSFEKNPIDFLEAKGYKEVKKDLIIKLPKYSLFELENGRKR

MLASAGELQKGNELALPSKYVNFLYLASHYEKLKGSPEDNEQKQLFVEQH

KHYLDEIIEQISEFSKRVILADANLDKVLSAYNKHRDKPIREQAENIIHL

FTLTNLGAPAAFKYFDTTIDRKRYTSTKEVLDATLIHQSITGLYETRIDL

SQLGGDSPKKKRKVEASGGGGSGGGGSGGGGSGPAMVSKGEEDNMAIIKE

FMRFKVHMEGSVNGHEFEIEGEGEGRPYEGTQTAKLKVTKGGPLPFAWDI

LSPQFMYGSKAYVKHPADIPDYLKLSFPEGFKWERVMNFEDGGVVTVTQD

SSLQDGEFIYKVKLRGTNFPSDGPVMQKKTMGWEASSERMYPEDGALKGE

IKQRLKLKDGGHYDAEVKTTYKAKKPVQLPGAYNVNIKLDITSHNEDYTI

VEQYERAEGRHSTGGMDELYKID
```

In the above sequence, the two NLS sequences are residues 30-36 and 1408-1414, dCas9 is residues 40-1406, mCherry is residues 1436-1671, and the HA tag is at residues 20-28.

>CBPHAT_4xNLS_PUFa_2xNLS
Key: CBPHAT NLS PUFa
(SEQ ID NO: 107)
MIFKPEELRQALMPTLEALYRQDPESLPFRQPVDPQLLGIPDYFDIVKNP
MDLSTIKRKLDTGQYQEPWQYVDDVWLMFNNAWLYNRKTSRVYKFCSKLA
EVFEQEIDPVMQSLGYCCGRKYEFSPQTLCCYGKQLCTIPRDAAYYSYQN
RYHFCEKCFTEIQGENVTLGDDPSQPQTTISKDQFEKKKNDTLDPEPFVD
CKECGRKMHQICVLHYDIIWPSGFVCDNCLKKTGRPRKENKFSAKRLQTT
RLGNHLEDRVNKFLRRQNHPEAGEVFVRVVASSDKTVEVKPGMKSRFVDS
GEMSESFPYRTKALFAFEEIDGVDVCFFGMHVQEYGSDCPPPNTRRVYIS
YLDSIHFFRPRCLRTAVYHEILIGYLEYVKKLGYVTGHIWACPPSEGDDY
IFHCHPPDQKIPKPKRLQEWYKKMLDKAFAERIINDYKDIFKQANEDRLT
SAKELPYFEGDFWPNVLEESIKELEQEEEERKKEESTAASETPEGSQGDS
KNAKKKNNKKTNKNKSSISRANKKKPSMPNVSNDLSQKLYATMEKHKEVF
FVIHLHAGPVISTQPPIVDPDPLLSCDLMDGRDAFLTLARDKHWEFSSLR
RSKWSTLCMLVELHTQGQDRFVYTCNECKHHVETRWHCTVCEDYDLCINC
YNTKSHTHKMVKWGLGLDDEGSSQGEPQSKSPQESRRLSIQRCIQSLVHA
CQCRNANCSLPSCQKMKRVVQHTKGCKRKTNGGCPVCKQLIALCCYHAKH
CQENKCPVPFCLNINDGGGGSDPKKKRKVDPKKKRKVDPKKKRKVGSTGS
RNDGGGGSGGGGSGGGGSGRAGILPPKKKRKVSRGRSRLLEDFRNNRYPN
LQLREIAGHIMEFSQDQHGSRFIQLKLERATPAERQLVFNEILQAAYQLM
VDVFGNYVIQKFFEFGSLEQKLALAERIRGHVLSLALQMYGSRVIEKALE
FIPSDQQNEMVRELDGHVLKCVKDQNGNHVVQKCIECVQPQSLQFIIDAF
KGQVFALSTHPYGCRVIQRILEHCLPDQTLPILEELHQHTEQLVQDQYGN
YVIQHVLEHGRPEDKSKIVAEIRGNVLVLSQHKFASNVVEKCVTHASRTE
RAVLIDEVCTMNDGPHSALYTMMKDQYANYVVQKMIDVAEPGQRKIVMHK
IRPHIATLRKYTYGKHILAKLEKYYMKNGVDLGDPKKKRKVDPKKKRKVG
GRGGGGSGGGGSGGGGSGPA

In the above sequence, the six 7-residue NLS sequences begin at residues 773, 781, 789, 826, 1185, and 1193, PUFa is residues 835-1183, and CBPHAT is residues 2-764.

>4xNLS_PUFa_2xNLS_CBPHAT
Key: NLS PUFa CBPHAT
(SEQ ID NO: 108)
MIDGGGGSDPKKKRKVDPKKKRKVDPKKKRKVGSTGSRNDGGGGSGGGGS
GGGGSGRAGILPPKKKRKVSRGRSRLLEDFRNNRYPNLQLREIAGHIMEF
SQDQHGSRFIQLKLERATPAERQLVFNEILQAAYQLMVDVFGNYVIQKFF
EFGSLEQKLALAERIRGHVLSLALQMYGSRVIEKALEFIPSDQQNEMVRE
LDGHVLKCVKDQNGNHVVQKCIECVQPQSLQFIIDAFKGQVFALSTHPYG
CRVIQRILEHCLPDQTLPILEELHQHTEQLVQDQYGNYVIQHVLEHGRPE
DKSKIVAEIRGNVLVLSQHKFASNVVEKCVTHASRTERAVLIDEVCTMND
GPHSALYTMMKDQYANYVVQKMIDVAEPGQRKIVMHKIRPHIATLRKYTY
GKHILAKLEKYYMKNGVDLGDPKKKRKVDPKKKRKVGGRGGGGSGGGGSG
GGGSGPAIFKPEELRQALMPTLEALYRQDPESLPFRQPVDPQLLGIPDYF
DIVKNPMDLSTIKRKLDTGQYQEPWQYVDDVWLMFNNAWLYNRKTSRVYK
FCSKLAEVFEQEIDPVMQSLGYCCGRKYEFSPQTLCCYGKQLCTIPRDAA
YYSYQNRYHFCEKCFTEIQGENVTLGDDPSQPQTTISKDQFEKKKNDTLD
PEPFVDCKECGRKMHQICVLHYDIIWPSGFVCDNCLKKTGRPRKENKFSA
KRLQTTRLGNHLEDRVNKFLRRQNHPEAGEVFVRVVASSDKTVEVKPGMK
SRFVDSGEMSESFPYRTKALFAFEEIDGVDVCFFGMHVQEYGSDCPPPNT
RRVYISYLDSIHFFRPRCLRTAVYHEILIGYLEYVKKLGYVTGHIWACPP
SEGDDYIFHCHPPDQKIPKPKRLQEWYKKMLDKAFAERIINDYKDIFKQA
NEDRLTSAKELPYFEGDFWPNVLEESIKELEQEEEERKKEESTAASETPE
GSQGDSKNAKKKNNKKTNKNKSSISRANKKKPSMPNVSNDLSQKLYATME
KHKEVFFVIHLHAGPVISTQPPIVDPDPLLSCDLMDGRDAFLTLARDKHW
EFSSLRRSKWSTLCMLVELHTQGQDRFVYTCNECKHHVETRWHCTVCEDY
DLCINCYNTKSHTHKMVKWGLGLDDEGSSQGEPQSKSPQESRRLSIQRCI
QSLVHACQCRNANCSLPSCQKMKRVVQHTKGCKRKTNGGCPVCKQLIALC
CYHAKHCQENKCPVPFCLNI

In the above sequence, the six 7-residue NLS sequences begin at residues 10, 18, 26, 63, 422, and 430, PUFa is residues 72-420, and CBPHAT is residues 458-1220.

| Name and Description | DNA sequence |
|---|---|
| sgRNA-PBS expression cassettes: | |
| U6::sgRNA-0xPBS expression cassette containing the target sequences as Ns without PBS sequences | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccAGATCTTTTTTTgttttagagctagaaatagcaagttaaaataaggct agtccgtagcgcgtgcgccaattctgcagacaaatggc (SEQ ID NO: 109) |
| U6::sgRNA-1xPBS32 expression cassette containing the target sequences as Ns and 1 copy of PBS32 (UGUAUGUA) | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt |

| Name and Description | DNA sequence |
|---|---|
| | ctccagatGCCTGTATGTAGCCagatCTTTTTTTgttttagagctagaaata gcaagttaaaataaggctagtccgtagcgcgtgcgccaattctgcagacaaa tggc (SEQ ID NO: 110) |
| U6::sgRNA-5xPBS32 expression cassette containing the target sequences as Ns and 5 copies of PBS32 (UGUAUGUA) separated by GCC spacer sequence attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt tccagatTGTATGTAGCCTGTATGTAGCCTGTATGTAGCCTGTATGTAGCC TGTATGTAagatCTTTTTTTgttttagagctagaaatagcaagttaaaataa ggctagtccgtagcgcgtgcgccaattctgcagacaaatggc (SEQ ID NO: 111) |
| U6::sgRNA-15xPBS32 expression and cloning cassette containing the target sequences as Ns and 15 copies of PBS32 (UGUAUGUA) separated by GCC spacer sequence attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccagatTGTATGTAGCCTGTATGTAGCCTGTATGTAGCCTGTATGTAGCC TGTATGTAAGATTGTATGTAGCCTGTATGTAGCCTGTATGTAGCCTGTATGTA GCCTGTATGTAAGATTGTATGTAGCCTGTATGTAGCCTGTATGTAGCCTGTA TGTAGCCTGTATGTAagatCTTTTTTTgttttagagctagaaatagcaagtt aaaataaggctagtccgtagcgcgtgcgccaattctgcagacaaatggc (SEQ ID NO: 112) |
| U6::sgRNA-25xPBS32 expression and cloning cassette containing the target sequences as Ns and 25 copies of PBS32 (UGUAUGUA) separated by GCC spacer sequence attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccagatTGTATGTAGCCTGTATGTAGCCTGTATGTAGCCTGTATGTAGCC TGTATGTAAGATTGTATGTAGCCTGTATGTAGCCTGTATGTAGCCTGTATGT AGCCTGTATGTAAGATTGTATGTAGCCTGTATGTAGCCTGTATGTAGCCTGT ATGTAGCCTGTATGTAAGATTGTATGTAGCCTGTATGTAGCCTGTATGTAGC CTGTATGTAGCCTGTATGTAAGATTGTATGTAGCCTGTATGTAGCCTGTATG TAGCCTGTATGTAGCCTGTATGTAagatCTTTTTTTgttttagagctagaaa tagcaagttaaaataaggctagtccgtagcgcgtgcgccaattctgcagaca aatggc (SEQ ID NO: 113) |
| U6::sgRNA-1xPBS6272 expression cassette containing the target sequences as Ns and 1 copy of PBS6272 (UUGAUAUA) | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccagatgccTtgATATAgccagatCTTTTTTTgttttagagctagaaata gcaagttaaaataaggctagtccgtagcgcgtgcgccaattctgcagacaaa tggc (SEQ ID NO: 114) |
| U6::sgRNA-2xPBS6272 expression cassette containing the target sequences as Ns and 2 copies of PBS6272 (UUGAUAUA) separated by GCC spacer sequence attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccagatTTGATATAGCCTTGATATAagatCTTTTTTTgttttagagctag aaatagcaagttaaaataaggctagtccgtagcgcgtgcgccaattctgcag acaaatggc (SEQ ID NO: 115) |
| U6::sgRNA-5xPBS6272 expression cassette containing the target sequences as Ns and 5 copies of PBS6272 (UUGAUAUA) separated by GCC spacer sequence | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt |

| Name and Description | DNA sequence |
| --- | --- |
| attached at 3' region of the sgRNA | ctccagatTTGATATAGCCTTGATATAGCCTTGATATAGCCTTGATATAGCC<br>TTGATATAagatCTTTTTTTgttttagagctagaaatagcaagttaaaataa<br>ggctagtccgtagcgcgtgcgccaattctgcagacaaatggc (SEQ ID NO: 116) |
| U6::sgRNA-10xPBS6272 expression cassette containing the target sequences as Ns and 10 copies of PBS6272 (UUGAUAUA) separated by GCC spacer sequence attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatTTGATATAGCCTTGATATAGCCTTGATATAGCCTTGATATAGCC<br>TTGATATAAGATTTGATATAGCCTTGATATAGCCTTGATATAGCCTTGATAT<br>AGCCTTGATATAagatCTTTTTTTgttttagagctagaaatagcaagttaaa<br>ataaggctagtccgtagcgcgtgcgccaattctgcagacaaatggc (SEQ ID NO: 117) |
| U6::sgRNA-15xPBS6272 expression cassette containing the target sequences as Ns and 15 copies of PBS6272 (UUGAUAUA) separated by GCC spacer sequence attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatTTGATATAGCCTTGATATAGCCTTGATATAGCCTTGATATAGCC<br>TTGATATAAGATTTGATATAGCCTTGATATAGCCTTGATATAGCCTTGATAT<br>AGCCTTGATATAAGATTTGATATAGCCTTGATATAGCCTTGATATAGCCTTG<br>ATATAGCCTTGATATAagatCTTTTTTTgttttagagctagaaatagcaagt<br>taaaataaggctagtccgtagcgcgtgcgccaattctgcagacaaatggc<br>(SEQ ID NO: 118) |
| U6::sgRNA-20xPBS6272 expression cassette containing the target sequences as Ns and 20 copies of PBS6272 (UUGAUAUA) separated by GCC spacer sequence attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatTTGATATAGCCTTGATATAGCCTTGATATAGCCTTGATATAGCC<br>TTGATATAAGATTTGATATAGCCTTGATATAGCCTTGATATAGCCTTGATAT<br>AGCCTTGATATAAGATTTGATATAGCCTTGATATAGCCTTGATATAGCCTTG<br>ATATAGCCTTGATATAAGATTTGATATAGCCTTGATATAGCCTTGATATAGC<br>CTTGATATAGCCTTGATATAagatCTTTTTTTgttttagagctagaaatagc<br>aagttaaaataaggctagtccgtagcgcgtgcgccaattctgcagacaaatg<br>gc (SEQ ID NO: 119) |
| U6::sgRNA-25xPBS6272 expression cassette containing the target sequences as Ns and 25 copies of PBS6272 (UUGAUAUA) separated by GCC spacer sequence attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatTTGATATAGCCTTGATATAGCCTTGATATAGCCTTGATATAGCC<br>TTGATATAAGATTTGATATAGCCTTGATATAGCCTTGATATAGCCTTGATAT<br>AGCCTTGATATAAGATTTGATATAGCCTTGATATAGCCTTGATATAGCCTTG<br>ATATAGCCTTGATATAAGATTTGATATAGCCTTGATATAGCCTTGATATAGC<br>CTTGATATAGCCTTGATATAAGATTTGATATAGCCTTGATATAGCCTTGATA<br>TAGCCTTGATATAGCCTTGATATAagatCTTTTTTTgttttagagctagaaa<br>tagcaagttaaaataaggctagtccgtagcgcgtgcgccaattctgcagaca<br>aatggc (SEQ ID NO: 120) |
| U6::sgRNA-47xPBS6272 expression cassette containing the target sequences as Ns and 47 copies of PBS6272 (UUGAUAUA) separated by GCC spacer sequence attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatTTGATATAGCCTTGATATAGCCTTGATATAGCCTTGATATAGCC<br>TTGATATAAGATTTGATATAGCCTTGATATAGCCTTGATATAGCCTTGATAT<br>AGCCTTGATATAAGATTTGATATACCTTGATATAGCCTTGATATAGCCTTGA<br>TATAGCCTTGATATAAGATTTGATATAGCCTTGATATAGCCTTGATATAGCC<br>TTGATATAGCCTTGATATAGCCTTGATATAGCCTTGATATAAGATTTGATAT<br>AGCCTTGATATAGCCTTGATATAGCCTTGATATAGCCTTGATATAAGATTTG<br>ATATAGCCTTGATATAGCCTTGATATAGCCTTGATATAGCCTTGATATAAGA |

| Name and Description | DNA sequence |
|---|---|
| | TTTGATATAGCCTTGATATAGCCTTGATATAGCCTTGATATAGCCTTGATAT<br>AAGATTTGATATAGCCTTGATATAGCCTTGATATAGCCTTGATATAGCCTTG<br>ATATAAGATTTGATATAGCCTTGATATAGCCTTGATATAGCCTTGATATAGC<br>CTTGATATAagatCTTTTTTTgttttagagctagaaatagcaagttaaaata<br>aggctagtccgtagcgcgtgcgccaattctgcagacaaatggc (SEQ ID<br>NO: 121) |
| U6::sgRNA-2xPBS6272-10Spacer expression cassette containing the target sequences as Ns and 2 copies of PBS6272 (UUGAUAUA) separated by GCCAGATGCC spacer sequence (SEQ ID NO: 173) attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatGCCTTGATATAGCCAGATGCCTTGATATAGCCagatCTTTTTTT<br>gttttagagctagaaatagcaagttaaaataaggctagtccgtagcgcgtgc<br>gccaattctgcagacaaatggc (SEQ ID NO: 122) |
| U6::sgRNA-6xPBS6272-10Spacer expression cassette containing the target sequences as Ns and 6 copies of PBS6272 (UUGAUAUA) separated by GCCAGATGCC spacer sequence (SEQ ID NO: 173) attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatGCCTTGATATAGCCAGATGCCTTGATATAGCCAGATGCCTTGAT<br>ATAGCCAGATGCCTTGATATAGCCAGATGCCTTGATATAGCCAGATGCCTTG<br>ATATAGCCagatCTTTTTTTgttttagagctagaaatagcaagttaaaataa<br>ggctagtccgtagcgcgtgcgccaattctgcagacaaatggc (SEQ ID<br>NO: 123) |
| U6::sgRNA-15xPBS6272-10Spacer expression cassette containing the target sequences as Ns and 15 copies of PBS6272 (UUGAUAUA) separated by GCCAGATGCC spacer sequence (SEQ ID NO: 173) attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatGCCTTGATATAGCCAGATGCCTTGATATAGCCAGATGCCTTGAT<br>ATAGCCAGATGCCTTGATATAGCCAGATGCCTTGATATAGCCAGATGCCTTG<br>ATATAGCCAGATGCCTTGATATAGCCAGATGCCTTGATATAGCCAGATGCCT<br>TGATATAGCCAGATGCCTTGATATAGCCAGATGCCTTGATATAGCCAGATGC<br>CTTGATATAGCCAGATGCCTTGATATAGCCAGATGCCTTGATATAGCCAGAT<br>GCCTTGATATAGCCagatCTTTTTTTgttttagagctagaaatagcaagtta<br>aaataaggctagtccgtagcgcgtgcgccaattctgcagacaaatggc<br>(SEQ ID NO: 124) |
| U6::sgRNA-20xPBS6272-10Spacer expression cassette containing the target sequences as Ns and 20 copies of PBS6272 (UUGAUAUA) separated by GCCAGATGCC spacer sequence (SEQ ID NO: 173) attached at 3' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCNNNNNNNNNNNN<br>NNNNNNNNNNgtttAagagctaTGCTGGAAACAGCAtagcaagttTaaataag<br>gctagtccgttatcaacttgaaaaagtggcaccgagtcggtgcCAATTGggt<br>ctccagatGCCTTGATATAGCCAGATGCCTTGATATAGCCAGATGCCTTGAT<br>ATAGCCAGATGCCTTGATATAGCCAGATGCCTTGATATAGCCAGATGCCTTG<br>ATATAGCCAGATGCCTTGATATAGCCAGATGCCTTGATATAGCCAGATGCCT<br>TGATATAGCCAGATGCCTTGATATAGCCAGATGCCTTGATATAGCCAGATGC<br>CTTGATATAGCCAGATGCCTTGATATAGCCAGATGCCTTGATATAGCCAGAT<br>GCCTTGATATAGCCAGATGCCTTGATATAGCCAGATGCCTTGATATAGCCAG<br>ATGCCTTGATATAGCCAGATCCTTGATATAGCCAGATGCCTTGATATAGCCa<br>gatCTTTTTTTgttttagagctagaaatagcaagttaaaataaggctagtcc<br>gtagcgcgtgcgccaattctgcagacaaatggc (SEQ ID NO: 125) |
| U6::5xPBS32-sgRNA expression cassette containing the target sequences as Ns and 5 copies of PBS32 (UGUAUGUA) separated by GCCAGATGCC spacer sequence (SEQ ID NO: 173) attached at 5' region of the sgRNA | gagggcctatttcccatgattccttcatatttgcatatacgatacaaggctg<br>ttagagagataattggaattaatttgactgtaaacacaaagatattagtaca<br>aaatacgtgacgtagaaagtaataatttcttgggtagtttgcagttttaaaa<br>ttatgttttaaaatggactatcatatgcttaccgtaacttgaaagtatttcg<br>atttcttggctttatatatcttGTGGAAAGGACGAAACACCgCAATTGggtc<br>tccAGATTGTATAGCCTGTATGTAGCCTGTATGTAGCCTGTATGTAGCCAT<br>GTATGTAAGATCTCACCNNNNNNNNNNNNNNNNNNNNNNgtttAagagctaTGC<br>TGGAAACAGCAtagcaagttTaaataaggctagtccgttatcaacttgaaaa<br>agtggcaccgagtcggtgcTTTTTTgttttagagctagaaatagcaagttaa<br>aataaggctagtccgtagcgcgtgcgccaattctgcagacaaatggc (SEQ<br>ID NO: 126) |

| Name and Description | DNA sequence |
|---|---|
| U6::sgRNA-2x[PBS32-PBS6272] expression cassette containing the target sequences as Ns and 2 copies of PBS32(UGUAUGUA)-PBS6272 (UUGAUAUA) clusters attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccagatTGTATGTAGTCTATTGATATAGTCTTGTCTATGTATGTAGTCTA TTGATATAagatCTTTTTTTgttttagagctagaaatagcaagttaaaataa ggctagtccgtagcgcgtgcgccaattctgcagacaaatggc (SEQ ID NO: 127) |
| U6::sgRNA-8x[PBS32-PBS6272] expression cassette containing the target sequences as Ns and 8 copies of PBS32(UGUAUGUA)-PBS6272 (UUGAUAUA) clusters attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccagatTGTATGTAGTCTATTGATATAGTCTTGTCTATGTATGTAG TCTATTGATATAAGATTGTATGTAGTCTATTGATATAGTCTTGTCTATGTAT GTAGTCTATTGATATAAGATTGTATGTAGTCTATTGATATAGTCTTGTCTAT GTATGTAGTCTATTGATATAagatCTTTTTTTgttttagagctagaaatagc aagttaaaataaggctagtccgtagcgcgtgcgccaattctgcagacaaatg gc (SEQ ID NO: 128) |
| U6::sgRNA-4x[PBS32-PBS6272] expression cassette containing the target sequences as Ns and 4 copies of PBS32(UGUAUGUA)-PBS6272 (UUGAUAUA) clusters attached at 3' region of the sgRNA | gagggcctatttcccatgattccttcatatttgcatatacgatacaaggctg ttagagagataattggaattaatttgactgtaaacacaaagatattagtaca aaatacgtgacgtagaaagtaataatttcttgggtagtttgcagttttaaaa ttatgttttaaaatggactatcatatgcttaccgtaacttgaaagtatttcg atttcttggctttatatatcttGTGGAAAGGACGAAACACCNNNNNNNNNNN NNNNNNNNNNgtttAagagctaTGCTGGAAACAGCAtagcaagttTaaataag gctagtccgttatcaacttgaaaaagtggcaccgagtcggtgcCAATTGggt ctccagatTGTATGTAGTCTATTGATATAGTCTTGTCTATGTATGTAGTCTA TTGATATAAGATTGTATGTAGTCTATTGATATAGTCTTGTCTATGTATGTAG TCTATTGATATAagatCTTTTTTTgttttagagctagaaatagcaagttaaa ataaggctagtccgtagcgcgtgcgccaattctgcagacaaatggc (SEQ ID NO: 129) |
| sgRNA target Sequences (sometimes an additional G is prepended to increase U6 transcriptional efficiency): | |
| Control Sequence | GTTCTCTTGCTGAAAGCTCGA (SEQ ID NO: 130) |
| TetO promoter | GCTTTTCTCTATCACTGATA (SEQ ID NO: 131) |
| SV40P1 | GCATACTTCTGCCTGCTGGGGAGCCTG (SEQ ID NO: 132) |
| SV40P2 | GAAAGTCCCCAGGCTCCCCAGC (SEQ ID NO: 133) |
| SV40P3 | GCATCTCAATTAGTCAGCAACC (SEQ ID NO: 134) |
| Telomere | GTTAGGGTTAGGGTTAGGGTTA (SEQ ID NO: 135) |
| Centromere | GTTGAGGCCTTCGTTGGAAAC (SEQ ID NO: 136) |
| MUC4-Nonrepeat-1 | GAAGAGTGGAGGCCGTGCGCGG (SEQ ID NO: 137) |
| MUC4-Nonrepeat-2 | GCAAGCAAGGGAAGCGACAAGG (SEQ ID NO: 138) |
| MUC4-Nonrepeat-3 | GATGTTTCAGGACTAGGCTGA (SEQ ID NO: 139) |
| MUC4-Nonrepeat-4 | GAGCTGGGCCAGGAGAGGAGA (SEQ ID NO: 140) |
| MUC4-Nonrepeat-5 | GAGGGGTCTGTGGAGAGTTT (SEQ ID NO: 141) |
| MUC4-Nonrepeat-6 | GGCTTGGTGTATTCAGAATG (SEQ ID NO: 142) |
| MUC4-Nonrepeat-7 | GTAGAGATGCCGCCCCGCCC (SEQ ID NO: 143) |
| OCT4-PP-1 | GGCCCCGCCCCCTGGATGGG (SEQ ID NO: 144) |
| OCT4-PP-2 | GGGGGGAGAAACTGAGGCGA (SEQ ID NO: 145) |
| OCT4-PP-3 | GGTGGTGGCAATGGTGTCTG (SEQ ID NO: 146) |

| Name and Description | DNA sequence |
|---|---|
| OCT4-PP-4 | GACACAACTGGCGCCCCTCC (SEQ ID NO: 147) |
| OCT4-PE-1 | GGCCCCTACTTCCCCTTCAA (SEQ ID NO: 148) |
| OCT4-PE-2 | GAGTGATAAGACACCCGCTT (SEQ ID NO: 149) |
| OCT4-PE-3 | GCCTGGGAGGGACTGGGGGA (SEQ ID NO: 150) |
| OCT4-PE-4 | GGACAATCCCGGTCCCCAGA (SEQ ID NO: 151) |
| OCT4-DE-1 | GGTCTGCCGGAAGGTCTACA (SEQ ID NO: 152) |
| OCT4-DE-2 | GGCAGGTAGATTATGGGGCC (SEQ ID NO: 153) |
| OCT4-DE-3 | GAAGACGGCCTCTCAGAGGA (SEQ ID NO: 154) |
| OCT4-DE-4 | GTATTTCTGGCCTGGGCAAG (SEQ ID NO: 155) |
| SOX2-PP-1 | GCATGTGACGGGGGCTGTCA (SEQ ID NO: 156) |
| SOX2-PP-2 | GCTGCCGGGTTTTGCATGAA (SEQ ID NO: 157) |
| SOX2-PP-3 | GCCGGCCGCGCGGGGAGGC (SEQ ID NO: 158) |
| SOX2-PP-4 | GGCAGGCGAGGAGGGGGAGG (SEQ ID NO: 159) |
| SV40-P1 | GCATACTTCTGCCTGCTGGGGAGCCTG (SEQ ID NO: 160) |

| Name | Peptide sequence |
|---|---|
| *S. pyrogene* NLS-dCas9-NLS | MYPYDVPDYASPKKKRKVEASDKKYSIGLAIGTNSVGWAVITDEYKVPSKKFKVLGNT DRHSIKKNLIGALLFDSGETAEATRLKRTARRRYTRRKNRICYLQEIFSNEMAKVDDS FFHRLEESFLVEEDKKHERHPIFGNIVDEVAYHEKYPTIYHLRKKLVDSTDKADLRLI YLALAHMIKFRGHFLIEGDLNPDNSDVDKLFIQLVQTYNQLFEENPINASGVDAKAIL SARLSKSRRLENLIAQLPGEKKNGLFGNLIALSLGLTPNFKSNFDLAEDAKLQLSKDT YDDDLDNLLAQIGDQYADLFLAAKNLSDAILLSDILRVNTEITKAPLSASMIKRYDEH HQDLTLLKALVRQQLPEKYKEIFFDQSKNGYAGYIDGGASQEEFYKFIKPILEKMDGT EELLVKLNREDLLRKQRTFDNGSIPHQIHLGELHAILRRQEDFYPFLKDNREKIEKIL TFRIPYYVGPLARGNSRFAWMTRKSEETITPWNFEEVVDKGASAQSFIERMTNFDKNL PNEKVLPKHSLLYEYFTVYNELTKVKYVTEGMRKPAFLSGEQKKAIVDLLFKTNRKVT VKQLKEDYFKKIECFDSVEISGVEDRFNASLGTYHDLLKIIKDKDFLDNEENEDILED IVLTLTLFEDREMIEERLKTYAHLFDDKVMKQLKRRRYTGWGRLSRKLINGIRDKQSG KTILDFLKSDGFANRNFMQLIHDDSLTFKEDIQKAQVSGQGDSLHEHIANLAGSPAIK KGILQTVKVVDELVKVMGRHKPENIVIEMARENQTTQKGQKNSRERMKRIEEGIKELG SQILKEHPVENTQLQNEKLYLYYLQNGRDMYVDQELDINRLSDYDVDAIVPQSFLKDD SIDNKVLTRSDKNRGKSDNVPSEEVVKKMKNYWRQLLNAKLITQRKFDNLTKAERGGL SELDKAGFIKRQLVETRQITKHVAQILDSRMNTKYDENDKLIREVKVITLKSKLVSDF RKDFQFYKVREINNYHHAHDAYLNAVVGTALIKKYPKLESEFVYGDYKVYDVRKMIAK SEQEIGKATAKYFFYSNIMNFFKTEITLANGEIRKRPLIETNGETGEIVWDKGRDFAT VRKVLSMPQVNIVKKTEVQTGGFSKESILPKRNSDKLIARKKDWDPKKYGGFDSPTVA YSVLVVAKVEKGKSKKLKSVKELLGITIMERSSFEKNPIDFLEAKGYKEVKKDLIIKL PKYSLFELENGRKRMLASAGELQKGNELALPSKYVNFLYLASHYEKLKGSPEDNEQKQ LFVEQHKHYLDEIIEQISEFSKRVILADANLDKVLSAYNKHRDKPIREQAENIIHLFT LTNLGAPAAFKYFDTTIDRKRYTSTKEVLDATLIHQSITGLYETRIDLSQLGGDSPKK KRKVEAS (SEQ ID NO: 161) |
| *S. pyogenes* NLS-Cas9WT-NLS | MYPYDVPDYASPKKKRKVEASDKKYSIGLDIGTNSVGWAVITDEYKVPSKKFKVLGNT DRHSIKKNLIGALLFDSGETAEATRLKRTARRRYTRRKNRICYLQEIFSNEMAKVDDS FFHRLEESFLVEEDKKHERHPIFGNIVDEVAYHEKYPTIYHLRKKLVDSTDKADLRLI YLALAHMIKFRGHFLIEGDLNPDNSDVDKLFIQLVQTYNQLFEENPINASGVDAKAIL SARLSKSRRLENLIAQLPGEKKNGLFGNLIALSLGLTPNFKSNFDLAEDAKLQLSKDT YDDDLDNLLAQIGDQYADLFLAAKNLSDAILLSDILRVNTEITKAPLSASMIKRYDEH HQDLTLLKALVRQQLPEKYKEIFFDQSKNGYAGYIDGGASQEEFYKFIKPILEKMDGT EELLVKLNREDLLRKQRTFDNGSIPHQIHLGELHAILRRQEDFYPFLKDNREKIEKIL TFRIPYYVGPLARGNSRFAWMTRKSEETITPWNFEEVVDKGASAQSFIERMTNFDKNL PNEKVLPKHSLLYEYFTVYNELTKVKYVTEGMRKPAFLSGEQKKAIVDLLFKTNRKVT VKQLKEDYFKKIECFDSVEISGVEDRFNASLGTYHDLLKIIKDKDFLDNEENEDILED IVLTLTLFEDREMIEERLKTYAHLFDDKVMKQLKRRRYTGWGRLSRKLINGIRDKQSG KTILDFLKSDGFANRNFMQLIHDDSLTFKEDIQKAQVSGQGDSLHEHIANLAGSPAIK KGILQTVKVVDELVKVMGRHKPENIVIEMARENQTTQKGQKNSRERMKRIEEGIKELG SQILKEHPVENTQLQNEKLYLYYLQNGRDMYVDQELDINRLSDYDVDHIVPQSFLKDD SIDNKVLTRSDKNRGKSDNVPSEEVVKKMKNYWRQLLNAKLITQRKFDNLTKAERGGL SELDKAGFIKRQLVETRQITKHVAQILDSRMNTKYDENDKLIREVKVITLKSKLVSDF RKDFQFYKVREINNYHHAHDAYLNAVVGTALIKKYPKLESEFVYGDYKVYDVRKMIAK |

| Name | Peptide sequence |
|---|---|
| | SEQEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPTVA<br>YSVLVVAKVEKGKSKKLKSVKELLGITIMERSSFEKNPIDFLEAKGYKEVKKDLIIKL<br>PKYSLFELENGRKRMLASAGELQKGNELALPSKYVNFLYLASHYEKLKGSPEDNEQKQ<br>LFVEQHKHYLDEIIEQISEFSKRVILADANLDKVLSAYNKHRDKPIREQAENIIHLFT<br>LTNLGAPAAFKYFDTTIDRKRYTSTKEVLDATLIHQSITGLYETRIDLSQLGGDSPKK<br>KRKVEAS (SEQ ID NO: 162) |
| *S. pyogenes* NLS-Cas9Nickase(D10A)-NLS | MYPYDVPDYASPKKKRKVEASDKKYSIGLAIGTNSVGWAVITDEYKVPSKKFKVLGNT<br>DRHSIKKNLIGALLFDSGETAEATRLKRTARRRYTRRKNRICYLQEIFSNEMAKVDDS<br>FFHRLEESFLVEEDKKHERHPIFGNIVDEVAYHEKYPTIYHLRKKLVDSTDKADLRLI<br>YLALAHMIKFRGHFLIEGDLNPDNSDVDKLFIQLVQTYNQLFEENPINASGVDAKAIL<br>SARLSKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKRYDEH<br>HQDLTLLKALVRQQLPEKYKEIFFDQSKNGYAGYIDGGASQEEFYKFIKPILEKMDGT<br>EELLVKLNREDLLRKQRTFDNGSIPHQIHLGELHAILRRQEDFYPFLKDNREKIEKIL<br>TFRIPYYVGPLARGNSRFAWMTRKSEETITPWNFEEVVDKGASAQSFIERMTNFDKNL<br>PNEKVLPKHSLLYEYFTVYNELTKVKYVTEGMRKPAFLSGEQKKAIVDLLFKTNRKVT<br>VKQLKEDYFKKIECFDSVEISGVEDRFNASLGTYHDLLKIIKDKDFLDNEENEDILED<br>IVLTLTLFEDREMIEERLKTYAHLFDDKVMKQLKRRRYTGWGRLSRKLINGIRDKQSG<br>KTILDFLKSDGFANRNFMQLIHDDSLTFKEDIQKAQVSGQGDSLHEHIANLAGSPAIK<br>KGILQTVKVVDELVKVMGRHKPENIVIEMARENQTTQKGQKNSRERMKRIEEGIKELG<br>SQILKEHPVENTQLQNEKLYLYYLQNGRDMYVDQELDINRLSDYDVDHIVPQSFLKDD<br>SIDNKVLTRSDKNRGKSDNVPSEEVVKKMKNYWRQLLNAKLITQRKFDNLTKAERGGL<br>SELDKAGFIKRQLVETRQITKHVAQILDSRMNTKYDENDKLIREVKVITLKSKLVSDF<br>RKDFQFYKVREINNYHHAHDAYLNAVVGTALIKKYPKLESEFVYGDYKVYDVRKMIAK<br>SEQEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPTVA<br>YSVLVVAKVEKGKSKKLKSVKELLGITIMERSSFEKNPIDFLEAKGYKEVKKDLIIKL<br>PKYSLFELENGRKRMLASAGELQKGNELALPSKYVNFLYLASHYEKLKGSPEDNEQKQ<br>LFVEQHKHYLDEIIEQISEFSKRVILADANLDKVLSAYNKHRDKPIREQAENIIHLFT<br>LTNLGAPAAFKYFDTTIDRKRYTSTKEVLDATLIHQSITGLYETRIDLSQLGGDSPKK<br>KRKVEAS (SEQ ID NO: 163) |
| *S. pyogenes* NLS-Cas9Nickase(H840A)-NLS | MYPYDVPDYASPKKKRKVEASDKKYSIGLDIGTNSVGWAVITDEYKVPSKKFKVLGNT<br>DRHSIKKNLIGALLFDSGETAEATRLKRTARRRYTRRKNRICYLQEIFSNEMAKVDDS<br>FFHRLEESFLVEEDKKHERHPIFGNIVDEVAYHEKYPTIYHLRKKLVDSTDKADLRLI<br>YLALAHMIKFRGHFLIEGDLNPDNSDVDKLFIQLVQTYNQLFEENPINASGVDAKAIL<br>SARLSKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKRYDEH<br>HQDLTLLKALVRQQLPEKYKEIFFDQSKNGYAGYIDGGASQEEFYKFIKPILEKMDGT<br>EELLVKLNREDLLRKQRTFDNGSIPHQIHLGELHAILRRQEDFYPFLKDNREKIEKIL<br>TFRIPYYVGPLARGNSRFAWMTRKSEETITPWNFEEVVDKGASAQSFIERMTNFDKNL<br>PNEKVLPKHSLLYEYFTVYNELTKVKYVTEGMRKPAFLSGEQKKAIVDLLFKTNRKVT<br>VKQLKEDYFKKIECFDSVEISGVEDRFNASLGTYHDLLKIIKDKDFLDNEENEDILED<br>IVLTLTLFEDREMIEERLKTYAHLFDDKVMKQLKRRRYTGWGRLSRKLINGIRDKQSG<br>KTILDFLKSDGFANRNFMQLIHDDSLTFKEDIQKAQVSGQGDSLHEHIANLAGSPAIK<br>KGILQTVKVVDELVKVMGRHKPENIVIEMARENQTTQKGQKNSRERMKRIEEGIKELG<br>SQILKEHPVENTQLQNEKLYLYYLQNGRDMYVDQELDINRLSDYDVDAIVPQSFLKDD<br>SIDNKVLTRSDKNRGKSDNVPSEEVVKKMKNYWRQLLNAKLITQRKFDNLTKAERGGL<br>SELDKAGFIKRQLVETRQITKHVAQILDSRMNTKYDENDKLIREVKVITLKSKLVSDF<br>RKDFQFYKVREINNYHHAHDAYLNAVVGTALIKKYPKLESEFVYGDYKVYDVRKMIAK<br>SEQEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPTVA<br>YSVLVVAKVEKGKSKKLKSVKELLGITIMERSSFEKNPIDFLEAKGYKEVKKDLIIKL<br>PKYSLFELENGRKRMLASAGELQKGNELALPSKYVNFLYLASHYEKLKGSPEDNEQKQ<br>LFVEQHKHYLDEIIEQISEFSKRVILADANLDKVLSAYNKHRDKPIREQAENIIHLFT<br>LTNLGAPAAFKYFDTTIDRKRYTSTKEVLDATLIHQSITGLYETRIDLSQLGGDSPKK<br>KRKVEAS (SEQ ID NO: 164) |
| Ruby::PUF(3-2) | MVRGSHHHHHGMASMTGGQQMGRDLYDDDDKDPMVSKGEELIKENMRMKVVMEGSVN<br>GHQFKCTGEGEGNPYMGTQTMRIKVIEGGPLPFAFDILATSFMYGSRTFIKYPKGIPD<br>FFKQSFPEGFTWERVTRYEDGGVVTVMQDTSLEDGCLVYHVQVRGVNFPSNGPVMQKK<br>TKGWEPNTEMMYPADGGLRGYTHMALKVDGGGHLSCSFVTTYRSKKTVGNIKMPGIHA<br>VDHRLERLEESDNEMFVVQREHAVAKFAGLGGGMDELYKGGGGSGPAGILPPKKKRKV<br>SRGRSRLLEDFRNNRYPNLQLREIAGHIMEFSQDQHGSRFIQLKLERATPAERQLVFN<br>EILQAAYQLMVDVFGNYVIQKFFEFGSLEQKLALAERIRGHVLSLALQMYGSRVIEKA<br>LEFIPSDQQNEMVRELDGHVLKCVKDQNGNHVVQKCIECVQPQSLQFIIDAFKGQVFA<br>LSTHPYGCRVIQRILEHCLPDQTLPILEELHQHTEQLVQDQYGNYVIQHVLEHGRPED<br>KSKIVAEIRGNVLVLSQHKFASNVVEKCVTHASRTERAVLIDEVCTMNDGPHSALYTM<br>MKDQYANYVVQKMIDVAEPGQRKIVMHKIRPHIATLRKYTYGKHILAKLEKYYMKNGV<br>DLG (SEQ ID NO: 165) |
| Ruby::PUF(6-2/7-2) | MVRGSHHHHHGMASMTGGQQMGRDLYDDDDKDPMVSKGEELIKENMRMKVVMEGSVN<br>GHQFKCTGEGEGNPYMGTQTMRIKVIEGGPLPFAFDILATSFMYGSRTFIKYPKGIPD<br>FFKQSFPEGFTWERVTRYEDGGVVTVMQDTSLEDGCLVYHVQVRGVNFPSNGPVMQKK<br>TKGWEPNTEMMYPADGGLRGYTHMALKVDGGGHLSCSFVTTYRSKKTVGNIKMPGIHA |

| Name | Peptide sequence |
|---|---|
| | VDHRLERLEESDNEMFVVQREHAVAKFAGLGGGMDELYKGGGGSGPAGILPPKKKRKV<br>SRGRSRLLEDFRNNRYPNLQLREIAGHIMEFSQDQHGSRFIQLKLERATPAERQLVFN<br>EILQAAYQLMVDVFGNYVIQKFFEFGSLEQKLALAERIRGHVLSLALQMYGCRVIQKA<br>LEFIPSDQQNEMVRELDGHVLKCVKDQNGNHVVQKCIECVQPQSLQFIIDAFKGQVFA<br>LSTHPYGCRVIQRILEHCLPDQTLPILEELHQHTEQLVQDQYGSYVIEHVLEHGRPED<br>KSKIVAEIRGNVLVLSQHKFANNVVQKCVTHASRTERAVLIDEVCTMNDGPHSALYTM<br>MKDQYANYVVQKMIDVAEPGQRKIVMHKIRPHIATLRKYTYGKHILAKLEKYYMKNGV<br>DLG (SEQ ID NO: 166) |
| Clover::PUF(3-2) | MVSKGEELFTGVVPILVELDGDVNGHKFSVRGEGEGDATNGKLTLKFICTTGKLPVPW<br>PTLVTTFGYGVACFSRYPDHMKQHDFFKSAMPEGYVQERTISFKDDGTYKTRAEVKFE<br>GDTLVNRIELKGIDFKEDGNILGHKLEYNFNSHNVYITADKQKNGIKANFKIRHNVED<br>GSVQLADHYQQNTPIGDGPVLLPDNHYLSHQSALSKDPNEKRDHMVLLEFVTAAGITH<br>GMDELYKSRGPYSIVSPKCGGGGSGPAGILPPKKKRKVSRGRSRLLEDFRNNRYPNLQ<br>LREIAGHIMEFSQDQHGSRFIQLKLERATPAERQLVFNEILQAAYQLMVDVFGNYVIQ<br>KFFEFGSLEQKLALAERIRGHVLSLALQMYGSRVIEKALEFIPSDQQNEMVRELDGHV<br>LKCVKDQNGNHVVQKCIECVQPQSLQFIIDAFKGQVFALSTHPYGCRVIQRILEHCLP<br>DQTLPILEELHQHTEQLVQDQYGNYVIQHVLEHGRPEDKSKIVAEIRGNVLVLSQHKF<br>ASNVVEKCVTHASRTERAVLIDEVCTMNDGPHSALYTMMKDQYANYVVQKMIDVAEPG<br>QRKIVMHKIRPHIATLRKYTYGKHILAKLEKYYMKNGVDLG (SEQ ID NO: 167) |
| Clover::PUF(6-2/7-2) | MVSKGEELFTGVVPILVELDGDVNGHKFSVRGEGEGDATNGKLTLKFICTTGKLPVPW<br>PTLVTTFGYGVACFSRYPDHMKQHDFFKSAMPEGYVQERTISFKDDGTYKTRAEVKFE<br>GDTLVNRIELKGIDFKEDGNILGHKLEYNFNSHNVYITADKQKNGIKANFKIRHNVED<br>GSVQLADHYQQNTPIGDGPVLLPDNHYLSHQSALSKDPNEKRDHMVLLEFVTAAGITH<br>GMDELYKSRGPYSIVSPKCGGGGSGPAGILPPKKKRKVSRGRSRLLEDFRNNRYPNLQ<br>LREIAGHIMEFSQDQHGSRFIQLKLERATPAERQLVFNEILQAAYQLMVDVFGNYVIQ<br>KFFEFGSLEQKLALAERIRGHVLSLALQMYGCRVIQKALEFIPSDQQNEMVRELDGHV<br>LKCVKDQNGNHVVQKCIECVQPQSLQFIIDAFKGQVFALSTHPYGCRVIQRILEHCLP<br>DQTLPILEELHQHTEQLVQDQYGSYVIEHVLEHGRPEDKSKIVAEIRGNVLVLSQHKF<br>ANNVVQKCVTHASRTERAVLIDEVCTMNDGPHSALYTMMKDQYANYVVQKMIDVAEPG<br>QRKIVMHKIRPHIATLRKYTYGKHILAKLEKYYMKNGVDLG (SEQ ID NO: 168) |
| PUF(3-2)::VP64 | MGILPPKKKRKVSRGRSRLLEDFRNNRYPNLQLREIAGHIMEFSQDQHGSRFIQLKLE<br>RATPAERQLVFNEILQAAYQLMVDVFGNYVIQKFFEFGSLEQKLALAERIRGHVLSLA<br>LQMYGSRVIEKALEFIPSDQQNEMVRELDGHVLKCVKDQNGNHVVQKCIECVQPQSLQ<br>FIIDAFKGQVFALSTHPYGCRVIQRILEHCLPDQTLPILEELHQHTEQLVQDQYGNYV<br>IQHVLEHGRPEDKSKIVAEIRGNVLVLSQHKFASNVVEKCVTHASRTERAVLIDEVCT<br>MNDGPHSALYTMMKDQYANYVVQKMIDVAEPGQRKIVMHKIRPHIATLRKYTYGKHIL<br>AKLEKYYMKNGVDLGGPAGSGRADALDDFDLDMLGSDALDDFDLDMLGSDALDDFDLD<br>MLGSDALDDFDLDMLYID (SEQ ID NO: 169) |
| PUF(6-2/7-2)::VP64 | MGILPPKKKRKVSRGRSRLLEDFRNNRYPNLQLREIAGHIMEFSQDQHGSRFIQLKLE<br>RATPAERQLVFNEILQAAYQLMVDVFGNYVIQKFFEFGSLEQKLALAERIRGHVLSLA<br>LQMYGCRVIQKALEFIPSDQQNEMVRELDGHVLKCVKDQNGNHVVQKCIECVQPQSLQ<br>FIIDAFKGQVFALSTHPYGCRVIQRILEHCLPDQTLPILEELHQHTEQLVQDQYGSYV<br>IEHVLEHGRPEDKSKIVAEIRGNVLVLSQHKFANNVVQKCVTHASRTERAVLIDEVCT<br>MNDGPHSALYTMMKDQYANYVVQKMIDVAEPGQRKIVMHKIRPHIATLRKYTYGKHIL<br>AKLEKYYMKNGVDLGGPAGSGRADALDDFDLDMLGSDALDDFDLDMLGSDALDDFDLD<br>MLGSDALDDFDLDMLYID (SEQ ID NO: 170) |
| PUF(6-2/7-2)::p65_HSF1 | MGILPPKKKRKVSRGRSRLLEDFRNNRYPNLQLREIAGHIMEFSQDQHGSRFIQLKLE<br>RATPAERQLVFNEILQAAYQLMVDVFGNYVIQKFFEFGSLEQKLALAERIRGHVLSLA<br>LQMYGCRVIQKALEFIPSDQQNEMVRELDGHVLKCVKDQNGNHVVQKCIECVQPQSLQ<br>FIIDAFKGQVFALSTHPYGCRVIQRILEHCLPDQTLPILEELHQHTEQLVQDQYGSYV<br>IEHVLEHGRPEDKSKIVAEIRGNVLVLSQHKFANNVVQKCVTHASRTERAVLIDEVCT<br>MNDGPHSALYTMMKDQYANYVVQKMIDVAEPGQRKIVMHKIRPHIATLRKYTYGKHIL<br>AKLEKYYMKNGVDLGGPAGGGSGGGGSGGGGSGPKKKRKVAAAGSPSGQISNQALAL<br>APSSAPVLAQTMVPSSAMVPLAQPPAPAPVLTPGPPQSLSAPVPKSTQAGEGTLSEAL<br>LHLQFDADEDLGALLGNSTDPGVFTDLASVDNSEFQQLLNQGVSMSHSTAEPMLMEYP<br>EAITRLVTGSQRPPDPAPTPLGTSGLPNGLSGDEDFSSIADMDFSALLSQISSSGQGG<br>GGSGFSVDTSALLDLFSPSVTVPDMSLPDLDSSLASIQELLSPQEPPRPPEAENSSPD<br>SGKQLVHYTAQPLFLLDPGSVDTGSNDLPVLFELGEGSYFSEGDGFAEDPTISLLTGS<br>EPPKAKDPTVSID (SEQ ID NO: 171) |
| KRAB::PUF(6-2/7-2) | MGSPKKKRKVEASMDAKSLTAWSRTLVTFKDVFVDFTREEWKLLDTAQQIVYRNVMLE<br>NYKNLVSLGYQLTKPDVILRLEKGEEPWLVSRGSIVGILPPKKKRKVSRGRSRLLEDF<br>RNNRYPNLQLREIAGHIMEFSQDQHGSRFIQLKLERATPAERQLVFNEILQAAYQLMV<br>DVFGNYVIQKFFEFGSLEQKLALAERIRGHVLSLALQMYGCRVIQKALEFIPSDQQNE<br>MVRELDGHVLKCVKDQNGNHVVQKCIECVQPQSLQFIIDAFKGQVFALSTHPYGCRVI<br>QRILEHCLPDQTLPILEELHQHTEQLVQDQYGSYVIEHVLEHGRPEDKSKIVAEIRGN<br>VLVLSQHKFANNVVQKCVTHASRTERAVLIDEVCTMNDGPHSALYTMMKDQYANYVVQ<br>KMIDVAEPGQRKIVMHKIRPHIATLRKYTYGKHILAKLEKYYMKNGVDLG (SEQ ID NO: 172) |

List of Vectors and their Addgene Accession Numbers

| pAC number | Descriptive name | Description |
|---|---|---|
| pAC164 | pmax-dCas9Master_VP64 | dCas9-VP64 driven by CAGGS promoter in expression vector pmax (Clontech) |
| pAC1119 | PB3-neo(−)-pmaxDEST(+) | PB gateway destination vector with neo selectable marker and pmax cassette (Clonetech) |
| pAC1355 | pmax-NLSPUFa_VP64 | NLSPUFa_VP64 in transient expression vector pmax |
| pAC1356 | pmax-NLSPUFb_VP64 | NLSPUFb_VP64 in expression vector pmax |
| pAC1357 | pmax-NLSPUFw_VP64 | NLSPUFw_VP64 in expression vector pmax |
| pAC1358 | pmax-NLSPUFc_VP64 | NLSPUFc_VP64 in expression vector pmax |
| pAC1360 | PB3-neo(−)-pmax-Clover_NLSPUFa | Clover_NLSPUFa in pAC1119 |
| pAC1362 | PB3-neo(−)-pmax-mRuby2_NLSPUFa | mRuby2_NLSPUFa in pAC1119 |
| pAC1364 | pmax-dCas9Master_mCBPHAT | dCas9Master_mCBPHAT in pmax expression vector |
| pAC1371 | pX-sgRNA-5xPBSa | Cloning vector for expression of sgRNA-5xPBSa |
| pAC1372 | pX-sgRNA-15xPBSa | Cloning vector for expression of sgRNA-15xPBSa |
| pAC1373 | pX-sgRNA-25xPBSa | Cloning vector for expression of sgRNA-25xPBSa |
| pAC1374 | pX-sgRNA-5xPBSb | Cloning vector for transient expression of sgRNA-5xPBSb |
| pAC1375 | pX-sgRNA-15xPBSb | Cloning vector for expression of sgRNA-15xPBSb |
| pAC1376 | pX-sgRNA-25xPBSb | Cloning vector for expression of sgRNA-25xPBSb |
| pAC1379 | pX-sgRNA-5xPBSw | Cloning vector for expression of sgRNA-5xPBSw |
| pAC1380 | pX-sgRNA-5xPBSc | Cloning vector for expression of sgRNA-5xPBSc |
| pAC1381 | PB3-neo(−)-pmax-Clover_NLSPUFc | Clover_NLSPUFc in pAC1119 |
| pAC1393 | pmax-NLSPUFa_p65HSF1 | NLSPUFa_p65HSF1 in pmax expression vector |
| pAC1394 | pX-sgRNA-0xPBS | Cloning vector for expression of sgRNA without PBS. It contains extra sequences for BsaI digestion for insertion of PBS |
| pAC1399 | pX-sgRNA-20xPBSc | Cloning vector for expression of sgRNA-20xPBSc |
| pAC1402 | pCR8-Clover_NLSPUFa | Clover_NLSPUFa in pCR8 gateway donor vector |
| pAC1403 | pCR8-Clover_NLSPUFc | Clover_NLSPUFc in pCR8 gateway donor vector |
| pAC1404 | pCR8-mRuby2_NLSPUFa | mRuby2_NLSPUFa in pCR8 gateway donor vector |
| pAC1405 | pCR8-4xNLS_PUFa_2xNLS | NLSPUFa pCR8 gateway donor vector for insertion of N-terminal domain (SgrAI or AgeI with ClaI) and C-terminal domain (FseI PacI). Grow in dcm- cells (e.g., NEB C3040) to prepare vector for ClaI digestion |
| pAC1406 | pCR8-4xNLS_PUFb_2xNLS | NLSPUFb pCR8 gateway donor vector for insertion of N-terminal domain (SgrAI or AgeI with ClaI) and C-terminal domain (FseI PacI). Grow in dcm- cells (e.g., NEB C3040) to prepare vector for ClaI digestion |
| pAC1407 | pCR8-4xNLS_PUFw_2xNLS | NLSPUFw pCR8 gateway donor vector for insertion of N-terminal domain (SgrAI or AgeI with ClaI) and C-terminal domain (FseI PacI). Grow in dcm- cells (e.g., NEB C3040) to prepare vector for ClaI digestion |
| pAC1408 | pCR8-4xNLS_PUFc_2xNLS | NLSPUFc pCR8 gateway donor vector for insertion of N-terminal domain (SgrAI or AgeI with ClaI) and C-terminal domain (FseI PacI). Grow in dcm- cells (e.g., NEB C3040) to prepare vector for ClaI digestion |
| pAC1410 | pmax-dCas9Master_p65HSF1 | dCas9Master_p65HSF1 in pmax expression vector |
| pAC1411 | pmax-NLSPUFc_p65HSF1 | NLSPUFc_p65HSF1 in pmax expression vector |
| pAC1412 | PB3-neo(−)-pmax-NLSKRAB_NLSPUFa | NLSKRAB_NLSPUFa in pAC1119 |
| pAC1413 | PB3-neo(−)-pmax-NLSPUFb_p65HSF1 | NLSPUFb_p65HSF1 in pAC1119 |
| pAC1414 | PB3-NLSPUFb_p65HSF1-neo(−)-BFPKRAB_NLSPUFa | Dual expression vector for NLSPUFb_p65HSF1 and BFPKRAB_NLSPUFa |
| pAC1415 | pCR8-4xNLS_PUFa_2xNLS_mCBPHAT | 4xNLS_PUFa_2xNLS_mCBPHAT in pCR8 Gateway donor vector |
| pAC1416 | pCR8-mCBPHAT_4xNLS_PUFa_2xNLS | mCBPHAT_4xNLS_PUFa_2xNLS in pCR8 Gateway donor vector |
| pAC1417 | pmax-4xNLS_PUFa_2xNLS_mCBPHAT | 4xNLS_PUFa_2xNLS_mCBPHAT in pmax expression vector |

-continued

| pAC number | Descriptive name | Description |
|---|---|---|
| pAC1418 | pmax-mCBPHAT_4xNLS_PUFa_2xNLS | mCBPHAT_4xNLS_PUFa_2xNLS in pmax expression vector |
| pAC1419 | PB3-neo(−)-pmax-dCas9Master_mCherry | dCas9Master_mCherry in pAC1119 |
| pAC1420 | pX-sgRNA-1xPBSa | Cloning vector for expression of sgRNA-1xPBSa |
| pAC1421 | pX-sgRNA-2xPBSa | Cloning vector for expression of sgRNA-2xPBSa |
| pAC1422 | pX-sgRNA-1xPBSb | Cloning vector for expression of sgRNA-1xPBSb |
| pAC1423 | pX-sgRNA-2xPBSb | Cloning vector for expression of sgRNA-2xPBSb |
| pAC1424 | pX-sgRNA-10xPBSb | Cloning vector for expression of sgRNA-10xPBSb |
| pAC1425 | pX-sgRNA-20xPBSb | Cloning vector for expression of sgRNA-20xPBSb |
| pAC1426 | pX-sgRNA-47xPBSb | Cloning vector for expression of sgRNA-47xPBSb |
| pAC1427 | pX-sgRNA-10xPBSw | Cloning vector for expression of sgRNA-10xPBSw |
| pAC1428 | pX-sgRNA-15xPBSw | Cloning vector for expression of sgRNA-15xPBSw |
| pAC1429 | pX-sgRNA-10xPBSc | Cloning vector for expression of sgRNA-10xPBSc |
| pAC1430 | pX-sgRNA-15xPBSc | Cloning vector for expression of sgRNA-15xPBSc |
| pAC1431 | PB3-LGFPL(−)-sgSOX2PP1-5xPBSa | Vector for expression of sgSOX2PP1-5xPBSa with a GFP marker flanked by loxP sites |
| pAC1432 | PB3-LGFPL(−)-sgSOX2PP2-5xPBSa(−) | Vector for expression of sgSOX2PP2-5xPBSa with a GFP marker flanked by loxP sites |
| pAC1433 | PB3-LGFPL(−)-sgSOX2PP3-5xPBSa | Vector for expression of sgSOX2PP3-5xPBSa with a GFP marker flanked by loxP sites |
| pAC1434 | PB3-LGFPL(−)-sgSOX2PP4-5xPBSa | Vector for expression of sgSOX2PP4-5xPBSa with a GFP marker flanked by loxP sites |
| pAC1435 | PB3-LGFPL(−)-sgOCT4PP1-5xPBSb | Vector for expression of sgOCT4PP1-5xPBSb with a GFP marker flanked by loxP sites |
| pAC1436 | PB3-LGFPL(−)-sgOCT4PP4-5xPBSb | Vector for expression of sgOCT4PP4-5xPBSb with a GFP marker flanked by loxP sites |
| pAC1437 | PB3-LGFPL(−)-sgOCT4PP3-5xPBSb | Vector for expression of sgOCT4PP3-5xPBSb with a GFP marker flanked by loxP sites |
| pAC1438 | PB3-LGFPL(−)-sgOCT4PP2-5xPBSb | Vector for expression of sgOCT4PP2-5xPBSb with a GFP marker flanked by loxP sites |

List of sgRNA-PBS Expression Vectors by Number and Type of PBS

| #PBS | PBSType | | | |
|---|---|---|---|---|
| | PUFa | PUFb | PUFw | PUFc |
| 1x | pAC1420 | pAC1422 | | |
| 2x | pAC1421 | pAC1423 | | |
| 5x | pAC1371 | pAC1374 | pAC1379 | pAC1380 |
| 10x | | pAC1424 | pAC1427 | pAC1429 |
| 15x | pAC1372 | pAC1375 | pAC1428 | pAC1430 |
| 20x | | pAC1425 | | pAC1399 |
| 25x | pAC1373 | pAC1376 | | |
| 47x | | pAC1426 | | |

The invention claimed is:

1. An RNA polynucleotide comprising:
   (1) a DNA-targeting sequence that is complementary to a target polynucleotide sequence;
   (2) a Cas9-binding sequence; and,
   (3) at least 5 tandem copies of a PUF domain-Binding Sequence (PBS).

2. The polynucleotide of claim 1, wherein the DNA-targeting sequence is complementary to the target polynucleotide sequence over about 12-22 nucleotides.

3. The polynucleotide of claim 1, wherein the DNA-targeting sequence has a 5' end nucleotide, and the 5' end nucleotide is G.

4. The polynucleotide of claim 1, further comprising a linker sequence linking the DNA-targeting sequence to the Cas9-binding sequence.

5. The polynucleotide of claim 1, wherein the Cas9-binding sequence
   (1) forms a hairpin structure, or
   (2) is about 37-47 nt or about 42 nt.

6. The polynucleotide of claim 1, wherein each of the multiple at least 5 tandem copies of the PBS has about 8 nucleotides.

7. The polynucleotide of claim 1, comprising
   a PBS of the sequence 5'-UGUAUGUA-3' that can be bound by the PUF domain PUF(3-2), or
   a PBS of the sequence 5'-UUGAUAUA-3' that can be bound by the PUF domain PUF(6-2/7-2).

8. The polynucleotide of claim 1, comprising 5-35 tandem copies of identical PUF domain-Binding Sequences.

9. The polynucleotide of claim 1, comprising 5-35 tandem copies of different PUF domain-Binding Sequences.

10. The polynucleotide of claim 1, comprising 5-10 tandem copies of identical PUF domain-Binding Sequences.

11. The polynucleotide of claim 1, comprising 5-10 tandem copies of different PUF domain-Binding Sequences.

12. The polynucleotide of claim 1, wherein the tandem copies of the PBS are separated from each other by a spacer sequence.

13. A vector comprising the polynucleotide of claim 1.

14. A plurality of vectors of claim 13, wherein the polynucleotides of the plurality of vectors have a different DNA-targeting sequence, Cas9-binding sequence, and/or PBS copy number or identity, relative to each other.

15. A complex comprising the polynucleotide of claim 1 and a Cas9 protein.

16. The complex of claim 15, further comprising a PUF domain bound to a PBS of the RNA polynucleotide.

17. The complex of claim 15, wherein the Cas9 protein is a nuclease-deficient dCas9 protein.

18. A host cell comprising the vector of claim 13.

* * * * *